US009938245B2

(12) United States Patent
Stockwell et al.

(10) Patent No.: US 9,938,245 B2
(45) Date of Patent: Apr. 10, 2018

(54) CARBONYL ERASTIN ANALOGS AND THEIR USE

(71) Applicant: THE TRUSTEES OF COLUMBIA UNIVERSITY IN THE CITY OF NEW YORK, New York, NY (US)

(72) Inventors: Brent R. Stockwell, New York, NY (US); Wan Seok Yang, New York, NY (US); Marie-Helene Larraufie, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/111,144

(22) PCT Filed: Jan. 14, 2015

(86) PCT No.: PCT/US2015/011451
§ 371 (c)(1),
(2) Date: Jul. 12, 2016

(87) PCT Pub. No.: WO2015/109009
PCT Pub. Date: Jul. 23, 2015

(65) Prior Publication Data
US 2016/0332974 A1   Nov. 17, 2016

Related U.S. Application Data

(60) Provisional application No. 61/927,601, filed on Jan. 15, 2014, provisional application No. 62/059,080, filed on Oct. 2, 2014.

(51) Int. Cl.
| | |
|---|---|
| *A61K 31/535* | (2006.01) |
| *C07D 239/91* | (2006.01) |
| *C07D 239/88* | (2006.01) |
| *C07D 403/10* | (2006.01) |

(52) U.S. Cl.
CPC ......... *C07D 239/91* (2013.01); *C07D 239/88* (2013.01); *C07D 403/10* (2013.01)

(58) Field of Classification Search
CPC ... C07D 239/88; C07D 239/91; C07D 403/10
USPC ........................................ 514/234.5; 544/290
See application file for complete search history.

(56) References Cited

U.S. PATENT DOCUMENTS

| | | | | |
|---|---|---|---|---|
| 7,615,554 B2* | 11/2009 | Selliah | .................. | A61K 31/495 514/218 |
| 8,518,959 B2* | 8/2013 | Becklin | .................. | A61K 31/495 514/266.1 |
| 9,695,133 B2* | 7/2017 | Stockwell | ............. | C07D 403/06 |
| 2006/0211683 A1 | 9/2006 | Selliah et al. | | |
| 2007/0161644 A1 | 7/2007 | Stockwell | | |
| 2008/0275067 A1 | 11/2008 | Fowler et al. | | |

OTHER PUBLICATIONS

Larraufie et al., "Incorporation of metabolically stable ketones into a small molecule probe to increase potency and water solubility!", 2015, Bioorganic & Medicinal Chemistry Letters, 25(21), pp. 4787-4792.*
Babij, C., et al. STK33 kinase activity is nonessential in KRAS-dependent cancer cells. Cancer Res 71, 5818-5826 (2011).
Barbie, D. A., et al. Systematic RNA interference reveals that oncogenic KRAS-driven cancers require TBK1. Nature 462, 108-112 (2009).
Boden, S. E., et al. MEK-1/2 inhibition prevents 5-lipoxygenase translocation in N-formylpeptide-challenged human neutrophils. Int J Biochem Cell Biol 32, 1069-1074 (2000).
Chen, B. K., et al. Overexpression of Ha-ras enhances the transcription of human arachidonate 12-lipoxygenase promoter in A431 cells. Biochim Biophys Acta 1344, 270-277 (1997).
Chen, X. S. & Funk, C. D. The N-terminal "beta-barrel" domain of 5-lipoxygenase is essential for nuclear membrane translocation. J Biol Chem 276, 811-818 (2001).
Chuang, J. I., et al. Glutathione depletion-induced apoptosis of Ha-ras-transformed NIH3T3 cells can be prevented by melatonin. Oncogene 22, 1349-1357 (2003).
Colles, S. M. & Chisolm, G. M. Lysophosphatidylcholine-induced cellular injury in cultured fibroblasts involves oxidative events. J Lipid Res 41, 1188-1198 (2000).

(Continued)

*Primary Examiner* — My-Chau T. Tran
(74) *Attorney, Agent, or Firm* — Bryan Cave LLP

(57) ABSTRACT

The present invention provides, inter alia, compounds having the structure of formula (I): Compositions containing such compounds are also provided. Methods for using such compounds or compositions for treating or ameliorating the effects of a cancer having a cell that harbors an oncogenic RAS mutation, for modulating a lipoxygenase in a ferroptosis cell death pathway, and for depleting reduced glutathione (GSH) in a cell harboring an oncogenic RAS mutation are further provided.

25 Claims, 92 Drawing Sheets

(56) References Cited

OTHER PUBLICATIONS

Dixon, S. J., et al. Systematic mapping of genetic interaction networks. Annu Rev Genet 43, 601-625 (2009).

Dixon, Scott J. et al. Ferroptosis: An Iron-Dependent Form of Nonapoptotic Cell Death. Cell 149, 1060-1072 (2012).

Dolma, S., et al. Identification of genotype-selective antitumor agents using synthetic lethal chemical screening in engineered human tumor cells. Cancer Cell 3, 285-296 (2003).

Downward, J. Targeting RAS signalling pathways in cancer therapy. Nat Rev Cancer 3, 11-22 (2003).

Fanelus, I. & Desrosiers, R. R. Reactive oxygen species generated by thiol-modifying phenylarsine oxide stimulate the expression of protein L-isoaspartyl methyltransferase. Biochem Biophys Res Commun 371, 203-208 (2008).

Haeggstrom, J. Z. & Funk, C. D. Lipoxygenase and leukotriene pathways: biochemistry, biology, and roles in disease. Chemical reviews 111, 5866-5898 (2011).

Hahn, W.C. et al. Creation of human tumour cells with defined genetic elements. Nature 400, 464-468 (1999).

Hartwell, L. H., et al. Integrating genetic approaches into the discovery of anticancer drugs. Science 278, 1064-1068 (1997).

Hussain, S. P., et al. Radical causes of cancer. Nat Rev Cancer 3, 276-285 (2003).

Imai, H. & Nakagawa, Y. Biological significance of phospholipid hydroperoxide glutathione peroxidase (PHGPx, GPx4) in mammalian cells. Free Radic Biol Med 34, 145-169 (2003).

International Search Report for PCT/US2015/011451, dated Apr. 3, 2015.

Irani, K. et al. Mitogenic signaling mediated by oxidants in Ras-transformed fibroblasts. Science 275, 1649-1652 (1997).

Ji, Z. et al. Chemical genetic screening of KRAS-based synthetic lethal inhibitors for pancreatic cancer. Frontiers in bioscience : a journal and virtual library 14, 2904-2910 (2009).

Kaelin, W. G., Jr. The concept of synthetic lethality in the context of anticancer therapy. Nat Rev Cancer 5, 689-698 (2005).

Kamphorst, J. J., et al. Liquid chromatography-high resolution mass spectrometry analysis of fatty acid metabolism. Analytical chemistry 83, 9114-9122 (2011).

Kang, Y. J. & Enger, M. D. Buthionine sulfoximine-induced cytostasis does not correlate with glutathione depletion. Am J Physiol 262, C122-127 (1992).

Kumar, M. S. et al. The GATA2 Transcriptional Network Is Requisite for RAS Oncogene-Driven Non-Small Cell Lung Cancer. Cell 149, 642-655 (2012).

Lebeau, A., et al. Blockade of 12-lipoxygenase expression protects cortical neurons from apoptosis induced by beta-amyloid peptide. Cell Death Differ 11, 875-884 (2004).

Li, Y., et al. A role for 12-lipoxygenase in nerve cell death caused by glutathione depletion. Neuron 19, 453-463 (1997).

Luo, J. et al. A genome-wide RNAi screen identifies multiple synthetic lethal interactions with the Ras oncogene. Cell 137, 835-848 (2009).

Luo, T. et al. STK33 kinase inhibitor BRD-8899 has no effect on KRAS-dependent cancer cell viability. Proc Natl Acad Sci U S A 109, 2860-2865, (2012).

Malumbres, M. & Barbacid, M. RAS oncogenes: the first 30 years. Nat Rev Cancer 3, 459-465 (2003).

McGarry, S. J. & Williams, A. J. Digoxin activates sarcoplasmic reticulum Ca(2+)-release channels: a possible role in cardiac inotropy. Br J Pharmacol 108, 1043-1050 (1993).

Patel, N. S. et al. Reduction of renal ischemia-reperfusion injury in 5-lipoxygenase knockout mice and by the 5-lipoxygenase inhibitor zileuton. Mol Pharmacol 66, 220-227 (2004).

Price, B. D., et al, Stimulation of phosphatidylcholine hydrolysis, diacylglycerol release, and arachidonic acid production by oncogenic ras is a consequence of protein kinase C activation. J Biol Chem 264, 16638-16643 (1989).

Ran, Q. et al. Embryonic fibroblasts from Gpx4+/-31 mice: a novel model for studying the role of membrane peroxidation in biological processes. Free Radic Biol Med 35, 1101-1109 (2003).

Root, D. E., et al. Biological mechanism profiling using an annotated compound library. Chemistry & biology 10, 881-892 (2003).

Scholl, C. et al. Synthetic lethal interaction between oncogenic KRAS dependency and STK33 suppression in human cancer cells. Cell 137, 821-834 (2009).

Seiler, A. et al. Glutathione peroxidase 4 senses and translates oxidative stress into 12/15-lipoxygenase dependent- and AIF-mediated cell death. Cell Metab 8, 237-248 (2008).

Shaw, A. T. et al. Selective killing of K-ras mutant cancer cells by small molecule inducers of oxidative stress. Proc Natl Acad Sci U S A 108, 8773-8778 (2011).

Shornick, L. P. & Holtzman, M. J. A cryptic, microsomal-type arachidonate 12-lipoxygenase is tonically inactivated by oxidation-reduction conditions in cultured epithelial cells. J Biol Chem 268, 371-376 (1993).

Szatrowski, T. P. & Nathan, C. F. Production of large amounts of hydrogen peroxide by human tumor cells. Cancer Res 51, 794-798 (1991).

Trachootham, D. et al. Selective killing of oncogenically transformed cells through a ROS-mediated mechanism by beta-phenylethyl isothiocyanate. Cancer Cell 10, 241-252 (2006).

Weiss, W. A., et al. Recognizing and exploiting differences between RNAi and small-molecule inhibitors. Nat Chem Biol 3, 739-744 (2007).

Weiwer, M. et al. Development of small-molecule probes that selectively kill cells induced to express mutant RAS. Bioorg Med Chem Lett 22, 1822-1826 (2012).

Wolpaw, A. J. et al. Modulatory profiling identifies mechanisms of small molecule-induced cell death. Proc Natl Acad Sci U S A 108, E771-780 (2011).

Written Opinion of the International Searching Authority for PCT/US2015/011451, dated Apr. 3, 2015.

Yagoda, N. et al. RAS-RAF-MEK-dependent oxidative cell death involving voltage-dependent anion channels. Nature 447, 864-868 (2007).

Yang, W. S. & Stockwell, B. R. Synthetic Lethal Screening Identifies Compounds Activating Iron-Dependent, Nonapoptotic Cell Death in Oncogenic-RAS-Harboring Cancer Cells. Chemistry & biology 15, 234-245 (2008a).

Yang, W. S. & Stockwell, B. R. Inhibition of casein kinase 1-epsilon induces cancer-cell-selective, PERIOD2-dependent growth arrest. Genome biology 9, R92 (2008b).

Yang, W. S. et al. Identification of Simple Compounds with Microtubule-Binding Activity That Inhibit Cancer Cell Growth with High Potency. ACS Med Chem Lett 3, 35-38 (2012).

Yu, Z., et al. The lipoxygenase gene ALOXE3 implicated in skin differentiation encodes a hydroperoxide isomerase. Proc Natl Acad Sci U S A 100, 9162-9167 (2003).

* cited by examiner d

PE (piperazine erastin)

c d e f g

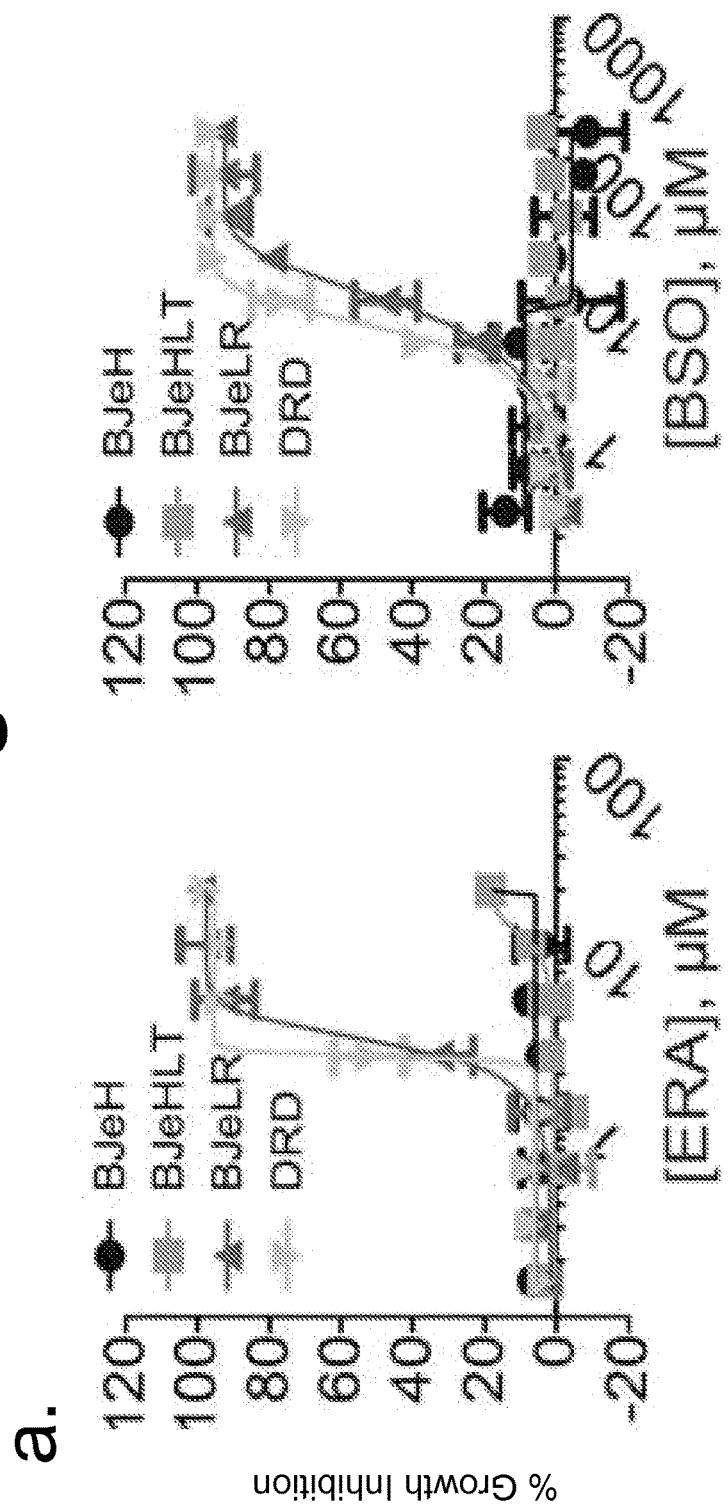

Fig. 6 continued b

| Abbr. | Full name | Target | Biological consequences |
|---|---|---|---|
| ERA | erastin | VDACs | Depletes GSH |
| BSO | Buthionine sulfoximine | GCLC | Prevents GSH synthesis |
| DETC | Sodium diethyldithiocarbamate trihydrate | SOD | Inhibits superoxide dismutase |
| DNCB | 1-Chloro-2,4-dinitrobenzene | TrxRs | Inhibits thioredoxin reductase irreversibly |
| IAA | Iodoacetamide | GRXs | Inhibits glutaredoxins irreversibly |
| DIA | Diamide | Cellular thiols | Reactive to cellular thiols including GSH |
| ATZ | 3-Amino-1,2,4-triazole | Catalase | Inhibition of catalase | a b a

| Abbreviation | Full name | Mechanism | Concentration (µM) | Incubation time (hour) |
|---|---|---|---|---|
| 9-AA | 9-Aminoacridine | DNA intercalating agent | 51.5 | 12 |
| CAN | Cantharidin | Protein phosphatase inhibitor | 51 | 30 |
| CAM | Camptothecin | Topoisomerase I inhibitor | 28.7 | 24 |
| COL | Colchicine | Microtubule depolymerizing agent | 2.5 | 30 |
| CCD | Cytochalasin D | Binds to actin and inhibits cytoskeletal function | 2 | 12 |
| DIG | Digoxin | Inhibits Na/K ATPase pump | 12.8 | 24 |
| ECH | Echinomycin | DNA intercalating agent | 0.9 | 30 |
| EMT | Emetine | Inhibits protein synthesis | 1.8 | 24 |
| ETO | Etoposide | Topoisomerase II inhibitor | 68 | 24 |
| PAO | Phenylarsine oxide | Metabolic poison, protein phosphatase inhibitor | 6 | 30 |
| STS | Staurosporine | Protein kinase inhibitor | 1 | 12 |

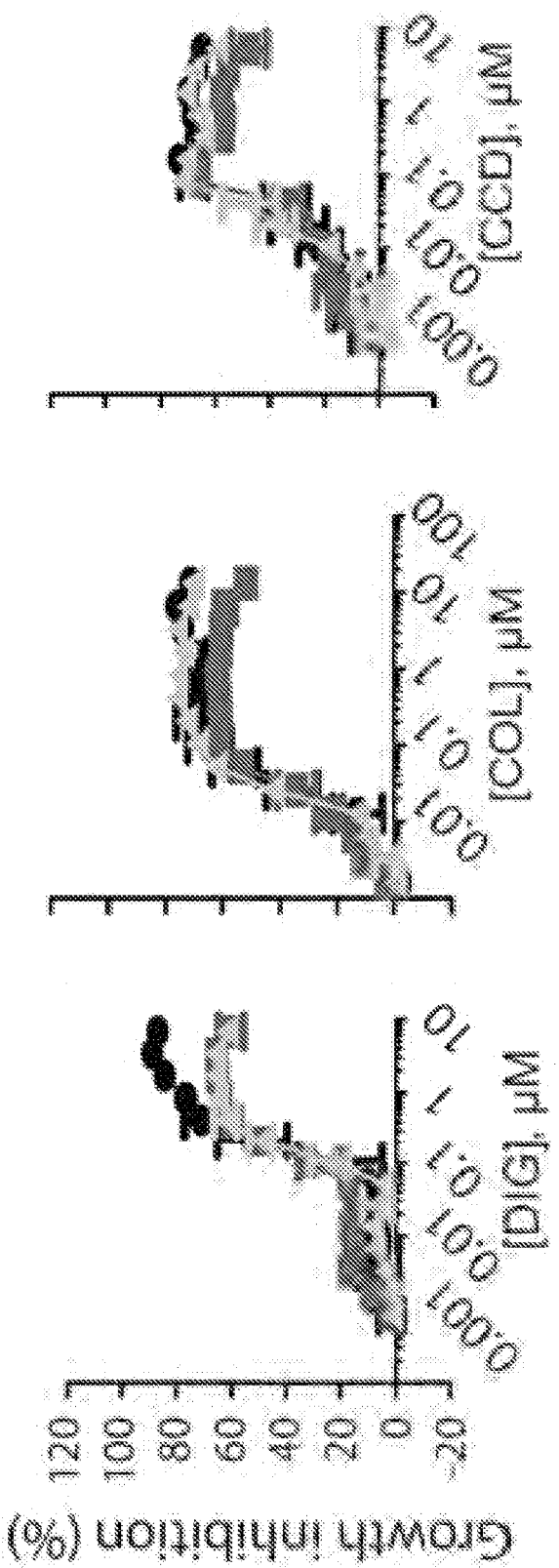

a
RSL compounds non-RSL compounds b

| Abbreviation | Full name | Concentration (µM) | Incubation time (day) |
|---|---|---|---|
| DPI2 | - | 40 | 1 |
| DPI6 | - | 12 | 0.5 |
| DPI7 | - | 0.2 | 0.5 |
| DPI9 | - | 2.2 | 0.5 |
| DPI10 | - | 10 | 1 |
| DPI12 | - | 3.3 | 0.5 |
| DPI13 | - | 13.9 | 0.5 |
| DPI17 | - | 2 | 0.5 |
| DPI18 | - | 3.6 | 0.5 |
| DPI19 | - | 3.5 | 0.5 |
| IONO | Ionomycin | 10 | 0.5 |
| STS | Staurosporine | 1 | 0.5 |
| 9-AA | 9-aminoacridine | 25.75 | 1 |
| CAN | Cantharidin | 25.5 | 1 |
| CAM | Camptothecin | 14.35 | 2 |
| COL | Colchicine | 0.5 | 1 |
| CCD | Cytochalasin D | 0.8 | 1 |
| DIG | Digoxin | 1.28 | 1 |
| ECH | Echinomycin | 0.09 | 1 |
| EMT | Emetine | 0.72 | 1 |
| ETO | Etoposide | 68 | 2 |
| PAO | Phenylarsine oxide | 0.6 | 1 | c

Cell line = BJeLR cells

Cell line = BJeLR cells

Cell line = BJeLR cells

Cell line = BJeLR cells

Cell line = BJeLR cells

Cell line = HT-1080 cells

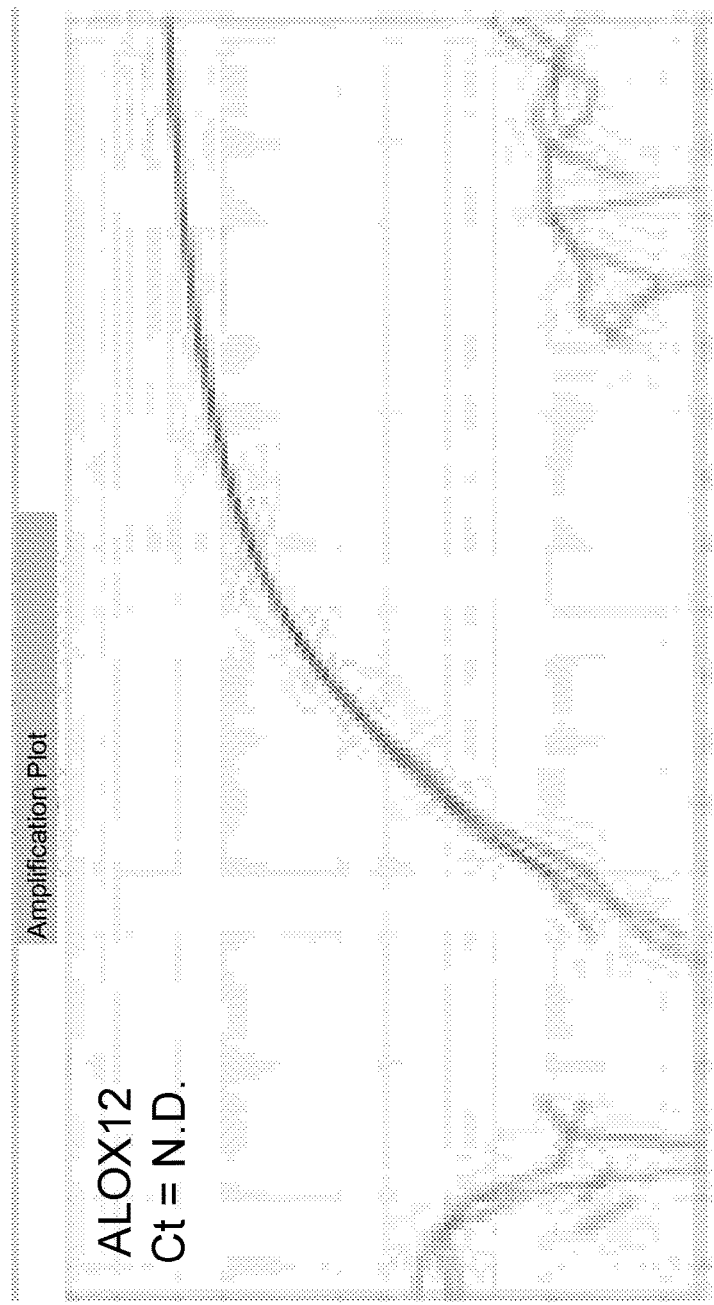

Cell line = HT-1080 cells

Cell line = HT-1080 cells

Cell line = HT-1080 cells

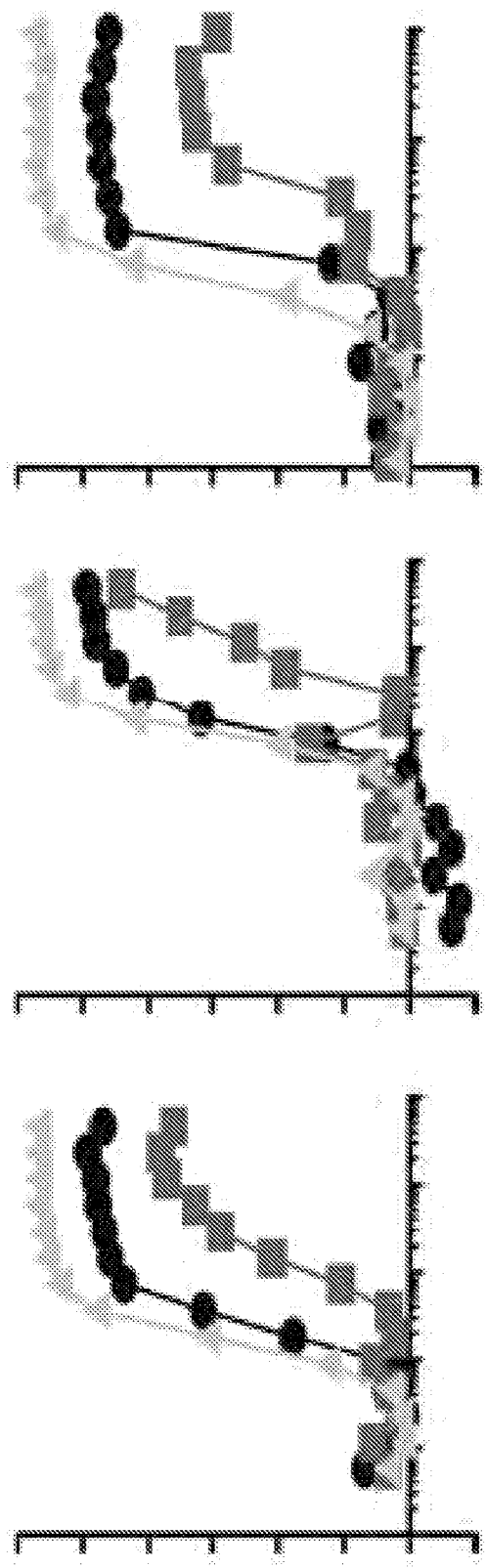

e a b

CARBONYL ERASTIN ANALOGS AND THEIR USE

CROSS-REFERENCES TO RELATED APPLICATIONS

The present application is the National Stage of International Application No. PCT/US2015/011451, filed on Jan. 14, 2015, which claims benefit to U.S. Provisional Patent Application Nos. 61/927,601, filed Jan. 15, 2014, and 62/059,080, filed Oct. 2, 2014. The entire contents of the above applications are incorporated by reference as if recited in full herein.

GOVERNMENT FUNDING

This invention was made with government support under grant no. CA097061 awarded by the National Institutes of Health. The government has certain rights in the invention.

FIELD OF INVENTION

The present invention provides, inter alia, carbonyl erastin analogs and compositions containing such compounds. Methods for using such compounds or compositions are also provided.

BACKGROUND OF THE INVENTION

Synthetic lethality describes a genetic interaction in which simultaneous mutations in two genes lead to synergistic cell death compared to individual mutations in the same genes (Kaelin, 2005; Yang et al., 2008a). The concept of synthetic lethality was originally used to study the buffering capacity of cells and organisms upon genetic variations, through which many gene-gene interactions have been discovered in multiple organisms, including bacteria, yeasts, and nematodes (Dixon et al., 2009; Malumbres, 2003). Soon after, it was recognized that this concept can be used as a framework for discovering anti-cancer drug leads with high therapeutic indices (Kaelin, 2005; Hartwell, 1997): one can search for small molecules that are only lethal in the presence of a specific oncogenic mutation.

Oncogenic RAS proteins have been targeted using this synthetic lethal screening approach, due to the widespread importance of mutant RAS proteins in the genesis and maintenance of human cancers (Malumbres et al., 2003), as well as the challenge of targeting oncogenic RAS proteins directly (Downward, 2003). Several synthetic lethal screens using RNA-interference-based (RNAi) libraries reported genes with synthetic lethal relationships with KRAS, such as PLK1 (Luo et al., 2009), TBK1 (Barbie et al., 2009), STK33 (Scholl et al., 2009), and GATA2 (Kumar et al., 2012). Some of these results may require further verification, because some follow-up studies did not support the originally postulated roles (Babij et al., 2011; Luo et al., 2012). The mechanism of synthetic lethality was attributed to increased dependence on mitotic function, NF-κB signaling, S6 kinase activity, and the GATA2 transcriptional network, respectively. The specific death-initiating mechanisms were different in these cases; however, cancer cells with oncogenic RAS mutations invariably died via apoptosis upon treatment with these RNAi reagents.

A different approach to targeting oncogenic RAS uses synthetic lethal screening with small molecules. Several RAS-synthetic-lethal (RSL) compounds were identified using this strategy (Yang et al., 2009; Yagoda et al., 2007; Weiwer et al., 2012; Shaw et al., 2011; Ji et al., 2009). The lethality of these RSL compounds, such as erastin and RSL3, was significantly enhanced upon activation of RAS-RAF-MEK signaling. In contrast to the results of RNAi screens, the small molecule approach yielded compounds that induced a distinct form of oxidative, non-apoptotic cell death. This mode of cell death was distinct from necrosis, and is a regulated form of oxidative cell death termed ferroptosis due to its unique morphology, inhibitor sensitivity and strict dependency on iron (Dixon et al., 2012). Thus, ferroptosis may be an efficient means of inducing synthetic lethality with small molecules in tumor cells harboring oncogenic RAS proteins. Defining the molecular pathways governing ferroptosis could aid in targeting RAS mutant tumors.

To define the core effectors of ferroptosis, erastin and RSL3 were further investigated, because both of these RSL compounds induce ferroptotic cell death via different triggering mechanisms. Erastin binds to VDAC2/3 (Yagoda et al., 2007), and inhibits system $xc^-$ (Dixon et al., 2012) to induce ferroptotic cell death. In contrast, RSL3 is not dependent on these proteins (Yang et al., 2008a), and its target has not been reported. Metabolomic profiling was used to evaluate comprehensively changes in metabolism upon erastin treatment, and it was found that a common lipoxygenase-mediated pathway executing ferroptotic cell death in response to RSL compounds.

RAS genes are among the most commonly mutated in human cancers, but their protein products have remained intractable to therapeutic agents. Thus, there is a need for, inter alia, anti-cancer drugs with high therapeutic indices that selectively target tumor cells, such as those harboring oncogenic RAS mutations. The present invention is directed to meeting these and other needs.

SUMMARY OF THE INVENTION

One embodiment of the present invention is a compound according to formula (I):

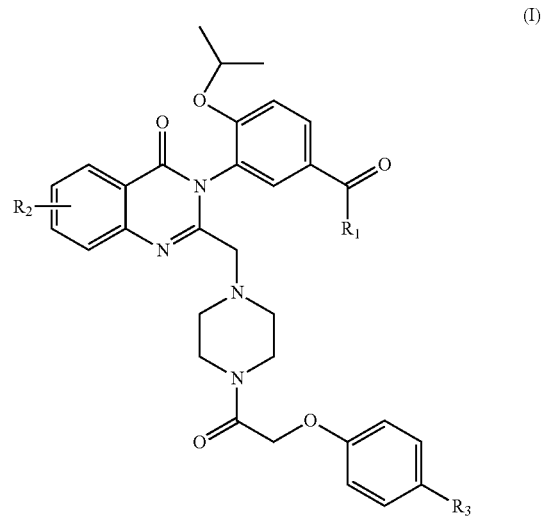

wherein:
R$_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;

$R_2$ is selected from the group consisting of H, halo, and $C_{1-6}$aliphatic; and $R_3$ is a halo atom;

or an N-oxide, crystalline form, hydrate, or pharmaceutically acceptable salt thereof.

Another embodiment of the present invention is a pharmaceutical composition. This pharmaceutical composition comprises a pharmaceutically acceptable carrier or diluent and a compound according to formula (I):

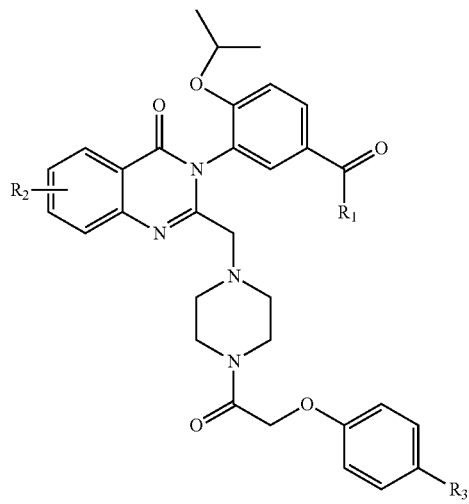

(I)

wherein:

$R_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;

$R_2$ is selected from the group consisting of H, halo, and $C_{1-6}$aliphatic; and $R_3$ is a halo atom;

or an N-oxide, crystalline form, hydrate, or pharmaceutically acceptable salt thereof.

An additional embodiment of the present invention is a method for treating or ameliorating the effects of a cancer comprising a cell that harbors an oncogenic RAS mutation. This method comprises administering to a subject in need thereof a therapeutically effective amount of any compound or pharmaceutical composition of the present invention.

Another embodiment of the present invention is a method for modulating a lipoxygenase in a ferroptosis cell death pathway. This method comprises contacting a cell with an effective amount of a compound having the structure of formula (I):

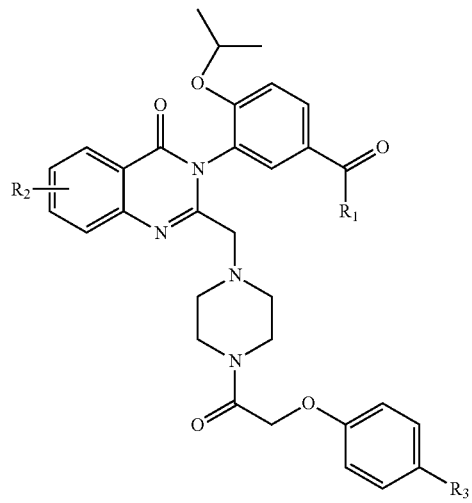

(I)

wherein:

$R_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;

$R_2$ is selected from the group consisting of H, halo, and $C_{1-6}$aliphatic; and $R_3$ is a halo atom;

or an N-oxide, crystalline form, hydrate, or pharmaceutically acceptable salt thereof.

Another embodiment of the present invention is a method for depleting reduced glutathione (GSH) in a cell harboring an oncogenic RAS mutation. This method comprises administering to the cell an effective amount of a compound having the structure of formula (I):

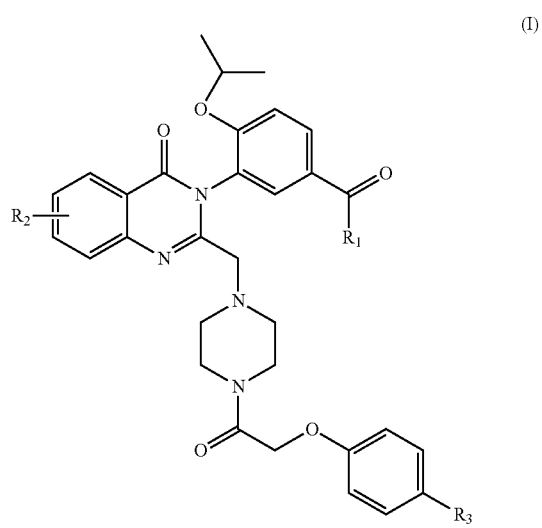

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;

R$_2$ is selected from the group consisting of H, halo, and C$_{1-6}$aliphatic; and R$_3$ is a halo atom;

or an N-oxide, crystalline form, hydrate, or pharmaceutically acceptable salt thereof.

An additional embodiment of the present invention is a method of inhibiting system xc$^-$ in a subject in need thereof. This method comprises administering to the subject an effective amount of a compound having the structure of formula (I):

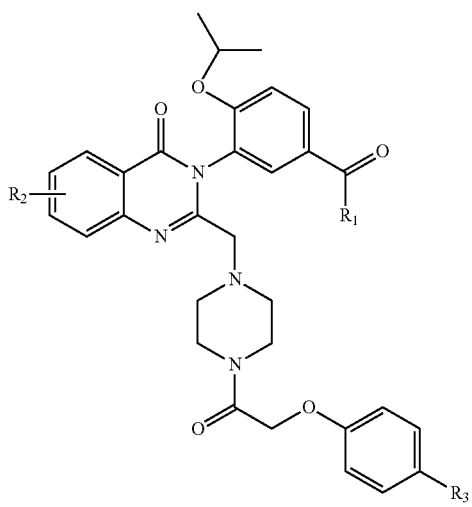

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;

R$_2$ is selected from the group consisting of H, halo, and C$_{1-6}$aliphatic; and R$_3$ is a halo atom;

or an N-oxide, crystalline form, hydrate, or pharmaceutically acceptable salt thereof.

A further embodiment of the present invention is a method of selectively killing a cell having a Ras$^{v12}$ mutation. This method comprises contacting the cell with an effective amount of a compound having the structure of formula (I):

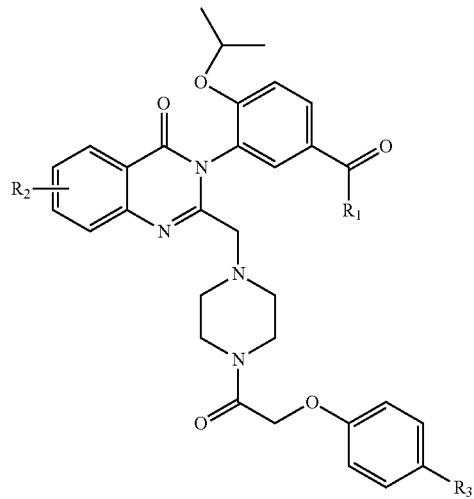

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;

R$_2$ is selected from the group consisting of H, halo, and C$_{1-6}$aliphatic; and R$_3$ is a halo atom;

or an N-oxide, crystalline form, hydrate, or pharmaceutically acceptable salt thereof.

Another embodiment of the present invention is a kit. This kit comprises any compound or pharmaceutical composition according to the present invention together with instructions for the use of the compound.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1a is a graph showing the fold changes in metabolites upon erastin treatment. 264 metabolites from HT-1080 cells were analyzed.

FIG. 1b are graphs showing dose-dependent depletion of GSH by erastin in HT-1080 cells and U-2 OS cells. Data are presented as mean±standard deviation (s.d.); n=3.

FIG. 1c is a plot showing GSH depletion by various erastin analogs. HT-1080 cells were incubated with 10 μM of erastin analogs for 5 hours or 100 μM buthioninesulfoximine (BSO) for 12 hours before measurement of GSH concentration. GSH in each sample was first normalized to the DMSO sample, then box-and-whisker plots were generated (n=3-8). Mid-line, median; box, 25th to 75th percentiles; and whiskers, minimum and maximum. , P<0.01, with respect to PYR-ERA; *, P<0.001.

FIG. 1d shows light microscopy images (top panel) and a growth inhibition plot (bottom panel) demonstrating that BSO induces the RSL phenotype. BJeLR and DRD are cells expressing HRAS$^{G12V}$, whereas BJeH and BJeHLT are isogenic counterparts lacking HRAS$^{G12V}$. Data are presented as mean±s.d.; n=3. Scale bars, 60 μm.

FIG. 1e is a plot showing that Erastin and BSO induced the RSL phenotype through a similar mechanism. The pattern of cell death inhibition was similar between erastin and BSO. The name of cell death inhibitors and the treatment condition is listed in Table 1 below.

TABLE 1

Figure 1:
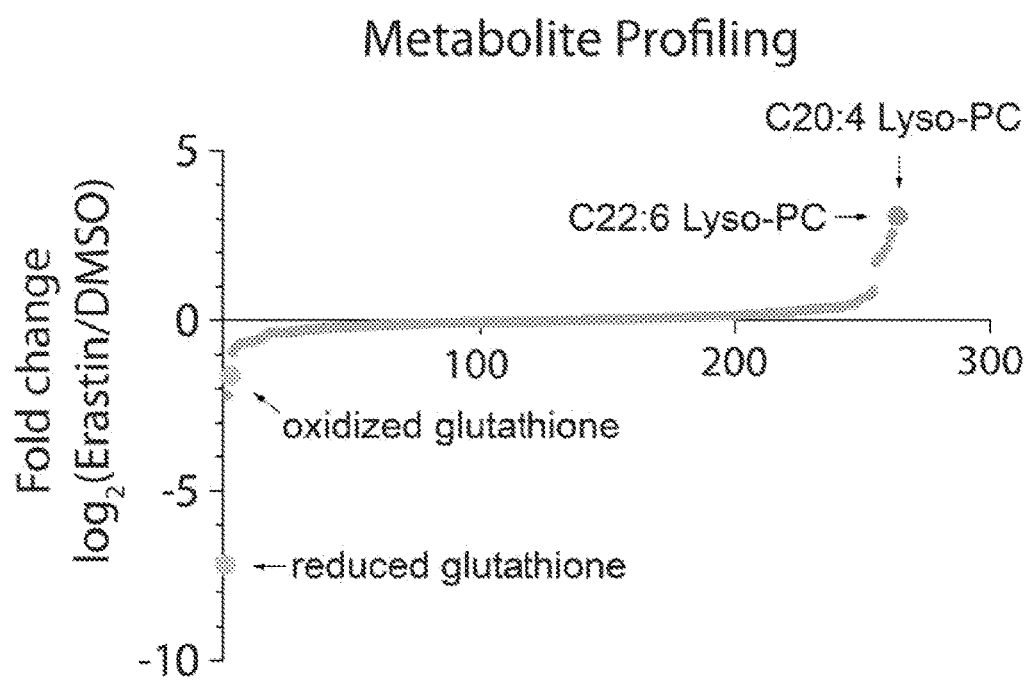
FIG. 1 shows that metabolite profiling revealed cellular glutathione (GSH) depletion as the most significant change upon erastin treatment.
Figure 1:
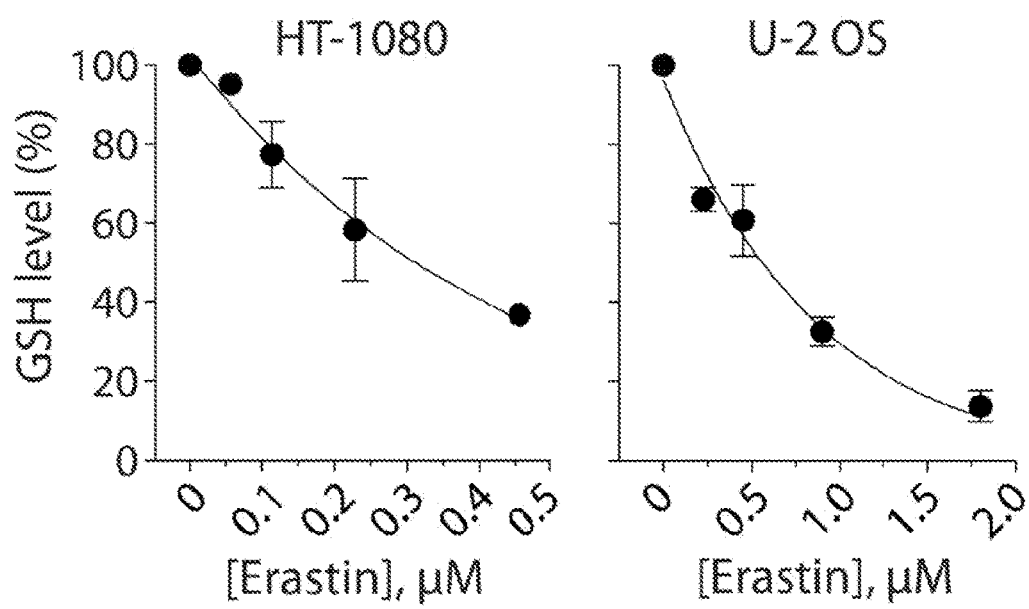
Figure 1:
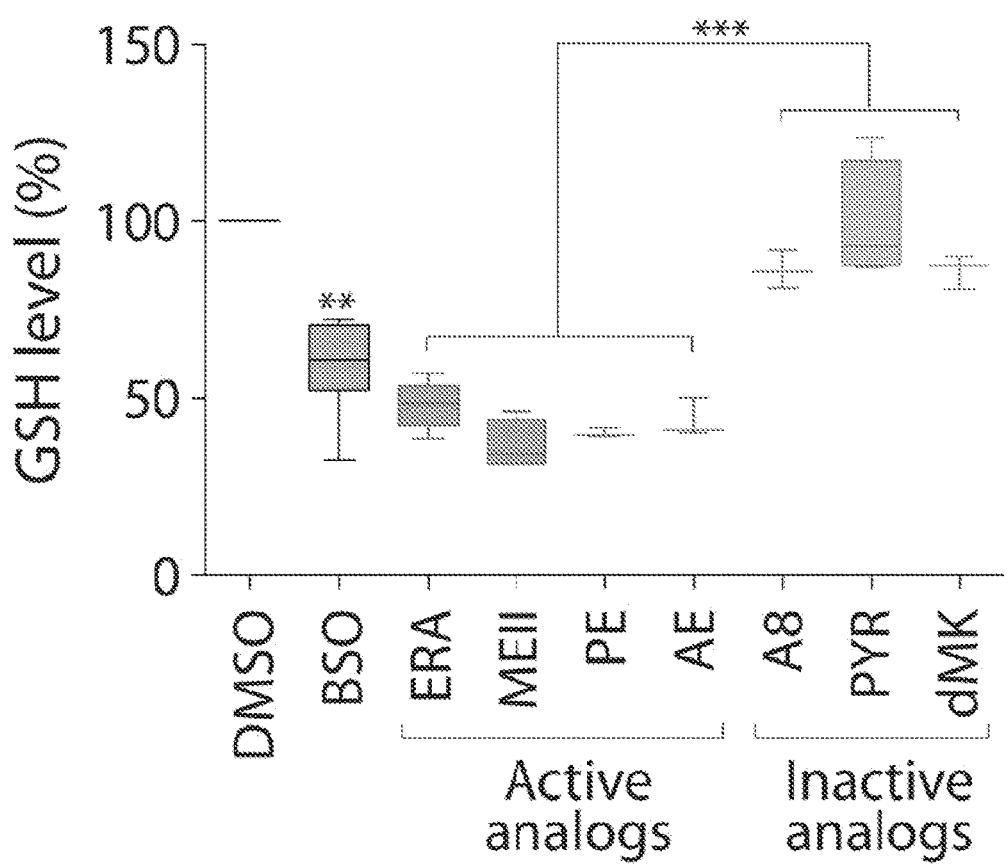
Figure 1:
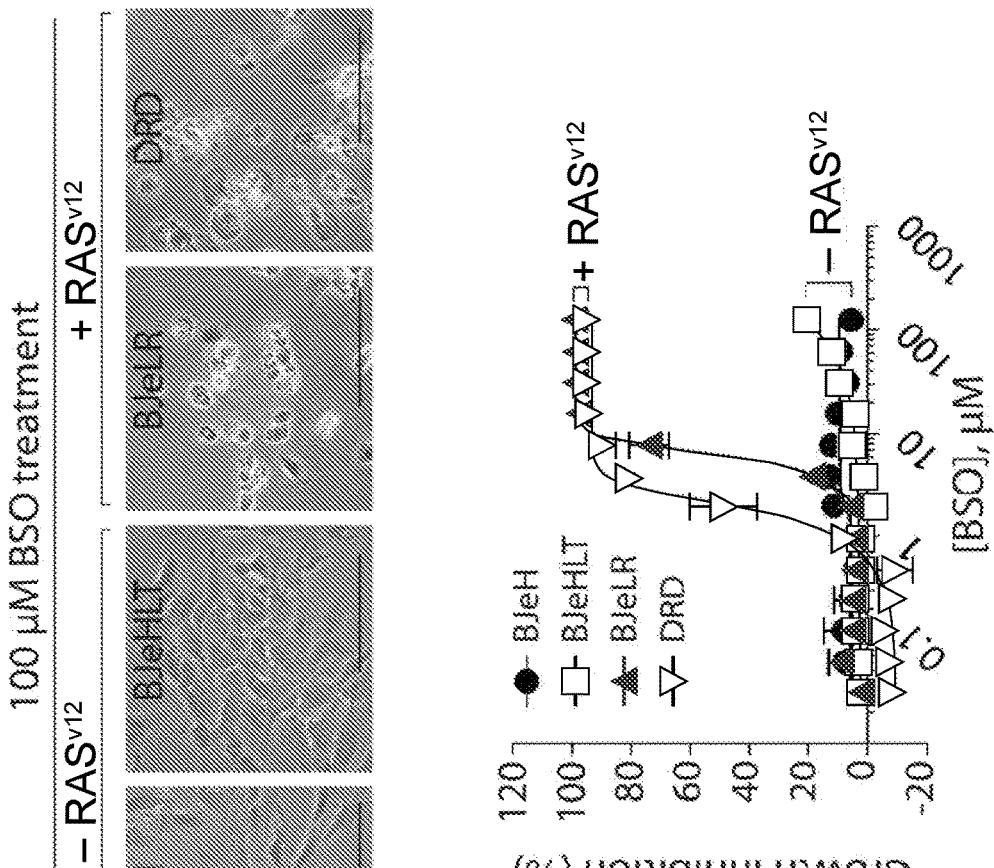
Figure 1:
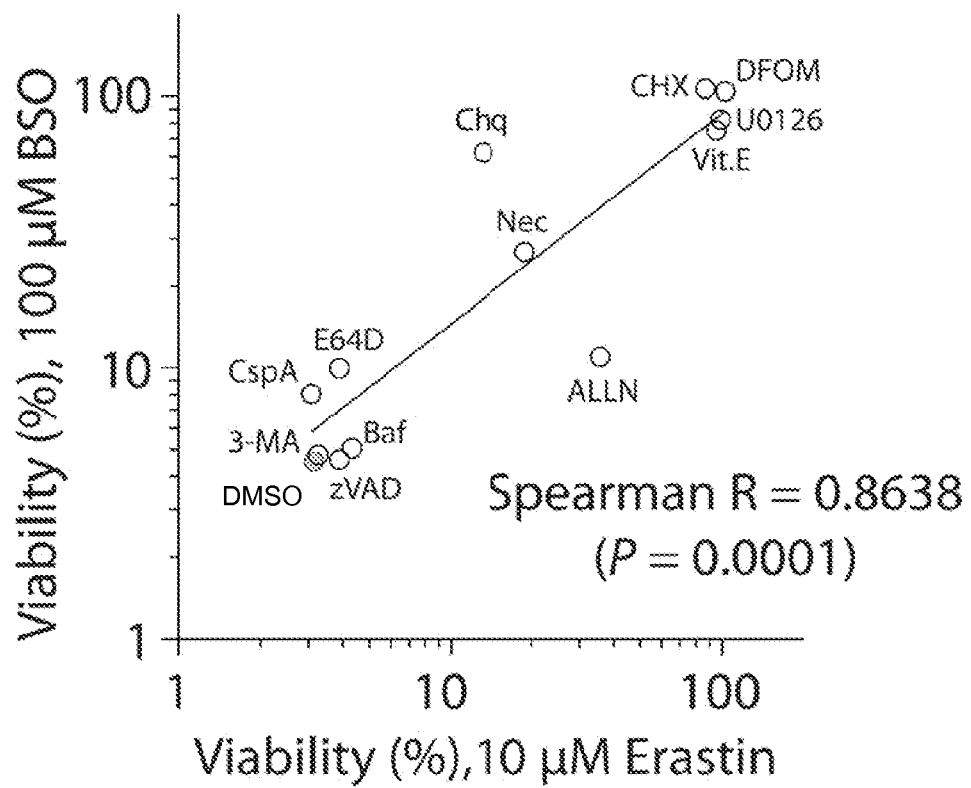

Name and treatment condition of cell death inhibitors used in FIG. 1e.

| Abbr. | Inhibitor | Target | Concentration, μM |
|---|---|---|---|
| 3-MA | 3-methyladenine | formation of preautophagosome | 1000 |
| zVAD | z-VAD-fmk | caspases | 50 |
| Baf | Bafilomycin A1 | autophagosome-lysosome fusion | 1 |
| CspA | Cyclosporin A | cyclophilin D | 5 |
| E64D | E64D | calpains/cathepsins | 100 |
| ALLN | ALLN | calpains | 2.5 |
| Nec | Necrostatin-1 | RIP1 kinase | 10 |
| Chq | Chloroquine | autophagosome-lysosome fusion | 10 |
| Vit. E | Vitamin E | lipophilic antioxidant | 100 |
| U0126 | U0126 | MEK inhibitor | 10 |
| CycH | Cycloheximide | Translation elongation | 1.5 |
| DFOM | Deferoxamine | iron chelator | 100 |

Figure 2:
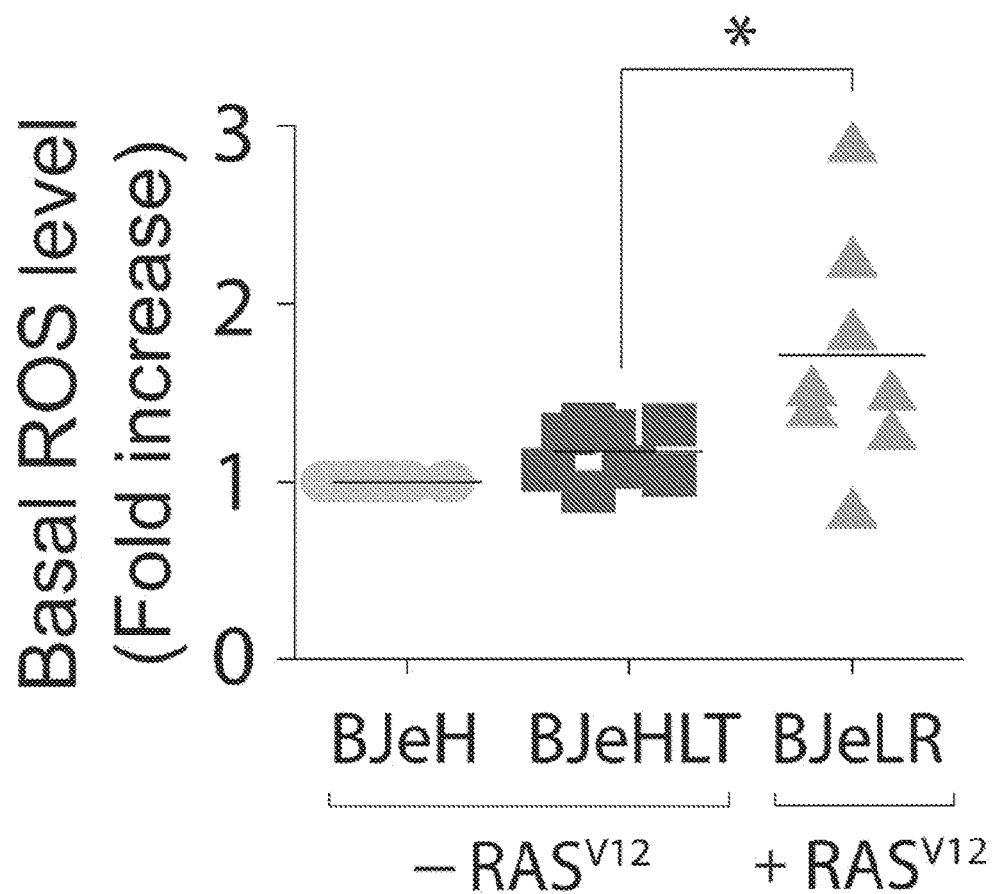
Figure 2:
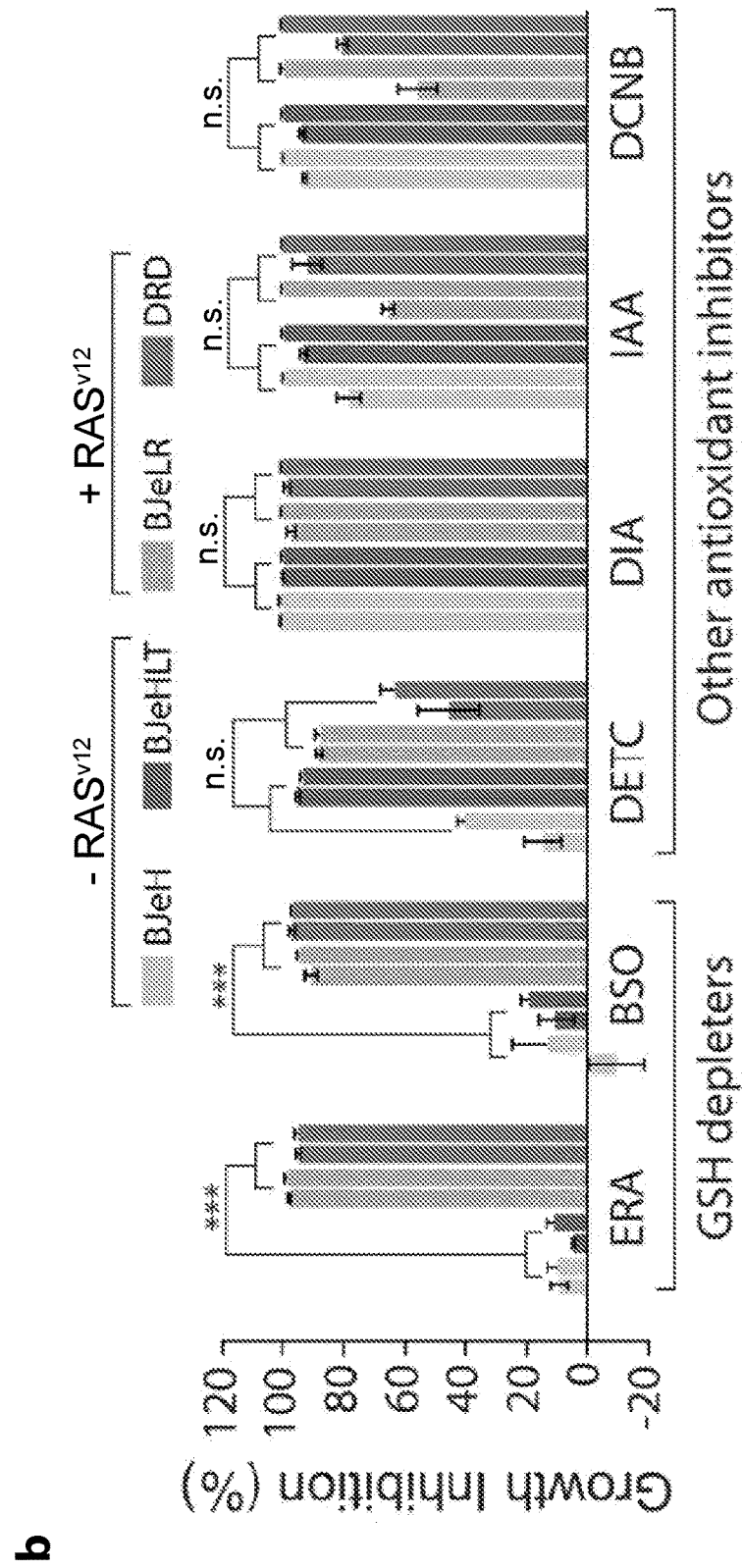
Figure 2:
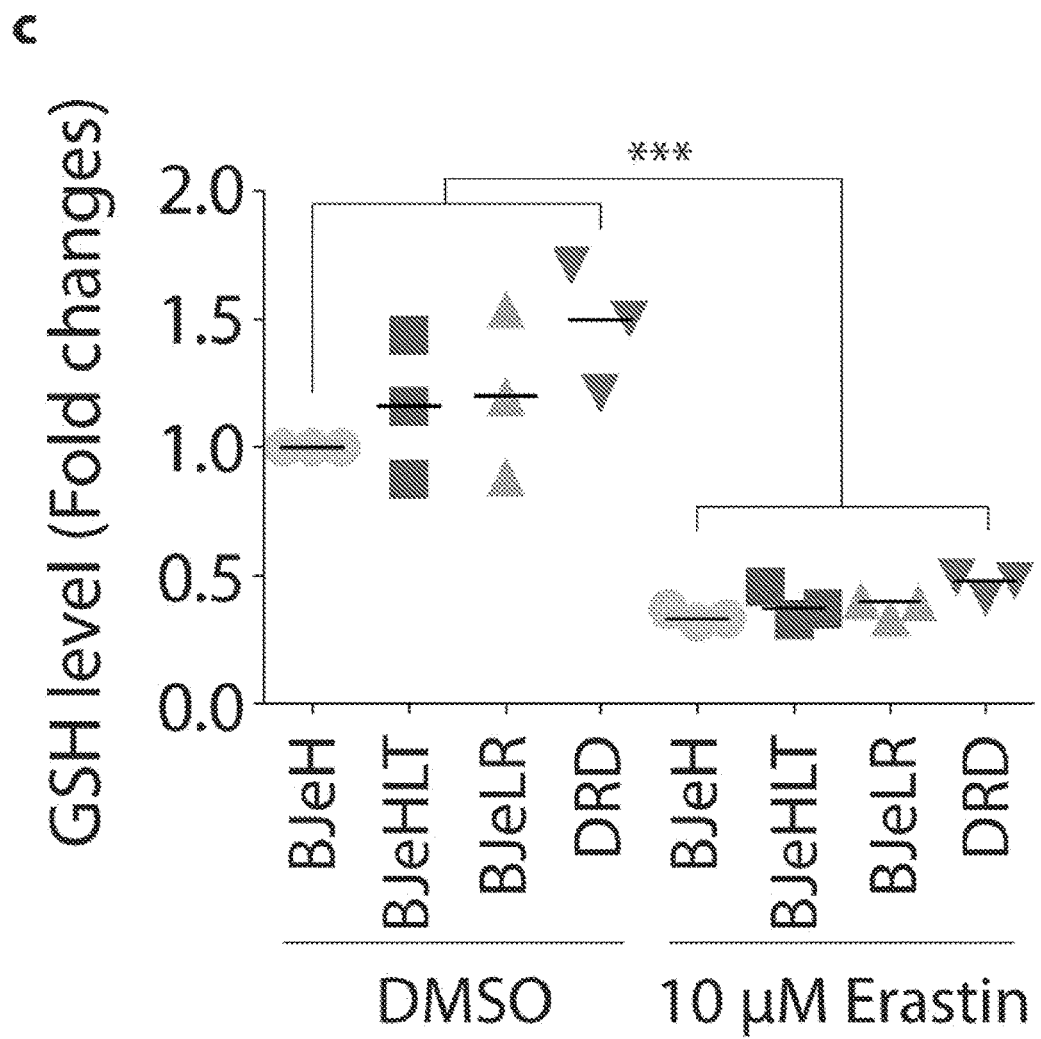
Figure 2:
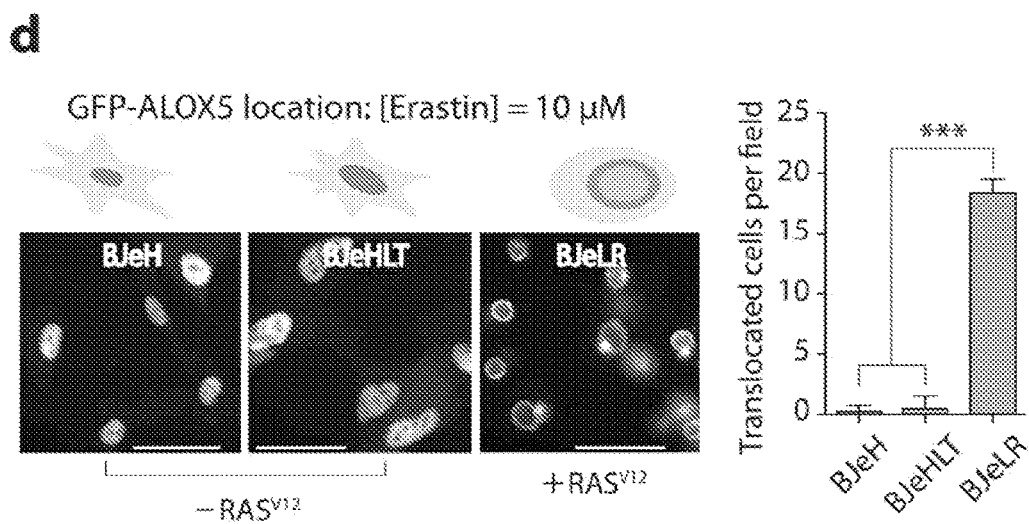
Figure 2:
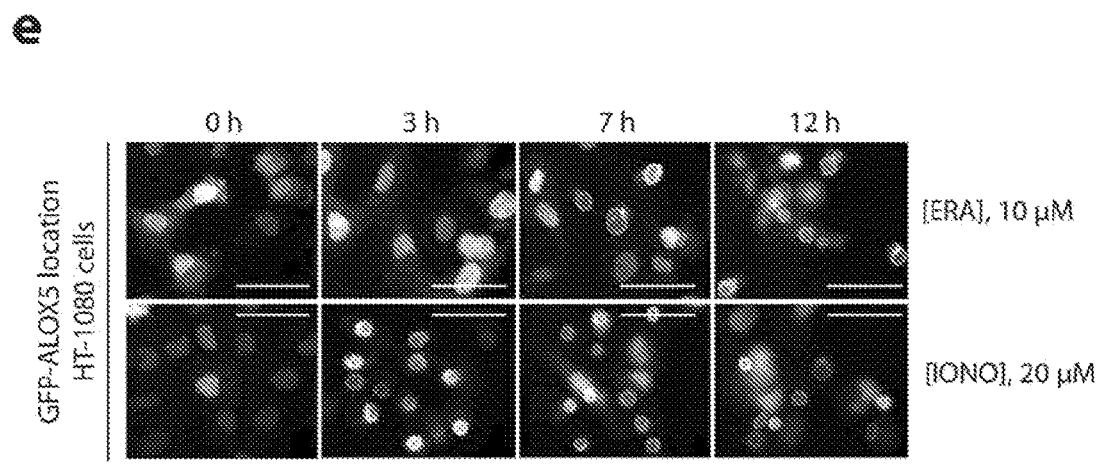
Figure 2:
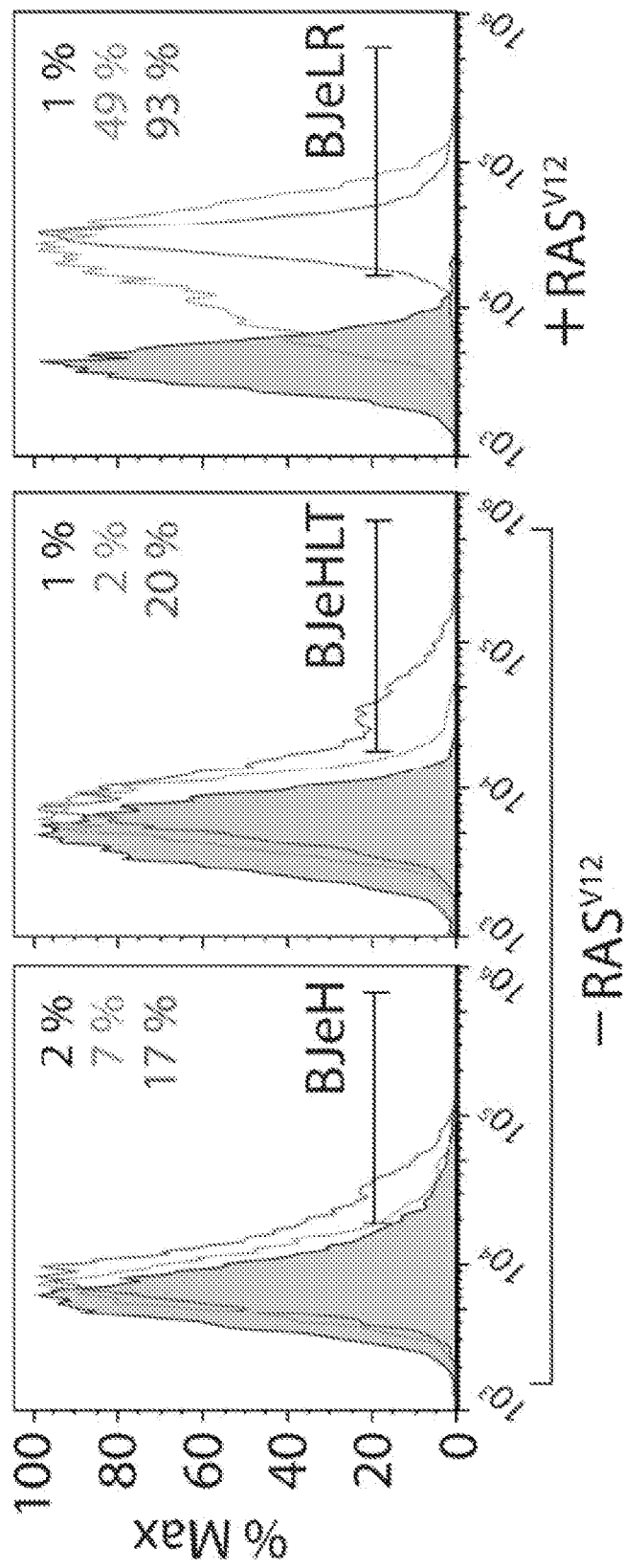
Figure 2:
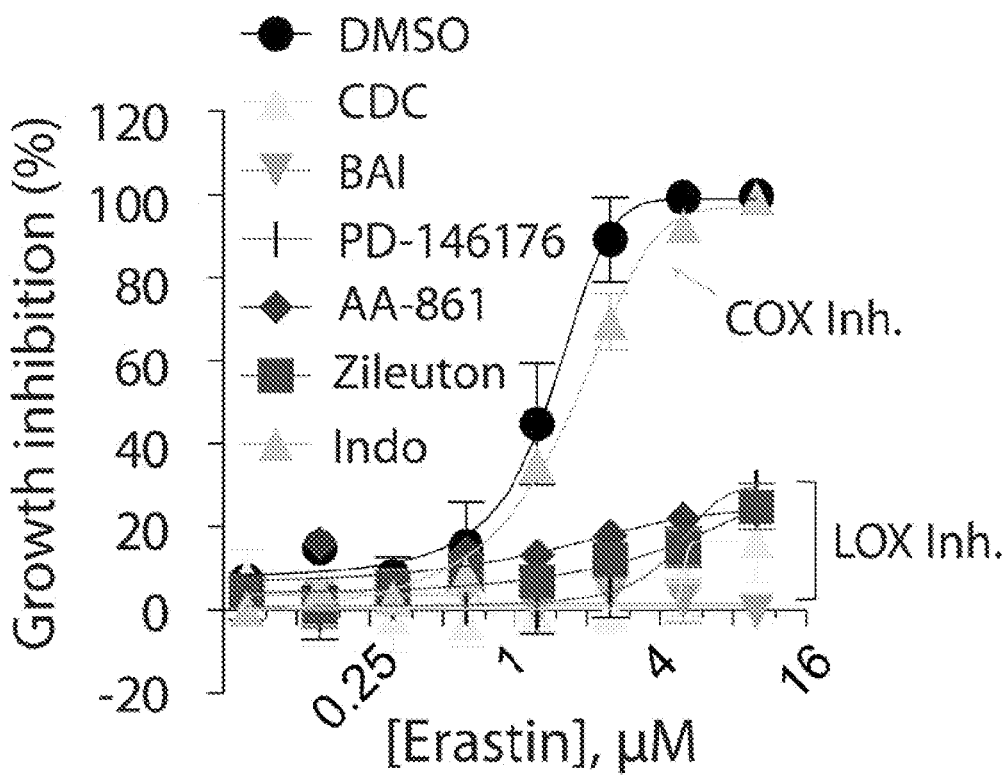

FIG. 2 shows that selective activation of lipoxygenases is responsible for the RSL phenotype of erastin.

FIG. 2a is a graph showing various basal ROS levels among BJ-derived cell lines, which were compared using H$_2$DCF, a ROS detection dye, and flow cytometric analysis. The horizontal lines indicate the mean of normalized ROS levels; n=8; *, P<0.05.

FIG. 2b is a series of bar graphs showing the results of experiments in which antioxidant-targeting compounds were tested in four BJ-derived cells to determine whether they exhibited an RSL phenotype. The graphs indicate growth inhibition in the 4 BJ-derived cell lines at two different concentrations (2×GI$_{50}$ and 4×GI$_{50}$ for each compound in BJeLR cells). Bar graph: mean±s.d.; n=3; n.s., not significant; ***, P<0.001.

FIG. 2c is a graph showing that erastin depletes cellular GSH equally in the 4 BJ-derived cell lines. Cells were treated with either DMSO or erastin for 12 hours followed by GSH quantification as described in Example 1 below. ***, P<0.001.

FIG. 2d shows a panel of microscopy images and a graph demonstrating that GFP-ALOX5 translocated to the nuclear membrane only in BJeLR cells upon 10 μM erastin treatment. Bar graph: mean+s.d.; n=3-4; ***, P<0.001. Scale bars, 60 μm.

FIG. 2e shows a series of time course microscopy images of GFP-ALOX5 translocation in HT-1080 cells upon treatment with erastin or ionomycin. Scale bars, 60 μm.

FIG. 2f is a series of graphs showing that erastin selectively generated lipid peroxides in BJeLR cells. The respective percentages in each graph indicate the percentage of the cell population that is BODIPY-C11 positive upon 0, 5, and 10 μM erastin treatment for 6 hours.

FIG. 2g is a graph showing that ALOX inhibitors, but not a COX inhibitor, strongly suppressed erastin-induced cell death. Five different ALOX inhibitors (CDC, BAI, PD-146176, AA-861, Zileuton) and one COX inhibitor (Indo) were tested for their ability to suppress erastin lethality. The detailed treatment condition is listed in Table 2 below. Data are presented as mean±s.d.; n=3.

TABLE 2

List of ALOX and COX inhibitors used in this study. The indicated concentration was used in the experiment of FIG. 2g and FIG. 3c.

| Abbr. | Full name | Concentration | Vendor | Cat# |
|---|---|---|---|---|
| CDC | cinnamyl-3,4-dihydroxy-a-cyanocinnamate | 20 μM | Santa Cruz | sc-200562 |
| BAI | Baicalein | 10 μM | Santa Cruz | sc-200494 |
| PD-146176 | PD-146176 | 5 μM | Santa Cruz | sc-200678 |
| AA-861 | AA-861 | 2 μM | Santa Cruz | sc-200570 |
| Zileuton | Zileuton | 50 μM | Santa Cruz | sc-204417 |
| Indo | Indomethacin | 200 μM | Santa Cruz | I-7378 |

Figure 3:
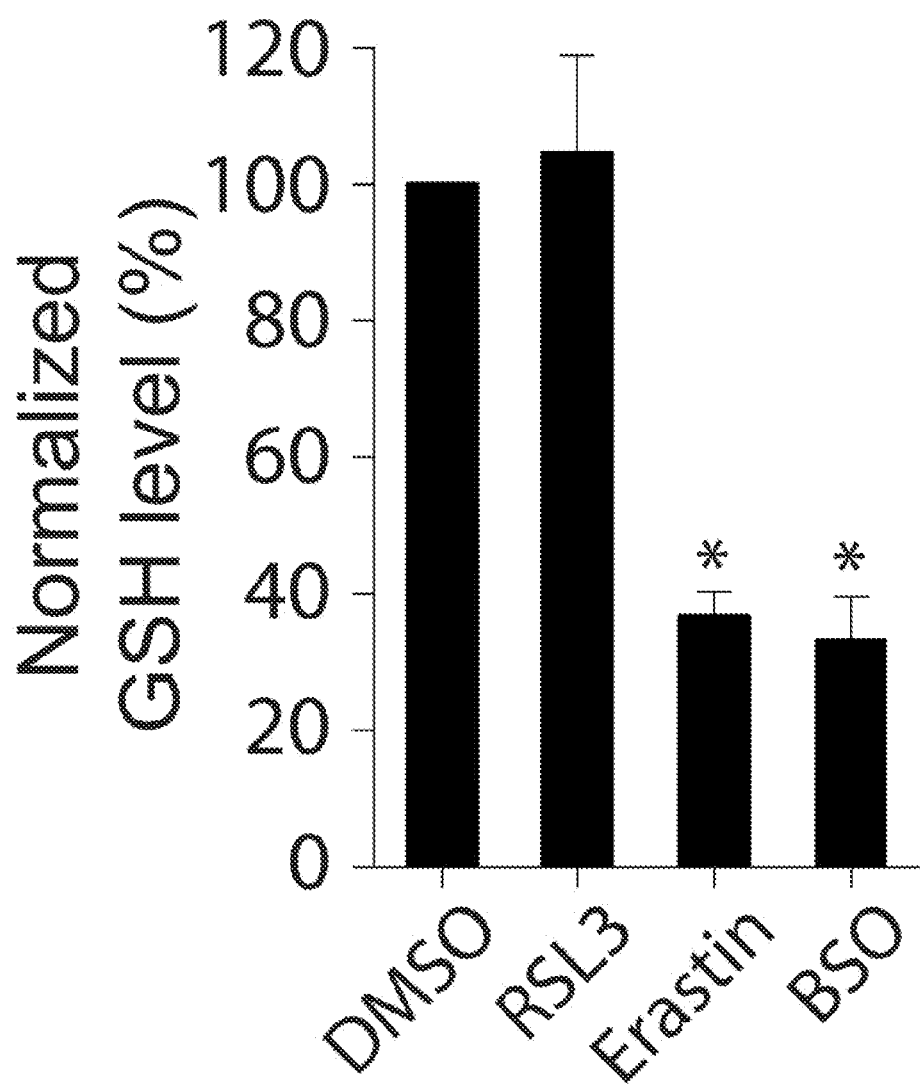
Figure 3:
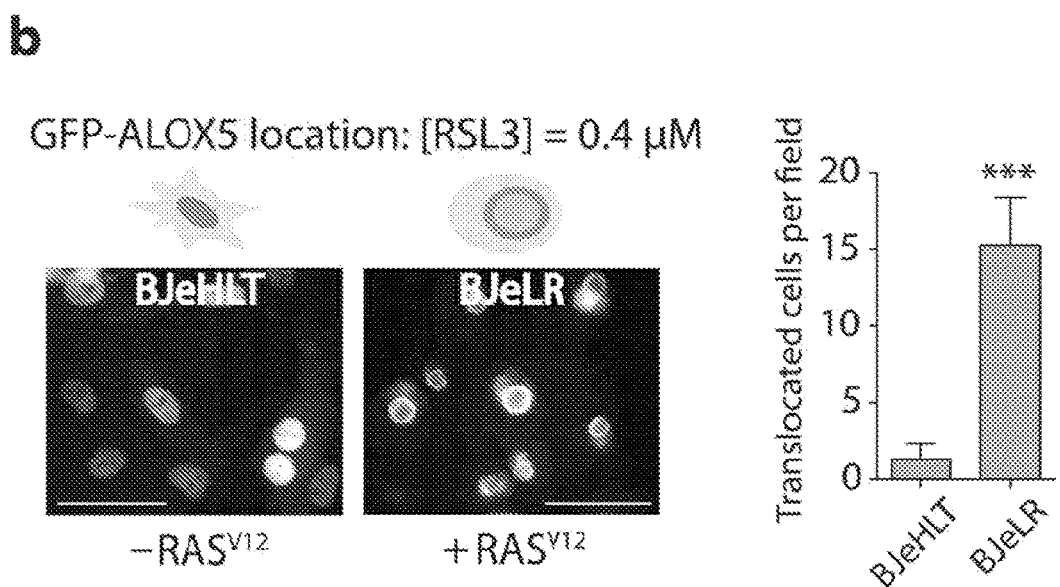
Figure 3:
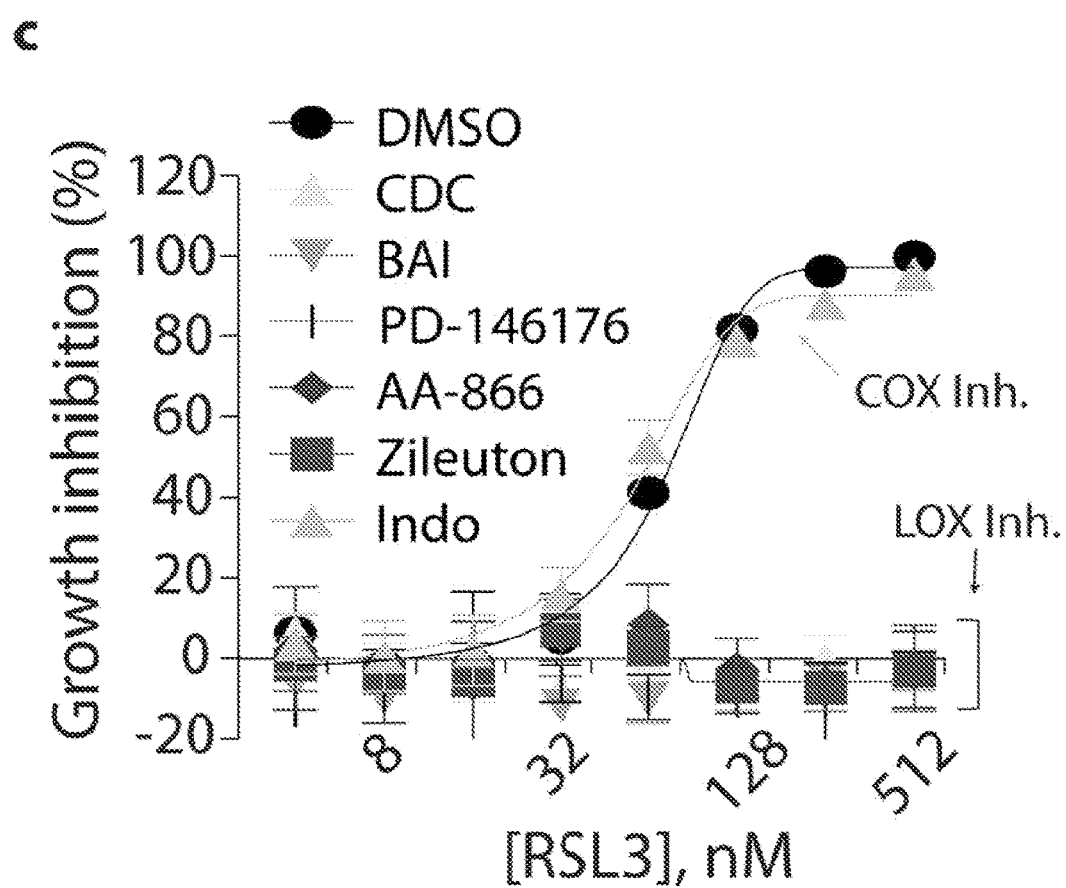
Figure 3:
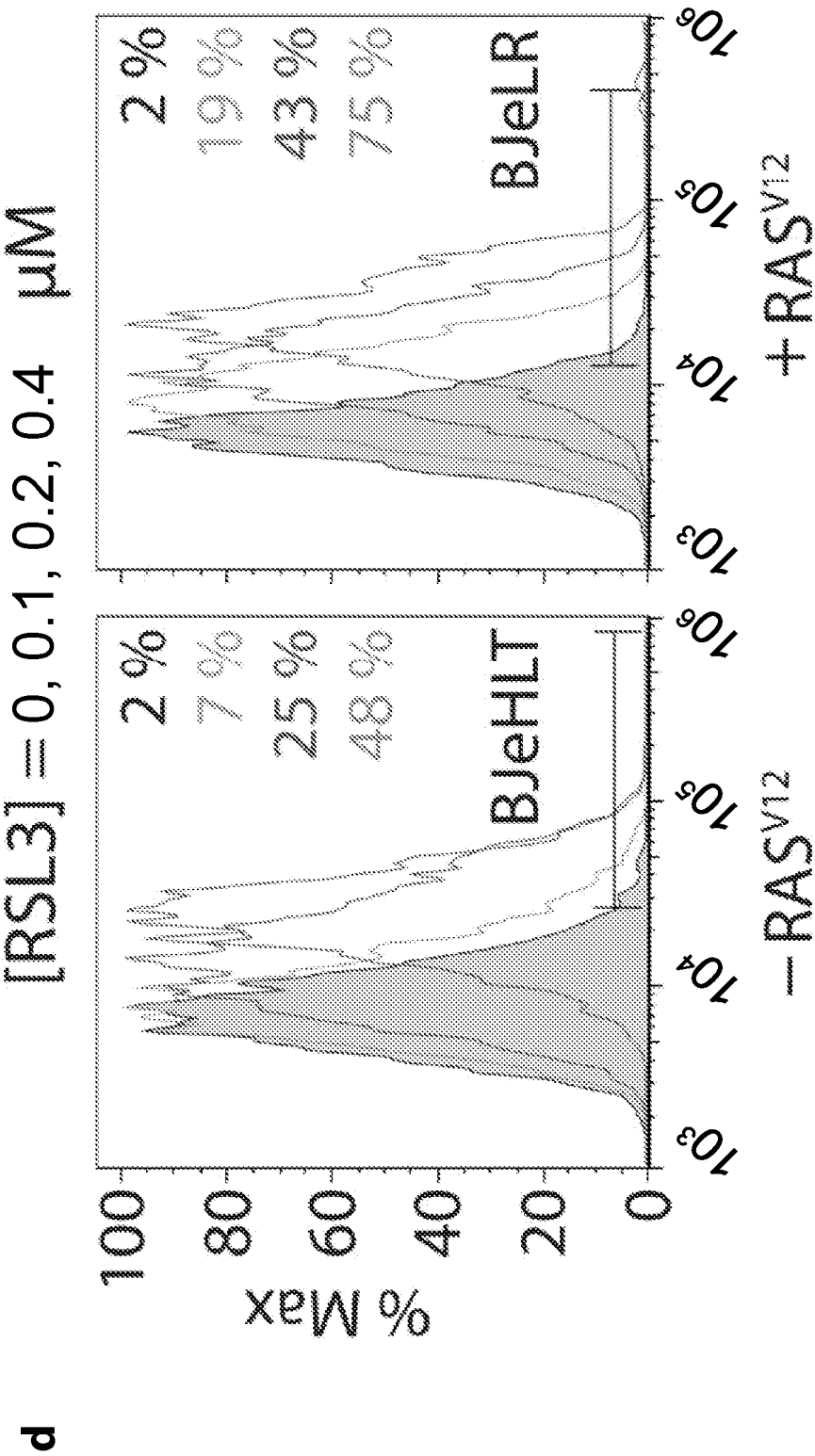
Figure 3:
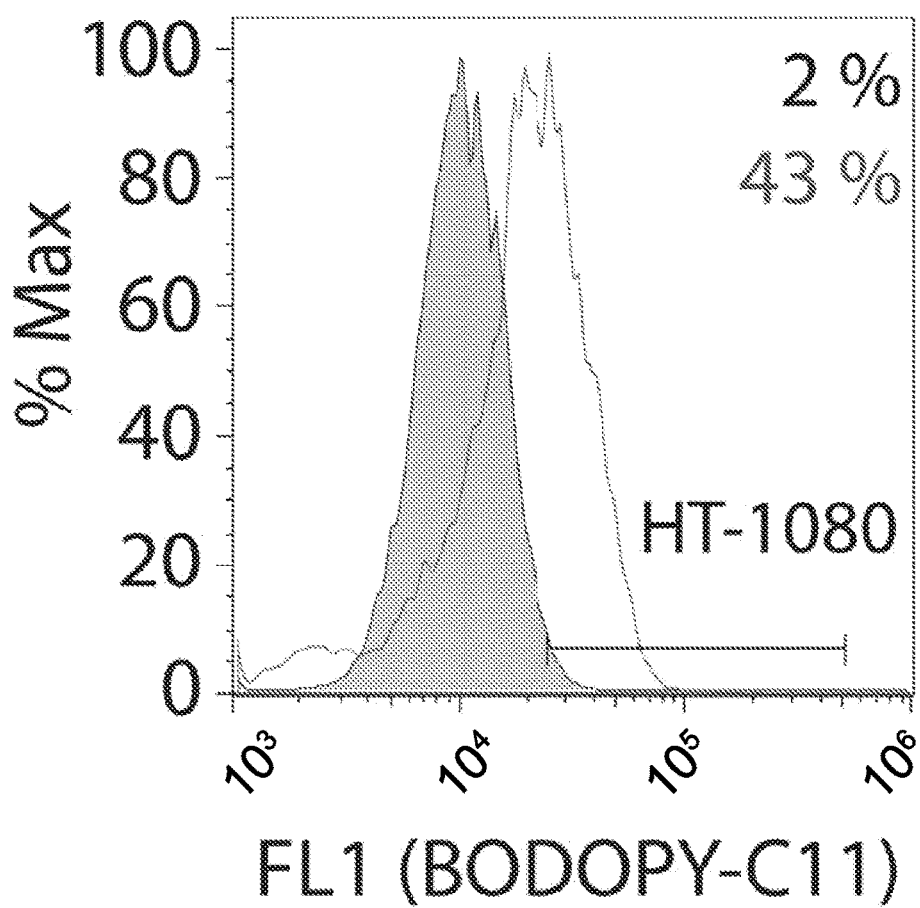
Figure 3:
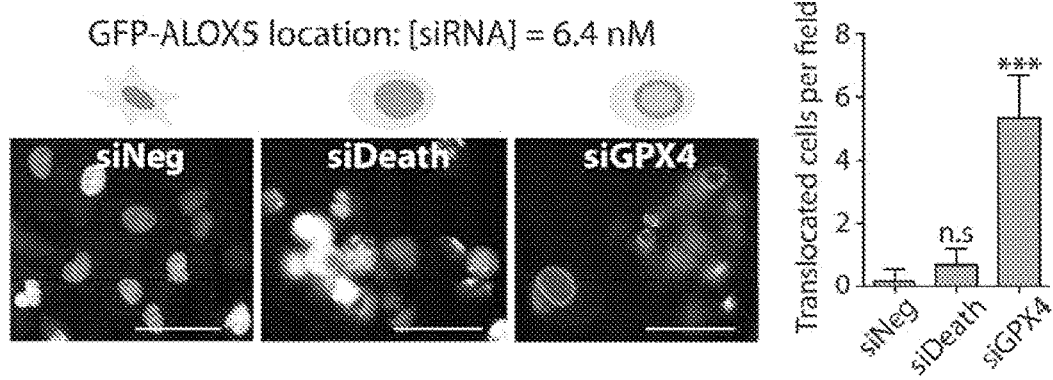
Figure 3:
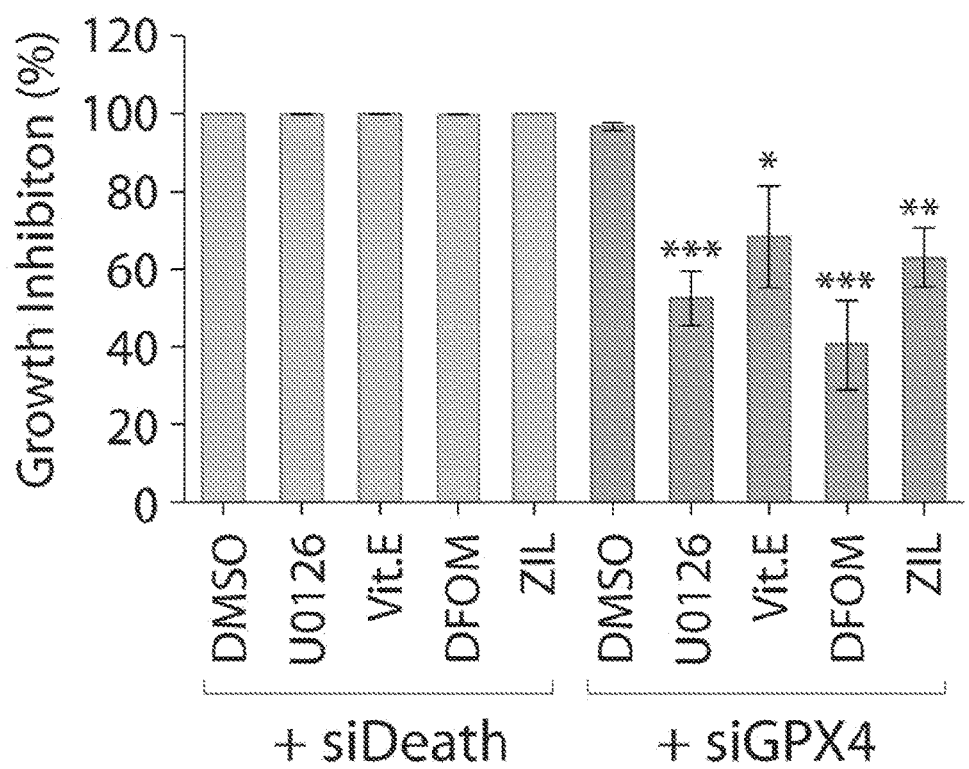
Figure 3:
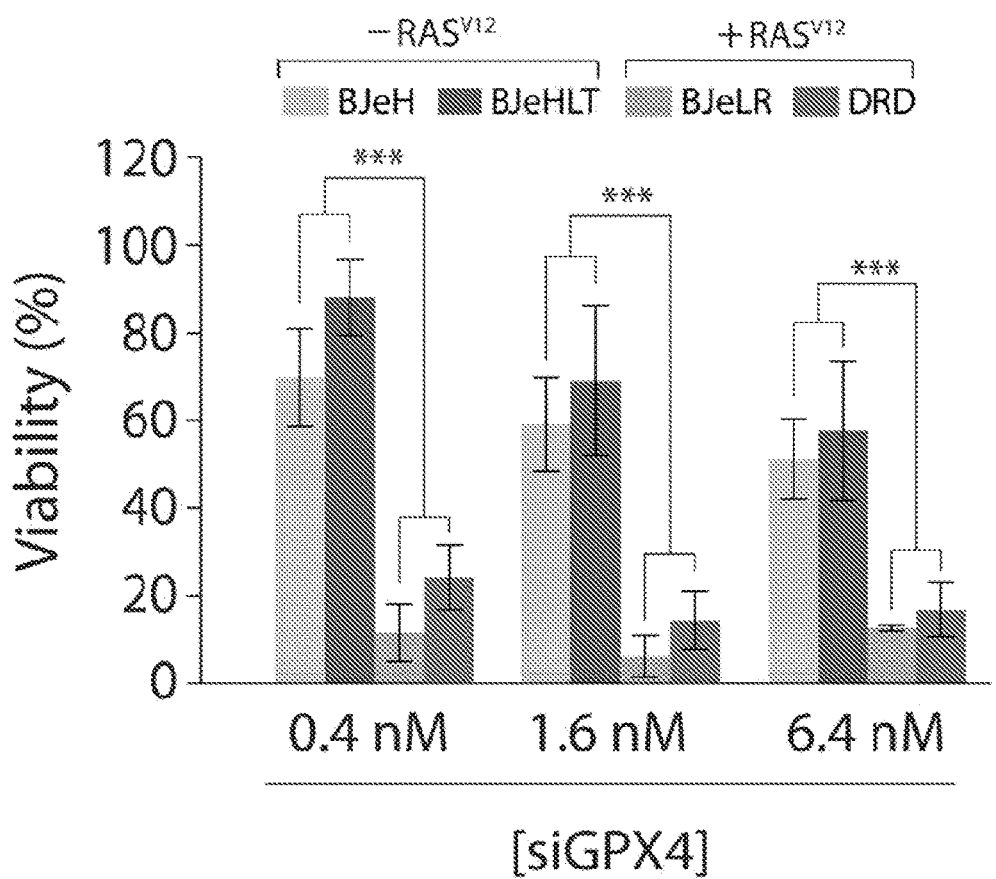

FIG. 3 shows that RSL3-induced ferroptosis activates an ALOX-dependent pathway.

FIG. 3a is a bar graph showing that RSL3 does not deplete GSH. The level of GSH was determined in BJeLR cells after treating with 2 μM RSL3, 10 μM erastin, or 1 mM BSO. Bar graph: mean+s.d.; n=3. *, P<0.05.

FIG. 3b shows microscopy images of GFP-ALOX5 and a bar graph demonstrating that GFP-ALOX5 translocated to the nuclear membrane upon RSL3 treatment (0.4 μM) in BJeLR cells, but not in BJeHLT cells. 0.4 μM RSL3 exhibited selective lethality in BJeLR cells. Bar graph: mean+s.d.; n=6 for BJeHLT, n=7 for BJeLR; ***, P<0.001. Scale bars, 60 μm FIG. 3c is a graph showing that the lethality of RSL3 was suppressed by ALOX inhibitors, but not by a COX inhibitor, in BJeLR cells. Data are presented as mean±s.d.; n=3.

FIG. 3d are graphs showing that RSL3 treatment generated lipid peroxides in the plasma membrane, as erastin did. The respective percentages in each graph indicate the percentage of BODIPY-C11 positive cell population upon 0, 0.1, 0.2, 0.4 μM RSL3 treatment.

FIG. 3e is a graph showing that HT-1080 cells transfected with a pool of siRNAs targeting GPX4 showed increased lipid peroxide level as assessed by BODIPY-C11 staining. siNeg has no homology to any known mammalian gene and was used as a negative control.

FIG. 3f shows a series of microscopy images of GFP-ALOX5 and a bar graph demonstrating that GFP-ALOX5 remained within the nucleus when siNeg was transfected; however, GFP-ALOX5 translocated to the nuclear membrane upon siGPX4 transfection. Another control siRNA, called siDeath, did not cause translocation during cell death. Bar graph: mean+s.d.; n=6, 7, 6 for siNeg, siDeath and siGPX4, respectively; n.s., not significant; ***, P<0.001. Scale bars, 60 μm FIG. 3g is a bar graph showing that known inhibitors of ferroptosis, 10 μM U0126, 100 μM Vit. E, 100 μM DFOM, or 50 μM ZIL, were able to suppress siGPX4-induced cell death. Cell death induced by siDeath could not be suppressed by any known ferroptosis inhibitor. Bar graph: mean±s.d.; n=3; *, P<0.05; , P<0.01; *, P<0.001.

FIG. 3h is a bar graph showing that knockdown of GPX4 displayed an RSL phenotype in the four BJ-derived isogenic cell lines. Bar graph: mean±s.d.; n=3; ***, P<0.001.

Figure 4:
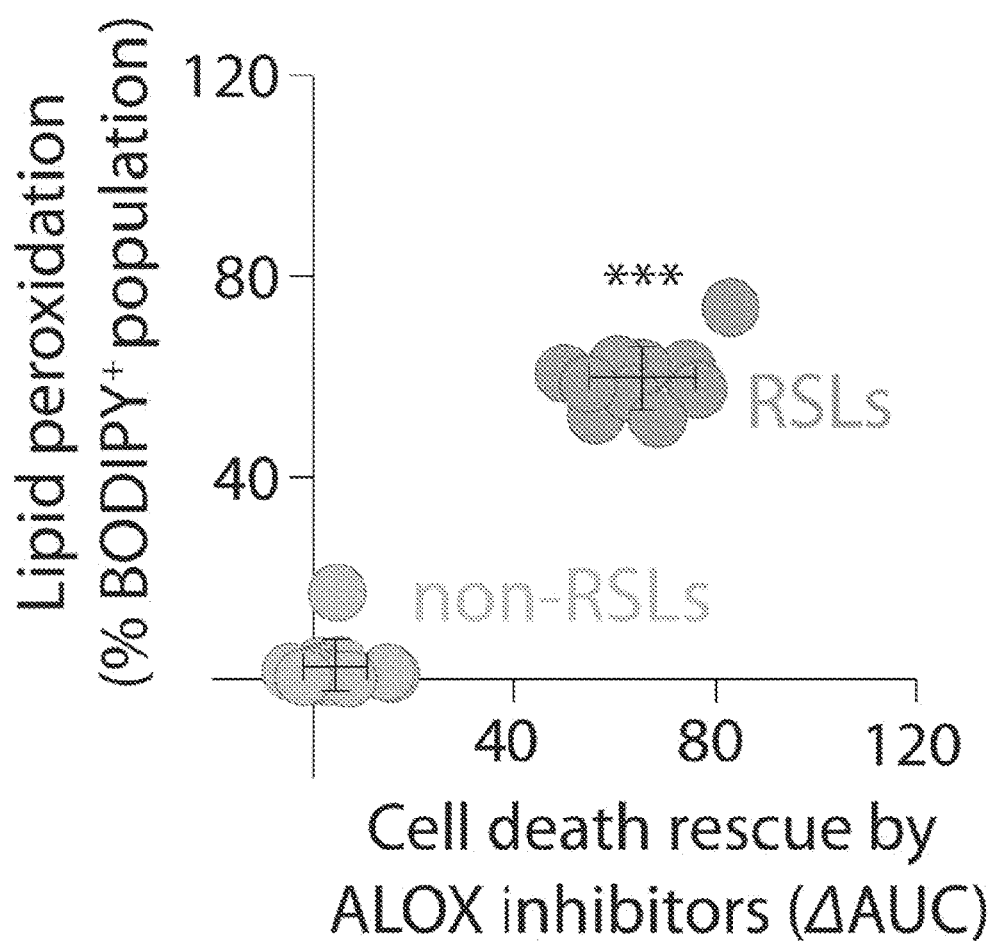
Figure 4:
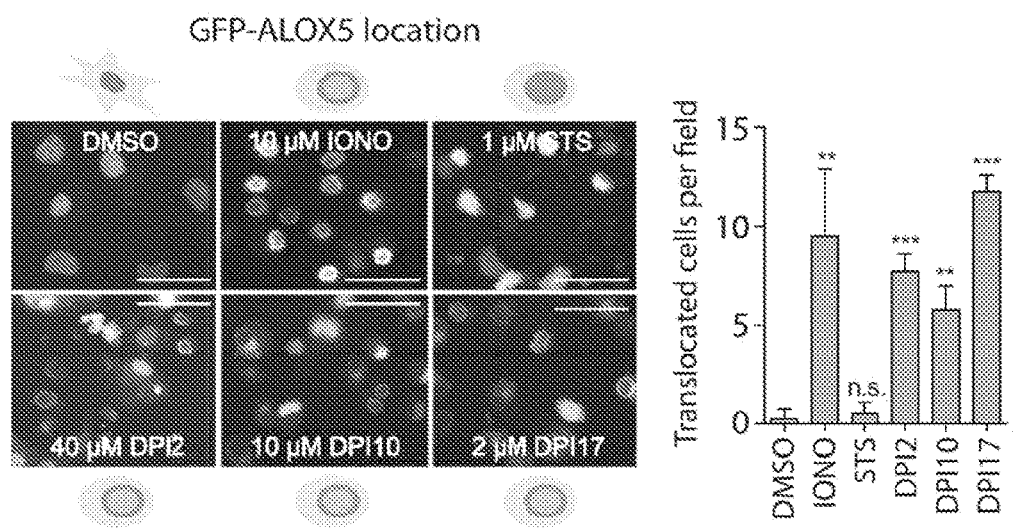
Figure 4:
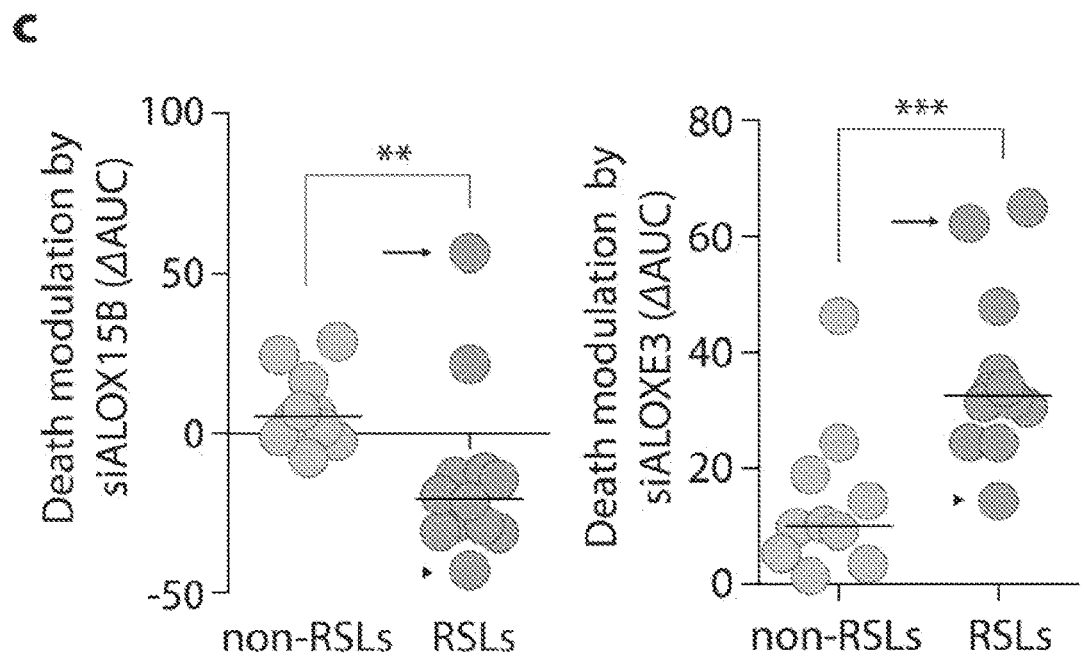
Figure 4:
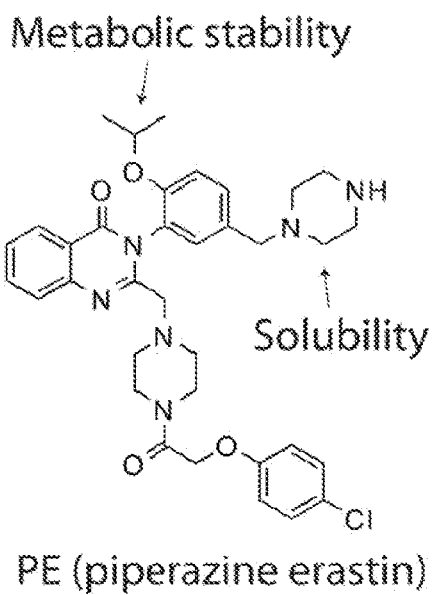
Figure 4:
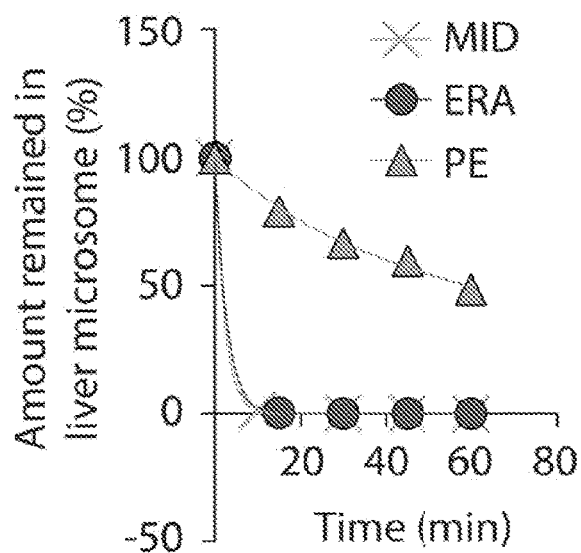
Figure 4:
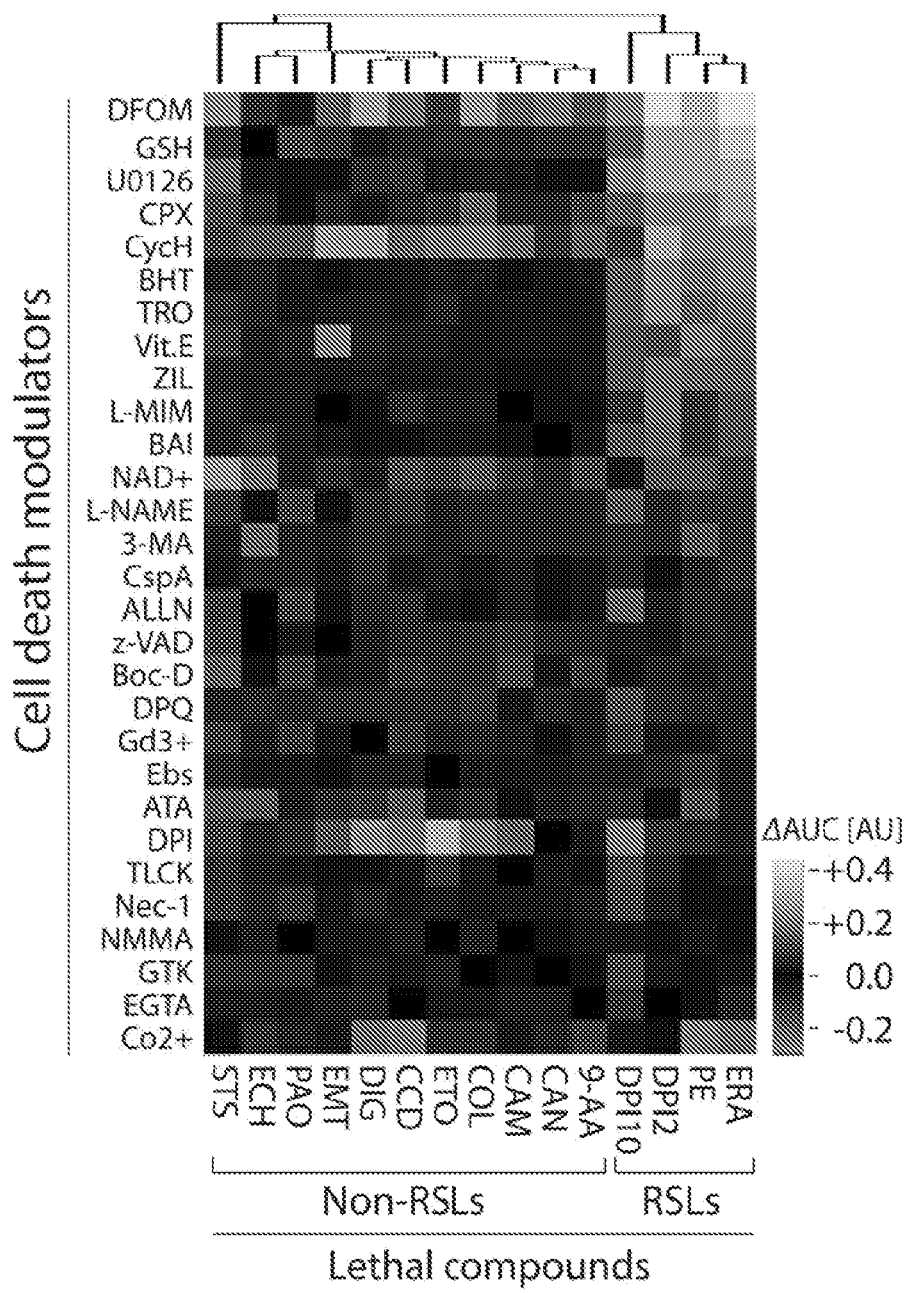
Figure 4:
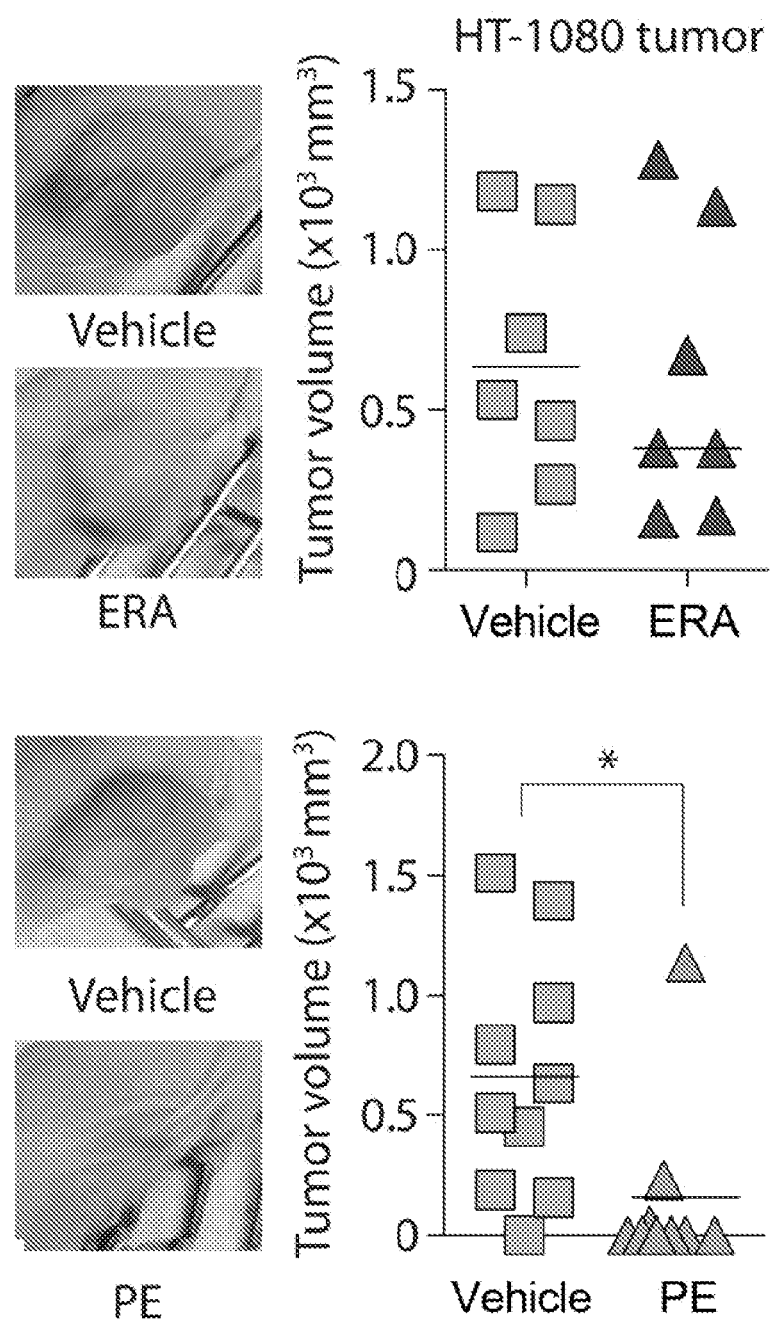
Figure 4:
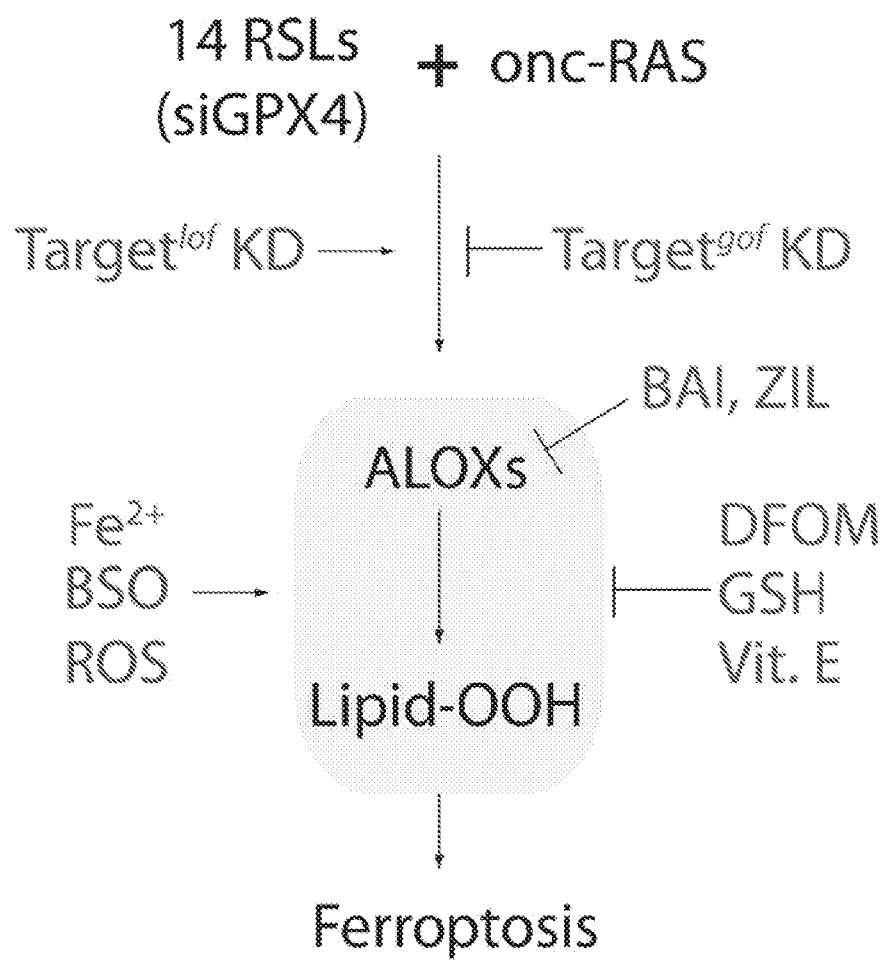

FIG. 4 shows that synthetic lethality with oncogenic-RAS occurs through a lipoxygenase-dependent pathway.

FIG. 4a is a graph showing that RSL compounds, but not non-RSL compounds, caused an increase in BODIPY-C11 fluorescence intensity, a measure of lipid peroxidation. Moreover, the lethality of RSL compounds depended on ALOX activity. The degree of cell death rescue by each ALOX inhibitor was calculated as ΔAUC. A larger ΔAUC indicates a greater rescue by the ALOX inhibitor. Capped lines indicates mean±s.d.; n=10 for RSLs, n=11 for non-RSLs; ***, P<0.001.

FIG. 4b shows a series of microscopy images of GFP-ALOX5 and a bar graph demonstrating that the administration of three structurally different RSL compounds, DPI2, DPI10, and DPI17 translocated GFP-ALOX5 to the nuclear membrane in HT-1080 cells, whereas the administration staurosporine (STS), a non-RSL compound, did not. Ionomycin (IONO) was used as a positive control for translocation. Bar graph presents mean+s.d.; n=4; n.s., not significant; , P<0.01; *, P<0.001. Scale bars, 60 μm.

FIG. 4c are graphs showing that knockdown of ALOXE3 rescued cells from death induced by 12 RSL compounds, whereas ALOX15B knockdown sensitized cells to RSL compounds in HT-1080 cells. Arrow and arrowhead indicate erastin and RSL3, respectively. The horizontal lines indicate median value of each group; n=10 for non-RSLs, n=12 for RSLs; , P<0.01; *, P<0.001.

FIG. 4d shows the structure of piperazine erastin (PE or Compound 30) and a graph demonstrating that PE has improved metabolic stability in comparison to erastin in a mouse liver microsome assay. Midazolam was used as a positive control for metabolic degradation. The structure of PE is shown on the left. Each data point is a mean of duplicates.

FIG. 4e is a graph showing modulatory profiling (Wolpaw et al., 2011) with PE, erastin, and other lethal molecules. This graph confirmed that PE induced a similar form of cell death as erastin in HT-1080 cells. ΔAUC with a positive sign indicates suppression of cell death, whereas a negative sign indicates sensitization by cell death modulators upon lethal compound treatment. Detailed treatment conditions are shown in Tables 3 and 4 below.

TABLE 3

The table shows the lethal compounds used in the modulatory profiling of FIG. 4e.

| Abbreviation | Full name | Mechanism | Highest conc. in 14-point, 2-fold dilution series (μM) |
|---|---|---|---|
| 9-AA | 9-Aminoacridine | DNA intercalating agent | 50 |
| CAN | Cantharidin | Protein phosphatase inhibitor | 200 |
| CAM | Camptothecin | Topoisomerase I inhibitor | 1 |
| COL | Colchicine | Microtubule depolymerizing agent | 0.6 |

TABLE 3-continued

The table shows the lethal compounds used in the modulatory profiling of FIG. 4e.

| Abbreviation | Full name | Mechanism | Highest conc. in 14-point, 2-fold dilution series (μM) |
|---|---|---|---|
| CCD | Cytochalasin D | Binds to actin and inhibits cytoskeletal function | 10 |
| DIG | Digoxin | Inhibits Na/K ATPase pump | 6.4 |
| ECH | Echinomycin | DNA intercalating agent | 0.002 |
| EMT | Emetine | Inhibits protein synthesis | 0.4 |
| ETO | Etoposide | Topoisomerase II inhibitor | 120 |
| PAO | Phenylarsine oxide | Metabolic poison, protein phosphatase inhibitor | 0.1 |
| STS | Staurosporine | Protein kinase inhibitor | 1 |
| DPI2 | — | unknown | 22.34 |
| DPI10 | — | unknown | 23 |
| ERA | Erastin | Targeting VDAC and system xc− | 18 |
| PE | Piperizine erastin | Targeting VDAC and system xc− | 8 |

TABLE 4

The table shows the cell death modulators used in the modulatory profiling of FIG. 4e.

| Abbreviation | Full name | Mechanism | Concentration (μM) |
|---|---|---|---|
| CspA | Cyclosporine A | Targets CypD | 5 |
| ALLN | ALLN | Inhibits calpains | 2.5 |
| Boc-D | Boc-D-fluoromethylketone | Inhibits caspases | 50 |
| z-VAD | z-VAD-fluoromethylketone | Inhibits caspases | 50 |
| L-NAME | L-NG-Nitroarginine methyl ester | Inhibits nitric oxide synthase | 300 |
| Gd3+ | Gadolinium | Calcium channel blocker | 656 |
| NMMA | NG-Methyl-L-arginine acetate | Inhibits nitric oxide synthase | 250 |
| NAD+ | beta-Nicotinamide adenine dinucleotide | Inhibits sirtuin | 2000 |
| ATA | aurintricarboxylic acid | Topoisomerase II inhibitor | 38 |
| ActD | Actinomycin D | Transcription inhibitor | 0.016 |
| 3-MA | 3-methyladenine | Inhibits pre-autophagosome | 1000 |
| CycH | Cycloheximide | Translation elongation inhibitor | 1.5 |
| Nec-1 | Necrostatin-1 | Inhibits RIP1 kinase | 10 |
| Vit. E | Vitamine E | Lipophilic antioxidant | 100 |
| DFOM | Deferoxamine | Iron chelator | 100 |
| U0126 | U0126 | MEK inhibitor | 10 |
| EGTA | EGTA | Calcium chelator | 2000 |
| DPQ | DPQ | PARP inhibitor | 10 |
| Co2+ | Cobalt chloride | Calcium channel blocker | 656 |
| TLCK | — | Serine protease inhibitor | 100 |

TABLE 4-continued

The table shows the cell death modulators used in the modulatory profiling of FIG. 4e.

| Abbreviation | Full name | Mechanism | Concentration (µM) |
|---|---|---|---|
| BHT | Butylated hydroxytoluene | Antioxidant | 400 |
| TRO | Trolox | Antioxidant | 100 |
| L-MIM | L-Mimosine | Cell cycle inhibitor/iron chelator | 200 |
| GSH | reduced glutathione | Antioxidant | 2000 |
| BAI | Baicalein | Inhibits lipoxygenase | 10 |
| ZIL | Zileuton | Inhibits lipoxygenase | 50 |
| DPI | NOX inhibitor1 | NOX inhibitor | 5 |
| GTK | GTK137831 | NOX inhibitor | 20 |
| CPX | Ciclopirox olamine | Lipophilic iron chelator | 5 |
| Ebs | Ebselen | Glutathion peroxidase mimetic | 5 |

FIG. 4f are photographs and plots showing that PE (Compound 30) has improved efficacy over erastinin (ERA) in preventing HT-1080 tumor formation in a mouse xenograft model. The images show representative tumors in live mice from each treatment group. The horizontal lines in the graphs indicate the mean value of tumor size in each group; n=7 in erastin testing; n=10 in PE testing; *, P<0.05.

FIG. 4g is a scheme showing a proposed molecular pathway enabling RAS-synthetic-lethality and ferroptotic cell death by the RSL compounds; lof: loss of function, gof: gain of function.

Figure 5:
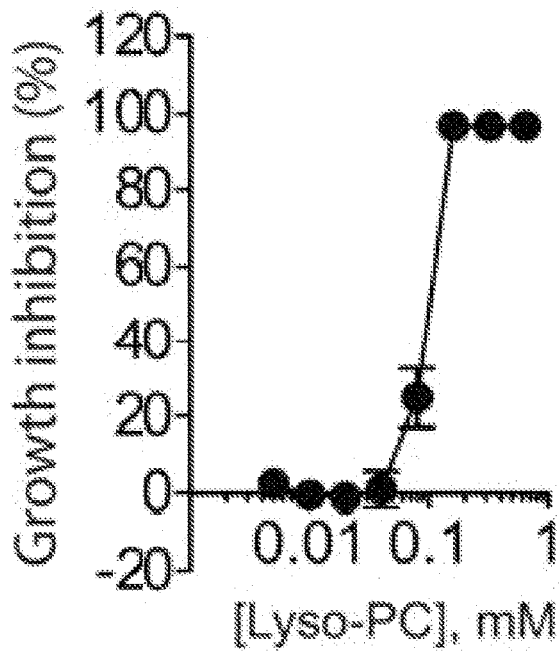
Figure 5:
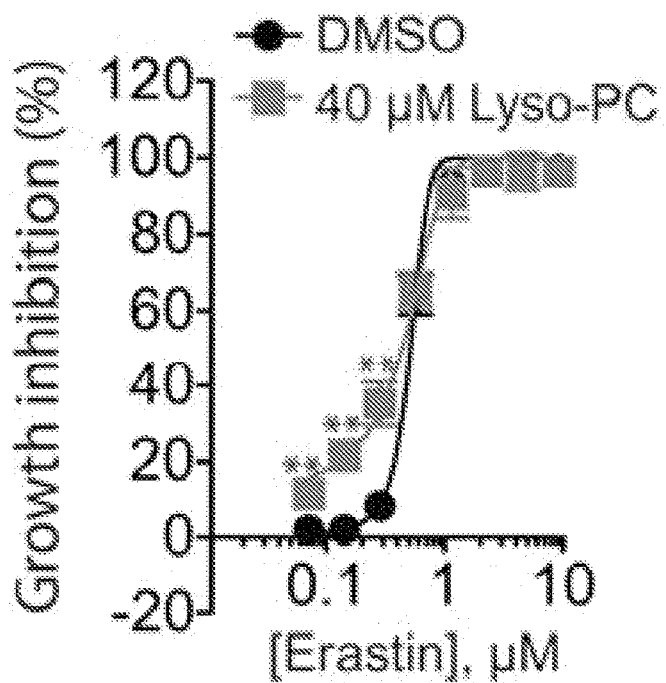
Figure 5:
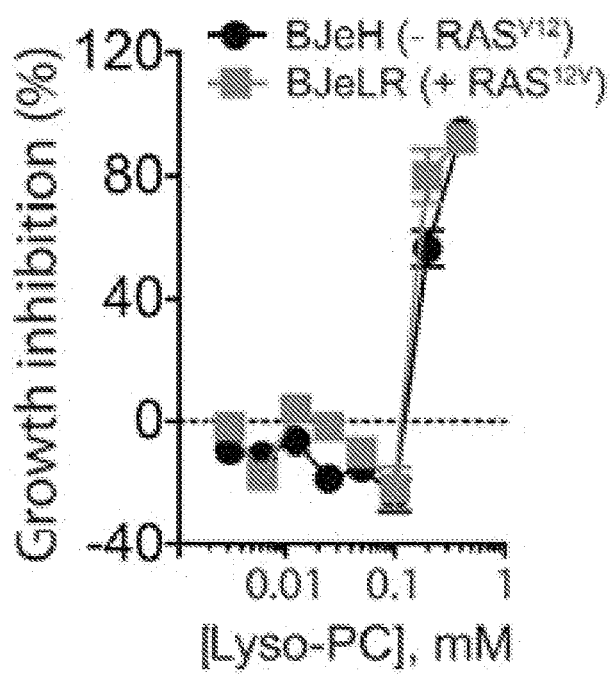
Figure 5:
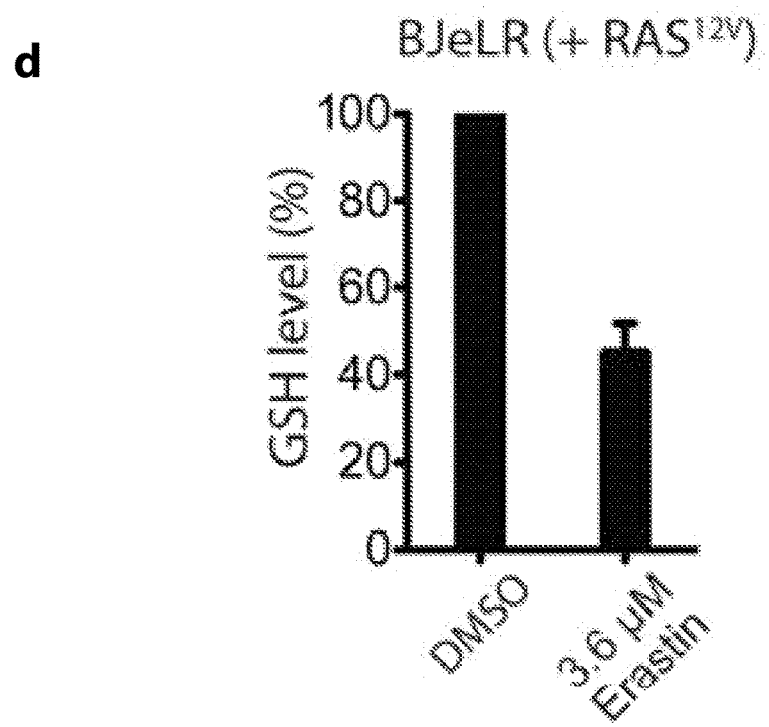
Figure 5:
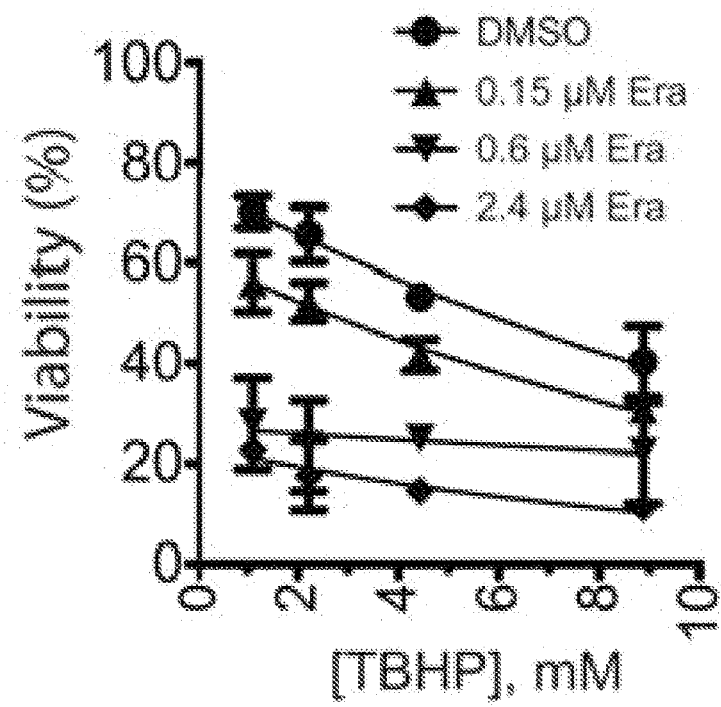
Figure 5:
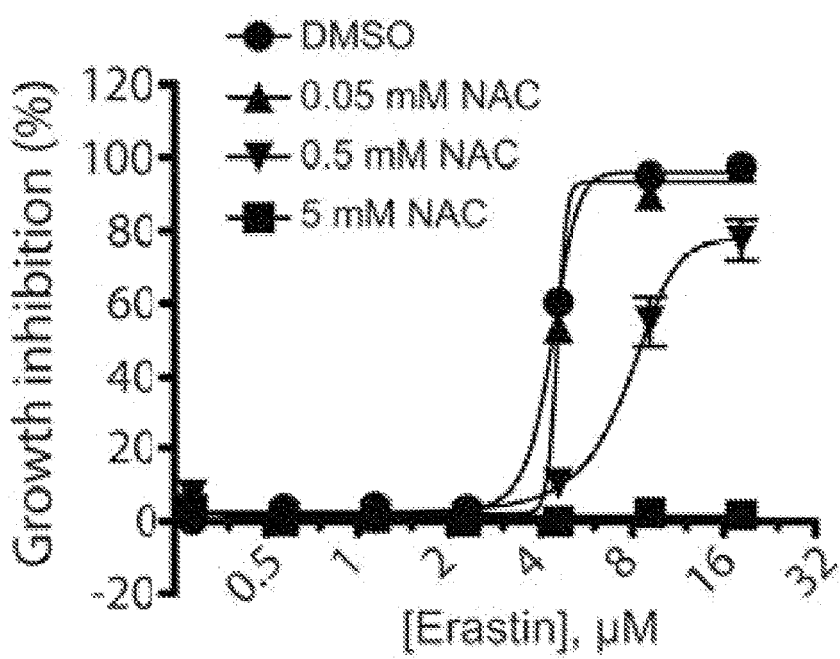
Figure 5:
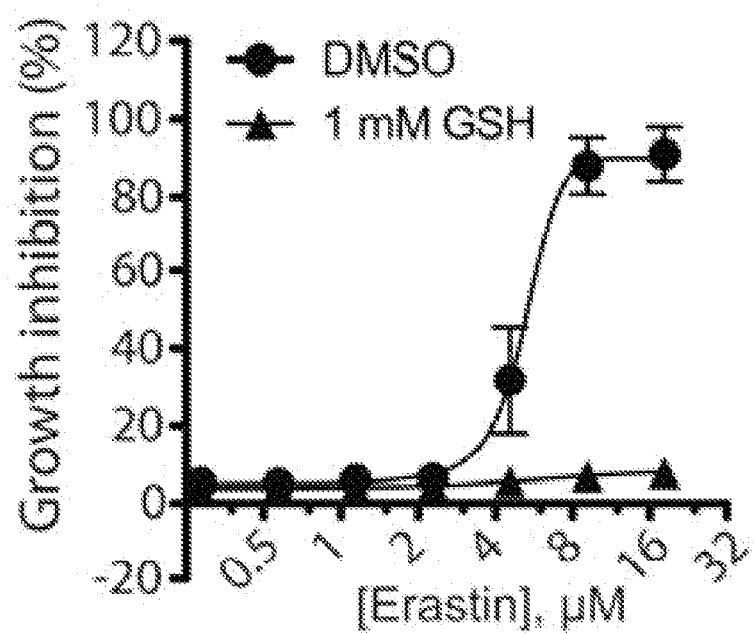

FIGS. 5a-c are graphs showing that lysophosphatidyl choline (Lyso-PC) contributes to the lethality of erastin but does not account for the selectivity toward oncogenic-RAS-expressing cells. Data are presented as mean±s.d.; n=3; **, P<0.01. Cell viability was determined using alamar blue after 24 hours of incubation with indicated compound. In FIG. 5a, HT-1080 cells were incubated with the indicated amount of Lyso-PC. In FIG. 5b, Erastin was added to HT-1080 cells in a 2-fold dilution series in the presence or absence of lyso-PC. In FIG. 5c, BJeH (wild type HRAS) or BJeLR (HRAS$_{G12V}$) cells were treated with lyso-PC.

FIGS. 5d-g are graphs showing that GSH depletion is a functionally important biochemical change in erastin-induced cell death. Data are presented as mean±s.d.; n=3; **, P<0.01. In FIGS. 5e-g, cell viability was determined using alamar blue after 24 hours of incubation with indicated compound. In FIG. 5d, Erastin was added to BJeLR cells for 24 hours. The cellular GSH level in each sample was determined as set forth in Example 1. FIG. 5e shows that GSH depletion by erastin sensitized cells to TBHP-induced oxidative stress in U-2 OS cells. FIG. 5f shows that supplementation with N-acetyl cystein (NAC), a GSH precursor, rescued U-2 OS cells from cell death by erastin. In FIG. 5g, HT-1080 cells were treated with erastin in the presence or absence of 1 mM GSH for 24 hours.

Figure 6A:
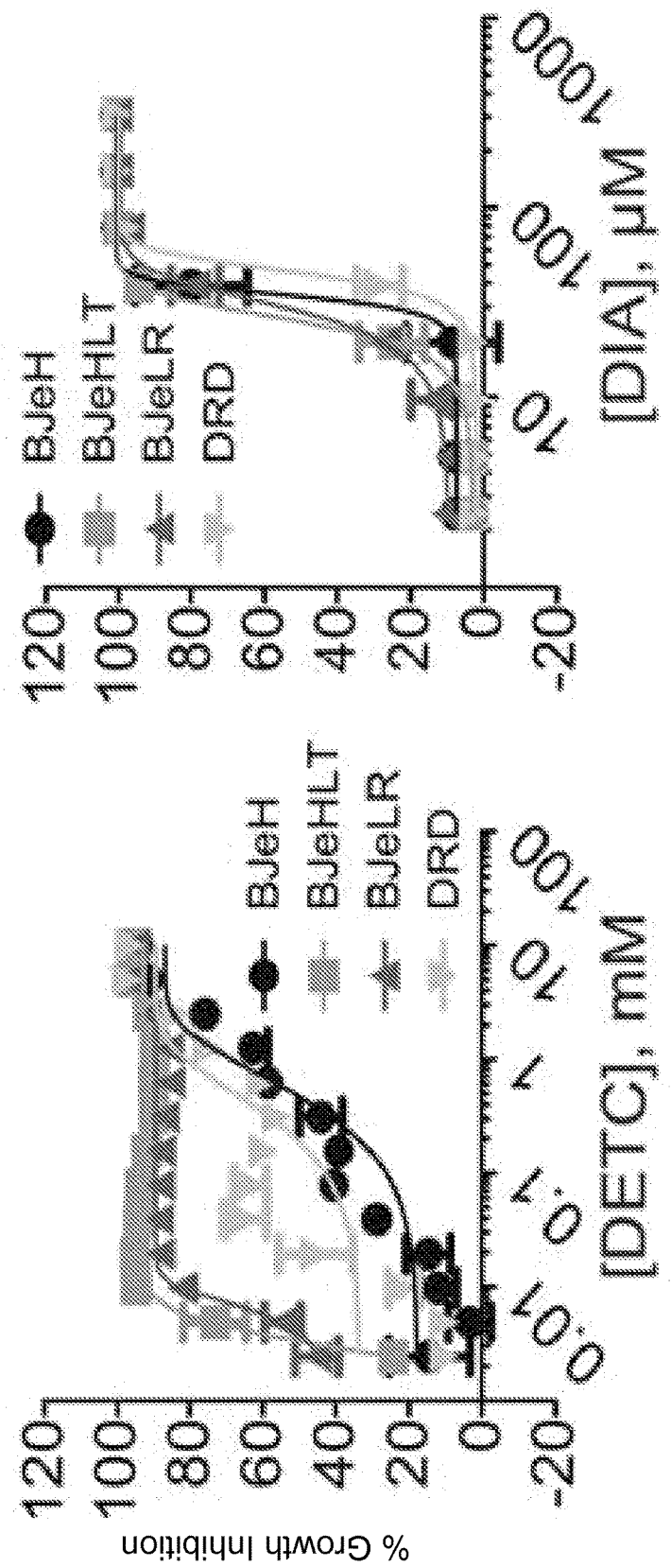
Figure 6A:
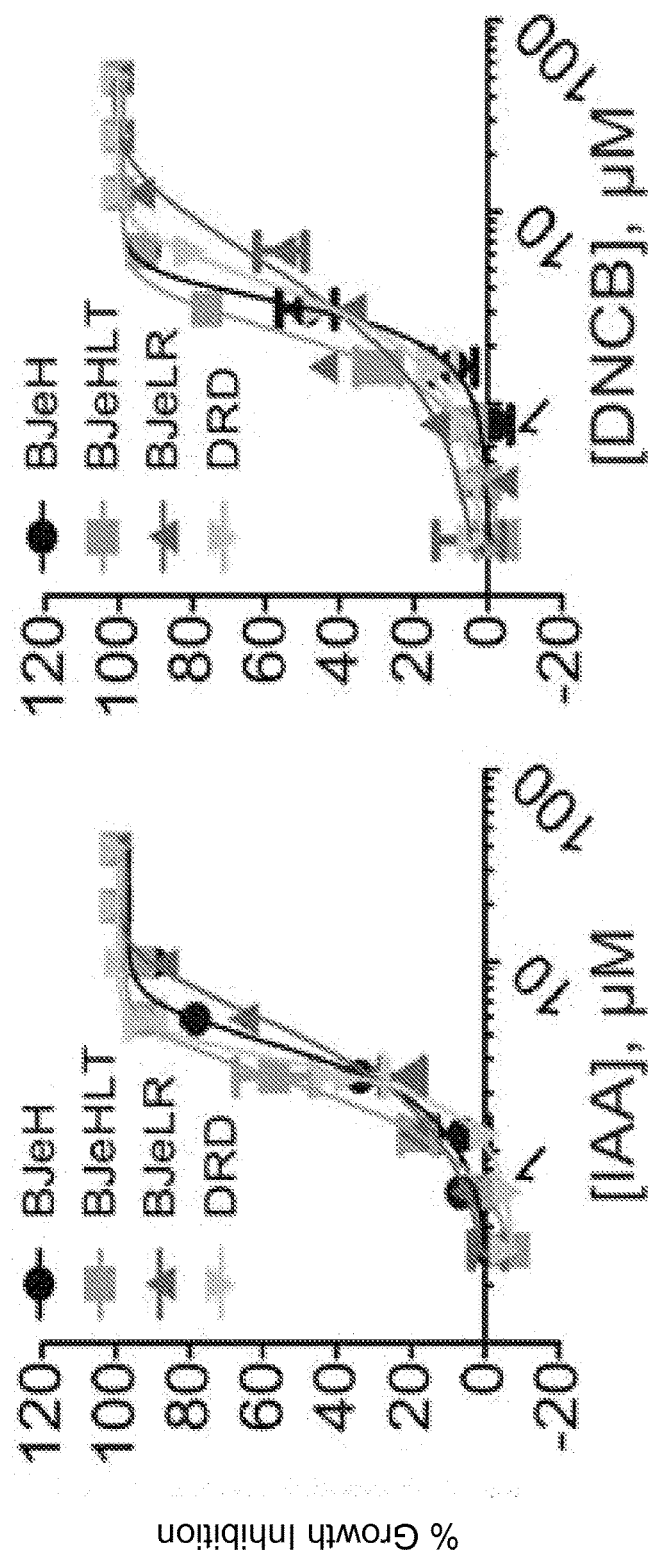
Figure 6A:
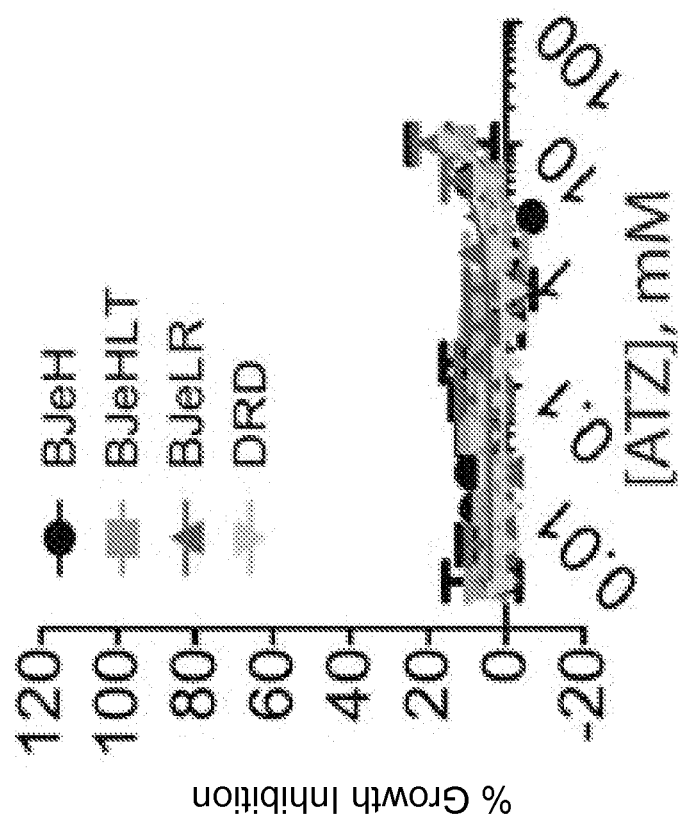

FIG. 6 shows testing of compounds targeting cellular antioxidant systems in the four BJ-derived cell lines. FIG. 6a shows a series of growth inhibition curves of antioxidant inhibitors in the 4 cell lines. FIG. 6b is a table listing the compounds used in the 4 BJ-derived cell line testing of FIG. 6a with the target information. Data are presented as mean±s.d.; n=3.

Figure 7:
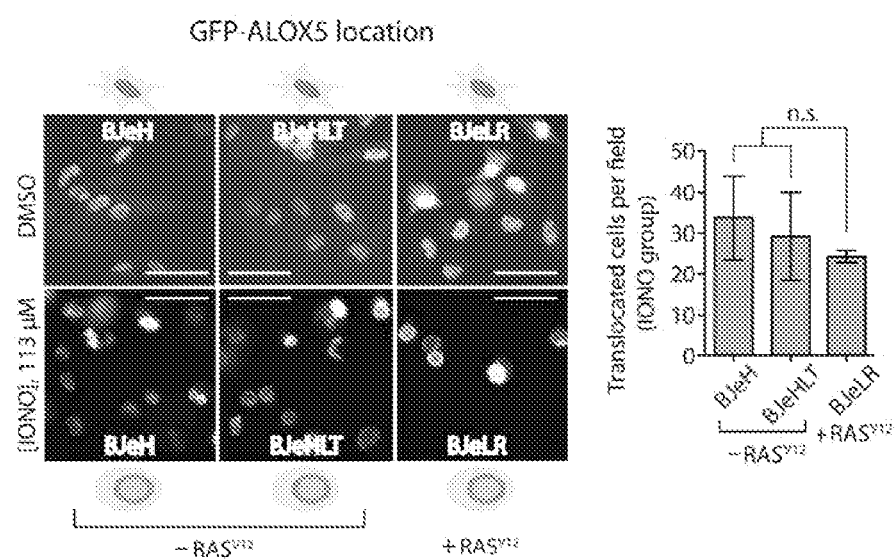

FIG. 7 shows a series of microscopy images and a graph demonstrating that GFP-ALOX5 translocated to the perinuclear membrane region upon ionomycin treatment. GPF-ALOX5 remained within the nucleus when expressed in BJeH, BJeHLT, and BJeLR cells (upper panel), but translocated to the perinuclear membrane region upon ionomycin treatment (lower panel). Unlike erastin-induced translocation (FIG. 2d), all three BJ cell lines responded equally to ionomycin treatment. BJ cells were treated with 113 µM ionomycin for 12 hours. Bar graph; n=3-4, n.s.=not significant. Scale bar=60 µm.

Figure 8:
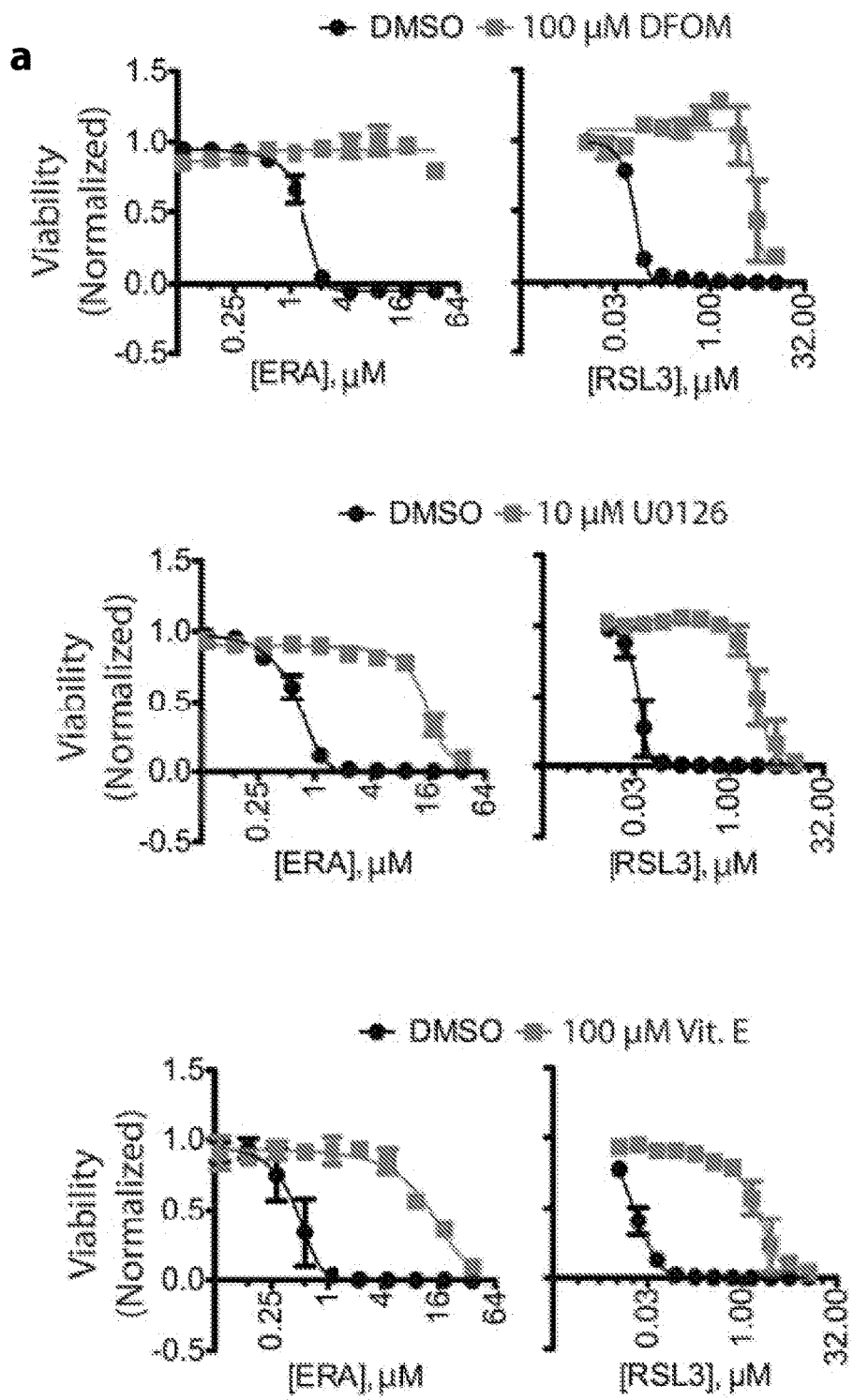
Figure 8:
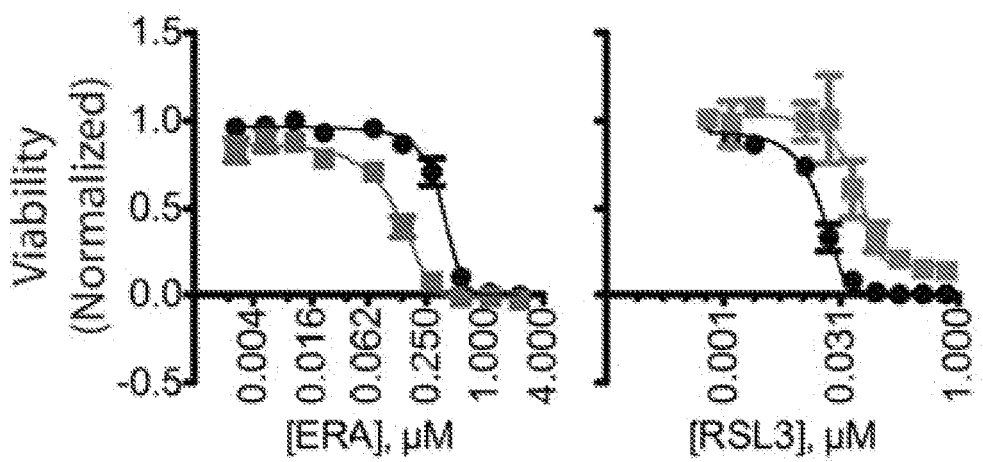
Figure 8:
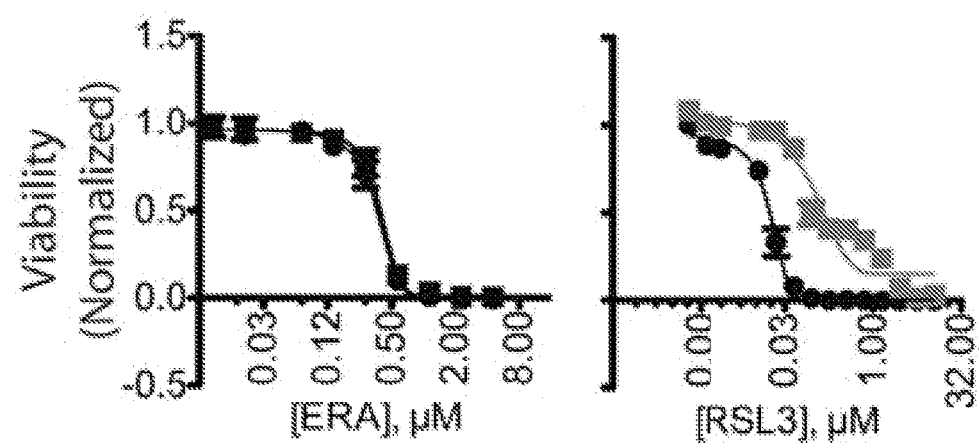
Figure 8B:
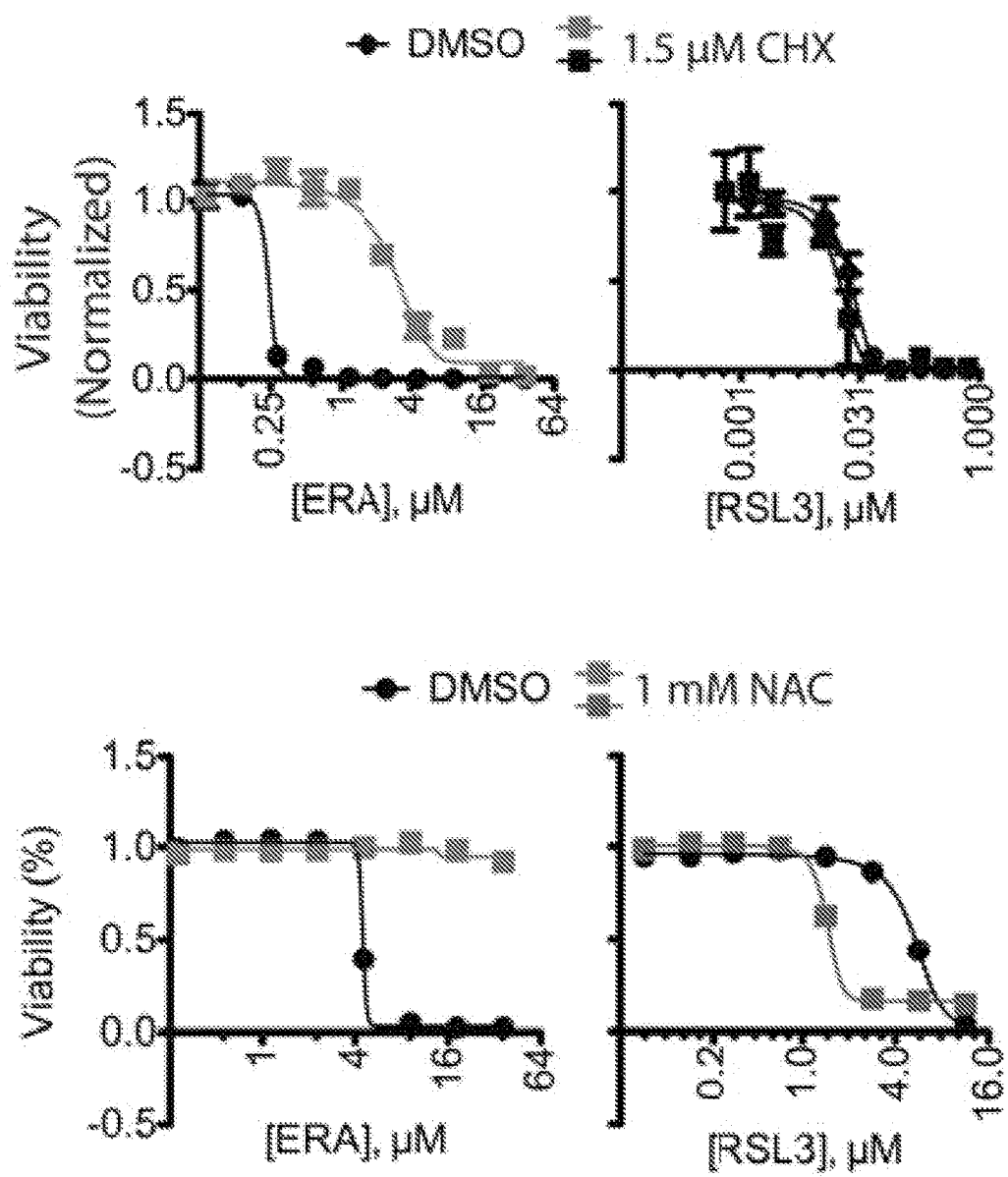

FIG. 8a shows a series of graphs demonstrating that erastin and RSL3 share a common dependency on iron, MEK, and reactive oxygen species. FIG. 8b shows a series of graphs demonstrating that erastin and RSL3 exhibited different responses to other cell death inhibitors. BJeLR cells were treated with erastin or RSL3 in the presence or absence of the indicated inhibitors for 24 hours followed by viability determination using alamar blue dye. DFOM: Deferoxamine, Vit. E: Vitamine E, Co$^{2+}$: CoCl$_2$, TLCK: serine protease inhibitor, CHX: Cycloheximide, NAC: N-acetylcystein. Data are presented as mean±s.d.; n=3.

Figure 9:
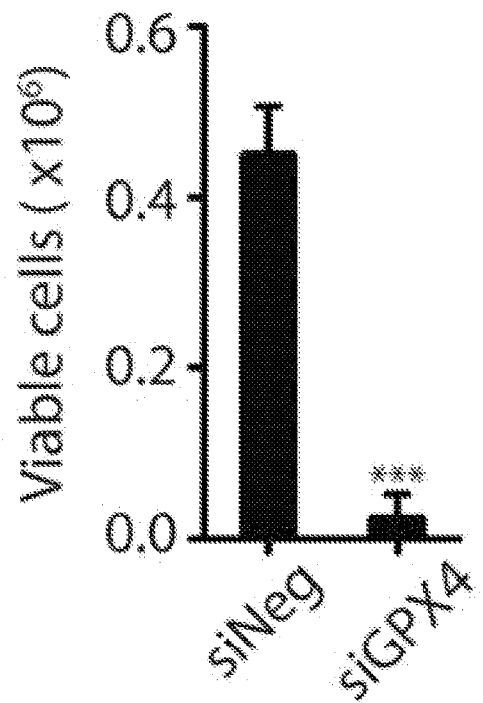
Figure 9:
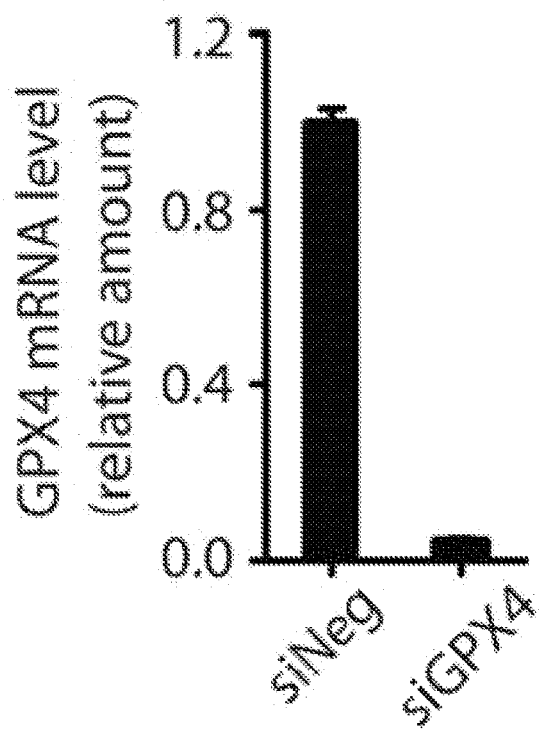
Figure 9:
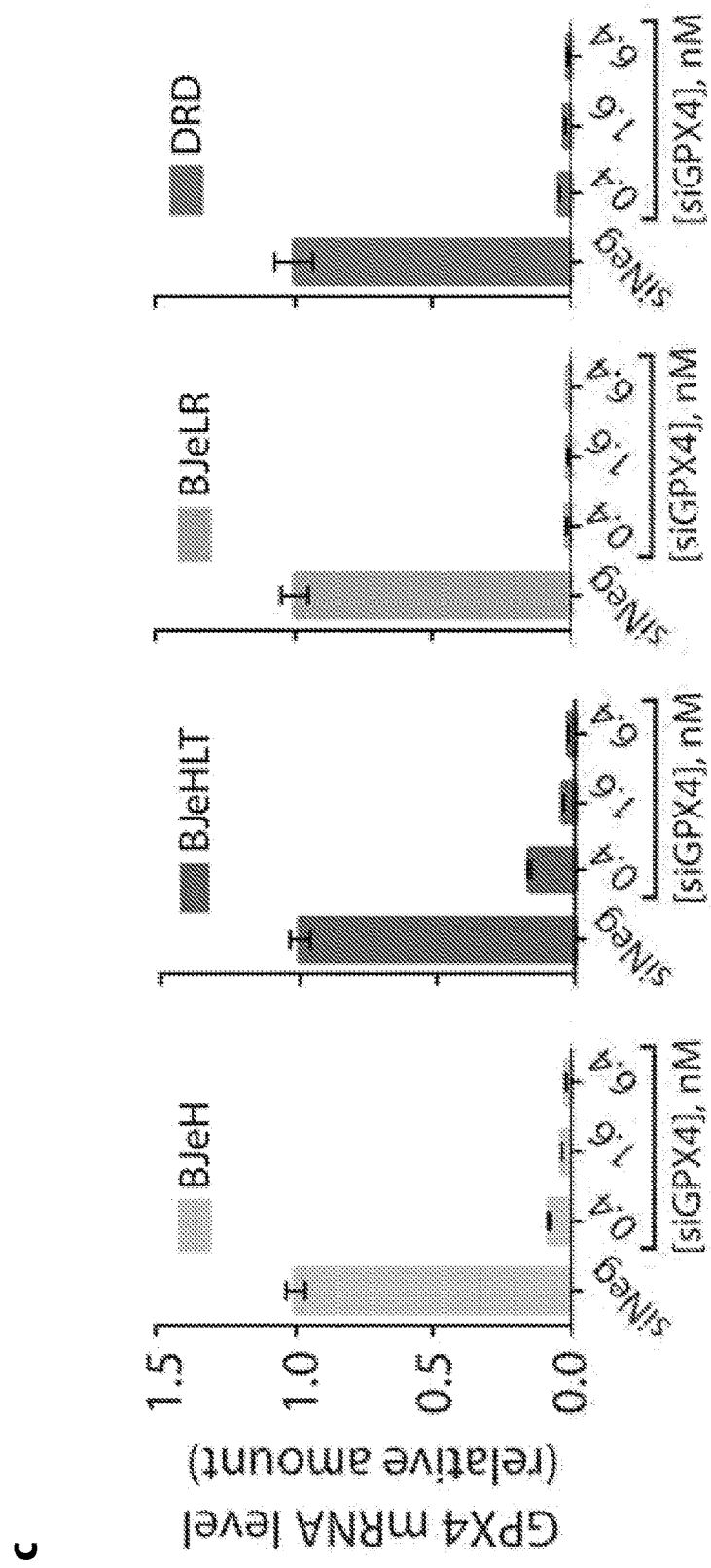

FIG. 9 shows the effect of siGPX4 on cell viability and GPX4 mRNA level. In FIG. 9a, HT-1080 cells were transfected with 6.4 nM siGPX4 for 4 days, and cell viability was determined by ViCell. FIG. 9b is a graph showing that a qPCR experiment confirmed the reduction of GPX4 expression in HT-1080 cells transfected with siGPX4. FIG. 9c is a series of graphs showing the confirmation of GPX4 knockdown by the siRNA pool using qPCR analysis in 4 BJ-derived cell lines. Comparative analysis was carried out using ACTB (human actin B) gene as an endogenous control. Data are presented as mean±s.d.; n=3.

Figure 10:
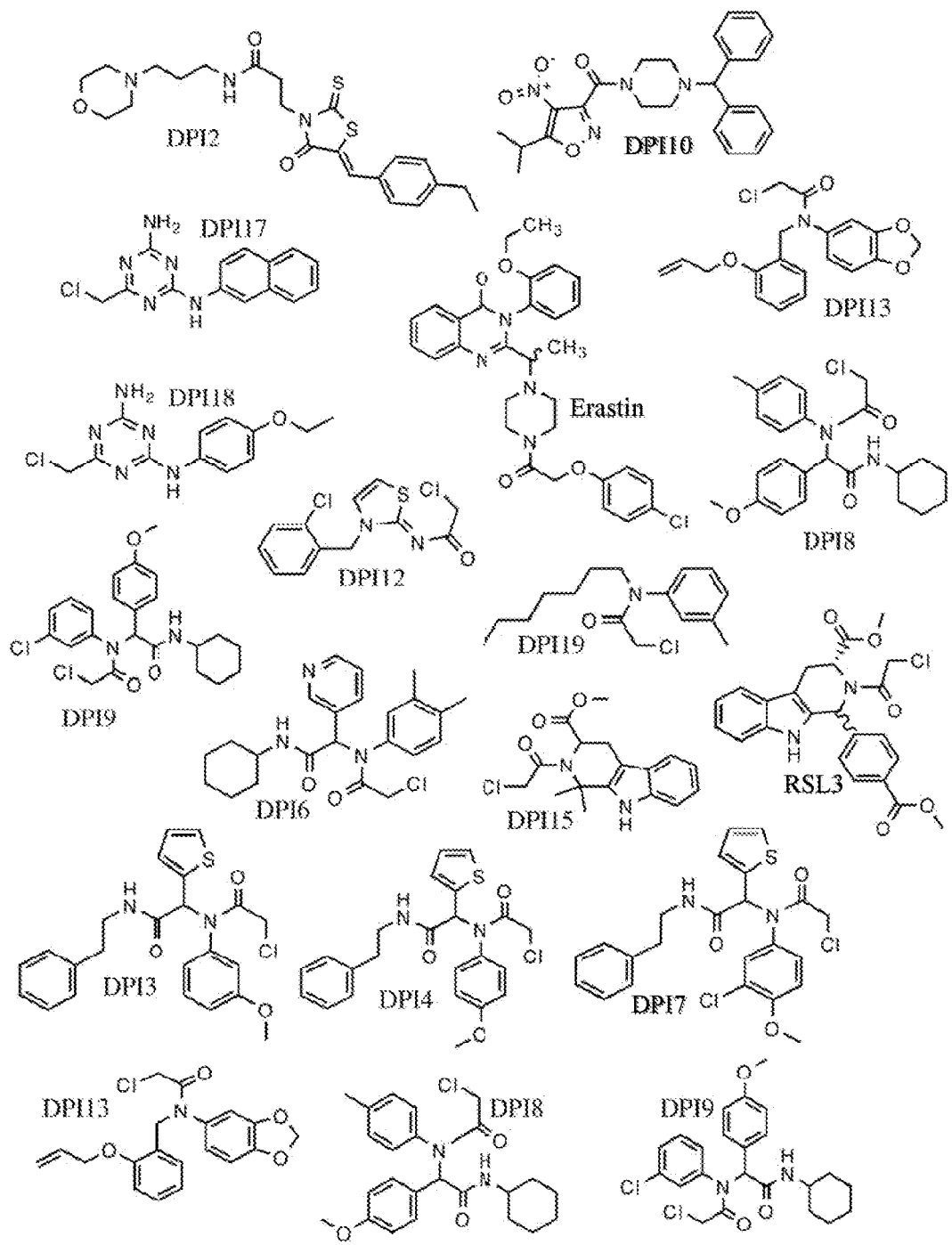

FIG. 10a shows the structure of certain RSL compounds discovered from a high throughput screening campaign of greater than 1 million compounds with the four BJ-derived cell lines. Of those compounds, 80,497 were purchased and synthesized in the inventors' laboratory, 303,282 compounds were obtained through the Molecular Libraries Probe Production Centers Network (MLPCN), and 658,301 compounds were made in collaboration with the Genomics Institute of the Novartis Research Foundation (GNF). Structure of erastin, RSL3, DPI7, and DPI10, were known previously.

Figure 10B:
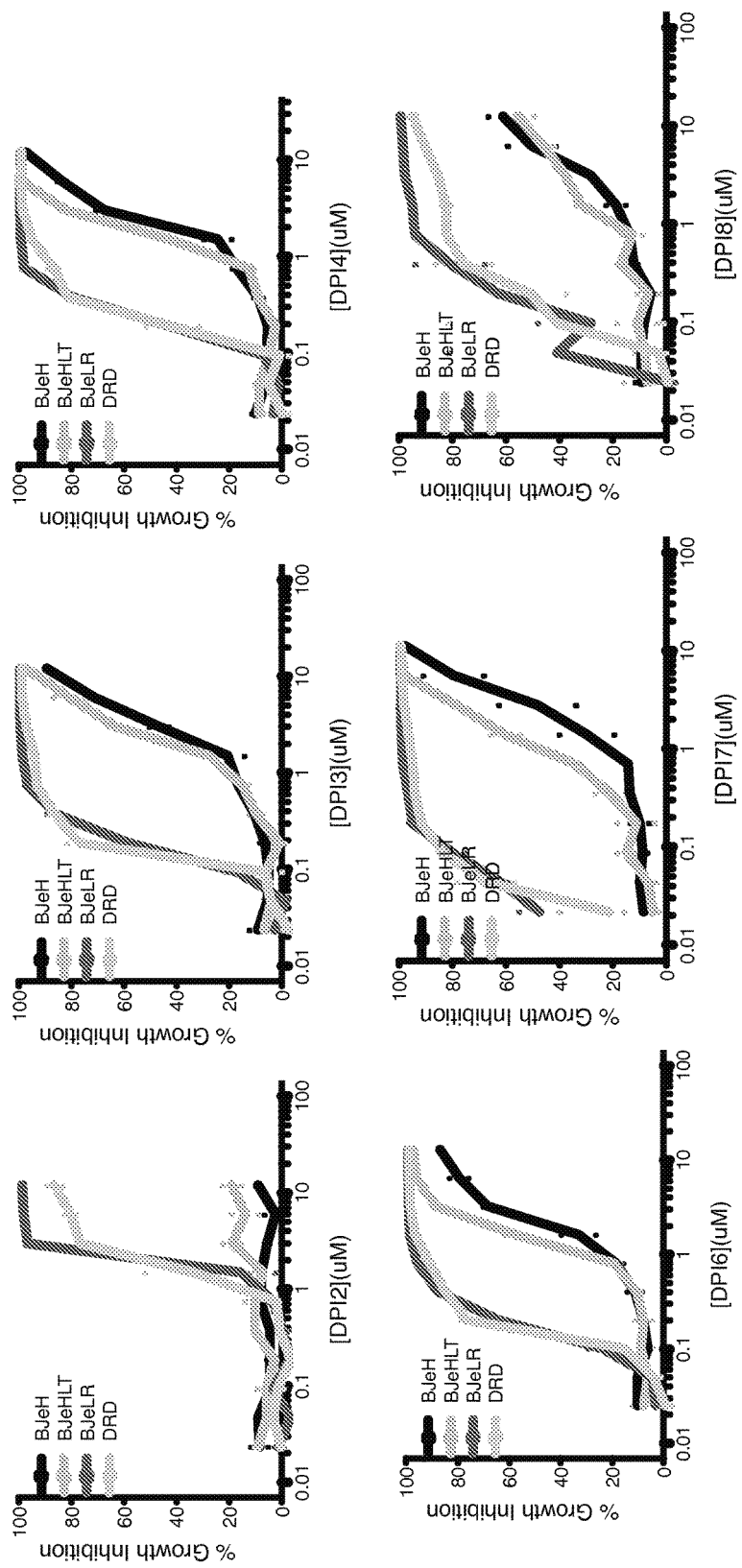
Figure 10B:
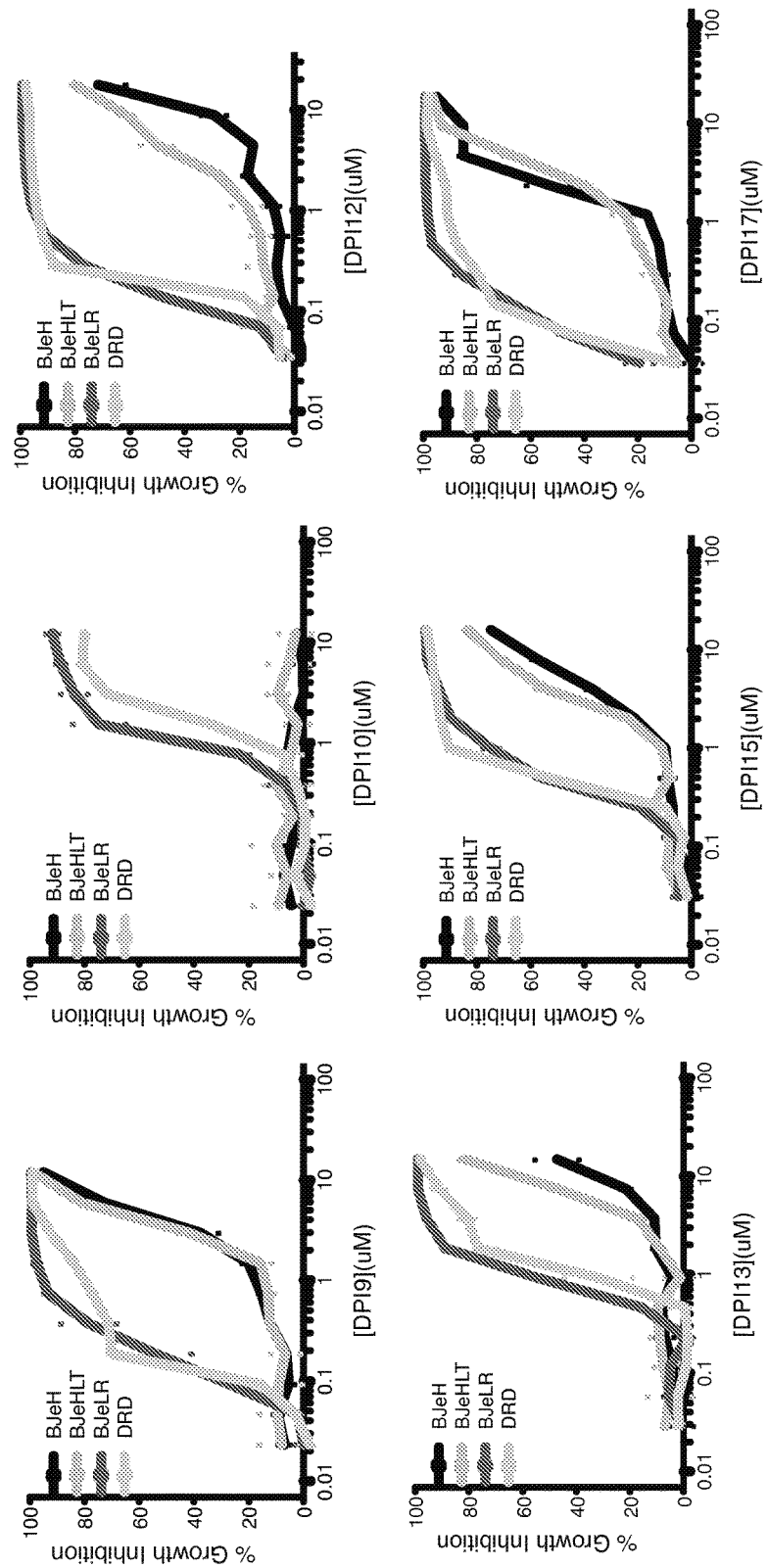
Figure 10B:
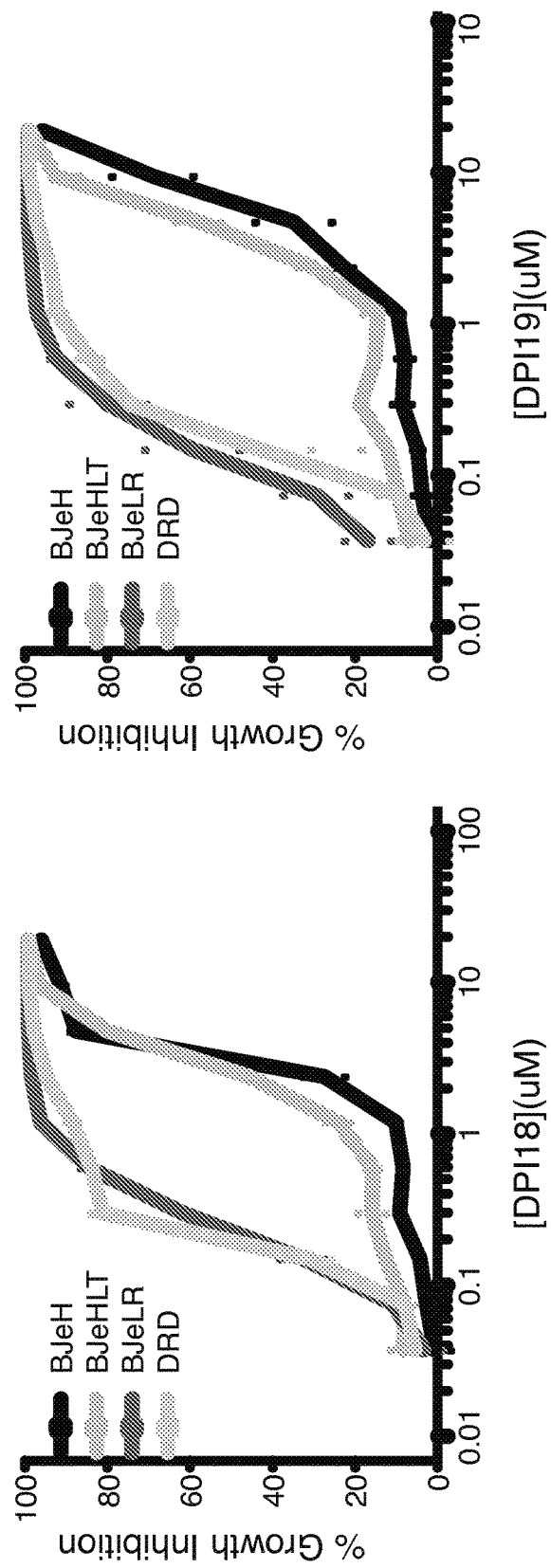
Figure 10:
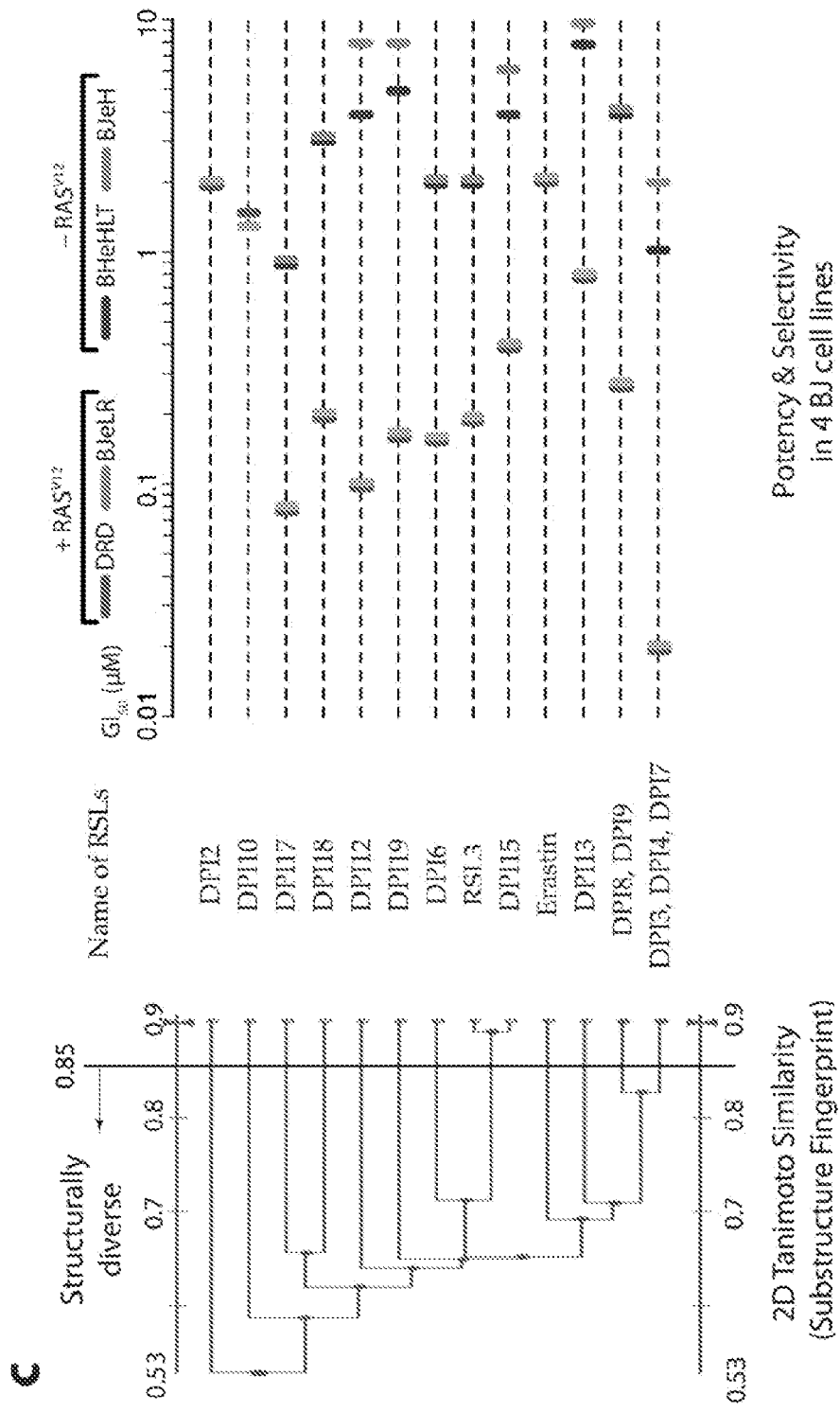

FIG. 10b shows a series of graphs demonstrating that the RSL phenotype of 14 compounds (as indicated) was confirmed in the 4-BJ cell system. The RSL compounds demonstrate increased potency in two cell lines with oncogenic-RAS (BJeLR and DRD) compared to two cell lines without oncogenic-RAS (BJeH and BJeHLT). Cells were incubated with each compound for 2 days followed by viability determination using alamar blue. The line shows mean of duplicate data points.

FIG. 10c is a graph showing the fourteen RSL compounds from FIG. 10b clustered based on 2-dimensional (2-D) structure similarity and their respective potency and selectivity. The Tanimoto equation was used to compute the degree of similarity. The Tanimoto score is a fraction between 0 and 1 where 0 means no similarity and 1 means identical. The inventors considered that compounds clustered with >0.85 Tanimoto similarity as a single group, which resulted in the characterization of 12 different groups.

Figure 11:
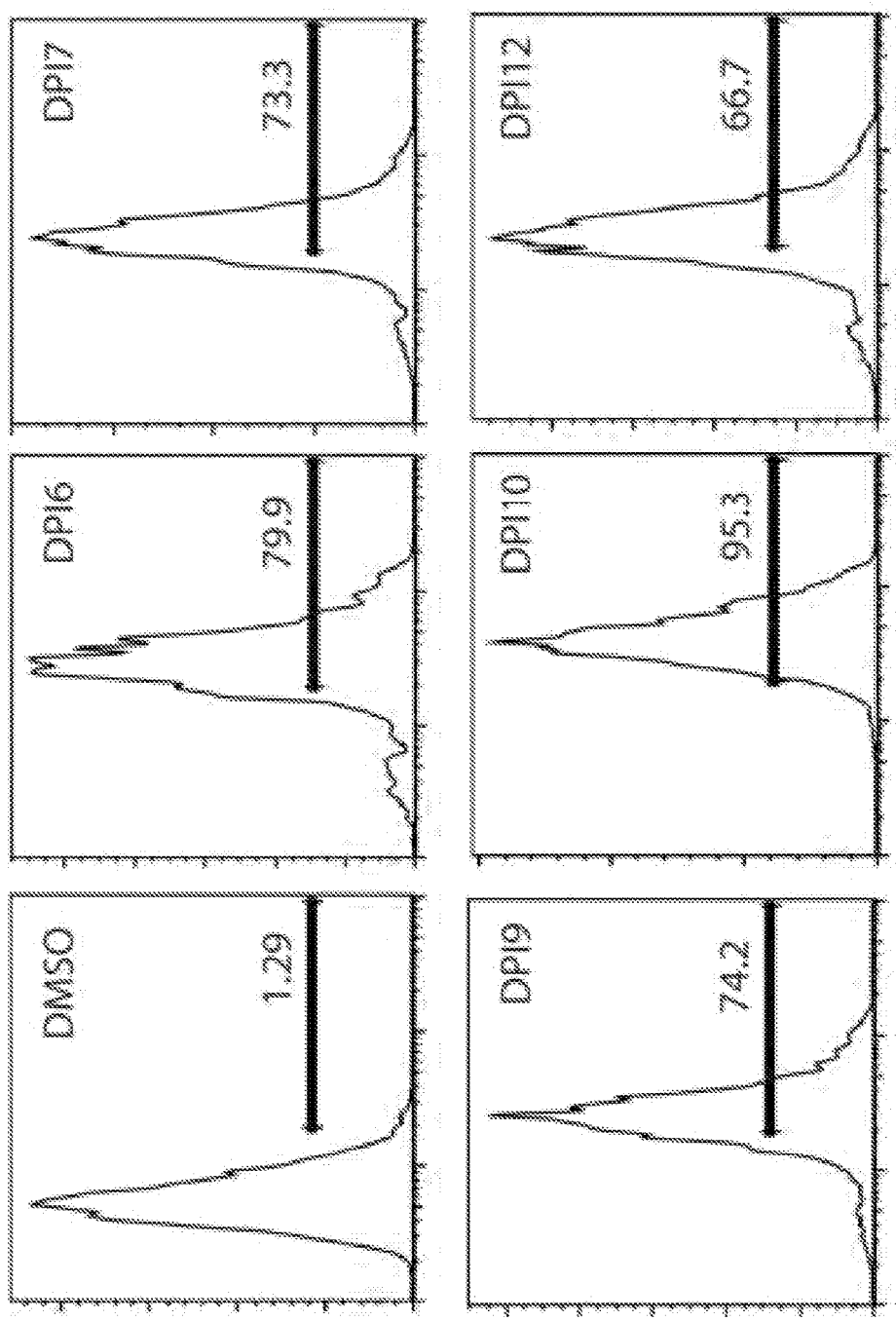
Figure 11A:
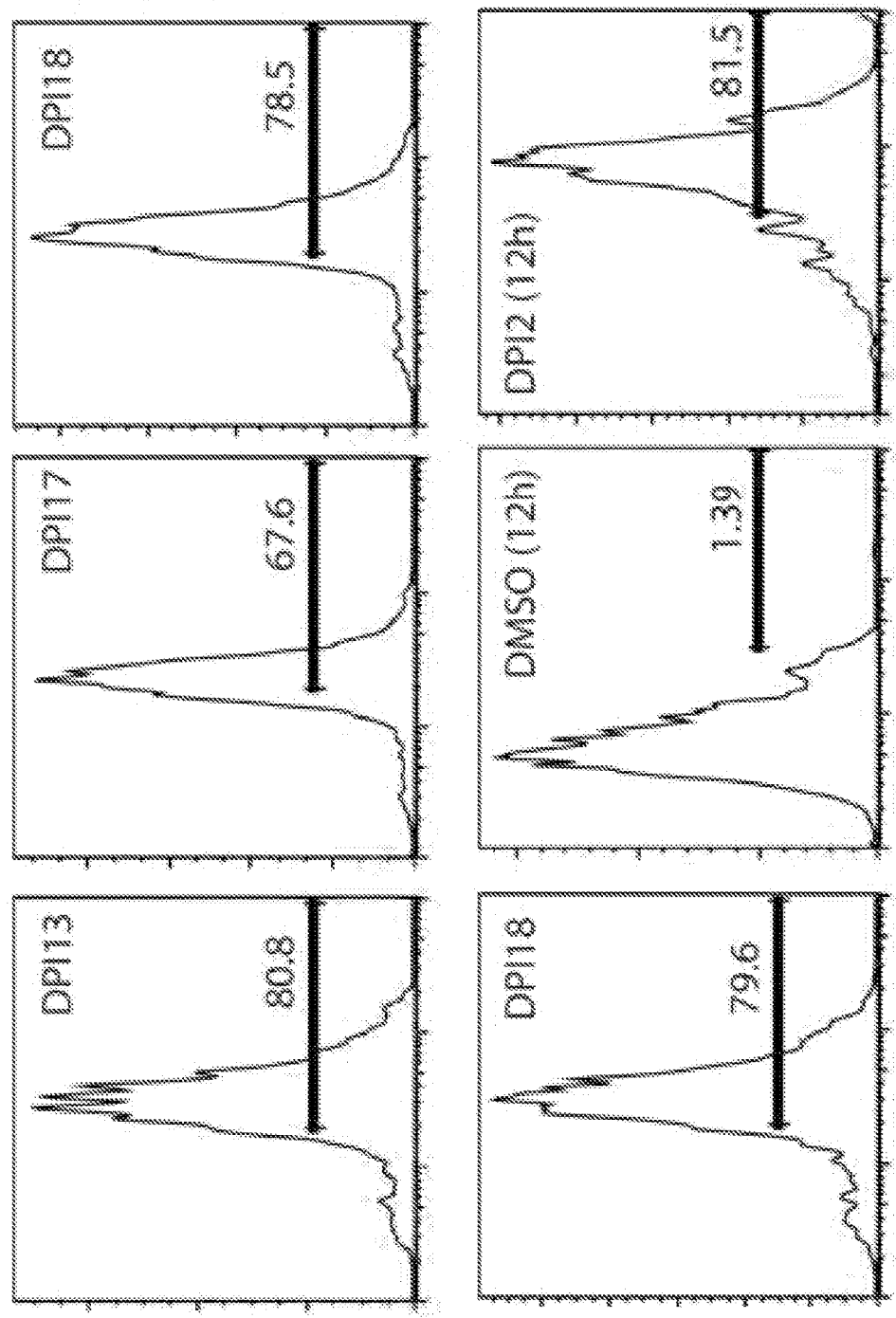
Figure 11:
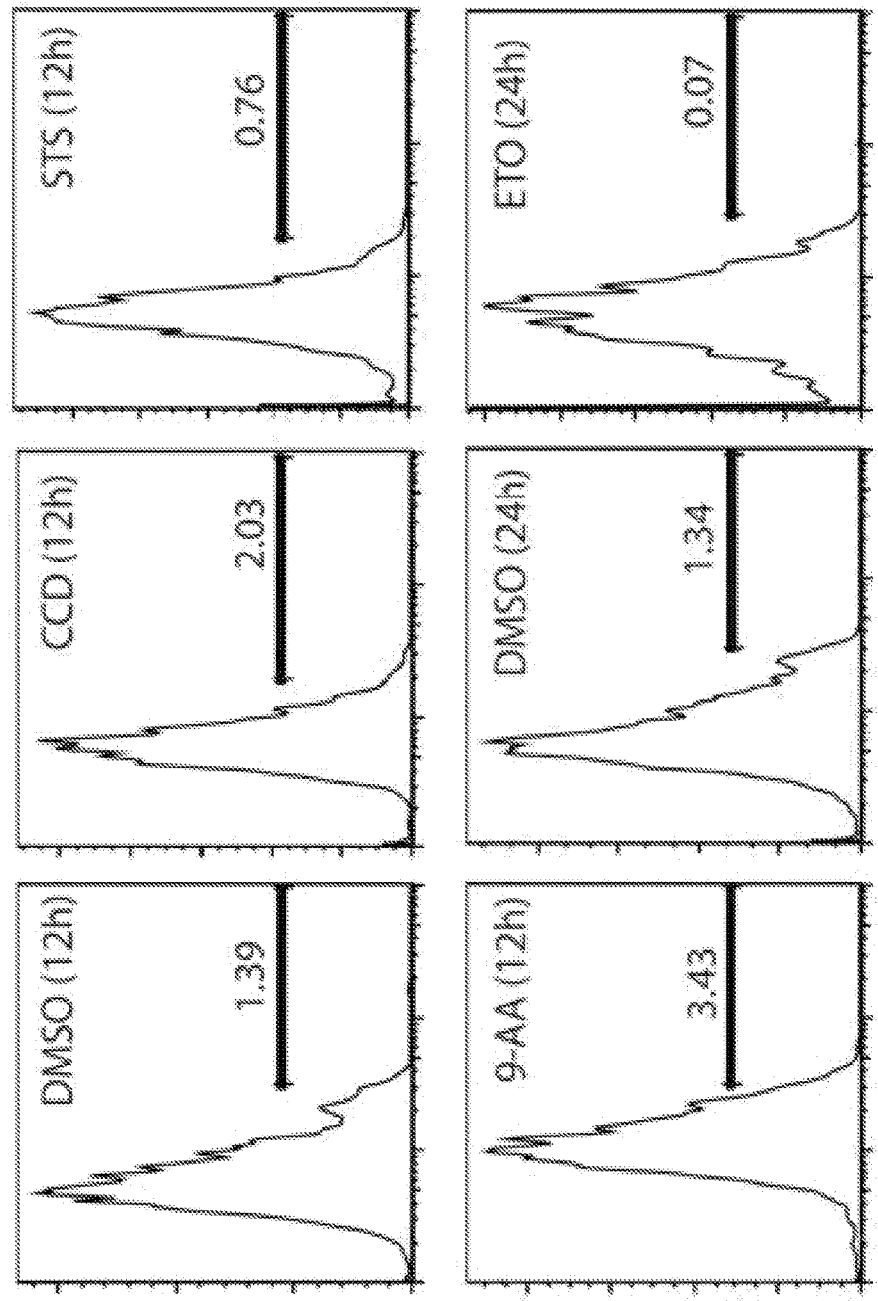
Figure 11B:
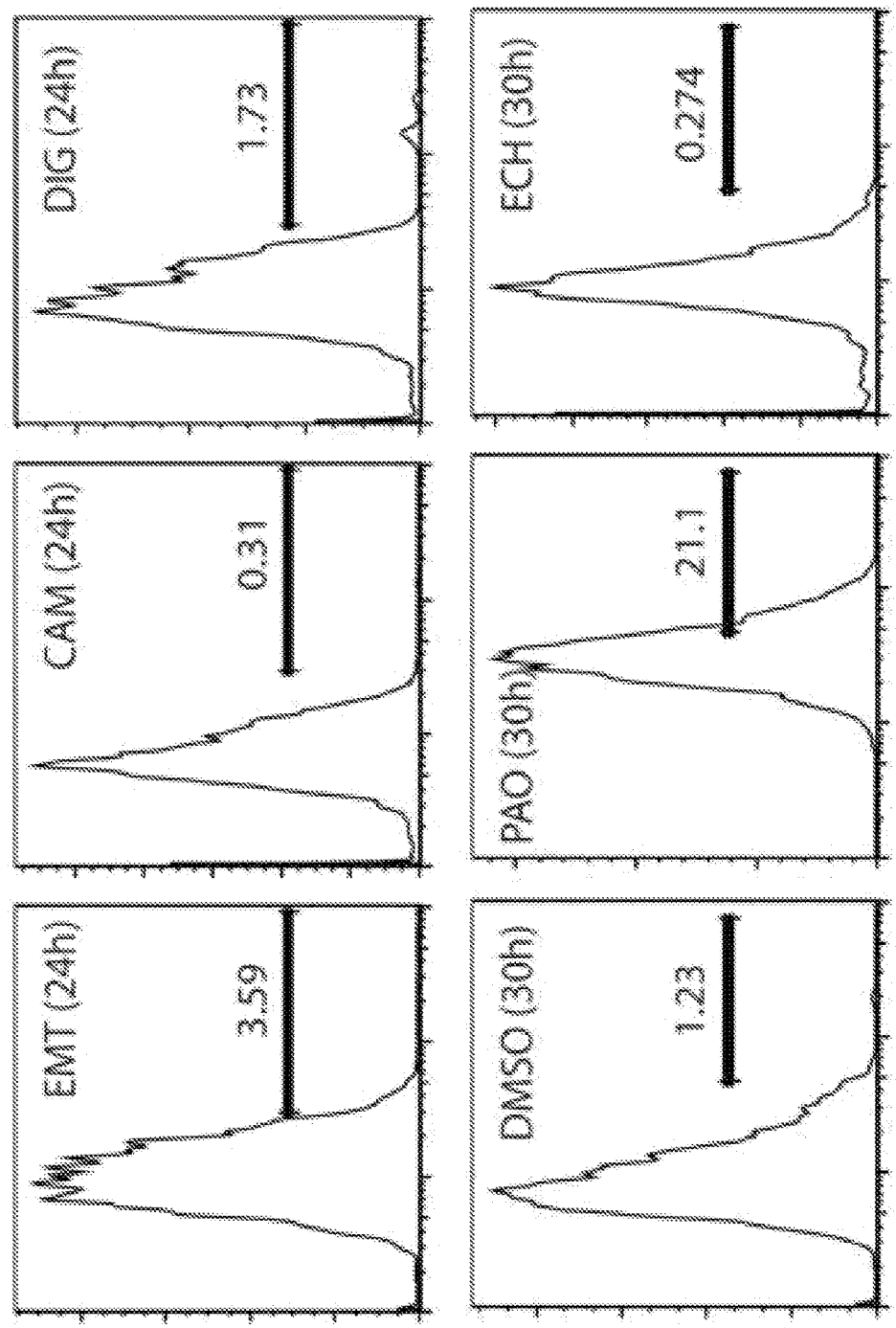
Figure 11B:
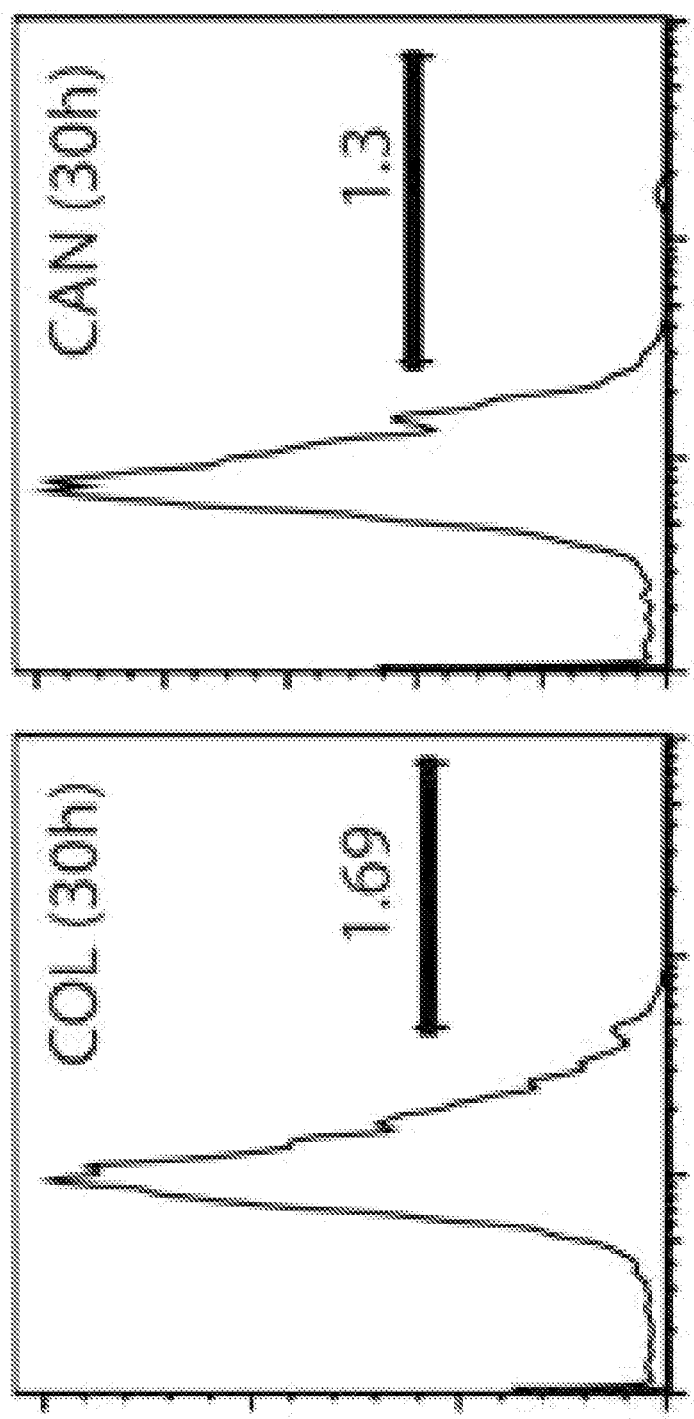

FIG. 11a shows a series of graphs demonstrating that ten additional RSL compounds were tested and were found to generate lipid peroxides. The indicated RSL compounds were added to BJeLR cells at 10 µM for 6 hours (or 12 hours for DPI2) to induce cell death. FIG. 11b shows a series of graphs demonstrating that eleven diverse non-RSL compounds were tested for lipid peroxide generation in BJeLR cells. Only phenylarsine oxide (PAO) showed weak generation of lipid peroxides, whereas all the other lethal compounds did not show any lipid peroxide generation. The indicated lethal compounds were administered to BJeLR cells to induce cell death according to the conditions shown in FIG. 11c. After cell death was initiated, cells were stained with BODIPY-C11 (581/591) and subjected to flow cytometric analysis to assess the level of lipid peroxidation. The number in each graph indicates percentage of BODIPY-C11 stain positive cells out of parental cell population. FIG. 11c is a table showing treatment conditions for the non-RSL compounds used in FIG. 4a and FIG. 11a.

Figure 12:
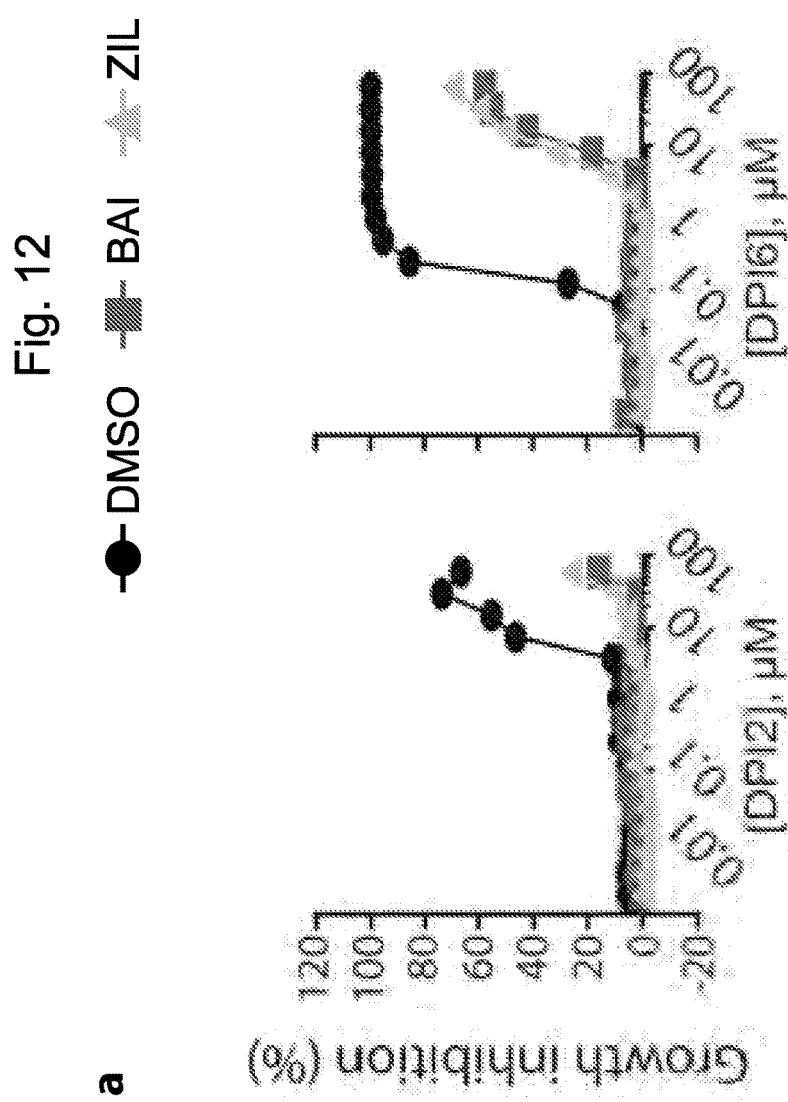
Figure 12A:
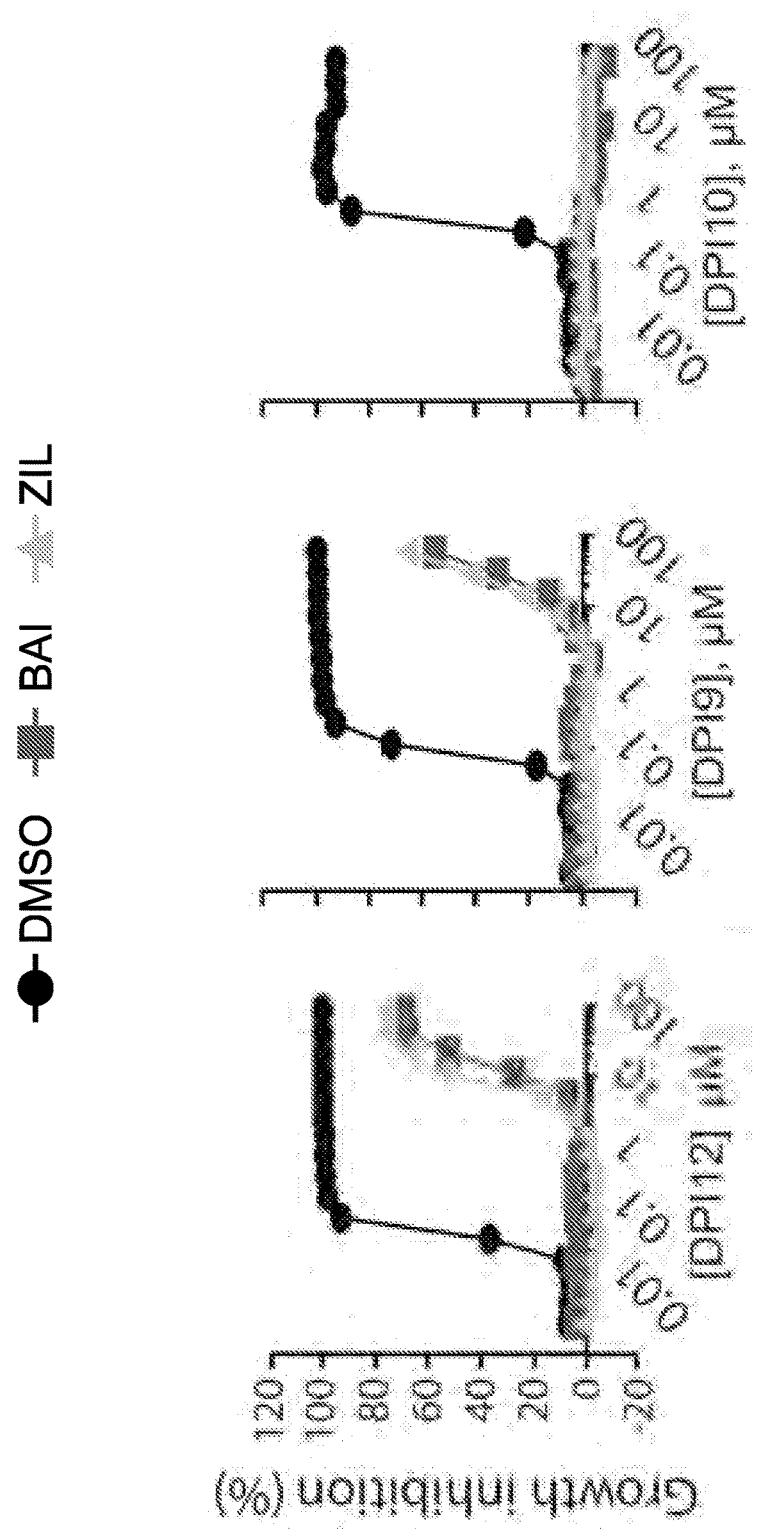
Figure 12A:
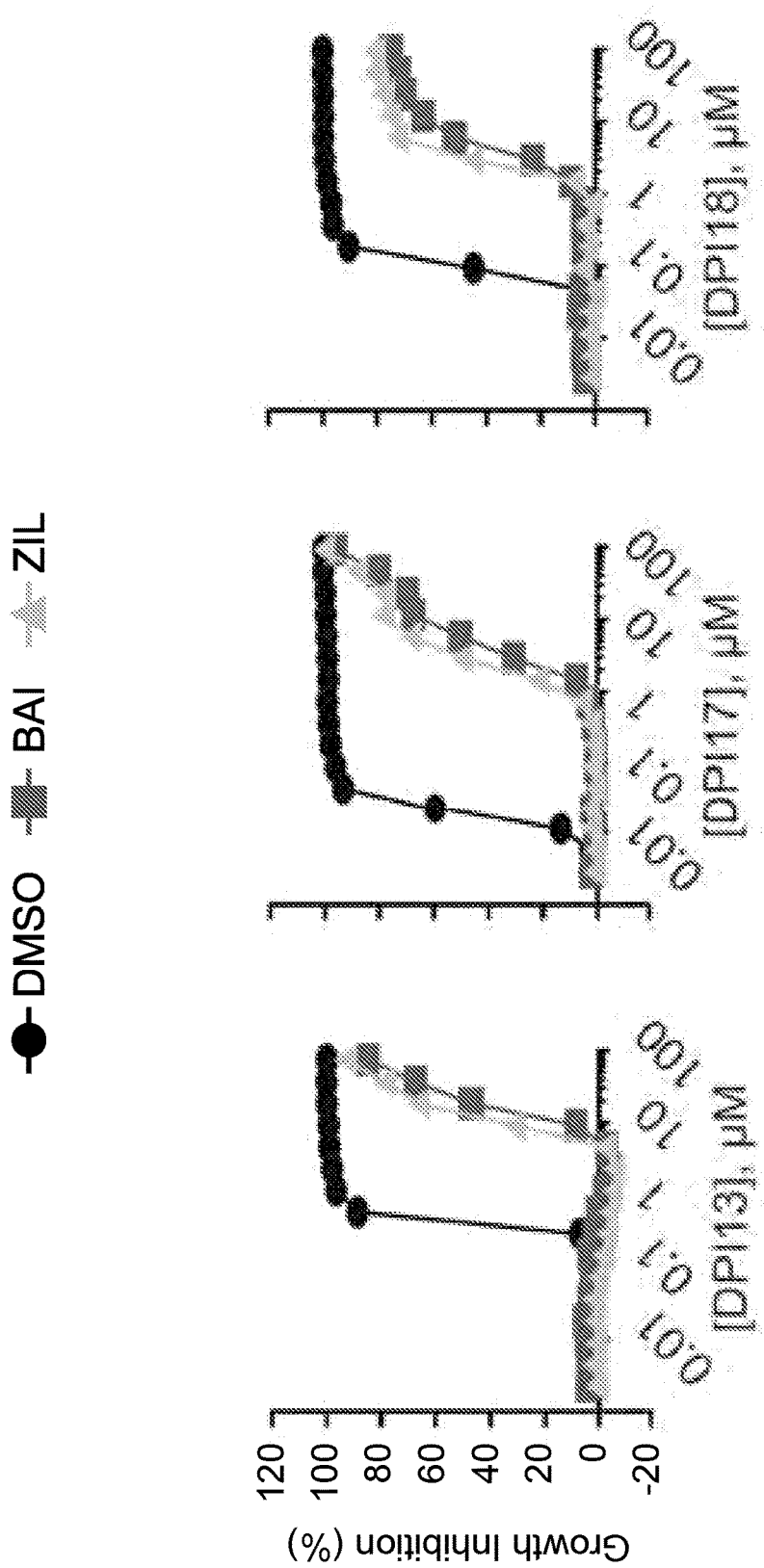
Figure 12A:
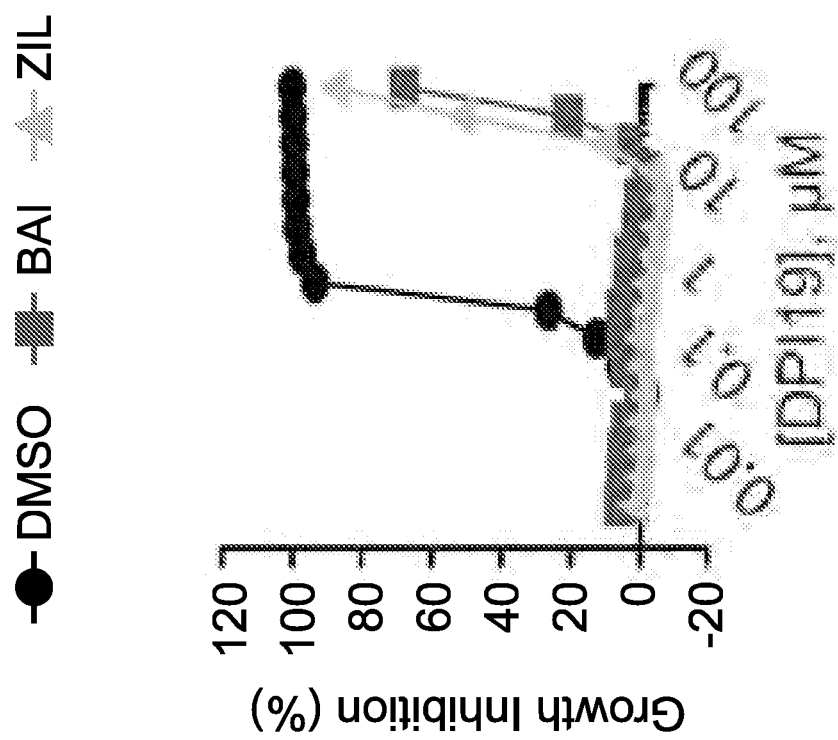
Figure 12:
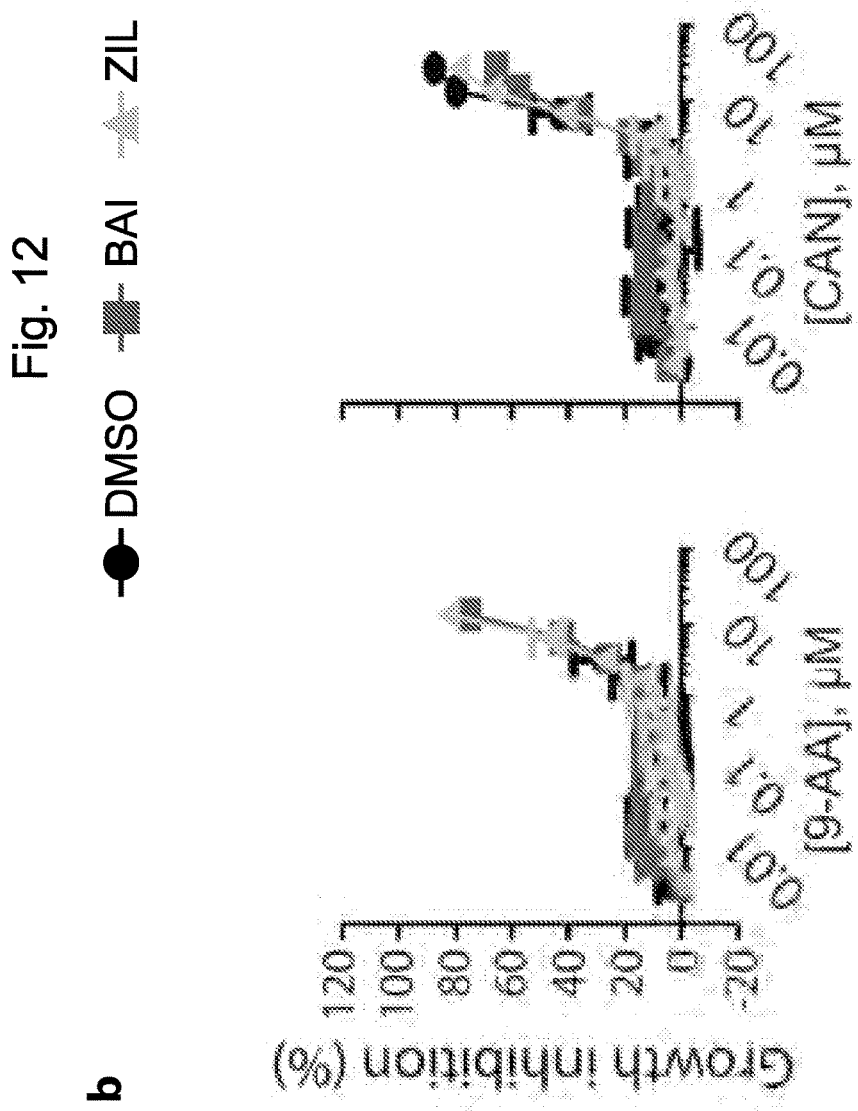
Figure 12B:
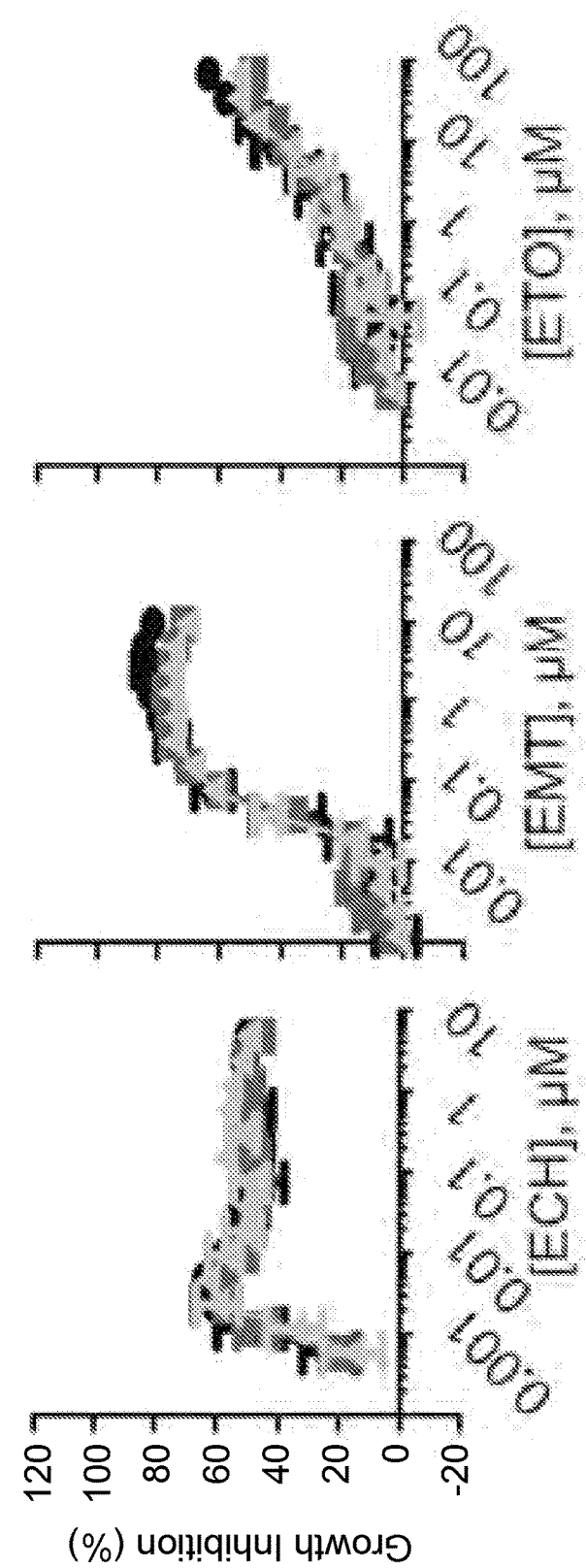
Figure 12B:
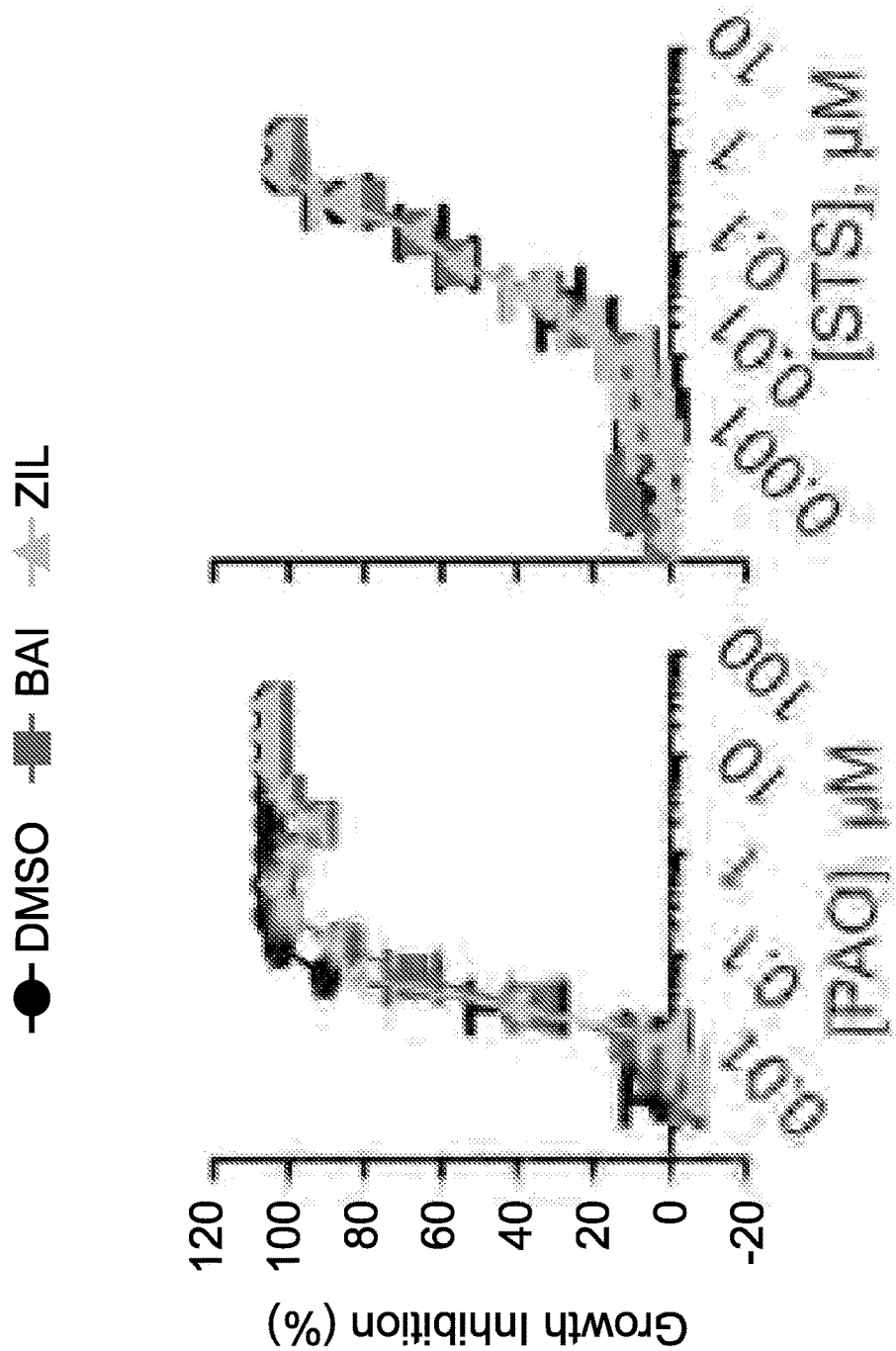

FIG. 12a shows a series of graphs demonstrating that ALOX inhibitors prevented cell death by all RSL compounds. Data points represent mean of duplicates. FIG. 12b show a series of graphs demonstrating that ALOX inhibitors did not rescue cell death induced by 11 diverse non-RSL compounds. HT-1080 cells were seeded in 384-well plates, treated with the indicated amount of compounds with or without 10 μM of BAI or 50 μM of ZIL for 24 hours. The percent growth inhibition was determined using alamar blue. Data are presented as mean±s.d.; n=3.

FIG. 13a shows a series of micrographs demonstrating that RSL compounds induced translocation of GFP-ALOX5 to the perinuclear membrane region, whereas non-RSL lethal compounds did not. HT-1080 cells stably expressing GFPALOX5 were treated with the indicated compounds under the conditions detailed in FIG. 13b. Under these conditions, cells were dying or dead (see the last photo of DMSO sample which shows untreated cells). Note that digioxin (DIG) did translocate GFP-ALOX5 to the perinuclear membrane region in a small portion of the cell population (arrow). Digioxin is known to increase cellular calcium concentration that can translocate GFP-ALOX5, similarly to ionomycin. Scale bars, 60 μm.

FIG. 13b is a table showing treatment conditions used in FIG. 4b and FIG. 13a.

FIG. 13c shows a series of microscopy images demonstrating that a few digoxin treated cells showed translocation but not selectively in three BJeLR cell lines (arrow). Scale bars=100 μm. Cells were treated with 10 μM digoxin for 12 hours.

Figure 14:
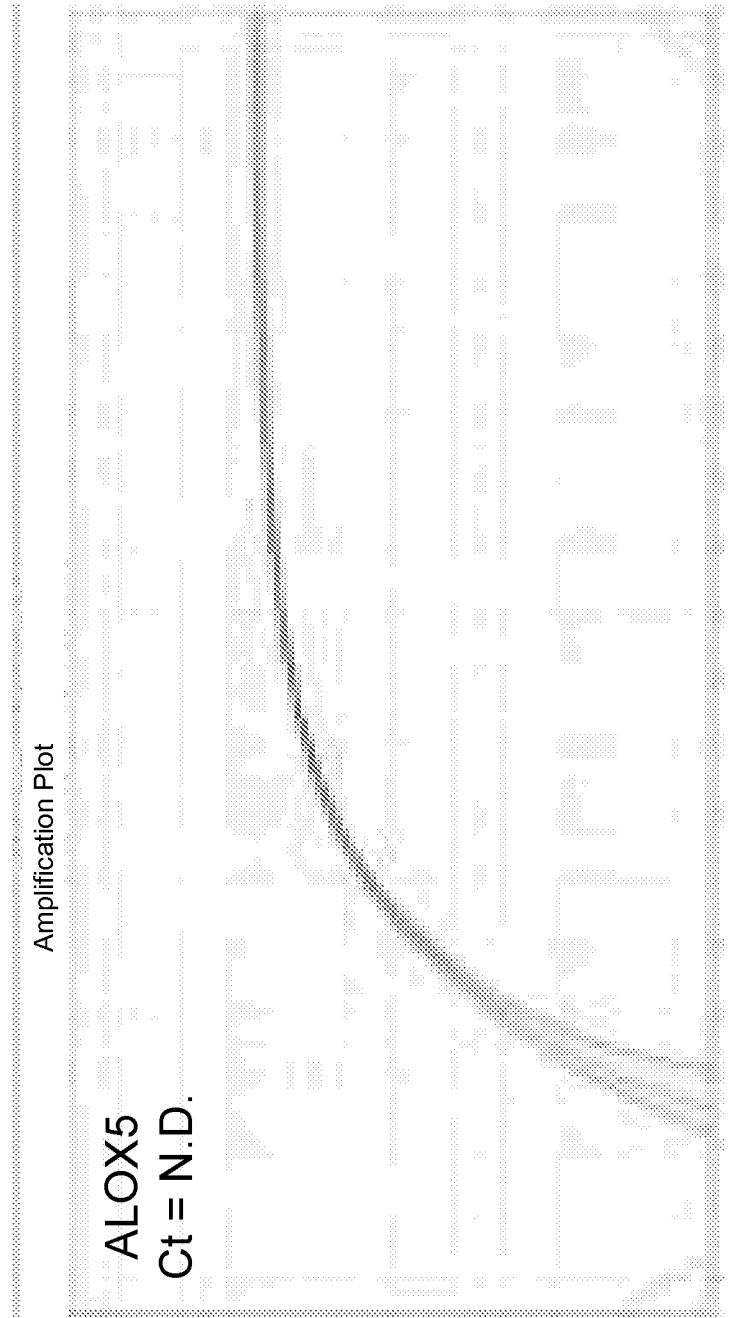
Figure 14A:
Figure 14A:
Figure 14A:
Figure 14A:
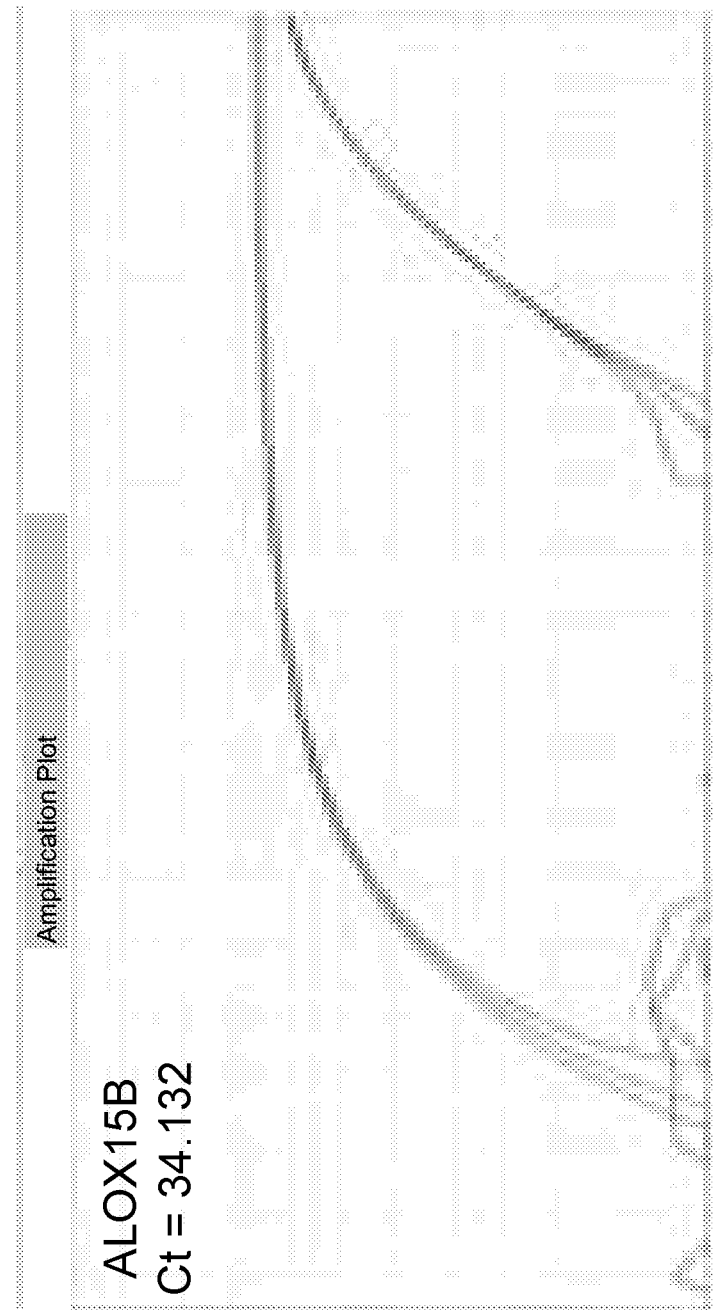
Figure 14A:
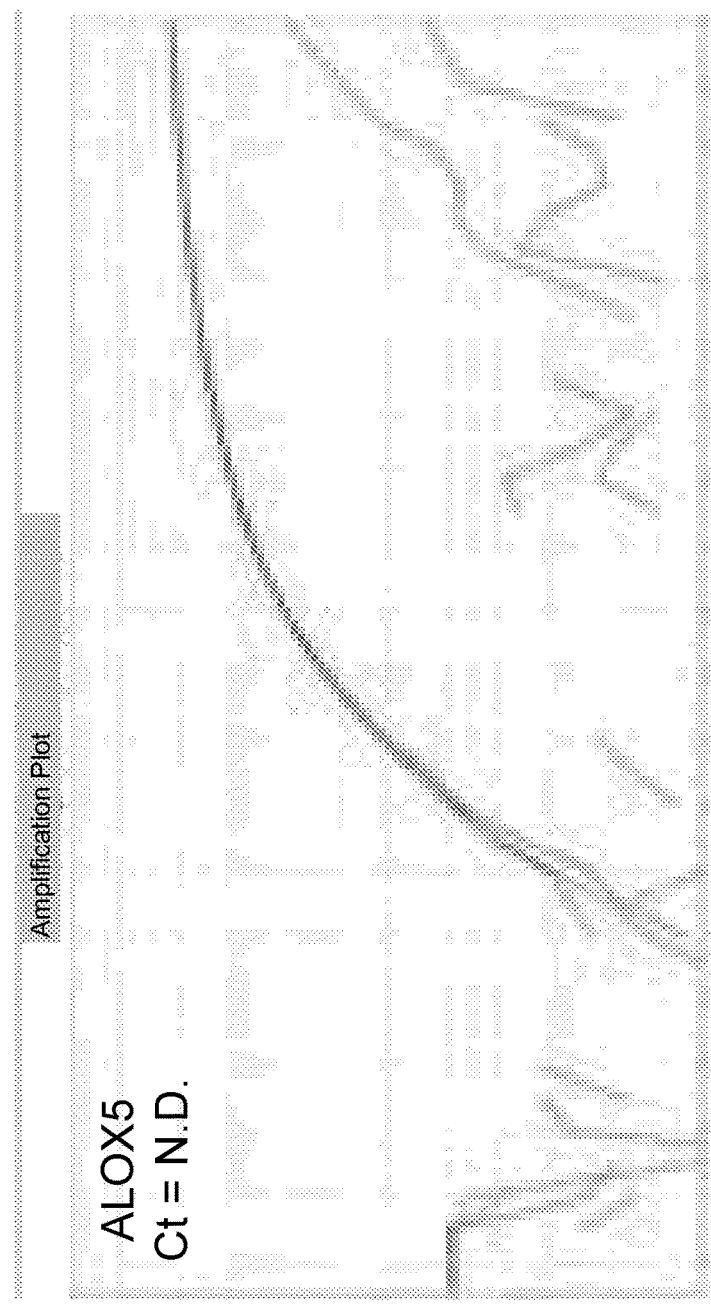
Figure 14A:
Figure 14A:
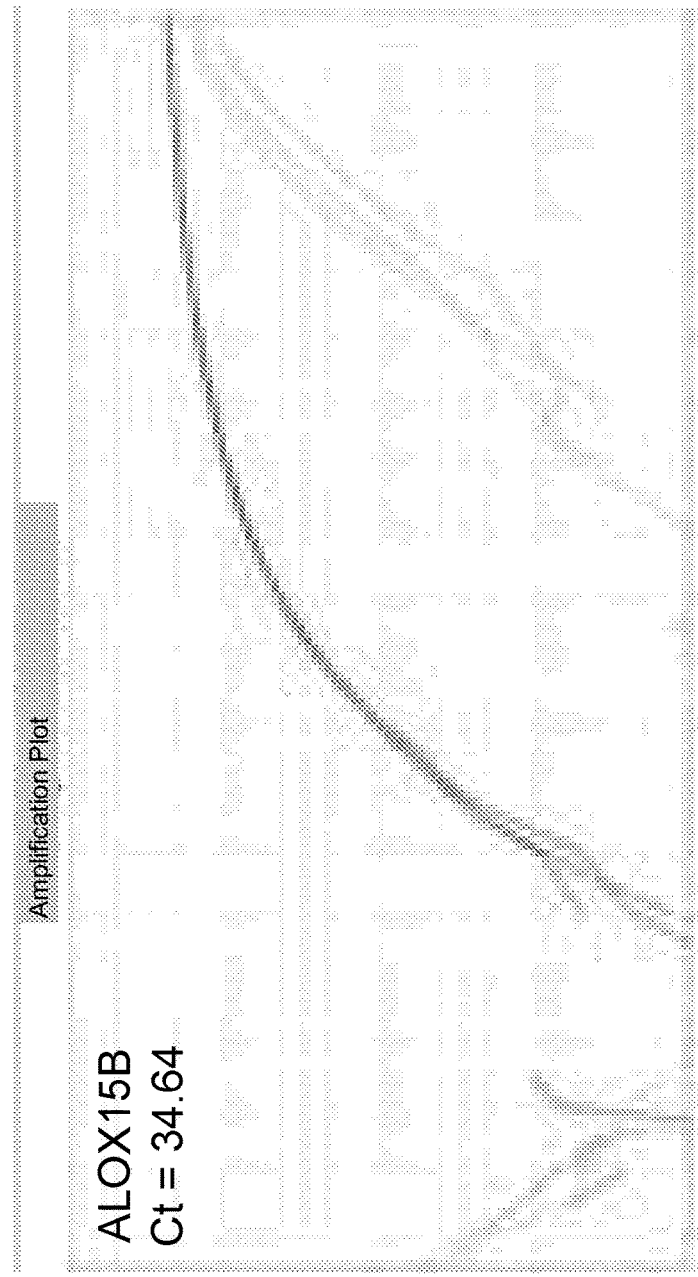
Figure 14A:
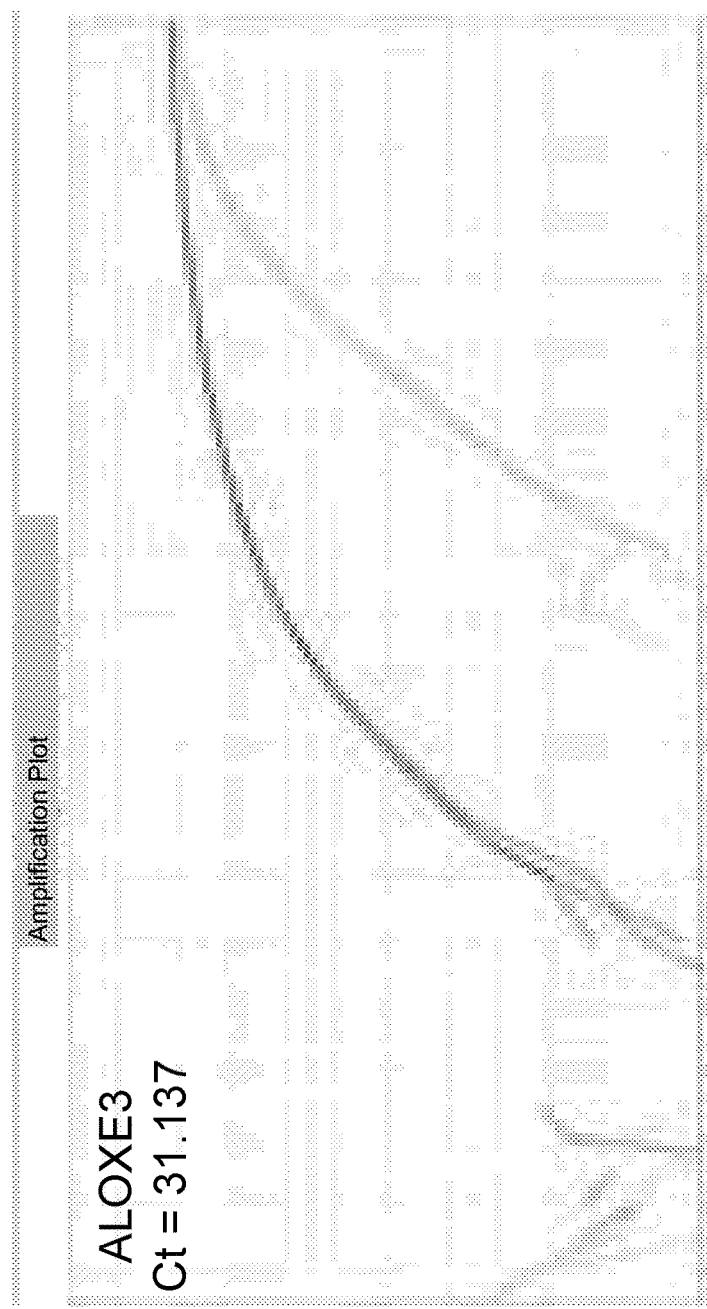
Figure 14:
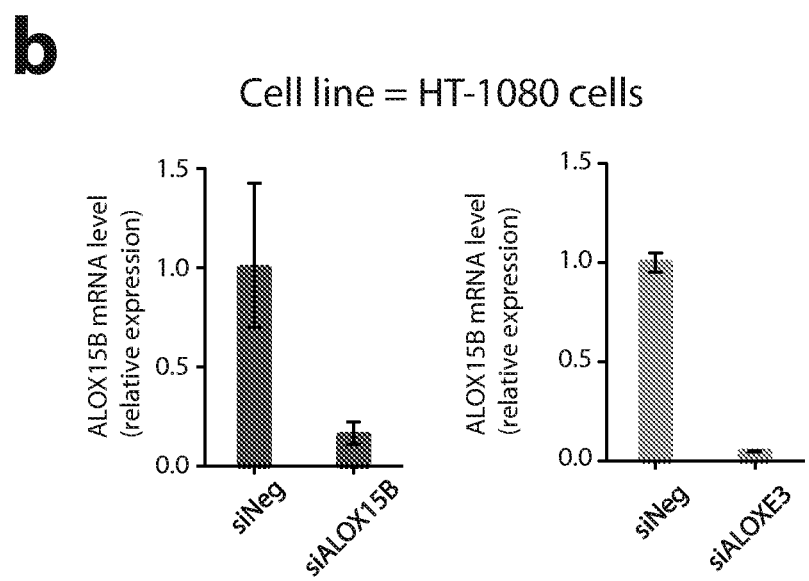

FIG. 14a shows a series of graphs demonstrating the expression analysis of ALOX genes in BJeLR and HT-1080 cells. The graphs show the amplification plot of each ALOX isoform. Triplicate samples were analyzed for each gene using mRNA from either cell line. ACTB gene amplification was served as endogenous control. The gene name and the Ct (cycle of threshold) number are presented. N.D.=not determined. Ct value of greater than 35 is considered weak expression, which suggests that ALOXE3 is the major isoform expressed in these cell lines.

FIG. 14b shows two graphs demonstrating that the knockdown of ALOX15B and ALOXE3 expression by a pool of siRNAs was confirmed using qPCR analysis. Data are presented as mean±s.d.; n=3.

Figure 15:
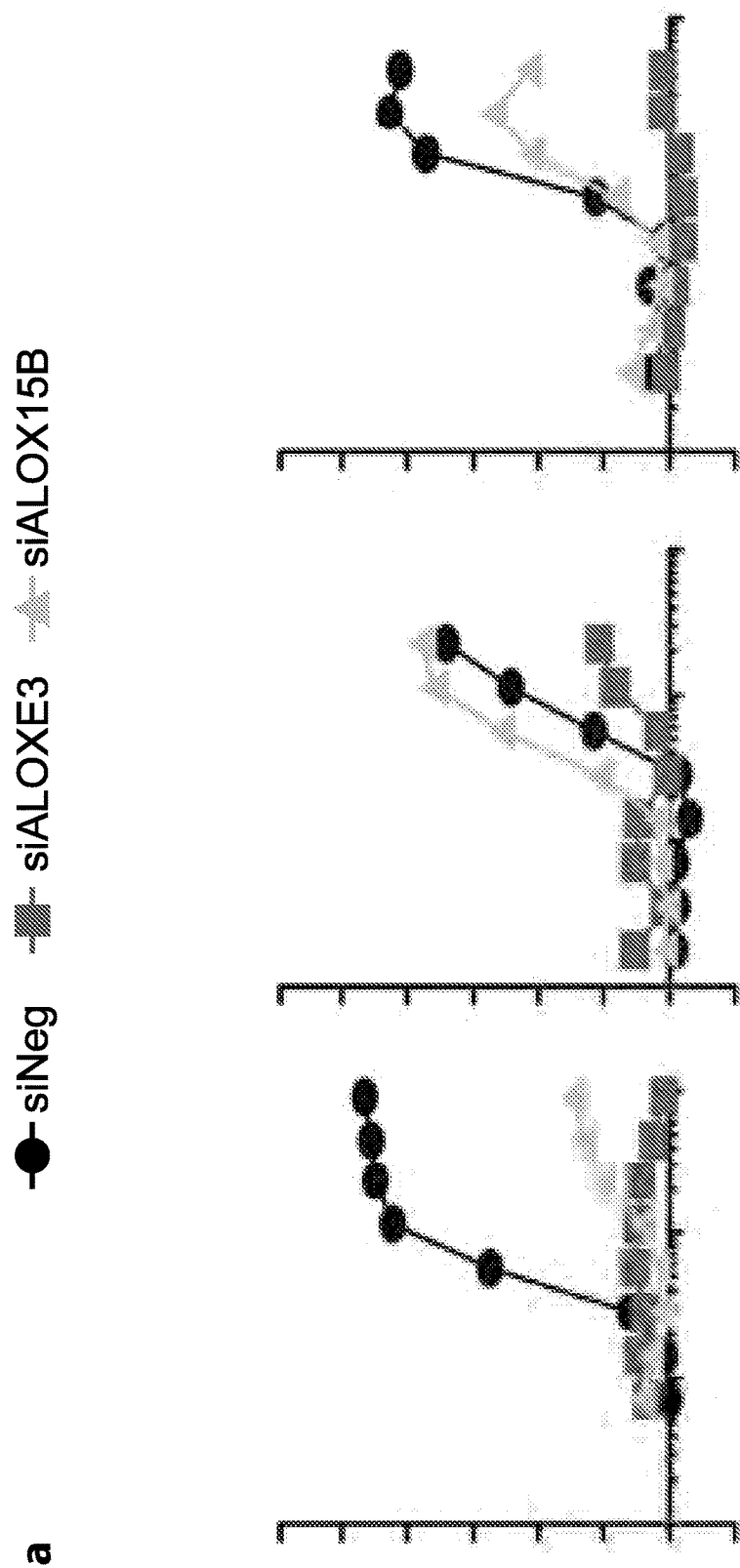
Figure 15A:
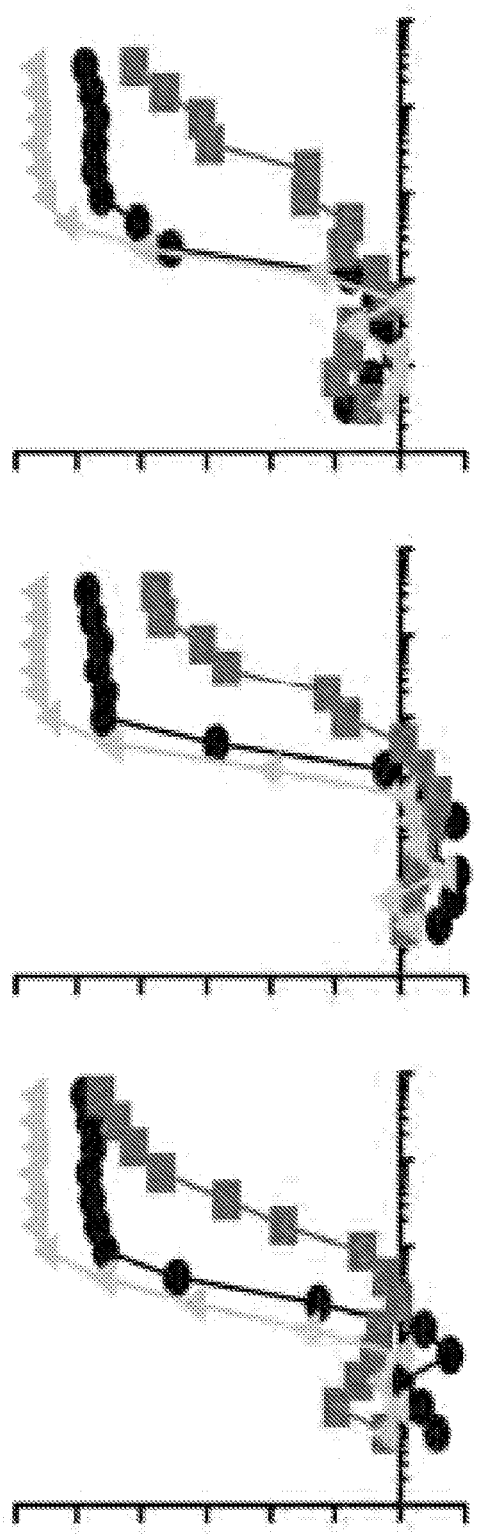
Figure 15A:
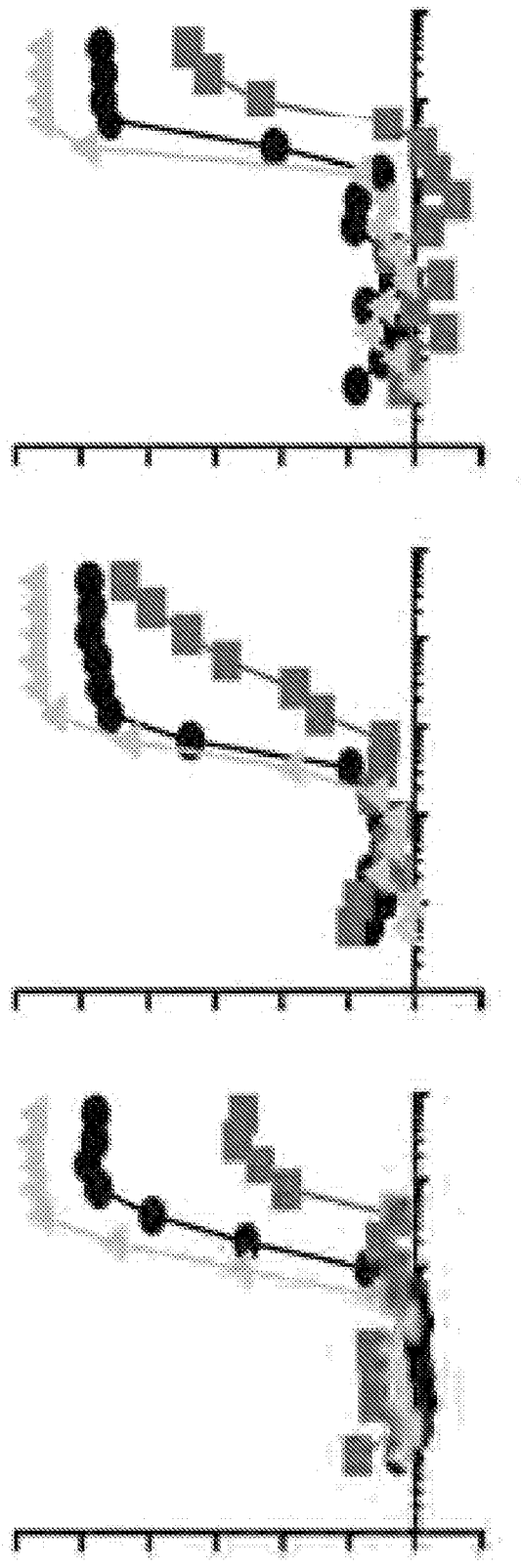
Figure 15B:
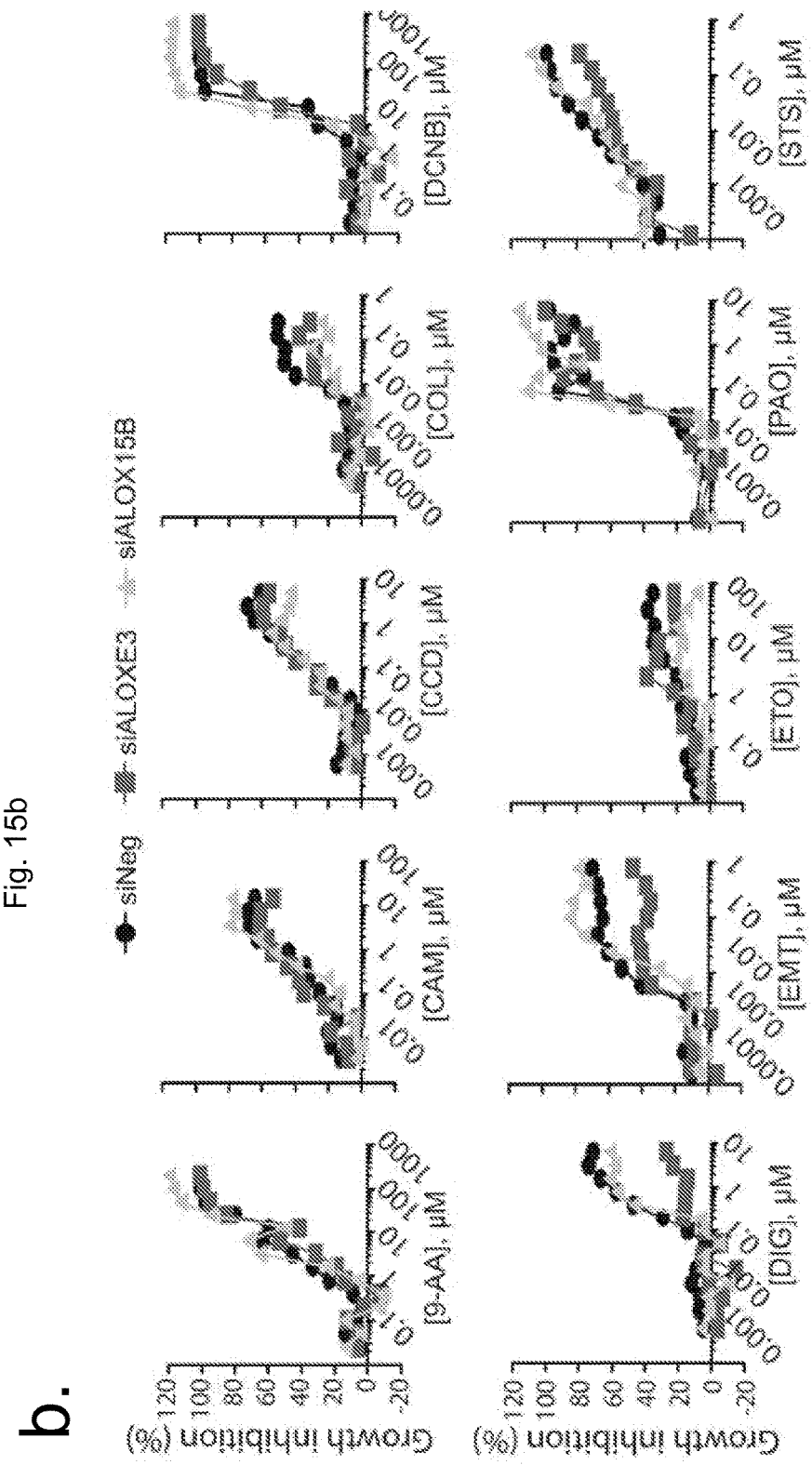

FIG. 15 shows modulation of RSL-induced cell death (FIG. 15a) or non-RSL-induced cell death (FIG. 15b) by knockdown of ALOX15B or ALOXE3. HT-1080 cells were transfected with siRNA pools targeting either ALOX15B or ALOXE3, and then, treated with the indicated RSL compounds in 2-fold dilution series. 24 hours after compound treatment, alamar blue was added to the culture at a final concentration of 10% in growth media to determine cell viability. The percent growth inhibition was calculated from the fluorescence intensity of each well in 384-well assay plates. Data points represent mean of duplicates.

FIGS. 16a-i show the concentration-dependent curves of various erastin analogs, which were tested in 4 isogenic cell lines: $HRAS^{G12V}$ overexpressing artificially transformed fibroblasts (BJeLR, BJeDRD) and non-transformed isogenic cells without mutant HRAS expression (BJeHLT, BJeH).

FIGS. 17a-e show the concentration-dependent curves of various erastin analogs, which were tested in HT1080, a human fibrosarcoma cell line.

Figure 18:
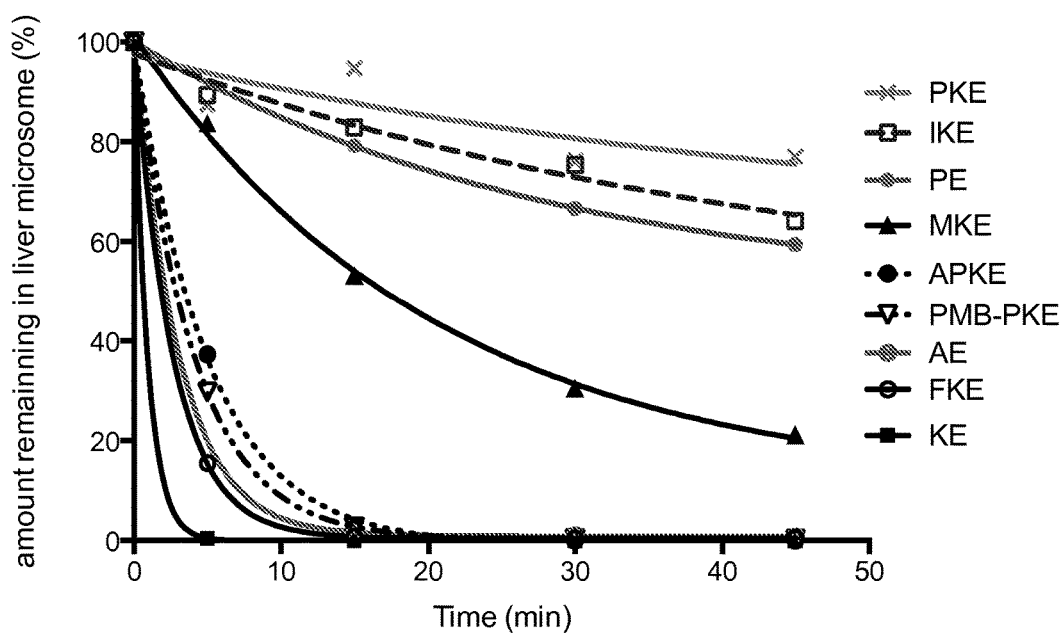

FIG. 18 shows the metabolic stability of various erastin analogs in mouse liver microsomes.

Figure 19:
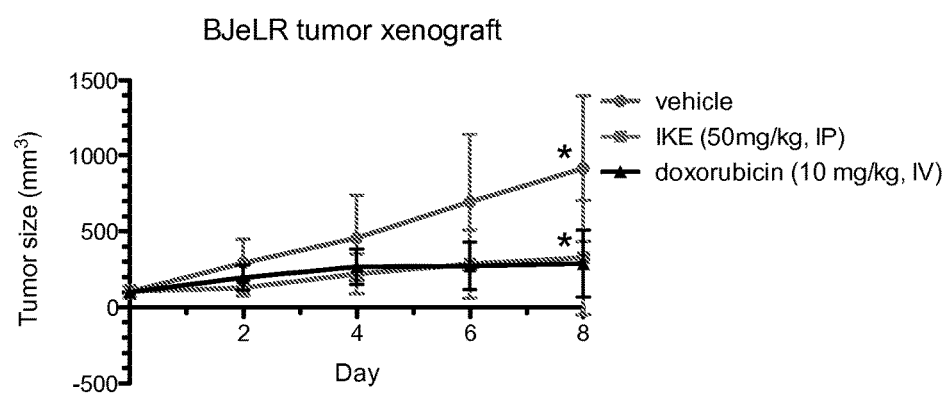
Figure 19:
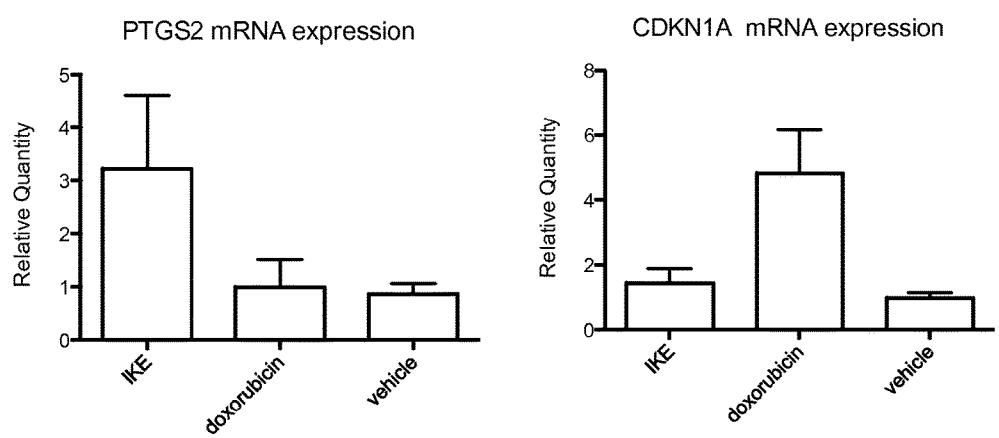

FIG. 19a shows the effect of IKE on tumor xenografts. N=6 or 7, eight week old nude mice with an average tumor size of about 60 mm³ received 7 doses of IKE at 50 mg/kg (I.P.), 4 doses of doxorubicin (I.V.), or 7 doses of vehicle (I.P.). *p=0.035 of IKE compared to vehicle treated.

FIG. 19b shows expression levels of PTGS2 and CDKN1A by qPCR.

Figure 20:
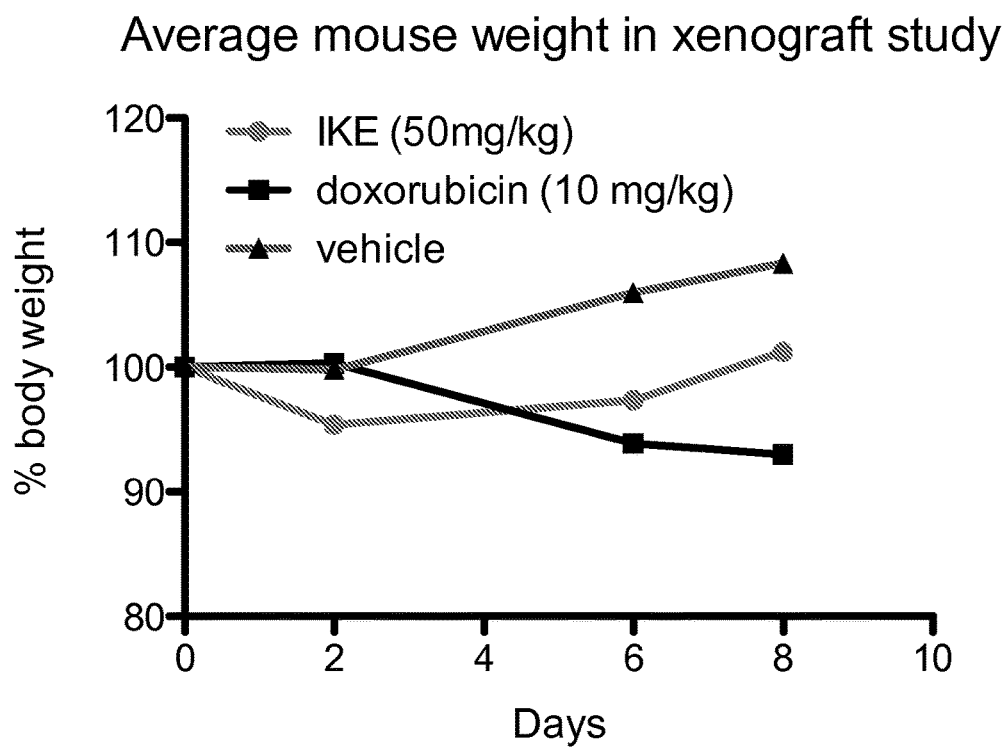

FIG. 20 shows that no overt toxicity was observed in either IKE or doxorubicin-treated mice throughout the study; as gauged by monitoring body weight.

DETAILED DESCRIPTION OF THE INVENTION

One embodiment of the present invention is a compound according to formula (I):

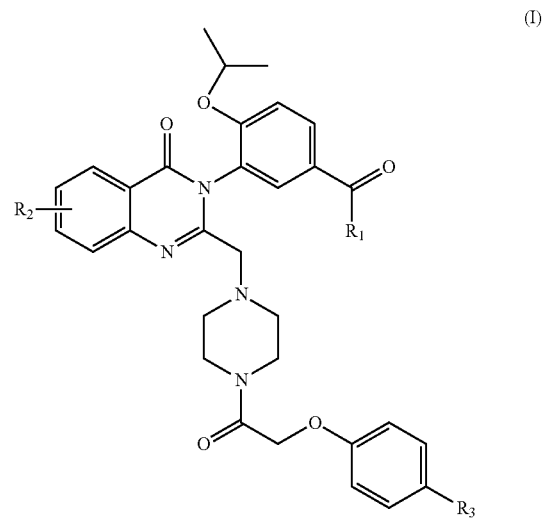

(I)

wherein:
R₁ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;
R₂ is selected from the group consisting of H, halo, and $C_{1-6}$aliphatic; and
R₃ is a halo atom;
or an N-oxide, crystalline form, hydrate, or pharmaceutically acceptable salt thereof.

The term "aliphatic", as used herein, refers to a group composed of carbon and hydrogen atoms that do not contain aromatic rings. Accordingly, aliphatic groups include alkyl, alkenyl, alkynyl, and carbocyclyl groups. Additionally, unless otherwise indicated, the term "aliphatic" is intended to include both "unsubstituted aliphatics" and "substituted aliphatics", the latter of which refers to aliphatic moieties having substituents replacing a hydrogen on one or more carbons of the aliphatic group. Such substituents can include, for example, a halogen, a deuterium, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic moiety.

The term "alkyl" refers to the radical of saturated aliphatic groups that does not have a ring structure, including straight-chain alkyl groups, and branched-chain alkyl groups. In certain embodiments, a straight chain or branched chain alkyl has 6 or fewer carbon atoms in its backbone (e.g., $C_1$-$C_6$ for straight chains, $C_3$-$C_6$ for branched chains). Such substituents include all those contemplated for aliphatic groups, except where stability is prohibitive.

Moreover, unless otherwise indicated, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "alkenyl", as used herein, refers to an aliphatic group containing at least one double bond and unless otherwise indicated, is intended to include both "unsubstituted alkenyls" and "substituted alkenyls", the latter of which refers to alkenyl moieties having substituents replacing a hydrogen on one or more carbons of the alkenyl group. Such substituents include all those contemplated for aliphatic groups, as discussed below, except where stability is prohibitive. For example, substitution of alkenyl groups by one or more alkyl, carbocyclyl, aryl, heterocyclyl, or heteroaryl groups is contemplated.

The term "$C_{x-y}$" when used in conjunction with a chemical moiety, such as, alkyl and cycloalkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc.

The terms "amine" and "amino" are art-recognized and refer to both unsubstituted and substituted amines and salts thereof, e.g., a moiety that can be represented by

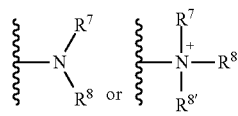

wherein $R^7$, $R^8$, and $R^{8'}$ each independently represent a hydrogen or a hydrocarbyl group, or $R^7$ and $R^8$ taken together with the N atom to which they are attached complete a heterocycle having from 4 to 8 atoms in the ring structure. The term "primary" amine means only one of $R^7$ and $R^8$ or one of $R^7$, $R^8$, and $R^{8'}$ is a hydrocarbyl group. Secondary amines have two hydrocarbyl groups bound to N. In tertiary amines, all three groups, $R^7$, $R^8$, and $R^{8'}$, are replaced by hydrocarbyl groups.

The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "alkyl-aryl" refers to an alkyl group substituted with at least one aryl group.

The terms "halo" and "halogen" are used interchangeably herein and mean halogen and include chloro, fluoro, bromo, and iodo.

The term "heterocycle" refers to substituted or unsubstituted non-aromatic ring structures, preferably 3- to 8-membered rings, whose ring structures include at least one heteroatom, preferably one to four heteroatoms, more preferably one or two heteroatoms. The term "heterocycle" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocycle groups include, for example, piperidine, piperazine, pyrrolidine, morpholine, lactones, lactams, and the like.

The term "heteroatom" as used herein means an atom of any element other than carbon or hydrogen. Preferred heteroatoms are nitrogen, oxygen, and sulfur; more preferably, nitrogen and oxygen.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As set forth previously, unless specifically stated as "unsubstituted," references to chemical moieties herein are understood to include substituted variants. For example, reference to an "aryl" group or moiety implicitly includes both substituted and unsubstituted variants.

As used herein, an "N-oxide" means a compound containing an N—O bond with three additional hydrogen and/or side chains attached to N, so that there is a positive charge on the nitrogen. The N-oxides of compounds of the present invention may be synthesized by simple oxidation procedures well known to those skilled in the art. For example, the oxidation procedure described by P. Brougham et al. (Synthesis, 1015-1017, 1987), allows the two nitrogen of a piperazine ring to be differentiated, enabling both the N-oxides and N,N'-dioxide to be obtained. Other oxidation procedures are disclosed in, e.g., U.S. Patent Publication No. 20070275977; S. L. Jain, J. K. Joseph, B. Sain, *Synlett*, 2006, 2661-2663; A. McKillop, D. Kemp, *Tetrahedron*, 1989, 45, 3299-3306; R. S. Varma, K. P. Naicker, *Org. Lett.*, 1999, 1, 189-191; and N. K. Jana, J. G. Verkade, *Org. Lett.*, 2003, 5, 3787-3790. Thus, the present invention includes these and other well known procedures for making N-oxides, so long as the end product is sufficiently effective as set forth in more detail below.

The term "crystalline form", as used herein, refers to the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

As used herein, a "hydrate" means a compound that contains water molecules in a definite ratio and in which water forms an integral part of the crystalline structure of the compound. Methods of making hydrates are known in the art. For example, some substances spontaneously absorb water from the air to form hydrates. Others may form hydrates upon contact with water. In most cases, however, hydrates are made by changes in temperature or pressure. Additionally, the compounds of the present invention as well as their salts may contain, e.g., when isolated in crystalline form, varying amounts of solvents, such as water. Included within the scope of the invention are, therefore, all hydrates of the compounds and all hydrates of salts of the compounds of the present invention, so long as such hydrates are sufficiently effective as set forth in more detail below.

In one aspect of this embodiment, the compound has the structure of formula (II):

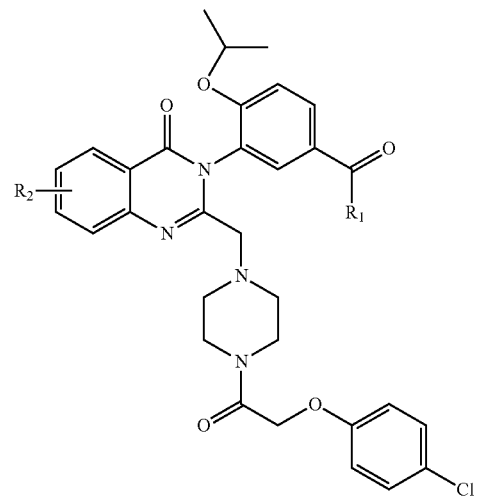

(II)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl; and
R$_2$ is selected from the group consisting of H, halo, and C$_{1-6}$aliphatic;
or an N-oxide, crystalline form, hydrate, or pharmaceutically acceptable salt thereof.

In an additional aspect of this embodiment, the compound has the structure of formula (III):

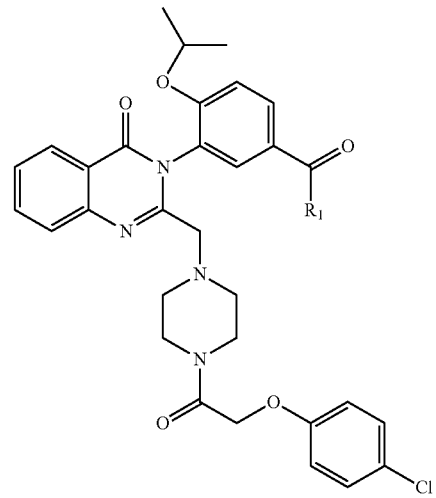

(III)

wherein R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl or an N-oxide, crystalline form, hydrate, or pharmaceutically acceptable salt thereof.
In another aspect of this embodiment, the compound is selected from the group consisting of:
KE
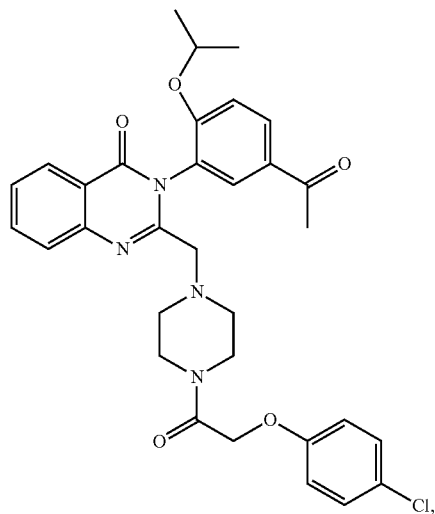
FKE
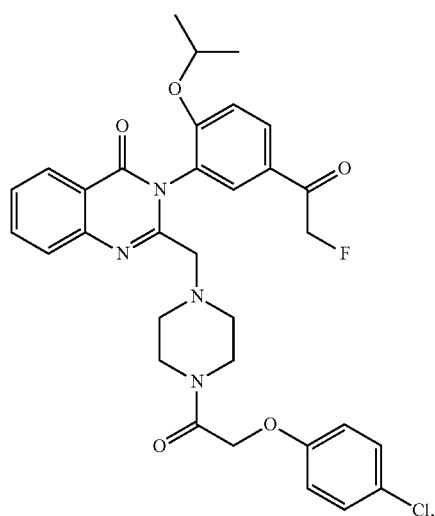
TFKE
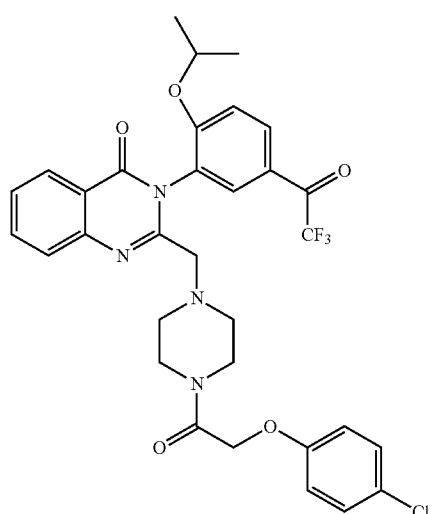
MKE
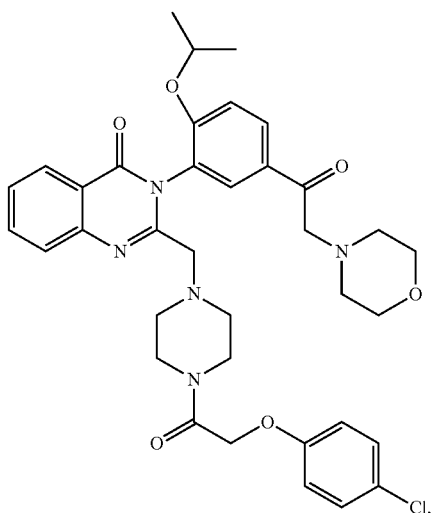
MPKE
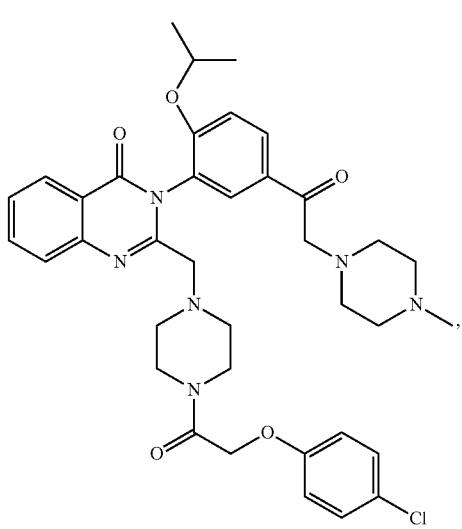
APKE
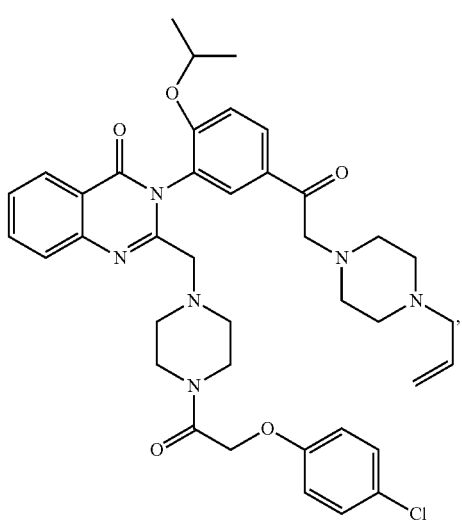

-continued
PMB-PKE
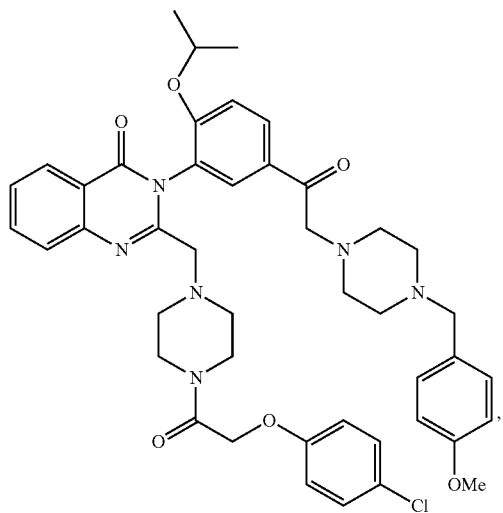
PKE
Preferably, the compound is selected from the group consisting of:
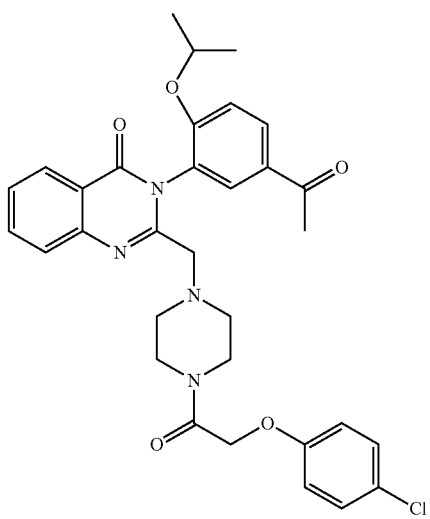
KE
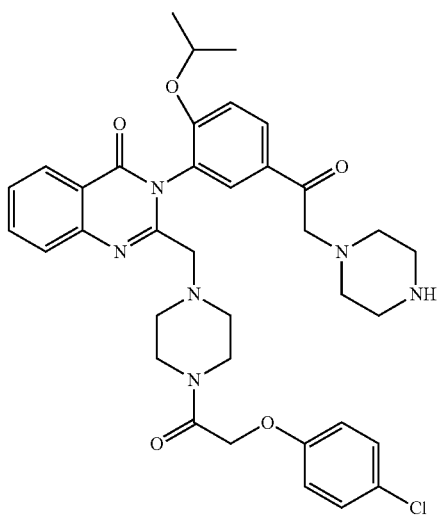
PKE
IKE
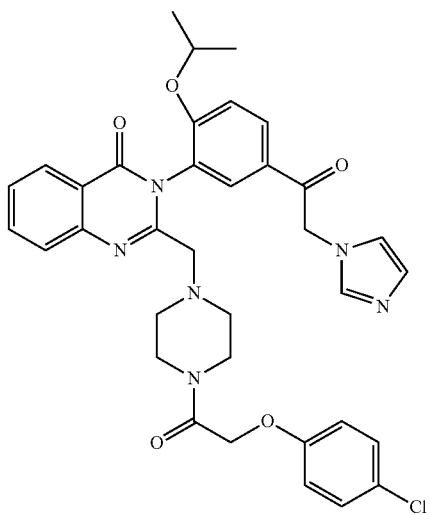
IKE
and combinations thereof or an N-oxide, crystalline form, hydrate, or pharmaceutically acceptable salt thereof.

and combinations thereof, or an N-oxide, crystalline form, hydrate, or pharmaceutically acceptable salt thereof.

Another embodiment of the present invention is a pharmaceutical composition. This pharmaceutical composition comprises a pharmaceutically acceptable carrier or diluent and a compound according to formula (I):

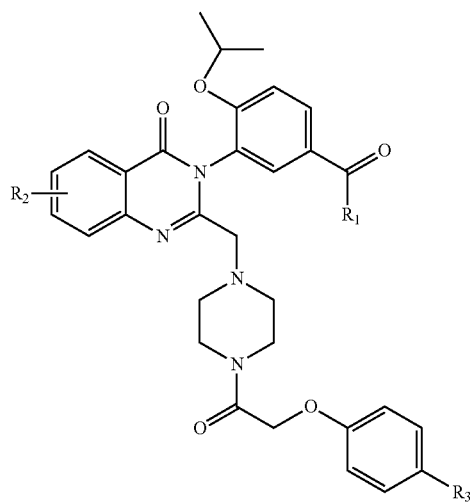

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;
R$_2$ is selected from the group consisting of H, halo, and C$_{1-6}$aliphatic; and
R$_3$ is a halo atom;
or an N-oxide, crystalline form, hydrate, or pharmaceutically acceptable salt thereof.

In this embodiment, suitable and preferred compounds are as disclosed herein, including the compounds of formula (II), formula (III), and KE, FKE, TFKE, MKE, MPKE, APKE, PMB-PKE, PKE, and IKE.

An additional embodiment of the present invention is a method for treating or ameliorating the effects of a cancer comprising a cell that harbors an oncogenic RAS mutation. This method comprises administering to a subject in need thereof a therapeutically effective amount of any compound or pharmaceutical composition disclosed herein.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt or reverse the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, "cancer" means uncontrolled growth of abnormal cells that harbor an oncogenic RAS mutation. The present invention includes those cancers selected from the following group that have one or more cells that harbor an oncogenic RAS mutation: adrenocortical carcinoma, anal cancer, bladder cancer, bone cancer, brain tumor, breast cancer, carcinoid tumor, carcinoma, cervical cancer, colon cancer, endometrial cancer, esophageal cancer, extrahepatic bile duct cancer, Ewing family of tumors, extracranial germ cell tumor, eye cancer, gallbladder cancer, gastric cancer, germ cell tumor, gestational trophoblastic tumor, head and neck cancer, hypopharyngeal cancer, islet cell carcinoma, kidney cancer, laryngeal cancer, leukemia, lip and oral cavity cancer, liver cancer, lung cancer, lymphoma, malignant mesothelioma, Merkel cell carcinoma, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, paranasal sinus and nasal cavity cancer, parathyroid cancer, penile cancer, pituitary cancer, plasma cell neoplasm, prostate cancer, rhabdomyosarcoma, rectal cancer, renal cell cancer, transitional cell cancer of the renal pelvis and ureter, salivary gland cancer, Sezary syndrome, skin cancer (such as cutaneous t-cell lymphoma, Kaposi's sarcoma, and melanoma), small intestine cancer, soft tissue sarcoma, stomach cancer, testicular cancer, thymoma, thyroid cancer, urethral cancer, uterine cancer, vaginal cancer, vulvar cancer, Wilms' tumor. Preferably, the cancer is a sarcoma.

As used herein, an "oncogenic RAS mutation" means a cellular change that results in the abnormal activation of any of the RAS family of genes (such as, e.g., H-RAS, K-RAS 4A, K-RAS 4B, M-RAS, N-RAS and R-RAS). RAS serves as a molecular switch in a large network of signaling pathways in cells. It cycles between the GDP-bound inactive form and the GTP-bound active form. Mutations in RAS have been found in about 30% of all human cancers. For example, various mutations, such as point mutations corresponding to amino acid numbers 12, 13, 59, 60 of H-RAS, may lead to impaired GTPase activity, resulting in inappropriate activation of RAS, such as constitutively activation of RAS.

As used herein, a "subject" is a mammal, preferably, a human. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include rats, mice, rabbits, guinea pigs, etc.

Another embodiment of the present invention is a method for modulating a lipoxygenase in a ferroptosis cell death pathway. This method comprises contacting a cell with an effective amount of a compound having the structure of formula (I):

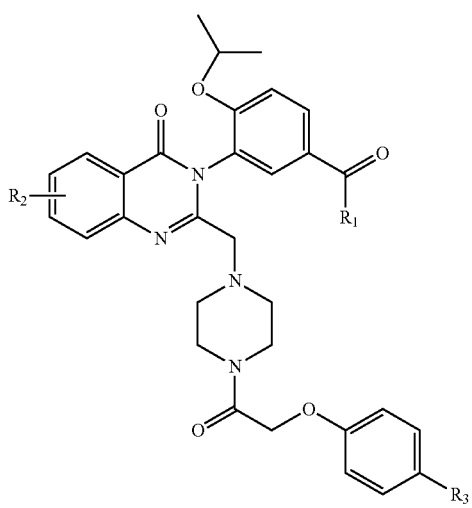

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;
R$_2$ is selected from the group consisting of H, halo, and C$_{1-6}$aliphatic; and
R$_3$ is a halo atom;
or an N-oxide, crystalline form, hydrate, or pharmaceutically acceptable salt thereof.

As used herein, the terms "modulate", "modulating" and grammatical variations thereof mean to change, such as increasing the activity or expression of lipoxygenase. A "lipoxygenase" means an enzyme that catalyzes the oxidation of unsaturated fatty acids with oxygen to form peroxides of the fatty acids. Lipoxygenases according to the present invention include those polypeptides encoded by the ALOX genes, including ALOX5, ALOX12, ALOX12B, ALOX15, ALOX15B, and ALOXE3. Preferably, the ALOX gene is the ALOXE3 gene as set forth in more detail below.

As used herein, "ferroptosis" means regulated cell death that is iron-dependent. Ferroptosis is characterized by the overwhelming, iron-dependent accumulation of lethal lipid reactive oxygen species. Ferroptosis is distinct from apoptosis, necrosis, and autophagy. Assays for ferroptosis are as disclosed, for instance, in Dixon et al., 2012.

As used herein, "contacting" means bringing, e.g., a compound or composition of the present invention into close proximity to, e.g., the cancer cells. This may be accomplished using conventional techniques of drug delivery to mammals or in the in vitro situation by, e.g., providing a compound or composition to a culture media in which the cancer cells are located.

Suitable cells for use in this embodiment may be a mammalian cell, preferably, a human cell. In addition to human cells, categories of mammalian cells within the scope of the present invention include, for example, cells from agricultural animals, veterinary animals, laboratory animals, etc. Examples of each type of these animals are as set forth above.

In this embodiment, suitable and preferred compounds are as disclosed herein, including the compounds of formula (II), formula (III), and KE, FKE, TFKE, MKE, MPKE, APKE, PMB-PKE, PKE, and IKE.

In one aspect of this embodiment, the modulation comprises activation of one or more polypeptides encoded by ALOX genes. As used herein, "ALOX" refers to arachidonate lipoxygenase such as, e.g., those identified above.

Another embodiment of the present invention is a method for depleting reduced glutathione (GSH) in a cell harboring an oncogenic RAS mutation. This method comprises administering to the cell an effective amount of a compound having the structure of formula (I):

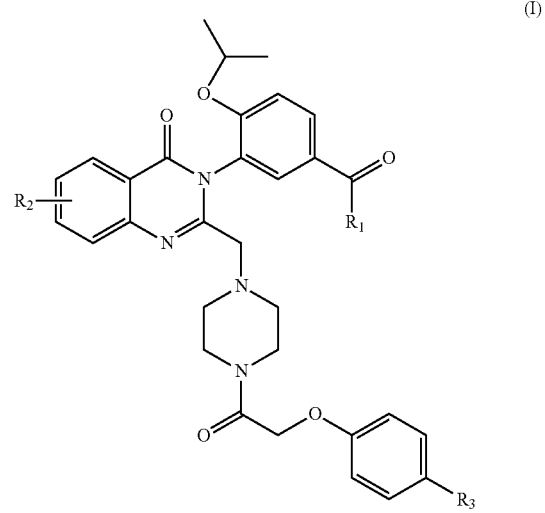

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;
R$_2$ is selected from the group consisting of H, halo, and C$_{1-6}$aliphatic; and
R$_3$ is a halo atom;
or an N-oxide, crystalline form, hydrate, or pharmaceutically acceptable salt thereof. In this embodiment, "depleting" means reducing or decreasing.

Additionally, in this embodiment, suitable and preferred compounds are as disclosed herein, including the compounds of formula (II), formula (III), and KE, FKE, TFKE, MKE, MPKE, APKE, PMB-PKE, PKE, and IKE. Suitable and preferred cells are as set forth above.

An additional embodiment of the present invention is a method of inhibiting system xc⁻ in a subject in need thereof. This method comprises administering to the subject an effective amount of a compound having the structure of formula (I):

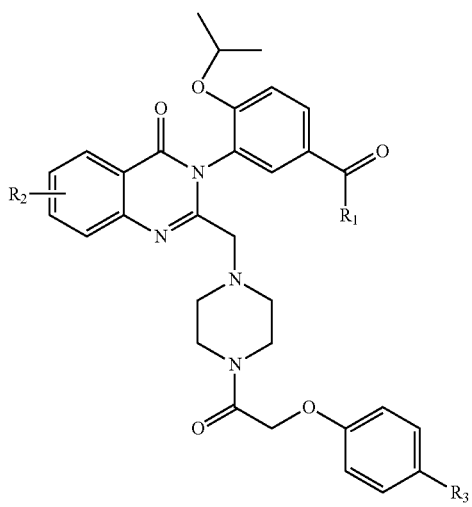

(I)

wherein:
- R₁ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;
- R₂ is selected from the group consisting of H, halo, and $C_{1-6}$aliphatic; and
- R₃ is a halo atom;
- or an N-oxide, crystalline form, hydrate, or pharmaceutically acceptable salt thereof.

As used herein, "inhibiting system xc⁻" means decreasing the activity of the antiporter which mediate the exchange of extracellular cystine and intracellular glutamate across the cellular plasma membrane.

Additionally, in this embodiment, suitable and preferred compounds are as disclosed herein, including the compounds of formula (II), formula (III), and KE, FKE, TFKE, MKE, MPKE, APKE, PMB-PKE, PKE, and IKE. Suitable and preferred cells are as set forth above.

A further embodiment of the present invention is a method of selectively killing a cell having a Ras$^{v12}$ mutation. This method comprises contacting the cell with an effective amount of a compound having the structure of formula (I):

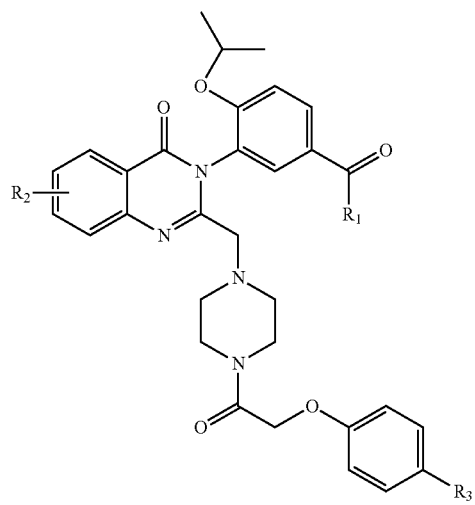

(I)

wherein:
- R₁ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;
- R₂ is selected from the group consisting of H, halo, and $C_{1-6}$aliphatic; and
- R₃ is a halo atom;
- or an N-oxide, crystalline form, hydrate, or pharmaceutically acceptable salt thereof.

As used herein, a "Ras$^{v12}$ mutation" means a mutation corresponding to amino acid number 12 of H-RAS (see, e.g., Hahn et al., 1999), which may lead to impaired GTPase activity, resulting in inappropriate activation of RAS, such as constitutively activation of RAS.

In this embodiment, suitable and preferred compounds are as disclosed herein, including the compounds of formula (II), formula (III), and KE, FKE, TFKE, MKE, MPKE, APKE, PMB-PKE, PKE, and IKE. Suitable and preferred cells are as set forth above.

Another embodiment of the present invention is a kit. This kit comprises any compound or pharmaceutical composition of the present invention together with instructions for the use of the compound.

The kits may also include suitable storage containers, e.g., ampules, vials, tubes, etc., for compound or pharmaceutical composition of the present invention and other reagents, e.g., buffers, balanced salt solutions, etc., for use in administering the anti-cancer agents to subjects. The compounds or pharmaceutical compositions may be present in the kits in any convenient form, such as, e.g., in a solution or in a powder form. The kits may further include a packaging container.

In the present invention, an "effective amount" or "therapeutically effective amount" of a compound or composition, is an amount of such a compound or composition that is sufficient to effect beneficial or desired results as described herein when administered to a subject or a cell. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of a compound or composition according to the invention will be that amount of the compound or composition, which is the lowest dose effective to produce the desired effect with no or minimal side effects. The effective dose of a compound or composition according to the present invention may be administered as two, three, four, five, six or more sub-doses, administered separately at appropriate intervals throughout the day.

A suitable, non-limiting example of a dosage of a compound according to the present invention or a composition comprising such a compound, is from about 1 ng/kg to about 1000 mg/kg, such as from about 1 mg/kg to about 100 mg/kg, including from about 5 mg/kg to about 50 mg/kg. Other representative dosages of a compound or a composition of the present invention include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

A compound or composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound or composition of the present invention may be administered in conjunction with other treatments. A compound or composition of the present invention may be encapsulated or otherwise protected against gastric or other secretions, if desired.

The compositions of the invention are preferably pharmaceutically acceptable and may comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy ($21^{st}$ Edition, Lippincott Williams and Wilkins, Philadelphia, Pa.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers are well known in the art (see, e.g., Remington, The Science and Practice of Pharmacy ($21^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The compositions of the invention may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that to the extent compounds of the present invention have a chiral center, they may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts as disclosed in more detail herein or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., antiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The following examples are provided to further illustrate the methods of the present invention. These examples are illustrative only and are not intended to limit the scope of the invention in any way.

EXAMPLES

Example 1

Materials And Methods

General Synthetic Route for Carbonyl Erastin Analogs

The general synthetic schemes for generating carbonyl erastin analogs according to the present invention are shown below.

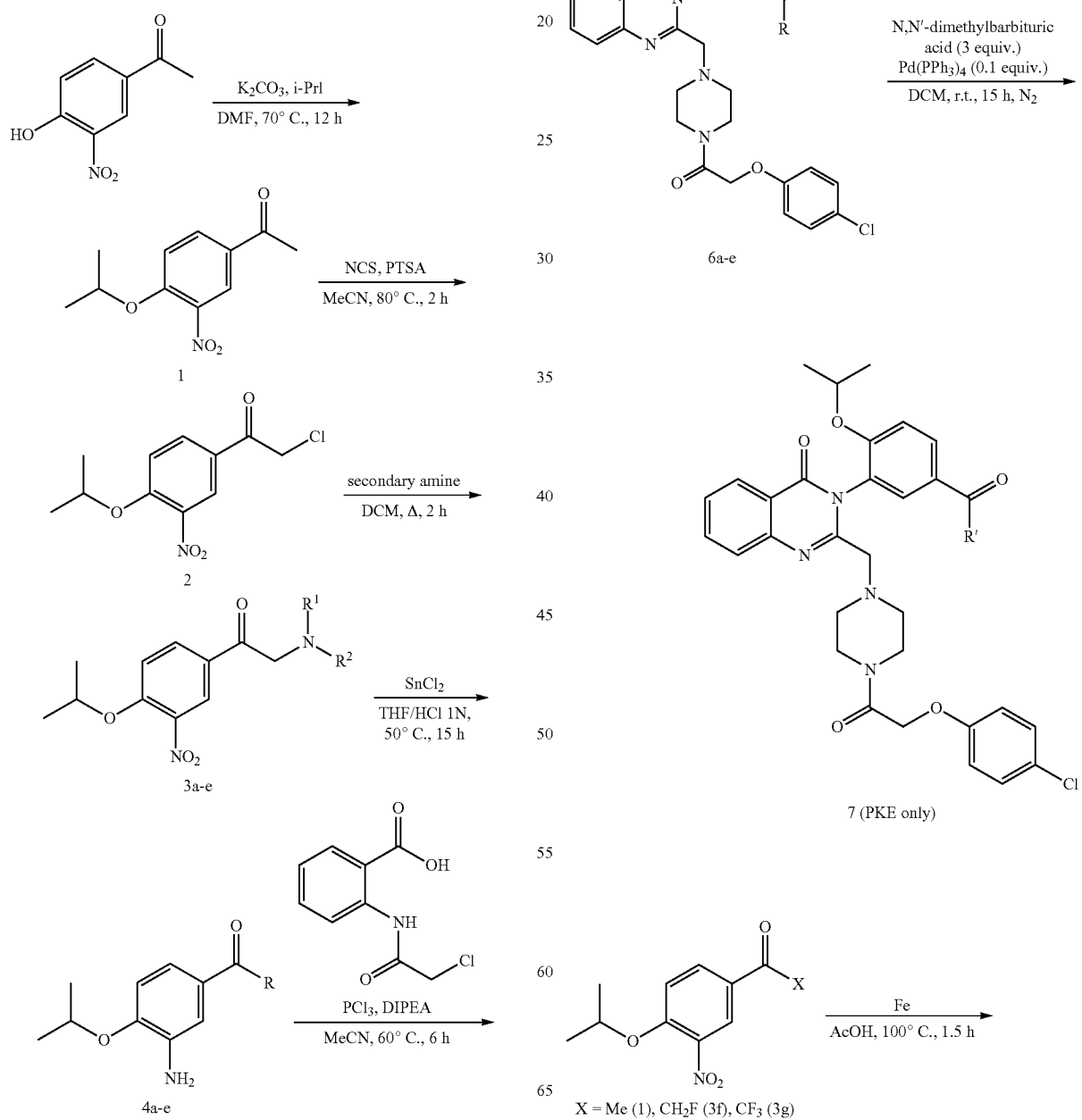

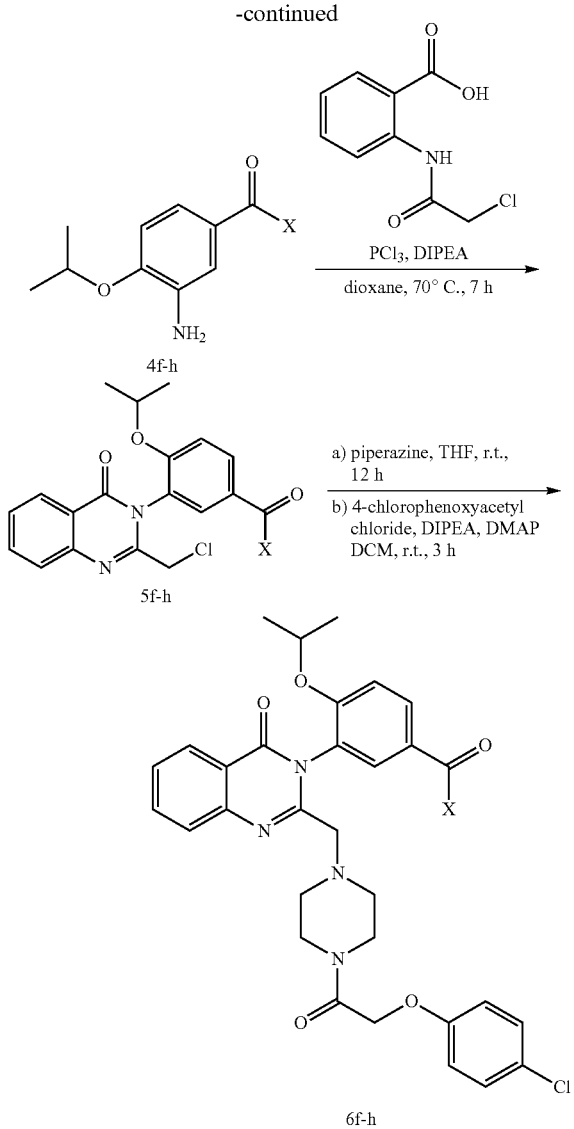

NaHCO₃=sodium bicarbonate, AcOH=acetic acid, DCM=dichloromethane, MeCN=acetonitrile, NEt₃=triethylamine, r.t.=room temperature, and THF=terahydrofuran.

General Procedure 1: Synthesis of α-Amino Acetophenones

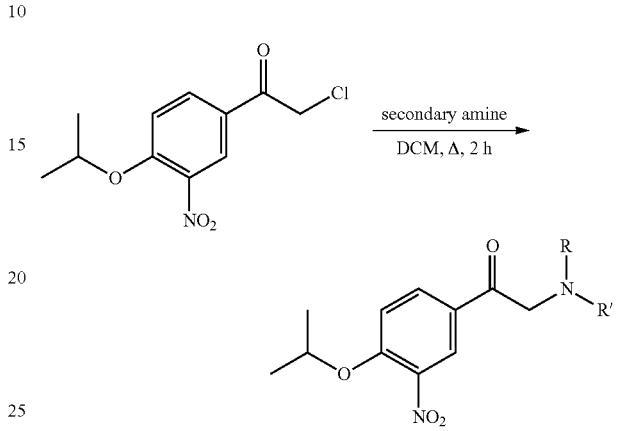

To a solution of 2-chloro-1-(4-isopropoxy-3-nitrophenyl)acetone (1 equivalent) in DCM (0.5 M) was added the secondary amine (3 equivalents). The reaction mixture was stirred under reflux for 2 hours, quenched with water, extracted two times with DCM. The combined organic layers were dried over sodium sulfate and concentrated under reduced pressure. Silica gel column chromatography (DCM/MeOH=100/0 to 95/5) afforded the corresponding α-amino acetophenone.

General Procedure 2a: Reduction of Substituted Nitrobenzenes to Anilines Using Stannous Chloride

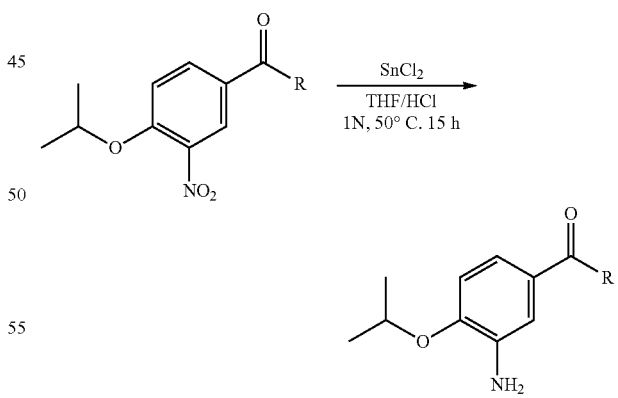

To a solution of substituted nitrobenzene (1 equivalent) in THF (0.25 M), HCl (1 N aqueous solution, 4 equivalents), and stannous chloride (3 equivalents) were added, and the reaction mixture was heated to 50° C. for 15 hours. Upon completion, the mixture was quenched with saturated aqueous sodium bicarbonate, filtered and the crude product was extracted twice with ethyl acetate. The combined organic layers were dried over sodium sulfate and concentrated Synthetic Procedures—General Information All reactions were carried out under a nitrogen atmosphere under anhydrous conditions unless indicated otherwise. Anhydrous methylene chloride (DCM), tetrahydrofuran (THF), N,N-dimethylformamide (DMF), acetonitrile (MeCN) were purchased from Sigma-Aldrich. Reactions were magnetically stirred and monitored by thin layer chromatography carried out on Merck pre-coated 0.25 mm silica plates containing a 254 nm fluorescence indicator. Flash chromatography was preformed on a Teledyne combiflash companion automatic flash chromatography system. Preparative thin layer chromatography was performed on 1 mm plates. Spectroscopy: NMR spectra were obtained on a Bruker DPX 400 MHz spectrometer. CI-MS spectra were taken on a Nermag R-10-10 instrument and high resolution MS were taken on a double focusing sector type mass spectrometer HX-110A (JEOL Ltd. Tokyo Japan).

The following abbreviations are used. DIPEA=diisopropylethyl amine, EtOAc=ethyl acetate, Et₂O=diethyl ether, MeOH=methanol, EtOH=ethanol, Pd(PPh₃)₄=Tetrakis(triphenylphosphine)palladium(0), Na₂SO₄=sodium sulfate, DMAP=4-dimethylaminopyridine, under reduced pressure. Silica gel column chromatography (DCM/MeOH=100/0 to 90/10) afforded the corresponding aniline.

General Procedure 2b: Reduction of Substituted Nitrobenzenes to Anilines Using Fe

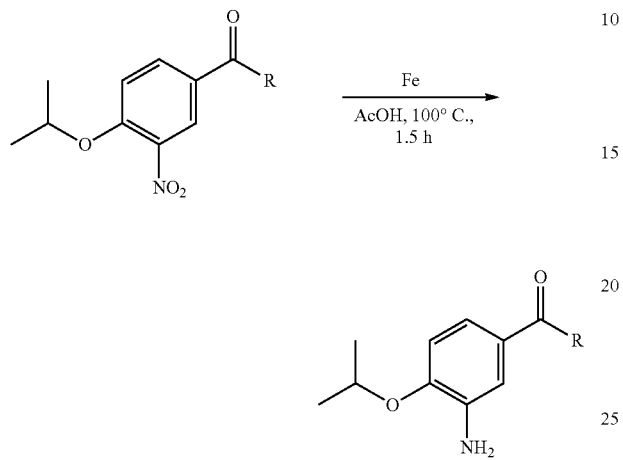

To a solution of substituted nitrobenzene (1 equivalent) in glacial acetic acid (0.10 M), iron powder (5 equivalents) was added in one batch and the reaction mixture was heated to 100° C. for 1.5 hours. Upon completion, the mixture was filtered through celite, and concentrated under reduced pressure. Silica gel column chromatography (hexane/EtOAc=100/0 to 40/60) afforded the corresponding aniline.

General Procedure 3a: Phosphorus Trichloride-Triggered Cyclocendensation in Acetonitrile (for the Most Polar Anilines)

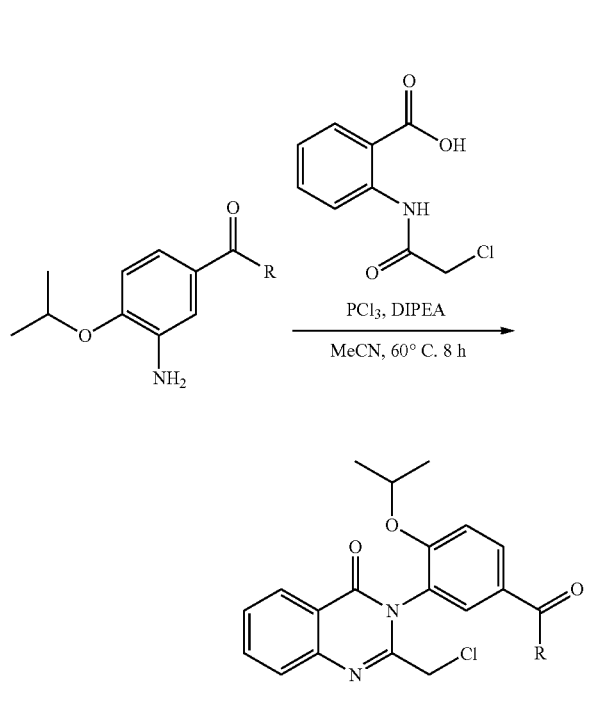

DIPEA (1.2 equivalents) was added to a solution of 2-(2-chloroethanamido)benzoic acid (1 equivalent) at room temperature in acetonitrile (0.03 M) and stirred for 2 minutes before the dropwise addition of phosphorous trichloride (1.2 equivalents). After 10 minutes of stirring at room temperature, the desired O-isopropoxyaniline (0.9 equivalents) was added dropwise as a 1.5 M solution in acetonitrile, and the resulting mixture was heated to 60° C. and stirred for an additional 8 hours. Upon completion the reaction was carefully quenched with saturated aqueous NaHCO$_3$, diluted with water, and extracted 3 times with EtOAc. The combined organic layers were dried (Na$_2$SO$_4$) and concentrated under reduce pressure. Silica gel column chromatography (DCM+0.5% NEt$_3$/MeOH=100/0 to 90/10) afforded the corresponding quinazolinones.

General Procedure 3b: Phosphorus Trichloride-Triggered Cyclocondensation in Dioxane (for the Less Polar Anilines)

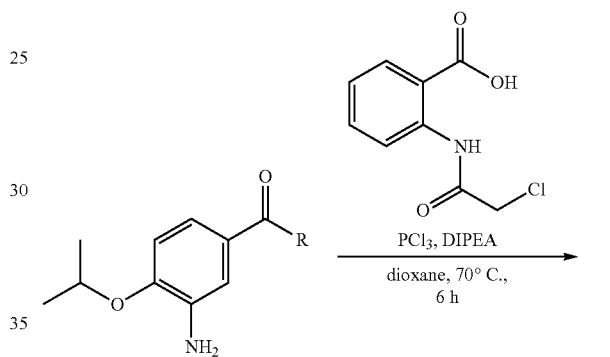

DIPEA (1.2 equivalents) was added to a solution of 2-(2-chloroethanamido)benzoic acid (1 equivalent) at room temperature in dioxane (0.2 M) and stirred for 2 minutes before the dropwise addition of phosphorous trichloride (1.2 equivalents). After 10 minutes of stirring at room temperature, the desired O-isopropoxyaniline (0.9 equivalents) was added dropwise as a 1.5 M solution in dioxane and the resulting mixture was heated to 70° C. and stirred for an additional 6 hours. Upon completion, the reaction was carefully quenched with saturated aqueous NaHCO$_3$, diluted with water, and extracted 3 times with EtOAc. The combined organic layers were dried (Na$_2$SO$_4$) and concentrated under reduce pressure. Silica gel column chromatography (hexane/EtOAc=100/0 to 50/50) afforded the corresponding quinazolinones.

General Procedure 4: Functionalization of the Quinazolinone Ring with (4-chlorophenoxy)acyl piperazine Moiety

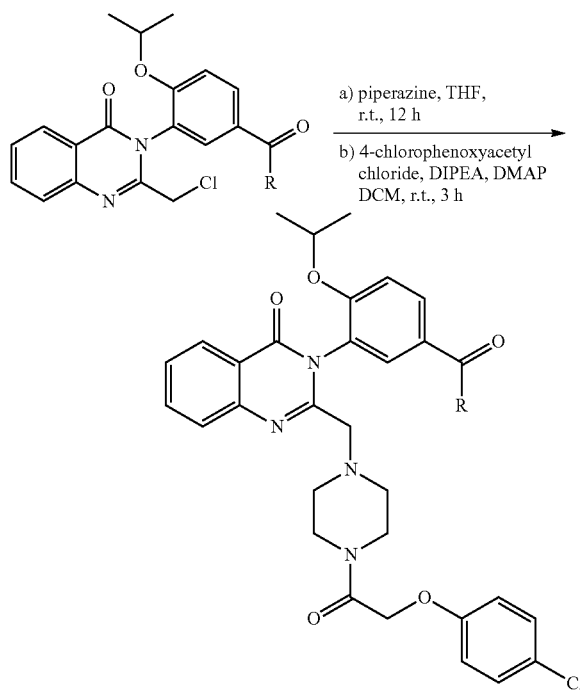

a) piperazine, THF, r.t., 12 h
b) 4-chlorophenoxyacetyl chloride, DIPEA, DMAP DCM, r.t., 3 h Piperazine (3.0 equivalents) was added to a solution of the chloromethyl quinazolinone (1 equivalent) in THF (0.2 M) and the resulting mixture was stirred at room temperature for 12 hours. The reaction mixture was then concentrated under reduce pressure. Silica gel column chromatography (DCM+0.5% NEt$_3$/MeOH=100/0 to 80/20) afforded the corresponding piperazine quinazolinone which was immediately used for the next step.

To a solution of the piperazine quinazolinine (1 equivalent) in DCM (0.1 M) was added EDIPA (1.2 equivalents) at room temperature. The mixture was then cooled to 0° C., before the sequential addition of 4-chlorophenoxyacetyl chloride (1.2 equivalents) and 4-DMAP (0.5 equivalents). The mixture was slowly warmed to room temperature and stirred for an additional 3 hours. Upon completion, the reaction was quenched with saturated aqueous NaHCO$_3$ and extracted 3 times with dichloromethane. The combined organic layers were dried (Na$_2$SO$_4$) and concentrated under reduced pressure. Silica gel column chromatography (DCM+0.5% NEt$_3$/MeOH=100/0 to 95/5) afforded the corresponding acylated quinazolinones.

General Procedure 5: Synthesis of Acetophenones

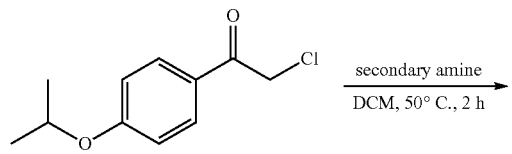

secondary amine
DCM, 50° C., 2 h

-continued

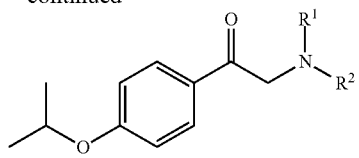

To a solution of 2-chloro-1-(4-isopropoxyphenyl)ethan-1-one (1 equiv.) in DCM (0.5 M) was added the secondary amine (3 equiv.). The reaction mixture was stirred under reflux for 2 hours, quenched with water, extracted two times with DCM. The combined organic layers were dried over sodium sulfate and concentrated under reduced pressure. Silica gel column chromatography (DCM/MeOH=100/0 to 90/10) afforded the corresponding acetophenone.

General Procedure 6: Synthesis of Amines Through Imine Intermediates

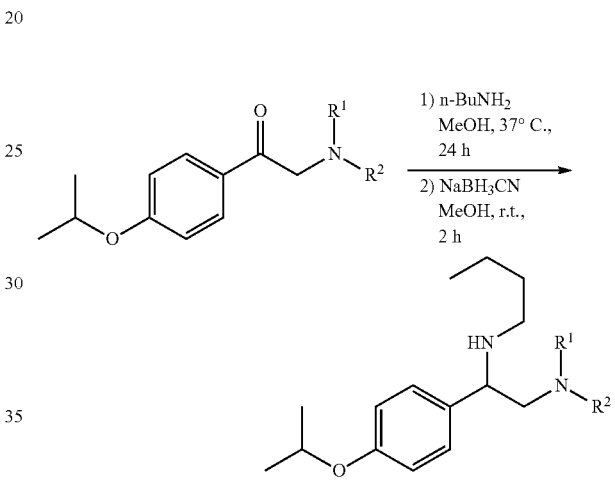

1) n-BuNH$_2$ MeOH, 37° C., 24 h
2) NaBH$_3$CN MeOH, r.t., 2 h

To a solution of the acetophenone (150 mg, 1 equiv.) in MeOH (2 mL), was added the n-butylamine (10 equiv). The reaction mixture was stirred at 37° C. for 24 hours, forming the imine intermediate. Subsequently NaCNBH$_3$ (1.2 equiv) was added and the mixture was stirred at room temperature for 2 hours. Upon completion the reaction mixture was concentrated under reduced pressure and purified by preparatory TLC (hexane:EtOAc=5:2) to afford both the starting acetophenone as well as the final amine. The masses of both were obtained and compared to determine the final amine/ketone ratio.

1-(4-isopropoxy-3-nitrophenyl)acetone (1)

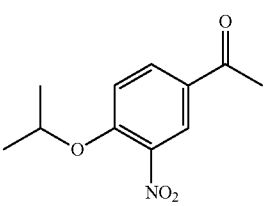

C$_{11}$H$_{13}$NO$_4$ MW=223.23 g/mol

To a solution of 4-hydroxy-3-nitroacetophenone (4.15 g, 22.9 mmol, 1 equivalent) in DMF (50 mL) at room temperature was added potassium carbonate (3.80 g, 27.5 mmol, 1.2 equivalents). The mixture was stirred at room temperature for 15 minutes and 2-iodopropane (4.60 mL, 45.8 mmol, 2.0 equivalents) was then added dropwise. The mixture was subsequently stirred at 70° C. for 12 hours. Upon completion, the reaction mixture was quenched with water and extracted twice with ethyl acetate. The combined organic layers were dried over sodium sulfate, concentrated under reduced pressure and purified by flash column chromatography (hexane/EtOAc=100/0 to 60/40) to afford 1-(4-isopropoxy-3-nitrophenyl)acetone 1 (4.43 g, 87% yield) as a yellow solid.

$^1$H NMR (400 MHz, CDCl$_3$) δ 8.31 (d, J=2.3 Hz, 1H), 8.07 (dd, J=8.8 Hz, J=2.3 Hz, 1H), 7.11 (d, J=8.9 Hz, 1H), 4.77 (sept, J=6.1 Hz, 1H), 2.55 (s, 3H), 1.38 (d, J=6.1 Hz, 6H). $^{13}$C NMR (101 MHz, CDCl$_3$) δ 194.9, 154.8, 140.3, 133.6, 129.1, 126.1, 115.0, 73.2, 26.3, 21.8 (2C). MS (m/z): [MH]$^+$ calculated for C$_{11}$H$_{14}$NO$_4$, 224.23; found 224.19.

2-chloro-1-(4-isopropoxy-3-nitrophenyl)acetone (2)

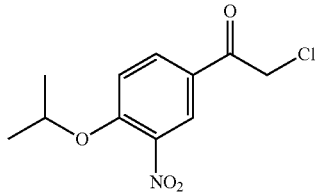 [SMILES: CC(C)Oc1ccc(C(=O)CCl)cc1[N+](=O)[O-]]

C$_{11}$H$_{12}$ClNO$_4$ MW=257.67 g/mol

To a solution of 1-(4-isopropoxy-3-nitrophenyl)acetone 1 (3.50 g, 15.7 mmol, 1 equivalent) in acetonitrile (60 mL) at room temperature were added p-toluenesulfonic acid (4.47 g, 23.5 mmol, 1.5 equivalents) and N-chlorosuccinimide (2.10 g, 15.7 mmol, 1 equivalent). The mixture was refluxed for 3 hours, concentrated under reduced pressure and purified by flash column chromatography (hexane/EtOAc=100/0 to 70/30) to afford 2-chloro-1-(4-isopropoxy-3-nitrophenyl) acetone 2 (3.0 g, 74% yield) as a yellow solid.

$^1$H NMR (400 MHz, CDCl$_3$) δ 8.31 (d, J=2.3 Hz, 1H), 8.08 (dd, J=8.9 Hz, J=2.3 Hz, 1H), 7.15 (d, J=8.9 Hz, 1H), 4.77 (sept, J=6.1 Hz, 1H), 4.64 (s, 2H), 1.38 (d, J=6.1 Hz, 6H). $^{13}$C NMR (101 MHz, CDCl$_3$) δ 188.4, 155.3, 140.3, 134.0, 126.3, 125.9, 115.2, 73.4, 45.4, 21.7 (2C). MS (m/z): [MH]+ calculated for C$_{11}$H$_{13}$ClNO$_4$, 258.04; found 258.14.

1-(4-isopropoxy-3-nitrophenyl)-2-morpholinoacetone (3a)

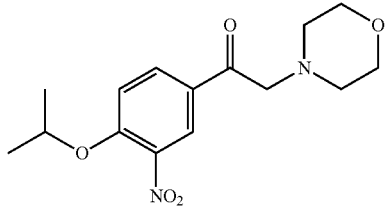

C$_{15}$H$_{20}$N$_2$O$_5$ MW=308.33 g/mol

Following general procedure 1 with 2-chloro-1-(4-isopropoxy-3-nitrophenyl)acetone 2 (230 mg, 0.89 mmol) and morpholine (232 mg, 2.67 mmol), 3a (180 mg, 66% yield) was obtained as a yellow oil.

$^1$H NMR (400 MHz, CDCl$_3$) δ 8.54 (d, J=2.2 Hz, 1H), 8.20 (dd, J=8.9 Hz, J=2.2 Hz, 1H), 7.11 (d, J=8.9 Hz, 1H), 4.79 (sept, J=6.1 Hz, 1H), 3.76-3.74 (m, 4H), 3.71 (s, 2H), 2.59-2.56 (m, 4H), 1.43 (d, J=6.1 Hz, 6H). $^{13}$C NMR (101 MHz, CDCl$_3$) δ 193.5, 154.9, 140.2, 133.8, 127.7, 126.3, 114.9, 73.2, 66.8 (2C), 65.1, 53.8 (2C), 21.8 (2C). MS (m/z): [MH]+ calculated for C$_{15}$H$_{21}$N$_2$O$_5$, 309.14; found 309.23.

1-(4-isopropoxy-3-nitrophenyl)-2-(4-methylpiperazin-1-yl)acetone (3b)

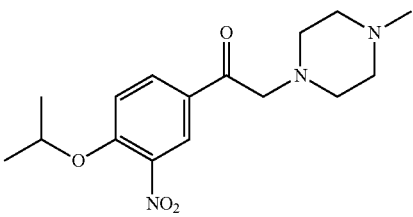 [SMILES: CC(C)Oc1ccc(C(=O)CN2CCN(C)CC2)cc1[N+](=O)[O-]]

C$_{16}$H$_{23}$N$_3$O$_4$ MW=321.37 g/mol

Following general procedure 1 with 2-chloro-1-(4-isopropoxy-3-nitrophenyl)acetone 2 (330 mg, 1.28 mmol) and 1-N-methylpiperazine (426 μL, 3.84 mmol), 3b (250 mg, 61% yield) was obtained as a yellow oil.

$^1$H NMR (400 MHz, CDCl$_3$) δ 8.44 (d, J=2.2 Hz, 1H), 8.11 (dd, J=8.9 Hz, J=2.2 Hz, 1H), 7.05 (d, J=8.9 Hz, 1H), 4.71 (sept, J=6.1 Hz, 1H), 3.64 (s, 2H), 2.55-2.40 (m, 8H), 2.20 (s, 3H), 1.34 (d, J=6.1 Hz, 6H). $^{13}$C NMR (101 MHz, CDCl$_3$) δ 193.7, 154.8, 140.1, 133.7, 127.7, 126.2, 114.8, 73.1, 64.7, 54.7 (2C), 53.2 (2C), 45.8, 21.7 (2C). HRMS (m/z): [MH]+ calculated for C$_{16}$H$_{24}$N$_3$O$_4$, 322.27; found 322.28.

2-(4-para-methoxybenzylpiperazin-1-yl)-1-(4-isopropoxy-3-nitrophenyl)acetone (3c)

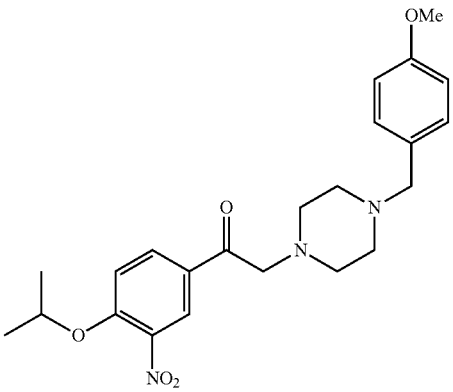 [SMILES: COc1ccc(CN2CCN(CC(=O)c3ccc(OC(C)C)c([N+](=O)[O-])c3)CC2)cc1]

C$_{23}$H$_{29}$N$_3$O$_5$ MW=427.49 g/mol

Following general procedure 1 with 2-chloro-1-(4-isopropoxy-3-nitrophenyl)acetone 2 (1.00 g, 3.88 mmol) and 1-N-para-methoxybenzylpiperazine (1.00 g, 4.85 mmol), 3c (1.60 g, 87% yield) was obtained as a yellow oil.

$^1$H NMR (400 MHz, CDCl$_3$) δ 8.52 (d, J=2.2 Hz, 1H), 8.17 (dd, J=8.9 Hz, J=2.2 Hz, 1H), 7.21 (d, J=8.6 Hz, 2H), 7.09 (d, J=9.0 Hz, 1H), 6.83 (d, J=8.6 Hz, 2H), 4.77 (sept, J=6.1 Hz, 1H), 3.78 (s, 3H), 3.70 (s, 2H), 3.49 (s, 2H), 2.65-2.45 (m, 8H), 1.41 (d, J=6.1 Hz, 6H). $^{13}$C NMR (101 MHz, CDCl$_3$) δ 193.7, 159.0, 154.9, 140.3, 133.8, 130.7 (2C), 129.2, 127.9, 126.4, 114.9, 113.7 (2C), 73.2, 64.8, 62.1, 55.3, 53.2 (2C), 52.5 (2C), 21.8 (2C). HRMS (m/z): [MH]+ calculated for C$_{23}$H$_{30}$N$_3$O$_5$, 428.2107; found 428.2110.

2-(4-allylpiperazin-1-yl)-1-(4-isopropoxy-3-nitrophenyl)acetone (3d)

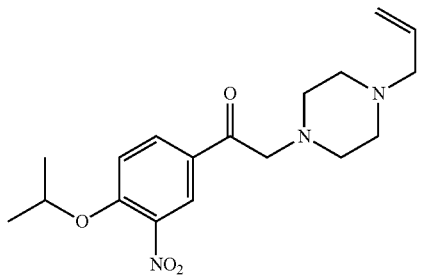 [SMILES: C=CCN1CCN(CC(=O)c2ccc(OC(C)C)c([N+](=O)[O-])c2)CC1]

C$_{18}$H$_{25}$N$_3$O$_4$ MW=347.41 g/mol

Following general procedure 1 with 2-chloro-1-(4-isopropoxy-3-nitrophenyl)acetone 2 (600 mg, 2.33 mmol) and 1-N-allylpiperazine (977 µL, 6.99 mmol), 3d (595 mg, 74% yield) was obtained as a yellow oil.

$^1$H NMR (400 MHz, CDCl$_3$) δ 8.56 (d, J=2.2 Hz, 1H), 8.19 (dd, J=8.9 Hz, J=2.2 Hz, 1H), 7.09 (d, J=8.9 Hz, 1H), 5.87-5.80 (m, 1H), 5.29-5.12 (m, 2H), 4.77 (sept, J=6.1 Hz, 1H), 3.69 (s, 2H), 2.99 (d, J=6.5 Hz, 1H), 2.60-2.45 (m, 8H), 1.43 (d, J=6.1 Hz, 6H). $^{13}$C NMR (101 MHz, CDCl$_3$) δ 194.0, 154.9, 140.1, 135.0, 133.9, 128.0, 126.6, 118.2, 114.9, 73.2, 65.2, 61.8, 53.6 (2C), 53.0 (2C), 21.9 (2C). MS (m/z): [MH]+ calculated for C$_{18}$H$_{26}$N$_3$O$_4$, 348.18; found 348.24.

2-(1H-imidazol-1-yl)-1-(4-isopropoxy-3-nitrophenyl)acetone (3e)

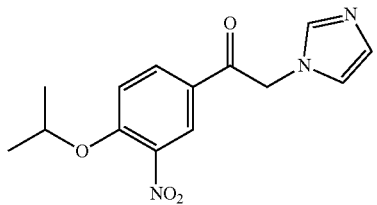 [SMILES: CC(C)Oc1ccc(C(=O)Cn2ccnc2)cc1[N+](=O)[O-]]

C$_{14}$H$_{15}$N$_3$O$_4$ MW=289.29 g/mol

Following general procedure 1 with 2-chloro-1-(4-isopropoxy-3-nitrophenyl)acetone 2 (460 mg, 1.78 mmol) and imidazole (363 mg, 5.34 mmol), 3e (350 mg, 68% yield) was obtained as a yellow oil.

$^1$H NMR (400 MHz, CDCl$_3$) δ 8.35 (d, J=2.0 Hz, 1H), 8.10 (dd, J=8.9 Hz, J=2.0 Hz, 1H), 7.48 (s, 1H), 7.17 (d, J=9.0 Hz, 1H), 7.10 (s, 1H), 6.92 (s, 1H), 5.37 (s, 2H), 4.81 (sept, J=6.0 Hz, 1H), 1.42 (d, J=6.0 Hz, 6H). $^{13}$C NMR (101 MHz, CDCl$_3$) δ 189.0, 155.8, 140.6, 138.3, 133.6, 129.9, 126.0, 125.9, 120.4, 115.6, 73.7, 52.3, 21.8 (2C). MS (m/z): [MH]+ calculated for C$_{14}$H$_{16}$N$_3$O$_4$, 290.10; found 290.19.

2-fluoro-1-(4-isopropoxy-3-nitrophenyl)acetone (3f)

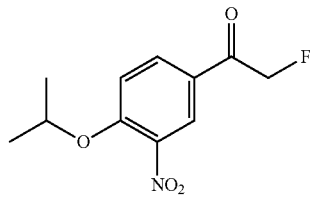 [SMILES: CC(C)Oc1ccc(C(=O)CF)cc1[N+](=O)[O-]]

C$_{11}$H$_{12}$FNO$_4$ MW=241.22 g/mol

Following general procedure 1 with 2-fluoro-1-(4-hydroxy-3-nitrophenyl)ethanone (500 mg, 2.50 mmol), 3f (351 mg, 58% yield) was obtained as a yellow oil.

$^1$H NMR (400 MHz, CDCl$_3$) δ 8.34 (d, J=2.0 Hz, 1H), 8.11 (dd, J=8.9 Hz, J=2.0 Hz, 1H), 7.16 (d, J=8.9 Hz, 1H), 5.43 (d, J$_{H-F}$=47 Hz, 2H), 4.80 (sept, J=6.0 Hz, 1H), 1.44 (d, J=6.0 Hz, 6H). MS (m/z): [MH]+ calculated for C$_{14}$H$_{16}$N$_3$O$_4$, 242.2157; found 242.2161.

trifluoro-1-(4-isopropoxy-3-nitrophenyl)acetone (3q)

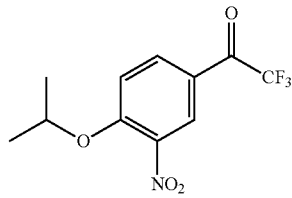 [SMILES: CC(C)Oc1ccc(C(=O)C(F)(F)F)cc1[N+](=O)[O-]]

C$_{11}$H$_{10}$F$_3$NO$_4$ MW=277.20 g/mol

Following general procedure 1 with trifluoro-1-(4-hydroxy-3-nitrophenyl)ethanone (238 mg, 1.01 mmol), 3g (140 mg, 51% yield) was obtained as a yellow oil.

$^1$H NMR (400 MHz, CDCl$_3$) δ 8.52 (s, 1H), 8.26-8.23 (m, 1H), 7.23 (d, J=9.0 Hz, 1H), 4.89 (sept, J=6.0 Hz, 1H), 1.50 (d, J=6.0 Hz, 6H). MS (m/z): [MH]+ calculated for C$_{11}$H$_{11}$F$_3$NO$_4$, 278.0562; found 278.0600.

1-(3-amino-4-isopropoxyphenyl)-2-morpholinoacetone (4a)

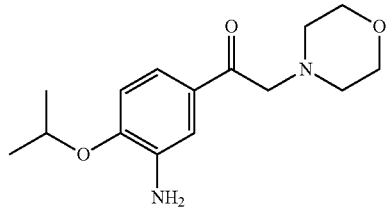

C$_{15}$H$_{22}$N$_2$O$_3$ MW=278.34 g/mol

Following general procedure 2a with 3a (500 mg, 1.62 mmol), 4a (236 mg, 52% yield) was obtained as a yellow solid.

¹H NMR (400 MHz, CDCl₃) δ 7.28-7.24 (m, 2H), 6.63 (d, J=8.5 Hz, 1H), 4.47 (sept, J=6.0 Hz, 1H), 3.93 (brs, 2H), 3.63-3.58 (m, 2H), 2.45-2.43 (m, 2H), 1.23 (d, J=6.1 Hz, 6H). ¹³C NMR (101 MHz, CDCl₃) δ 194.7, 149.2, 136.9, 128.6, 119.2, 113.6, 110.9, 70.2, 66.4 (2C), 63.9, 53.6 (2C), 53.3, 21.7 (2C). MS (m/z): [MH]⁺ calculated for $C_{15}H_{23}N_2O_3$, 279.1709; found 279.1700.

1-(3-amino-4-isopropoxyphenyl)-2-(4-methylpiperazin-1-yl)acetone (4b)

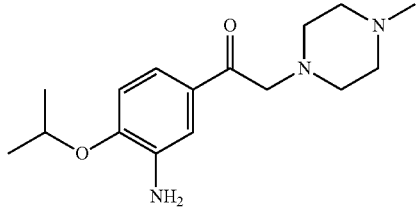

$C_{16}H_{25}N_3O_2$ MW=291.39 g/mol

Following general procedure 2a with 3b (150 mg, 0.47 mmol), 4b (120 mg, 88% yield) was obtained as a yellow solid.

¹H NMR (400 MHz, CDCl₃) δ 7.37 (d, J=8.4 Hz, 1H), 7.32 (s, 1H), 6.72 (d, J=8.5 Hz, 1H), 4.59 (sept, J=6.1 Hz, 1H), 3.91 (brs, 2H), 3.70 (s, 2H), 2.58-2.49 (m, 8H), 2.26 (s, 3H), 1.33 (d, J=6.1 Hz, 6H). ¹³C NMR (101 MHz, CDCl₃) δ 195.1, 149.6, 137.0, 129.2, 119.8, 114.2, 111.3, 70.6, 64.1, 54.9 (2C), 53.5 (2C), 46.0, 22.1 (2C).

1-(3-amino-4-isopropoxyphenyl)-2-(4-(4-methoxybenzyl)piperazin-1-yl)acetone (4c)

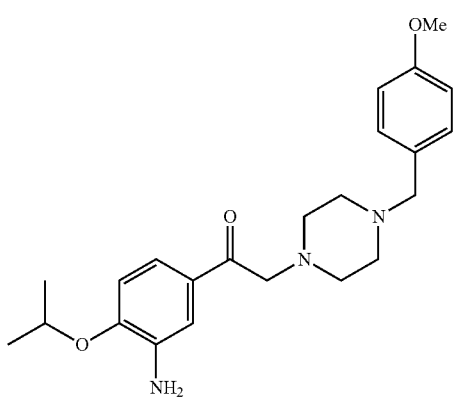

$C_{23}H_{31}N_3O_3$ MW=397.51

Following general procedure 2a with 3c (1.6 g, 3.7 mmol), 4c (930 mg, 63% yield) was obtained as a yellow solid.

¹H NMR (400 MHz, CDCl₃) δ 7.40 (dd, J=8.9 Hz, J=2.1 Hz, 1H), 7.35 (d, J=2.1 Hz, 1H), 7.21 (d, J=8.6 Hz, 2H), 6.83 (d, J=8.6 Hz, 2H), 6.75 (d, J=8.5 Hz, 1H), 4.63 (sept, J=6.0 Hz, 1H), 3.83 (brs, 2H), 3.78 (s, 3H), 3.72 (s, 2H), 3.45 (s, 2H), 2.65-2.45 (m, 8H), 1.36 (d, J=6.1 Hz, 6H). ¹³C NMR (101 MHz, CDCl₃) δ 195.2, 158.8, 149.6, 137.0, 130.4 (2C), 130.1, 129.2, 119.8, 114.2, 113.6 (2C), 111.3, 70.7, 64.1, 62.4, 55.3, 53.6 (2C), 52.8 (2C), 22.1 (2C). MS (m/z): [MH]⁺ calculated for $C_{23}H_{32}N_3O_3$, 398.2444; found 398.2444.

1-(3-amino-4-isopropoxyphenyl)-2-(4-allylpiperazin-1-yl)acetone (4d)

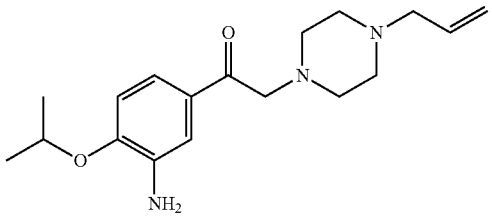 [SMILES: C=CCN1CCN(CC(=O)c2ccc(OC(C)C)c(N)c2)CC1]

$C_{18}H_{27}N_3O_2$ MW=317.43 g/mol

Following general procedure 2a with 3d (350 mg, 1.00 mmol), 4d (250 mg, 79% yield) was obtained as a yellow solid.

¹H NMR (400 MHz, CDCl₃) δ 7.39 (dd, J=8.4 Hz, J=2.2 Hz, 1H), 7.34 (d, J=2.2 Hz, 1H), 6.74 (d, J=8.4 Hz, 1H), 5.88-5.79 (m, 1H), 5.27-5.10 (m, 2H), 4.63 (sept, J=6.0 Hz, 1H), 3.87 (bs, 2H), 3.71 (s, 2H), 2.98 (d, J=6.2 Hz, 1H), 2.62-2.45 (m, 8H), 1.35 (d, J=6.0 Hz, 6H). ¹³C NMR (101 MHz, CDCl₃) δ 195.2, 149.6, 137.0, 135.1, 129.3, 119.9, 118.1, 114.3, 111.3, 70.7, 64.2, 61.8, 53.7 (2C), 53.0 (2C), 22.2 (2C). MS (m/z): [MH]⁺ calculated for $C_{18}H_{28}N_3O_2$, 318.2182; found 318.2193.

1-(3-amino-4-isopropoxyphenyl)-2-(1H-imidazol-1-yl) acetone (4e)

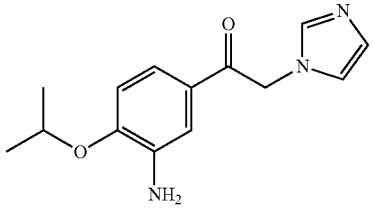 [SMILES: CC(C)Oc1ccc(C(=O)Cn2ccnc2)cc1N]

$C_{14}H_{17}N_3O_2$ MW=259.30

Following general procedure 2a with 3e (350 mg, 1.2 mmol), 4e (210 mg, 67% yield) was obtained as a yellow solid.

¹H NMR (400 MHz, CDCl₃) δ 7.50 (s, 1H), 7.36-7.33 (m, 2H), 7.13 (s, 1H), 6.94 (s, 1H), 6.82 (d, J=8.3 Hz, 1H), 5.30 (s, 2H), 4.69 (sept, J=6.0 Hz, 1H), 4.11 (brs, 2H), 1.40 (d, J=6.0 Hz, 6H). ¹³C NMR (101 MHz, CDCl₃) δ 190.3, 150.5, 138.3, 137.7, 129.5, 120.4, 119.7, 113.7, 111.4, 71.1, 52.1, 22.2 (2C). MS (m/z): [MH]⁺ calculated for $C_{14}H_{18}N_3O_2$, 260.1399; found 260.1395.

1-(3-amino-4-isopropoxyphenyl)acetone (4f)

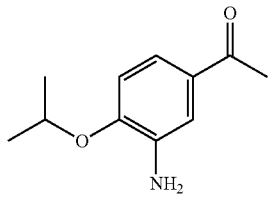

C$_{11}$H$_{15}$NO$_2$ MW=193.24 g/mol

Following general procedure 2b with 1 (900 mg, 4.03 mmol), 4f (600 mg, 77% yield) was obtained as a yellow oil.

$^1$H NMR (400 MHz, CDCl$_3$) δ 7.35-7.33 (m, 2H), 6.77 (d, J=8.1 Hz, 1H), 4.63 (sept, J=6.0 Hz, 1H), 3.85 (brs, 2H), 2.50 (s, 3H), 1.36 (d, J=6.1 Hz, 6H). $^{13}$C NMR (101 MHz, CDCl$_3$) δ 197.4, 149.6, 137.0, 130.4, 120.4, 114.4, 111.4, 70.7, 26.3, 22.2 (2C). MS (m/z): [M]$^+$ calculated for C$_{11}$H$_{15}$NO$_2$, 193.1103; found 193.1098.

1-(3-amino-4-isopropoxyphenyl)-2-fluoroacetone (4g)

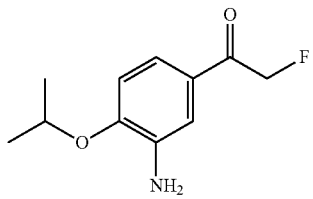

C$_{11}$H$_{14}$FNO$_2$ MW=211.23 g/mol

Following general procedure 2b with 3f (50 mg, 0.2 mmol), 4g (43 mg, 100% yield) was obtained as a yellow oil.

$^1$H NMR (400 MHz, CDCl$_3$) δ 7.26-7.17 (m, 2H), 6.71 (d, J=8.5 Hz, 1H), 5.37 (d, J$_{H-F}$=47 Hz, 2H), 4.57 (sept, J=6.0 Hz, 1H), 3.84 (brs, 2H), 1.31 (d, J=6.1 Hz, 6H). MS (m/z): [M]$^+$ calculated for C$_{11}$H$_{15}$FNO$_2$, 212.1009; found 212.1010.

1-(3-amino-4-isopropoxyphenyl)-2,2,2-trifluoroacetone (4h)

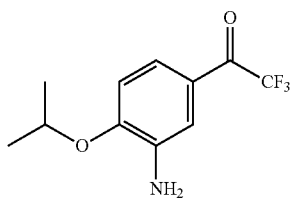

C$_{11}$H$_{12}$F$_3$NO$_2$ MW=247.21 g/mol

Following general procedure 2b with 3g (140 mg, 0.5 mmol), 4h (65 mg, 53% yield) was obtained as a yellow oil.

$^1$H NMR (400 MHz, CDCl$_3$) δ 7.50-7.48 (m, 1H), 7.40 (s, 1H), 6.83 (d, J=8.6 Hz, 1H), 4.71 (sept, J=6.0 Hz, 1H), 4.00 (brs, 2H), 1.41 (d, J=6.1 Hz, 6H). MS (m/z): [M]$^+$ calculated for C$_{11}$H$_{13}$F$_3$NO$_2$, 248.0820; found 248.0815.

2-(chloromethyl)-3-(2-isopropoxy-5-(2-morpholinoethanoyl)phenyl)quinazolin-4(3H)-one (5a)

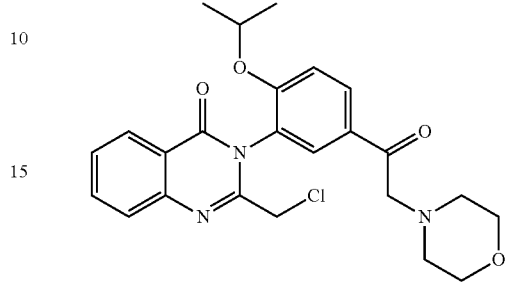

C$_{24}$H$_{26}$ClN$_3$O$_4$ MW=455.94 g/mol

Following general procedure 3b with 4a (155 mg, 0.55 mmol), 5a (76 mg, 31% yield) was obtained as a white oily solid.

$^1$H NMR (400 MHz, CDCl$_3$) δ 8.27 (d, J=7.6 Hz, 1H), 8.19 (dd, J=8.8 Hz, J=2.0 Hz, 1H), 8.06 (d, J=2.0 Hz, 1H), 7.80-7.75 (m, 2H), 7.54-7.52 (m, 1H), 7.10 (d, J=8.8 Hz, 1H), 4.67 (sept, J=6.1 Hz, 1H), 4.36, 4.13 (ABq, J$_{AB}$=11.9 Hz, 2H), 3.74-3.70 (m, 4H), 2.59-2.49 (m, 4H), 1.26 (d, J=6.0 Hz, 3H), 1.20 (d, J=6.0 Hz, 3H). $^{13}$C NMR (101 MHz, CDCl$_3$) δ 194.0, 161.5, 157.4, 151.8, 147.1, 134.8, 131.9, 131.7, 128.9, 127.9, 127.8 127.3, 125.0, 121.3, 113.4, 72.0, 66.9 (2C), 65.0, 53.9 (2C), 43.8, 21.9, 21.8.

2-(chloromethyl)-3-(2-isopropoxy-5-(2-(4-methylpiperazin-1-yl)ethanoyl)phenyl)quinazolin-4(3H)-one (5b)

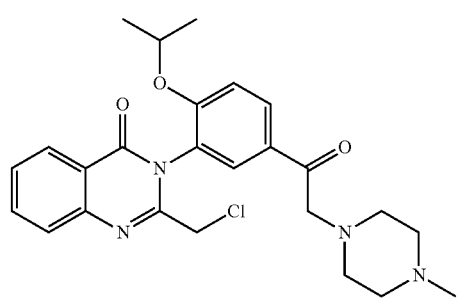 [SMILES: CC(C)Oc1ccc(C(=O)CN2CCN(C)CC2)cc1-n1c(CCl)nc2ccccc2c1=O]

C$_{25}$H$_{29}$ClN$_4$O$_3$ MW=468.98 g/mol

Following general procedure 3a with 4b (380 mg, 1.30 mmol), 5b (275 mg, 45% yield) was obtained as a beige oily solid.

$^1$H NMR (400 MHz, CDCl$_3$) δ 8.28 (d, J=7.4 Hz, 1H), 8.20 (dd, J=8.8 Hz, J=2.1 Hz, 1H), 8.06 (s, 1H), 7.81-7.77 (m, 2H), 7.27-7.23 (m, 1H), 7.10 (d, J=8.9 Hz, 1H), 4.67 (sept, J=6.1 Hz, 1H), 4.36, 4.13 (ABq, J$_{AB}$=11.9 Hz, 2H), 3.77, 3.65 (ABq, J$_{AB}$=16.0 Hz, 2H), 2.65-2.45 (m, 8H), 2.26 (s, 3H), 1.25 (d, J=6.0 Hz, 3H), 1.20 (d, J=6.0 Hz, 3H). $^{13}$C NMR (101 MHz, CDCl$_3$) δ 194.2, 161.5, 157.3, 151.9, 147.1, 134.8, 132.0, 131.7, 129.0, 127.8, 127.3, 124.9, 121.3, 113.3, 71.9, 64.8, 55.0 (2C), 53.6 (2C), 46.2, 46.1, 43.8, 21.9, 21.8.

2-(chloromethyl)-3-(2-isopropoxy-5-(2-(4-(4-methoxybenzyl)piperazin-1-yl)ethanoyl)phenyl)quinazolin-4(3H)-one (5c)

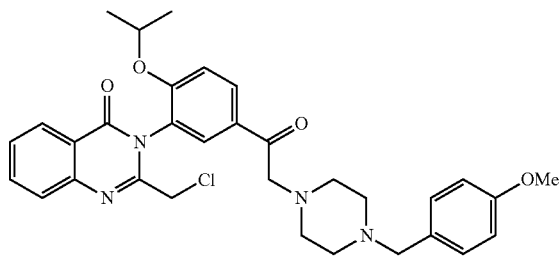 [SMILES: COc1ccc(CN2CCN(CC(=O)c3ccc(OC(C)C)c(-n4c(CCl)nc5ccccc5c4=O)c3)CC2)cc1]

$C_{32}H_{35}ClN_4O_4$ MW=575.10 g/mol

Following general procedure 3a with 4c (230 mg, 0.52 mmol), 5c (134 mg, 45% yield) was obtained as a white oily solid.

$^1$H NMR (400 MHz, CDCl$_3$) δ 8.32 (d, J=7.4 Hz, 1H), 8.20 (dd, J=8.8 Hz, J=2.2 Hz, 1H), 8.06 (d, J=2.1 Hz, 1H), 7.82-7.77 (m, 2H), 7.59-7.51 (m, 1H), 7.21 (d, J=7.4 Hz, 2H), 7.10 (d, J=9.0 Hz, 1H), 6.84 (d, J=7.4 Hz, 2H), 4.67 (sept, J=6.1 Hz, 1H), 4.37, 4.13 (ABq, J$_{AB}$=11.9 Hz, 2H), 3.75 (s, 3H), 3.74-3.64 (m, 2H), 3.44 (s, 2H), 2.62-2.45 (m, 8H), 1.28 (d, J=6.0 Hz, 3H), 1.21 (d, J=6.0 Hz, 3H).

3-(5-(2-(4-allylpiperazin-1-yl)ethanoyl)-2-isopropoxyphenyl)-2-(chloromethyl)quinazolin-4(3H)-one (5d)

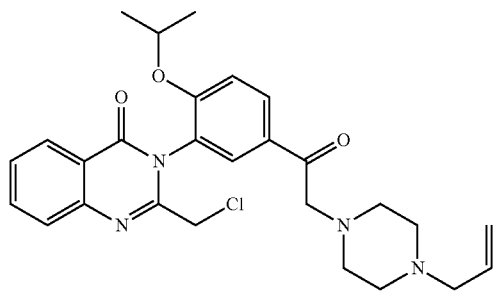 [SMILES: C=CCN1CCN(CC(=O)c2ccc(OC(C)C)c(-n3c(CCl)nc4ccccc4c3=O)c2)CC1]

$C_{27}H_{31}ClN_4O_3$ MW=495.01 g/mol

Following general procedure 3a with 4d (800 mg, 2.52 mmol), 5d (800 mg, 64% yield) was obtained as a beige oily solid.

$^1$H NMR (400 MHz, CDCl$_3$) δ 8.28 (d, J=7.4 Hz, 1H), 8.20 (dd, J=8.8 Hz, J=2.1 Hz, 1H), 8.05 (s, 1H), 7.79-7.74 (m, 2H), 7.53-7.49 (m, 1H), 7.09 (d, J=8.9 Hz, 1H), 5.87-5.78 (m, 1H), 5.26-5.10 (m, 2H), 4.64 (sept, J=6.0 Hz, 1H), 4.35, 4.12 (ABq, J$_{AB}$=11.9 Hz, 2H), 3.76, 3.65 (ABq, J$_{AB}$=16.1 Hz, 2H), 2.98 (d, J=6.6 Hz, 2H), 2.65-2.45 (m, 8H), 1.24 (d, J=6.0 Hz, 3H), 1.18 (d, J=6.0 Hz, 3H). $^{13}$C NMR (101 MHz, CDCl$_3$) δ 194.2, 161.5, 157.3, 151.9, 147.1, 134.8, 134.7, 132.0, 131.7, 129.0, 127.8 (2C), 127.3, 124.9, 121.3, 118.4, 113.3, 71.9, 64.8, 61.7, 53.4 (2C), 52.8 (2C), 43.8, 21.9, 21.8.

3-(5-(2-(1H-imidazol-1-yl)ethanoyl)-2-isopropoxyphenyl)-2-(chloromethyl)quinazolin-4(3H)-one (5e)

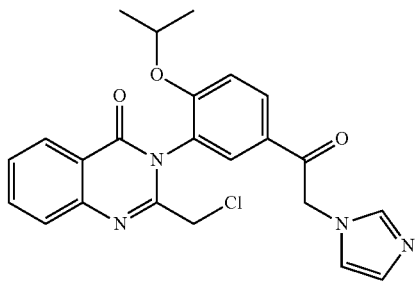 [SMILES: CC(C)Oc1ccc(C(=O)Cn2ccnc2)cc1-n1c(CCl)nc2ccccc2c1=O]

$C_{23}H_{21}ClN_4O_3$ MW=436.89 g/mol

Following general procedure 3a with 4e (190 mg, 0.73 mmol), 5e (170 mg, 53% yield) was obtained as a beige oily solid.

$^1$H NMR (400 MHz, CDCl$_3$) δ 8.28 (d, J=7.4 Hz, 1H), 8.20 (dd, J=8.8 Hz, J=2.1 Hz, 1H), 8.00 (s, 1H), 7.78-7.71 (m, 2H), 7.52-7.50 (m, 1H), 7.45 (s, 1H), 7.13 (d, J=8.9 Hz, 1H), 7.07 (s, 1H), 6.90 (s, 1H), 5.53 (s, 2H), 4.67 (sept, J=6.1 Hz, 1H), 4.35, 4.08 (ABq, J$_{AB}$=11.9 Hz, 2H), 1.25 (d, J=6.0 Hz, 3H), 1.19 (d, J=6.0 Hz, 3H). $^{13}$C NMR (101 MHz, CDCl$_3$) δ 189.5, 161.4, 158.1, 151.4, 147.0, 138.2, 134.9, 131.8, 131.4, 129.5, 128.0, 127.8, 127.1, 127.0, 125.5, 121.0, 120.4, 113.8, 72.3, 52.2, 43.8, 21.8, 21.7.

2-(chloromethyl)-3-(5-ethanoyl-2-isopropoxyphenyl)quinazolin-4(3H)-one (5f)

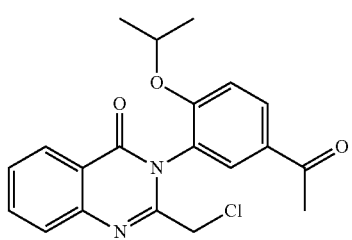 [SMILES: CC(=O)c1ccc(OC(C)C)c(-n2c(CCl)nc3ccccc3c2=O)c1]

$C_{20}H_{19}ClN_2O_3$ MW=370.83 g/mol

Following general procedure 3a with 4f (610 mg, 3.15 mmol), 5f (553 mg, 47% yield) was obtained as a beige oily solid.

$^1$H NMR (400 MHz, CDCl$_3$) δ 8.28 (d, J=7.8 Hz, 1H), 8.12 (dd, J=8.7 Hz, J=1.8 Hz, 1H), 7.97 (s, 1H), 7.83-7.76 (m, 2H), 7.55-7.51 (m, 1H), 7.12 (d, J=8.7 Hz, 1H), 4.67 (sept, J=6.1 Hz, 1H), 4.36, 4.12 (ABq, J$_{AB}$=11.9 Hz, 2H), 2.56 (s, 3H), 1.26 (d, J=6.0 Hz, 3H), 1.21 (d, J=6.0 Hz, 3H). $^{13}$C NMR (101 MHz, CDCl$_3$) δ 195.7, 161.5, 157.3, 151.9, 147.1, 134.9, 131.9, 131.7, 130.3, 127.9, 127.8, 127.3, 125.2, 121.3, 113.4, 72.0, 43.8, 26.4, 22.0, 21.8.

2-(chloromethyl)-3-(5-(2-fluoroethanoyl)-2-isopropoxyphenyl)quinazolin-4(3H)-one (5g)

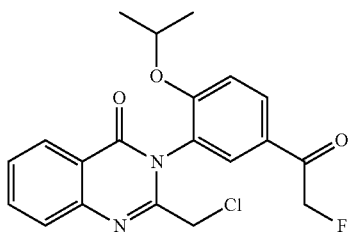 [SMILES: CC(C)Oc1ccc(C(=O)CF)cc1-n1c(CCl)nc2ccccc2c1=O]

C$_{20}$H$_{18}$ClFN$_2$O$_3$ MW=388.82 g/mol

Following general procedure 3a with 4g (64 mg, 0.28 mmol), 5g (65 mg, 60% yield) was obtained as a beige oily solid.

$^1$H NMR (400 MHz, CDCl$_3$) δ 8.29 (d, J=7.8 Hz, 1H), 8.14-8.10 (m, 1H), 7.95 (s, 1H), 7.83-7.76 (m, 2H), 7.55-7.51 (m, 1H), 7.14 (d, J=8.7 Hz, 1H), 5.46 (d, J$_{H-F}$=47 Hz, 2H), 4.67 (sept, J=6.1 Hz, 1H), 4.36, 4.13 (ABq, J$_{AB}$=11.9 Hz, 2H), 1.27 (d, J=6.0 Hz, 3H), 1.22 (d, J=6.0 Hz, 3H).

2-(chloromethyl)-3-(2-isopropoxy-5-(2,2,2-trifluoroethanoyl)phenyl)quinazolin-4(3H)-one (5h)

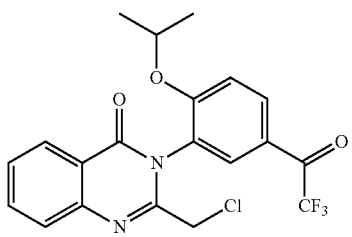 [SMILES: CC(C)Oc1ccc(C(=O)C(F)(F)F)cc1-n1c(CCl)nc2ccccc2c1=O]

C$_{20}$H$_{16}$ClF$_3$N$_2$O$_3$ MW=424.80 g/mol

Following general procedure 3a with 4h (65 mg, 0.26 mmol), 5h (55 mg, 49% yield) was obtained as a beige oily solid.

$^1$H NMR (400 MHz, CDCl$_3$) δ 8.30-8.25 (m, 2H), 8.11 (s, 1H), 7.83-7.76 (m, 2H), 7.57-7.51 (m, 1H), 7.19 (d, J=9.0 Hz, 1H), 4.75 (sept, J=6.1 Hz, 1H), 4.37, 4.11 (ABq, J$_{AB}$=11.9 Hz, 2H), 1.27 (d, J=6.0 Hz, 3H), 1.22 (d, J=6.0 Hz, 3H).

MKE (6a)

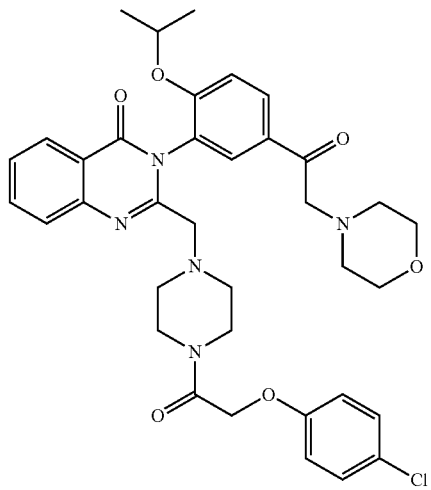 [SMILES: CC(C)Oc1ccc(C(=O)CN2CCOCC2)cc1-n1c(CN2CCN(C(=O)COc3ccc(Cl)cc3)CC2)nc2ccccc2c1=O]

C$_{36}$H$_{40}$ClN$_5$O$_6$ MW=674.19 g/mol

Following general procedure 4 with 5a (75 mg, 0.16 mmol), MKE (63 mg, 62% yield, 2 steps) was obtained as a white solid.

$^1$H NMR (400 MHz, CDCl$_3$) δ 8.26 (d, J=8.0 Hz, 1H), 8.10 (dd, J=8.7 Hz, J=2.2 Hz, 1H), 7.98 (d, J=2.2 Hz, 1H), 7.80-7.71 (m, 2H), 7.51-7.47 (m, 1H), 7.20 (d, J=8.9 Hz, 2H), 7.05 (d, J=8.9 Hz, 1H), 6.82 (d, J=8.9 Hz, 2H), 4.65 (sept, J=6.0 Hz, 1H), 4.58 (s, 2H), 3.75-3.73 (m, 4H), 3.50-3.40 (m, 4H), 3.25, 3.18 (ABq, J$_{AB}$=14.0 Hz, 2H), 2.61-2.35 (m, 8H), 2.18-2.05 (m, 2H), 1.23 (d, J=6.0 Hz, 3H), 1.19 (d, J=6.0 Hz, 3H). $^{13}$C NMR (101 MHz, CDCl$_3$) δ 193.9, 166.0, 161.8, 157.4, 156.5, 152.8, 147.0, 134.6, 131.5, 131.2, 129.6 (2C), 128.7, 127.6, 127.3, 127.2, 126.7, 126.4, 121.2, 116.0 (2C), 113.0, 72.0, 67.9, 66.9 (2C), 64.9, 61.2, 54.0 (2C), 53.0, 52.7, 45.2, 42.0, 22.2, 21.7.

MPKE (6b)

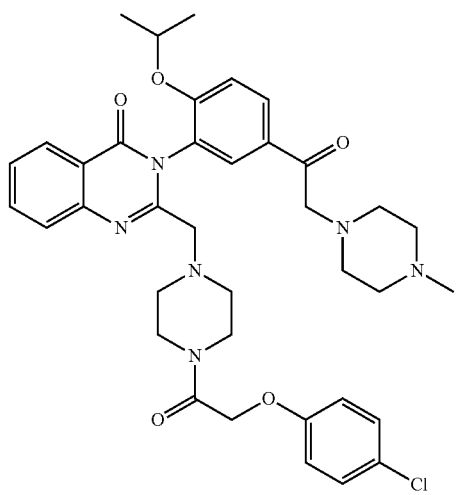 [SMILES: CC(C)Oc1ccc(C(=O)CN2CCN(C)CC2)cc1-n1c(CN2CCN(C(=O)COc3ccc(Cl)cc3)CC2)nc2ccccc2c1=O]

C$_{37}$H$_{43}$ClN$_6$O$_5$ MW=687.23 g/mol

Following general procedure 4 with 5b (70 mg, 0.15 mmol), MPKE (13 mg, 20% yield, 2 steps) was obtained as a white solid.

$^1$H NMR (400 MHz, CDCl$_3$) δ 8.28 (d, J=7.9 Hz, 1H), 8.13 (dd, J=8.7 Hz, J=2.1 Hz, 1H), 8.00 (d, J=2.1 Hz, 1H), 7.79-7.72 (m, 2H), 7.53-7.48 (m, 1H), 7.22 (d, J=8.9 Hz, 2H), 7.06 (d, J=8.8 Hz, 1H), 6.83 (d, J=8.9 Hz, 2H), 4.65 (sept, J=6.0 Hz, 1H), 4.60 (s, 2H), 3.75-3.73 (m, 2H), 3.50-3.40 (m, 4H), 3.27, 3.19 (ABq, J$_{AB}$=14.0 Hz, 2H), 2.61-2.35 (m, 10H), 2.30 (s, 3H), 2.18-2.05 (m, 2H), 1.25 (d, J=6.0 Hz, 3H), 1.21 (d, J=6.0 Hz, 3H). $^{13}$C NMR (101 MHz, CDCl$_3$) δ 194.2, 166.0, 161.9, 157.5, 156.6, 152.9, 147.0, 134.7, 131.6, 131.3, 129.7 (2C), 128.9, 127.6, 127.5, 127.3, 127.2, 126.4, 121.3, 116.1 (2C), 113.1, 72.0, 68.0, 64.7, 61.3, 55.0 (2C), 53.7 (2C), 53.1, 52.7, 46.1, 45.3, 42.1, 22.3, 21.7.

PMB-PKE (6c)

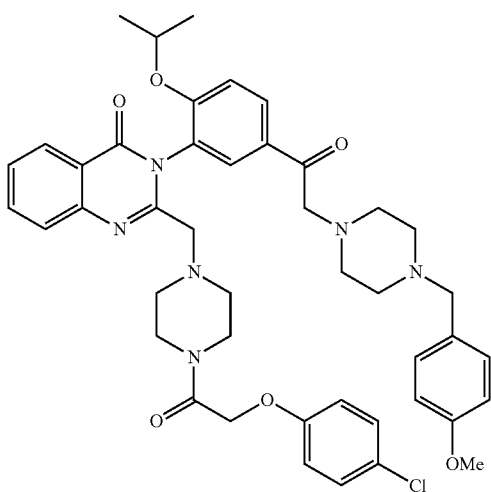 [SMILES: COc1ccc(CN2CCN(CC(=O)c3ccc(OC(C)C)c(-n4c(CN5CCN(C(=O)COc6ccc(Cl)cc6)CC5)nc5ccccc5c4=O)c3)CC2)cc1]

C$_{44}$H$_{49}$ClN$_6$O$_6$ MW=793.34 g/mol

Following general procedure 4 with 5c (104 mg, 0.18 mmol), PMB-PKE (61 mg, 43% yield, 2 steps) was obtained as a white solid.

$^1$H NMR (400 MHz, CDCl$_3$) δ 8.28 (d, J=7.9 Hz, 1H), 8.12 (d, J=8.7 Hz, 1H), 7.99 (s, 1H), 7.81-7.72 (m, 2H), 7.52-7.48 (m, 1H), 7.21 (d, J=8.4 Hz, 4H), 7.06 (d, J=8.8 Hz, 1H), 6.83 (d, J=8.8 Hz, 4H), 4.66 (sept, J=6.0 Hz, 1H), 4.60 (s, 2H), 3.79 (s, 3H), 3.72 (s, 2H), 3.47-3.40 (m, 6H), 3.27, 3.19 (ABq, J$_{AB}$=14.0 Hz, 2H), 2.61-2.35 (m, 10H), 2.19-2.13 (m, 2H), 1.24 (d, J=6.0 Hz, 3H), 1.21 (d, J=6.0 Hz, 3H). $^{13}$C NMR (101 MHz, CDCl$_3$) δ 194.3, 165.9, 161.8, 157.4, 156.5, 152.8, 147.1, 134.6, 131.5, 131.3, 130.5 (2C), 129.6 (4C), 128.8, 127.6, 127.3, 127.2, 126.7, 126.4, 121.2, 116.0 (4C), 113.7 (2C), 113.0, 71.9, 67.9, 64.7, 62.4, 61.2, 55.3, 53.6 (2C), 53.0, 52.8 (2C), 52.6, 45.2, 42.0, 22.2, 21.7.

APKE (6d)

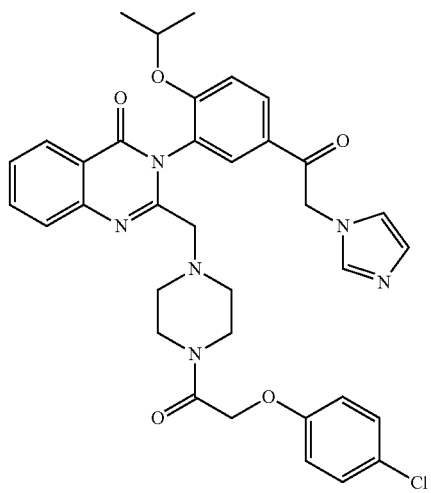 [SMILES: CC(C)Oc1ccc(C(=O)Cn2ccnc2)cc1-n1c(CN2CCN(C(=O)COc3ccc(Cl)cc3)CC2)nc2ccccc2c1=O]

C$_{39}$H$_{45}$ClN$_6$O$_5$ MW=713.26 g/mol

Following general procedure 4 with 5d (80 mg, 0.16 mmol), APKE (65 mg, 59% yield, 2 steps) was obtained as a white solid.

$^1$H NMR (400 MHz, CDCl$_3$) δ 8.29 (d, J=7.9 Hz, 1H), 8.12 (dd, J=8.7 Hz, J=2.1 Hz, 1H), 7.99 (d, J=2.1 Hz, 1H), 7.79-7.72 (m, 2H), 7.52-7.48 (m, 1H), 7.22 (d, J=8.9 Hz, 2H), 7.06 (d, J=8.8 Hz, 1H), 6.84 (d, J=8.9 Hz, 2H), 5.88-5.81 (m, 1H), 5.27-5.13 (m, 2H), 4.69 (sept, J=6.0 Hz, 1H), 4.60 (s, 2H), 3.74-3.73 (m, 2H), 3.46-3.39 (m, 4H), 3.26, 3.19 (ABq, J$_{AB}$=14.0 Hz, 2H), 3.00 (d, J=6.6 Hz, 2H), 2.61-2.35 (m, 10H), 2.18-2.05 (m, 2H), 1.25 (d, J=6.0 Hz, 3H), 1.21 (d, J=6.0 Hz, 3H). $^{13}$C NMR (101 MHz, CDCl$_3$) δ 195.1, 166.0, 162.6, 157.5, 156.6, 152.9, 134.6, 131.6, 131.3, 129.6 (2C), 128.7, 127.6, 127.5, 127.3, 127.2, 127.1, 124.1, 121.3, 118.4, 116.1 (2C), 113.2, 72.0, 68.0, 64.7, 61.3, 53.7 (2C), 52.9 (2C), 52.8, 52.7, 46.5, 45.3, 42.1, 22.3, 21.7.

IKE (6e)

C$_{35}$H$_{35}$ClN$_6$O$_5$ MW=655.14 g/mol

Following general procedure 4 with 5e (120 mg, 0.27 mmol), IKE (110 mg, 61% yield, 2 steps) was obtained as a white solid.

$^1$H NMR (400 MHz, CDCl$_3$) δ 8.22 (d, J=7.9 Hz, 1H), 8.01 (dd, J=8.7 Hz, J=2.1 Hz, 1H), 7.99 (d, J=2.1 Hz, 1H), 7.77-7.70 (m, 2H), 7.50-7.45 (m, 2H), 7.19 (d, J=9.0 Hz, 2H), 7.50-7.45 (m, 2H), 6.90 (s, 1H), 6.81 (d, J=8.9 Hz, 2H), 5.40-5.25 (m, 2H), 4.66 (sept, J=6.0 Hz, 1H), 4.57 (s, 2H), 3.43-3.35 (m, 4H), 3.24, 3.16 (ABq, J$_{AB}$=14.0 Hz, 2H), 2.40-2.01 (m, 4H), 1.25 (d, J=6.0 Hz, 3H), 1.21 (d, J=6.0 Hz, 3H). $^{13}$C NMR (101 MHz, CDCl$_3$) δ 189.7, 166.0, 161.8, 158.3, 156.5, 152.4, 147.0, 138.2, 134.7, 131.4, 130.9, 129.7, 129.5 (2C), 127.7, 127.3, 127.2, 127.0, 126.9, 126.7, 121.0, 120.3, 116.0 (2C), 113.4, 72.3, 67.8, 61.1, 52.7, 52.6, 52.2, 45.1, 41.9, 22.2, 21.6.

KE (6f)

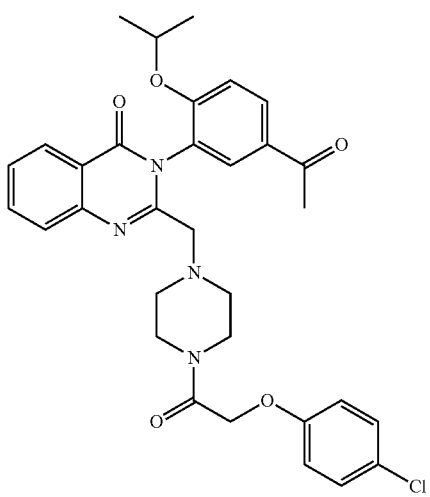 [SMILES: CC(=O)c1ccc(OC(C)C)c(-n2c(CN3CCN(C(=O)COc4ccc(Cl)cc4)CC3)nc3ccccc3c2=O)c1]

C$_{32}$H$_{33}$ClN$_4$O$_5$ MW=589.08 g/mol

Following general procedure 4 with 5f (365 mg, 0.88 mmol), KE (282 mg, 54% yield, 2 steps) was obtained as a white solid.

$^1$H NMR (400 MHz, CDCl$_3$) δ 8.28 (d, J=7.4 Hz, 1H), 8.04 (dd, J=8.7 Hz, J=2.1 Hz, 1H), 7.95 (d, J=2.1 Hz, 1H), 7.79-7.72 (m, 2H), 7.52-7.48 (m, 1H), 7.21 (d, J=8.9 Hz, 2H), 7.07 (d, J=8.8 Hz, 1H), 6.83 (d, J=8.9 Hz, 2H), 4.65 (sept, J=6.0 Hz, 1H), 4.60 (s, 2H), 3.50-3.40 (m, 4H), 3.25, 3.18 (ABq, J$_{AB}$=14.0 Hz, 2H), 2.56 (s, 3H), 2.44-2.40 (m, 2H), 2.21-2.12 (m, 2H), 1.24 (d, J=6.0 Hz, 3H), 1.20 (d, J=6.0 Hz, 3H). $^{13}$C NMR (101 MHz, CDCl$_3$) δ 195.8, 166.1, 161.9, 157.3, 156.6, 152.9, 147.1, 134.7, 131.6, 131.5, 130.1, 129.6 (2C), 127.6, 127.3, 127.2, 126.8, 126.5, 121.3, 116.1 (2C), 113.2, 72.0, 68.0, 61.3, 53.1, 52.7, 45.3, 42.1, 26.5, 22.3, 21.7.

FKE (6g)

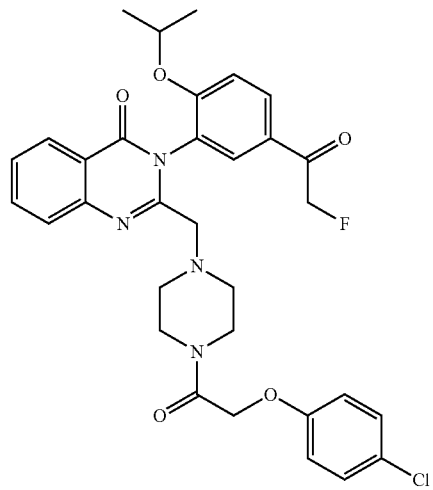 [SMILES: CC(C)Oc1ccc(C(=O)CF)cc1-n1c(CN2CCN(C(=O)COc3ccc(Cl)cc3)CC2)nc2ccccc2c1=O]

C$_{32}$H$_{32}$ClFN$_4$O$_5$ MW=607.07 g/mol

Following general procedure 4 with 5g (25 mg, 0.06 mmol), FKE (19 mg, 51% yield, 2 steps) was obtained as a white solid.

$^1$H NMR (400 MHz, CDCl$_3$) δ 8.28 (d, J=7.4 Hz, 1H), 8.05-7.96 (m, 2H), 7.80-7.74 (m, 2H), 7.52-7.48 (m, 1H), 7.21 (d, J=8.9 Hz, 2H), 7.09 (d, J=8.8 Hz, 1H), 6.83 (d, J=8.9 Hz, 2H), 5.42 (d, J$_{F-H}$=47 Hz, 2H), 4.67 (sept, J=6.0 Hz, 1H), 4.60 (s, 2H), 3.48-3.40 (m, 4H), 3.26, 3.18 (ABq, J$_{AB}$=13.9 Hz, 2H), 2.44-2.40 (m, 2H), 2.21-2.12 (m, 2H), 1.24 (d, J=6.0 Hz, 3H), 1.20 (d, J=6.0 Hz, 3H).

TFKE (6h)

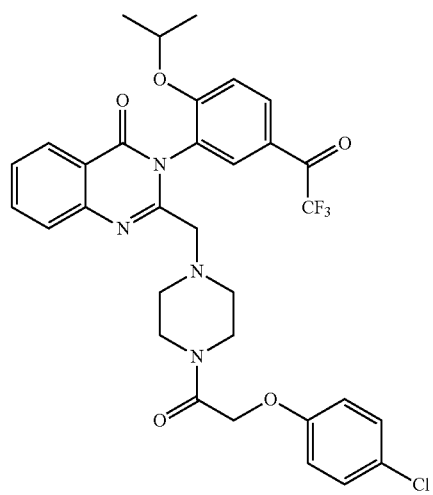 [SMILES: CC(C)Oc1ccc(C(=O)C(F)(F)F)cc1-n1c(CN2CCN(C(=O)COc3ccc(Cl)cc3)CC2)nc2ccccc2c1=O]

C$_{32}$H$_{30}$ClF$_3$N$_4$O$_5$ MW=643.05 g/mol

Following general procedure 4 with 5h (50 mg, 0.12 mmol), TFKE (28 mg, 37% yield, 2 steps) was obtained as a white solid.

$^1$H NMR (400 MHz, CDCl$_3$) δ 8.29 (d, J=7.9 Hz, 1H), 8.15 (d, J=7.9 Hz, 1H), 8.09 (s, 1H), 7.81-7.73 (m, 2H), 7.52-7.48 (m, 1H), 7.23 (d, J=8.9 Hz, 2H), 7.15 (d, J=9.0 Hz, 1H), 6.85 (d, J=8.9 Hz, 2H), 4.71 (sept, J=6.0 Hz, 1H), 4.60 (s, 2H), 3.48-3.16 (m, 6H), 2.44-2.40 (m, 2H), 2.21-2.12 (m, 2H), 1.28 (d, J=6.1 Hz, 3H), 1.25 (d, J=6.1 Hz, 3H).

PKE (7)

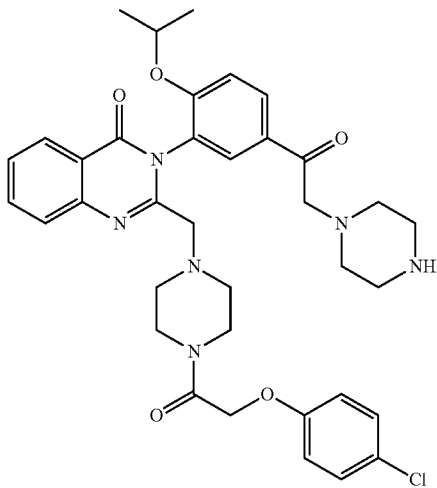 [SMILES: CC(C)Oc1ccc(C(=O)CN2CCNCC2)cc1-n1c(CN2CCN(C(=O)COc3ccc(Cl)cc3)CC2)nc2ccccc2c1=O]

$C_{36}H_{41}ClN_6O_5$ MW=673.20 g/mol

To a Schlenk reactor containing APKE (700 mg, 0.98 mmol, 1 equivalent) in DCM (20 mL) was added under nitrogen N,N-dimethylbarbituric acid (460 mg, 2.94 mmol, 3 equivalents) followed by Pd(PPh$_3$)$_4$ (115 mg, 0.1 mmol, 0.1 equivalent). The reaction mixture was stirred under nitrogen for 15 hours at 40° C. Upon completion, the reaction mixture was quenched with 2N aqueous HCl solution (10 mL), and the aqueous phase containing the desired product was extracted with DCM (2×10 mL). The aqueous phase was then basified with 6N aqueous NaOH, and the desired product was extracted into the organic phase (5×10 mL DCM/MeOH 5%). The organic phases were combined, dried over Na$_2$SO$_4$ and concentrated under reduced pressure to yield PKE (571 mg, 87%) as a white solid.

$^1$H NMR (400 MHz, CD$_3$OD) δ 8.24-8.22 (m, 2H), 8.15 (d, J=1.6 Hz, 1H), 7.91-7.89 (m, 1H), 7.79 (d, J=8.2 Hz, 1H), 7.63-7.59 (m, 1H), 7.33 (d, J=8.8 Hz, 1H), 7.26 (d, J=8.9 Hz, 2H), 6.93 (d, J=8.9 Hz, 2H), 4.85 (sept, J=6.0 Hz, 1H), 4.75 (s, 2H), 3.91 (s, 2H), 3.46-3.27 (m, 6H), 2.93-2.91 (m, 4H), 2.64-2.61 (m, 4H), 2.36-2.17 (m, 4H), 1.27 (d, J=6.0 Hz, 3H), 1.21 (d, J=6.0 Hz, 3H). $^{13}$C NMR (101 MHz, CD$_3$OD) δ 196.1, 168.4, 163.6, 158.9, 158.2, 155.0, 148.2, 136.2, 132.7, 132.5, 130.3, 129.8 (2C), 128.7, 128.2, 127.7, 127.4, 127.3, 122.0, 117.3 (2C), 114.5, 73.1, 67.7, 62.0, 54.6 (2C), 53.8, 53.5, 50.0, 45.9 (3C), 42.9, 22.5, 21.8.

1-(4-isopropoxyphenyl)ethan-1-one (8b)

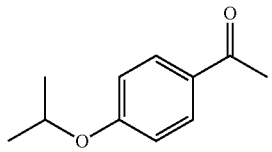

$C_{11}H_{14}O_2$ MW=178.23

To a solution of 1-(4-hydroxyphenyl)ethan-1-one (5.00 g, 36.6 mmol, 1 equiv.) in DMF (50 mL) at room temperature was added potassium carbonate (5.80 g, 43.9 mmol, 1.2 equiv.). The mixture was stirred at room temperature for 15 minutes and 2-iodopropane (7.31 mL, 73.3 mmol, 2.0 eq) was then added dropwise. The mixture was subsequently stirred at 70° C. for 12 hours. Upon completion the reaction mixture was quenched with water and extracted twice with ethyl acetate. The combined organic layers were dried over sodium sulfate, concentrated under reduced pressure and purified by flash column chromatography (hexane/EtOAc=100/0 to 60/40) to afford 1-(4-isopropoxyphenyl)ethan-1-one (4.27 g, 65% yield) as a clear oil.

$^1$H NMR (400 MHz, Chloroform-d) δ 8.32-7.66 (m, 2H), 6.91 (d, J=8.9 Hz, 2H), 4.66 (p, J=6.1 Hz, 1H), 2.56 (s, 3H), 1.38 (d, J=6.1 Hz, 6H). $^{13}$C NMR (101 MHz, CDCl$_3$) δ 196.67, 161.99, 130.59, 129.93, 115.05, 70.08, 26.27, 21.90. MS (m/z): [MH+] calculated for $C_{11}H_{14}O_2$, 178.23; found 178.55.

2-chloro-1-(4-isopropoxyphenyl)ethan-1-one

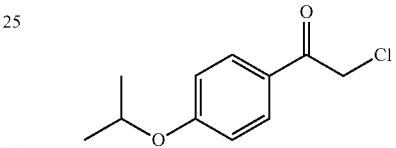

$C_{11}H_{13}ClO_2$ MW=212.67

To a solution of 8b (4.27 g, 23.9 mmol, 1 equiv.) in acetonitrile (60 mL) at room temperature were added p-toluenesulfonic acid (6.84 g, 35.9 mmol, 1.5 equiv.) and N-chlorosuccinimide (3.52 g, 26.40 mmol, 1.1 equiv.). The mixture was refluxed for 3 hours, concentrated under reduced pressure and purified by flash column chromatography (hexane/EtOAc=100/0 to 70/30) to afford 2-chloro-1-(4-isopropoxyphenyl)ethan-1-one (2.88 g, 57% yield) as a white solid.

$^1$H NMR (400 MHz, Chloroform-d) δ 7.95-7.93 (d, J=2.9 Hz, 2H), 6.96-6.94 (d, 2H), 4.71-4.65 (m, 3H), 1.40 (d, J=6.1 Hz, 6H). $^{13}$C NMR (101 MHz, CDCl$_3$) δ 189.73, 162.88, 131.11, 126.87, 115.51, 70.46, 45.75, 22.011 MS (m/z): [MH+] calculated for $C_{11}H_{13}ClO_2$, 212.67; found 212.53.

N-(4-isopropoxybenzyl)butan-1-amine (9a)

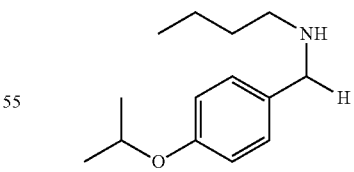

$C_{14}H_{23}NO$ MW=221.18

Following general procedure 6 with 4-isopropoxybenzaldehyde (50 mg, 0.30 mmol), N-(4-isopropoxybenzyl)butan-1-amine (53 mg, 79% yield) was obtained as a yellow oil. Remaining starting material, 4-isopropoxybenzaldehyde, was also obtained (4 mg, 8% yield), giving an amine/ketone ratio of 9.5:1.

¹H NMR (400 MHz, Chloroform-d) δ 7.24 (d, J=8.5 Hz, 2H), 6.95-6.72 (m, 2H), 4.54 (p, J=6.1 Hz, 1H), 3.74 (s, 2H), 2.72-2.52 (m, 2H), 1.70-1.36 (m, 5H), 1.35 (d, J=6.0 Hz, 7H), 0.93 (t, J=7.3 Hz, 4H). ¹³C NMR (101 MHz, CDCl₃) δ 156.95, 132.11, 129.36, 115.85, 69.92, 53.35, 48.98, 46.99, 32.03, 22.07, 20.48, 13.99. MS (m/z): [MH+] calculated for C₁₄H₂₃NO, 222.18; found 222.19.

N-(1-(4-isopropoxyphenyl)ethyl)butan-1-amine (9b)

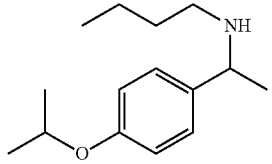 [SMILES: CCCCNC(C)c1ccc(OC(C)C)cc1]

C₁₅H₂₅NO MW=235.37

Following general procedure 6 with 1-(4-isopropoxyphenyl)ethan-1-one 8b (100 mg, 0.56 mmol), N-(1-(4-isopropoxyphenyl)ethyl)butan-1-amine (69 mg, 52% yield) was obtained as a yellow oil. Remaining starting material, 1-(4-isopropoxyphenyl)ethan-1-one, was also obtained (18 mg, 18% yield), giving an amine/ketone ratio of 3:1.

¹H NMR (400 MHz, Chloroform-d) δ 7.24-7.09 (m, 2H), 6.96-6.63 (m, 2H), 4.54 (p, J=6.1 Hz, 1H), 3.72 (q, J=6.6 Hz, 1H), 2.67-2.31 (m, 2H), 2.19 (s, 1H), 1.63-1.39 (m, 2H), 1.37-1.25 (m, 11H), 0.89 (t, J=7.3 Hz, 3H). ¹³C NMR (101 MHz, CDCl₃) δ 156.76, 137.82, 127.50, 115.67, 69.84, 57.71, 47.53, 32.43, 24.27, 22.14, 20.51, 14.00. MS (m/z): [MH+] calculated for C₁₅H₂₅NO 235.19; found 235.47.

2-fluoro-1-(4-isopropoxyphenyl)ethan-1-one (8c)

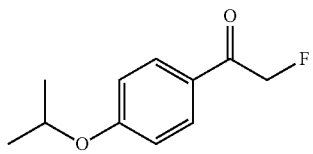

C₁₁H₁₃FO₂ MW=196.22

To a solution of LiHMDS (1 M in THF, 3.76 mL, 3.76 mmol, 1.2 equiv.) in THF (25 mL) at room temperature, was added a solution of 1-(4-isopropoxyphenyl)ethan-1-one (1.0 g, 5.6 mmol, 1 equiv.) in THF (1 mL) dropwise over 30 minutes. The reaction mixture was stirred at room temperature for 15 minutes, then concentrated under reduced pressure, dissolved in MeCN (20 mL) and filtered. To a solution of selectfluor (1.45 g, 4.1 mmol, 1.3 equiv.) in acetonitrile (6 mL) at 0° C. was added the crude filtrate dropwise. The reaction mixture was stirred at room temperature for 30 minutes and concentrated under reduced pressure. The crude residue was dissolved in EtOAc (30 mL) and washed with water (2×30 mL). The organic layer was dried over sodium sulfate, concentrated under reduced pressure and purified by flash column chromatography (hexane/EtOAc=100/0 to 60/40) to 2-fluoro-1-(4-isopropoxyphenyl)ethan-1-one 8c (601 mg, 55% yield) as a yellow oil.

¹H NMR (400 MHz, Chloroform-d) δ 8.06 (dt, J=8.0, 1.1 Hz, 2H), 7.10-6.82 (m, 2H), 4.72 (p, J=6.1 Hz, 1H), 1.42 (d, J=6.2 Hz, 6H). ¹³C NMR (101 MHz, CDCl₃) δ 191.92, 191.77, 162.82, 130.29, 130.26, 126.29, 115.44, 84.35, 82.55, 70.32, 21.87. MS (m/z): [MH+] calculated for C₁₁H₁₃FO₂ 196.09; found 196.45.

(E)-N-butyl-2-fluoro-1-(4-isopropoxyphenyl)ethan-1-imine (9c)

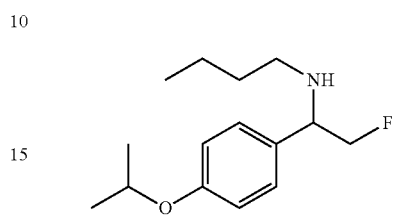

C₁₅H₂₂FNO MW=253.36

Following general procedure 6 with 2-fluoro-1-(4-isopropoxyphenyl)ethan-1-one 8c (90 mg, 0.46 mmol), (E)-N-butyl-2-fluoro-1-(4-isopropoxyphenyl)ethan-1-imine 9c (47 mg, 40% yield) was obtained as a yellow oil. Remaining starting material, 2-fluoro-1-(4-isopropoxyphenyl)ethan-1-one, was also obtained (36 mg, 40% yield), giving an amine/ketone ratio of 1:1.

¹H NMR (400 MHz, Chloroform-d) δ 7.27 (d, J=8.6 Hz, 2H), 6.88 (d, J=8.6 Hz, 2H), 4.60, 4.51 (m, 1H), 4.49, 4.25 (m, 2H), 3.97 (ddd, J=12.7, 8.6, 4.1 Hz, 1H), 2.50 (t, J=7.1 Hz, 2H), 1.52, 1.43 (m, 2H), 1.40 (d, J=6.1 Hz, 9H), 0.90 (t, J=7.3 Hz, 4H). ¹³C NMR (101 MHz, CDCl₃) δ 157.60, 130.33, 128.71, 115.41, 84.39, 70.29, 62.54, 62.35, 47.17, 32.36, 21.87, 20.40, 13.97. MS (m/z): [MH+] calculated for C₁₅H₂₂FNO 251.35; found 253.36.

1-(4-isopropoxyphenyl)-2-morpholinoethan-1-one (8d)

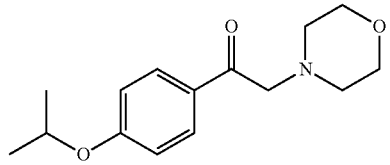 [SMILES: CC(C)Oc1ccc(C(=O)CN2CCOCC2)cc1]

C₁₅H₂₁NO₃ MW=263.34

Following general procedure 5 with 2-chloro-1-(4-isopropoxyphenyl)ethan-1-one (550 mg, 2.6 mmol) and morpholine (680 μL, 678 mg, 7.8 mmol), 1-(4-isopropoxyphenyl)-2-morpholinoethan-1-one 8d (482 mg, 71% yield) was obtained as a yellow oil.

¹H NMR (400 MHz, Chloroform-d) δ 7.96 (d, J=8.9 Hz, 2H), 6.89 (d, J=8.9 Hz, 2H), 4.64 (p, J=6.1 Hz, 1H), 3.92-3.64 (m, 6H), 3.01-2.32 (m, 4H), 1.36 (d, J=6.1 Hz, 7H), 1.25 (s, 1H). ¹³C NMR (101 MHz, CDCl₃) δ 194.67, 162.24, 130.52, 128.65, 115.12, 70.18, 66.89, 64.57, 60.45, 53.98, 50.73, 21.95, 21.09, 14.25. MS (m/z): [MH+] calculated for C₁₅H₂₁NO₃ 263.44; found 263.44.

N-(1-(4-isopropoxyphenyl)-2-morpholinoethyl)butan-1-amine (9d)

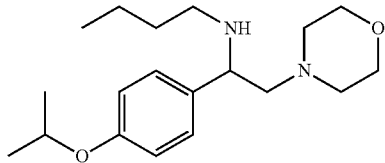 [SMILES: CCCCNC(CN1CCOCC1)c1ccc(OC(C)C)cc1]

$C_{19}H_{32}N_2O_2$ MW=320.48

Following general procedure 6 with 1-(4-isopropoxyphenyl)-2-morpholinoethan-1-one (150 mg, 0.57 mmol), N-(1-(4-isopropoxyphenyl)-2-morpholinoethyl)butan-1-amine 9d (62 mg, 34% yield) was obtained as a yellow oil. Remaining starting material, 1-(4-isopropoxyphenyl)-2-morpholinoethan-1-one, was also obtained (62.3 mg, 42% yield), giving an amine/ketone ratio of 1:1.2.

$^1$H NMR (400 MHz, Chloroform-d) δ 7.26 (d, J=8.5 Hz, 2H), 6.86 (d, J=8.5 Hz, 2H), 4.55-4.45 (m, 1H), 3.87-3.56 (m, 6H), 3.37 (s, 1H), 2.75-2.05 (m, 9H), 1.33 (dd, J=6.2, 0.8 Hz, 9H), 0.89 (td, J=7.4, 0.8 Hz, 3H). $^{13}$C NMR (101 MHz, CDCl$_3$) δ 157.57, 132.11, 128.66, 115.91, 69.94, 67.12, 65.18, 60.48, 59.10, 46.96, 31.35, 22.14, 20.38, 13.92. MS (m/z): [MH]+ calculated for $C_{19}H_{32}N_2O_2$ 320.48; found 320.40.

1-(4-isopropoxyphenyl)-2-(4-methylpiperazin-1-yl)ethan-1-one (8e)

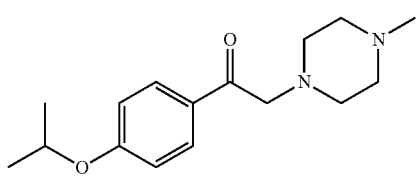 [SMILES: CC(C)Oc1ccc(C(=O)CN2CCN(C)CC2)cc1]

$C_{16}H_{24}N_2O_2$ MW=276.38

Following general procedure 5 with 2-chloro-1-(4-isopropoxyphenyl)ethan-1-one (550 mg, 2.6 mmol) and methylpiperazine (860 μL, 777 mg, 7.8 mmol), 1-(4-isopropoxyphenyl)-2-(4-methylpiperazin-1-yl)ethan-1-one 8e (311 mg, 43% yield) was obtained as a yellow oil.

$^1$H NMR (400 MHz, Chloroform-d) δ 7.99 (d, J=8.9 Hz, 2H), 6.90 (d, J=8.9 Hz, 2H), 4.65 (p, J=6.1 Hz, 1H), 3.75 (s, 2H), 2.80-2.43 (m, 8H), 2.30 (s, 4H), 1.37 (d, J=6.1 Hz, 7H). $^{13}$C NMR (101 MHz, CDCl$_3$) δ 194.95, 162.17, 130.59, 128.87, 115.11, 70.18, 64.47, 55.05, 53.70, 46.16, 22.02. MS (m/z): [MH]+ calculated for $C_{16}H_{24}N_2O_2$ 276.38; found 276.45.

N-(1-(4-isopropoxyphenyl)-2-(4-methylpiperazin-1-yl)ethyl)butan-1-amine (9e)

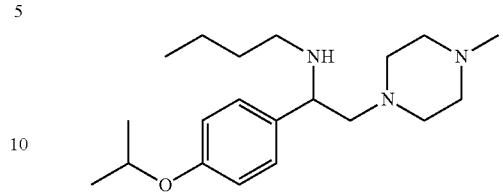

$C_{20}H_{35}N_3O$ MW=333.53

Following general procedure 6 with 1-(4-isopropoxyphenyl)-2-(4-methylpiperazin-1-yl)ethan-1-one 8e (150 mg, 0.54 mmol), N-(1-(4-isopropoxyphenyl)-2-(4-methylpiperazin-1-yl)ethyl)butan-1-amine 9e (11.5 mg, 6% yield) was obtained as a yellow oil. Remaining starting material, 1-(4-isopropoxyphenyl)-2-(4-methylpiperazin-1-yl)ethan-1-one, was also obtained (24.2 mg, 16% yield), giving an amine/ketone ratio of 1:2.5.

$^1$H NMR (400 MHz, Chloroform-d) δ 7.35-7.14 (m, 2H), 6.85 (d, J=8.6 Hz, 2H), 4.53 (p, J=6.1 Hz, 1H), 3.70 (dd, J=11.1, 3.4 Hz, 1H), 2.80-2.35 (m, 11H), 2.31 (s, 5H), 1.62-1.37 (m, 3H), 1.34 (d, J=6.0 Hz, 8H), 0.90 (t, J=7.3 Hz, 4H). $^{13}$C NMR (101 MHz, CDCl$_3$) δ 157.15, 134.77, 128.44, 115.77, 69.95, 65.84, 59.36, 55.46, 47.55, 46.21, 32.32, 22.27, 20.59, 14.12. MS (m/z): [MH]+ calculated for $C_{20}H_{35}N_3O$ 333.53; found: 333.40.

2-(4-allylpiperazin-1-yl)-1-(4-isopropoxyphenyl)ethan-1-one (8f)

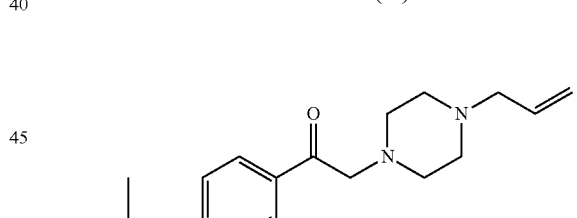

$C_{18}H_{26}N_2O_2$ MW=302.20

Following general procedure 5 with 2-chloro-1-(4-isopropoxyphenyl)ethan-1-one (550 mg, 2.6 mmol) and allylpiperazine (1.73 mL, 984 mg, 7.8 mmol,) 2-(4-allylpiperazin-1-yl)-1-(4-isopropoxyphenyl)ethan-1-one 8f (451 mg, 57% yield) was obtained as a yellow oil.

$^1$H NMR (400 MHz, Chloroform-d) δ 8.00 (d, J=8.9 Hz, 2H), 6.98-6.63 (m, 2H), 5.90 (ddt, J=16.9, 10.2, 6.6 Hz, 1H), 5.29-5.07 (m, 2H), 4.66 (p, J=6.1 Hz, 1H), 3.77 (s, 2H), 3.06 (dt, J=6.7, 1.2 Hz, 2H), 2.63 (d, J=30.0 Hz, 7H), 1.38 (d, J=6.1 Hz, 5H). $^{13}$C NMR (101 MHz, CDCl$_3$) δ 194.68, 162.29, 133.29, 130.50, 119.73, 115.15, 70.20, 63.89, 61.61, 61.41, 52.96, 52.64, 21.96. MS (m/z): [MH]+ calculated for $C_{18}H_{26}N_2O_2$ 302.20; found: 302.80.

N-(2-(4-allylpiperazin-1-yl)-1-(4-isopropoxyphenyl)ethyl)butan-1-amine (9f)

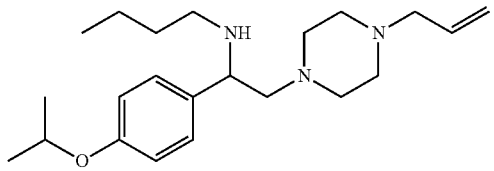 [SMILES: C=CCN1CCN(CC(NCCCC)c2ccc(OC(C)C)cc2)CC1]

C₂₂H₃₇N₃O MW=359.56

Following general procedure 6 with 2-(4-allylpiperazin-1-yl)-1-(4-isopropoxyphenyl)ethan-1-one 8f (150 mg, 0.49 mmol), N-(2-(4-allylpiperazin-1-yl)-1-(4-isopropoxyphenyl)ethyl)butan-1-amine 9f (51 mg, 28% yield) was obtained as a yellow oil. Remaining starting material, 2-(4-allylpiperazin-1-yl)-1-(4-isopropoxyphenyl)ethan-1-one, was also obtained (52 mg, 35% yield), giving an amine/ketone ratio of 1:1.2.

$^1$H NMR (400 MHz, Chloroform-d) δ 7.35 (d, J=8.3 Hz, 2H), 6.92 (d, J=8.2 Hz, 2H), 5.97-5.73 (m, 1H), 4.56 (p, J=6.1 Hz, 1H), 4.30-3.90 (m, 1H), 3.43-3.26 (m, 2H), 3.24-3.01 (m, 2H), 1.66 (dt, J=22.7, 7.3 Hz, 3H), 1.34 (d, J=6.0 Hz, 7H), 0.88 (t, J=7.3 Hz, 3H). $^{13}$C NMR (101 MHz, CDCl₃) δ 159.18, 129.71, 123.65, 122.59, 116.59, 70.12, 60.64, 60.38, 59.89, 52.28, 51.65, 45.42, 28.31, 22.04, 22.02, 19.90, 13.59. MS (m/z): [MH]+ calculated for C₂₂H₃₇N₃O 359.56; found: 360.83.

1-(4-isopropoxyphenyl)-2-(4-(4-methoxybenzyl)piperazin-1-yl)ethan-1-one (8g)

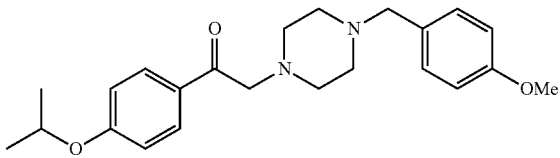 [SMILES: COc1ccc(CN2CCN(CC(=O)c3ccc(OC(C)C)cc3)CC2)cc1]

C₂₃H₃₀N₂O₃ MW=382.50

Following general procedure 5 with 2-chloro-1-(4-isopropoxyphenyl)ethan-1-one (300 mg, 1.4 mmol) and 1-(4-methoxybenzyl)piperazine (872 mg, 4.2 mmol), 1-(4-isopropoxyphenyl)-2-(4-(4-methoxybenzyl)piperazin-1-yl)ethan-1-one 8g (522 mg, 91% yield) was obtained as a yellow oil.

$^1$H NMR (400 MHz, Chloroform-d) δ 7.98 (d, J=8.9 Hz, 2H), 7.24 (d, J=8.6 Hz, 2H), 6.88 (dd, J=13.8, 8.7 Hz, 4H), 4.65 (p, J=6.1 Hz, 1H), 3.80 (s, 3H), 3.75 (s, 2H), 3.49 (s, 2H), 2.77-2.31 (m, 8H), 2.05 (s, 2H), 1.37 (d, J=6.1 Hz, 6H). $^{13}$C NMR (101 MHz, CDCl₃) δ 194.96, 162.15, 158.85, 130.54, 129.85, 128.81, 115.08, 113.67, 70.15, 64.36, 62.43, 60.46, 55.32, 53.56, 52.82, 21.99, 21.13, 14.28. MS (m/z): [MH]+ calculated for C₂₃H₃₀N₂O₃ 382.50; found: 382.66.

N-(1-(4-isopropoxyphenyl)-2-(4-(4-methoxybenzyl)piperazin-1-yl)ethyl)butan-1-amine (9g)

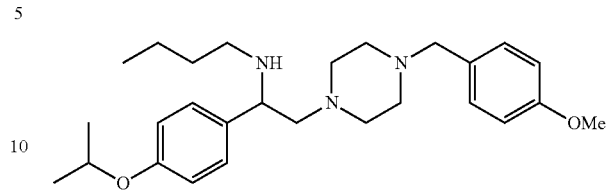

C₂₇H₄₁N₃O₂ MW=439.64

Following general procedure 2 with 1-(4-isopropoxyphenyl)-2-(4-(4-methoxybenzyl)piperazin-1-yl)ethan-1-one 8g (100 mg, 0.26 mmol), N-(1-(4-isopropoxyphenyl)-2-(4-(4-methoxybenzyl)piperazin-1-yl)ethyl)butan-1-amine 9g (9 mg, 8% yield) was obtained as a yellow oil. Remaining starting material, 1-(4-isopropoxyphenyl)-2-(4-(4-methoxybenzyl)piperazin-1-yl)ethan-1-one, was also obtained (32 mg, 32% yield), giving an amine/ketone ratio of 1:4.

$^1$H NMR (400 MHz, Chloroform-d) δ 7.48-7.17 (m, 4H), 7.07-6.56 (m, 4H), 4.59-4.54 (m, 2H), 3.94 (dd, J=11.7, 3.5 Hz, 1H), 3.82 (s, 3H), 3.66 (s, 1H), 3.02 (t, J=12.5 Hz, 2H), 2.91-2.46 (m, 8H), 1.65 (td, J=17.8, 16.1, 8.2 Hz, 3H), 1.35 (d, J=6.0 Hz, 9H), 1.28 (t, J=7.1 Hz, 1H), 0.94-0.85 (m, 3H). $^{13}$C NMR (101 MHz, CDCl₃) δ 158.90, 131.07, 129.52, 116.49, 114.06, 70.14, 61.95, 59.80, 55.43, 52.57, 45.62, 29.12, 22.12, 20.06, 13.70. MS (m/z) [MH]+ calculated for C₂₇H₄₁N₃O₂ 439.64; found: 439.55.

1-(4-isopropoxyphenyl)-2-(piperazin-1-yl)ethan-1-one (8h)

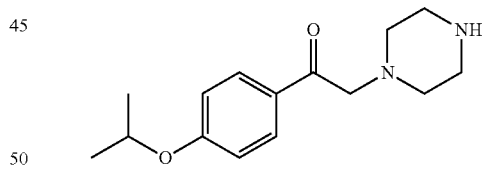

C₁₅H₂₂N₂O₂ MW=262.17

Following general procedure 5 with 2-chloro-1-(4-isopropoxyphenyl)ethan-1-one (550 mg, 2.6 mmol) and piperazine (668 mg, 7.8 mmol), 1-(4-isopropoxyphenyl)-2-(piperazin-1-yl)ethan-1-one 8h (404 mg, 59% yield) was obtained as a yellow oil.

$^1$H NMR (400 MHz, Chloroform-d) δ 8.11-7.76 (m, 2H), 6.91 (d, J=9.0 Hz, 2H), 4.67 (ddt, J=12.2, 8.5, 4.3 Hz, 1H), 3.95-3.69 (m, 2H), 3.29-2.79 (m, 4H), 2.59 (dd, J=7.4, 3.0 Hz, 4H), 2.27-1.61 (m, 2H), 1.39 (d, J=6.0 Hz, 6H). $^{13}$C NMR (101 MHz, CDCl₃) δ 194.94, 162.34, 130.54, 128.54, 115.19, 70.22, 64.39, 53.69, 45.34, 22.15, 21.97. MS (m/z) [MH]+ calculated for C₁₅H₂₂N₂O₂ 262.17; found 262.63.

N-(1-(4-isopropoxyphenyl)-2-(piperazin-1-yl)ethyl)butan-1-amine (9h)

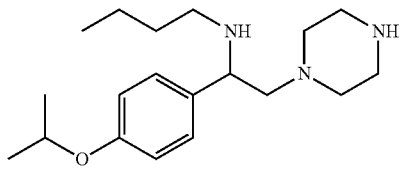 [SMILES: CCCCNC(CN1CCNCC1)c1ccc(OC(C)C)cc1]

C$_{19}$H$_{33}$N$_3$O MW=319.26

Following general procedure 2 with 1-(4-isopropoxyphenyl)-2-(piperazin-1-yl)ethan-1-one 8h (150 mg, 0.57 mmol), N-(1-(4-isopropoxyphenyl)-2-(piperazin-1-yl)ethyl)butan-1-amine 9h (6 mg, 3% yield) was obtained as a yellow oil. Remaining starting material, 1-(4-isopropoxyphenyl)-2-(piperazin-1-yl)ethan-1-one, was also obtained (37 mg, 25% yield), giving an amine/ketone ratio of 1:7.

$^1$H NMR (400 MHz, Chloroform-d) δ 7.31 (d, J=9.1 Hz, 2H), 6.88 (d, J=8.6 Hz, 2H), 4.55 (p, J=6.1 Hz, 1H), 3.84-3.60 (m, 1H), 2.90-2.65 (m, 3H), 2.65-2.31 (m, 5H), 1.53 (q, J=7.3 Hz, 2H), 1.36 (d, J=6.0 Hz, 6H), 0.90 (t, J=7.3 Hz, 3H). $^{13}$C NMR (101 MHz, CDCl$_3$) δ 157.66, 128.79, 116.00, 70.02, 59.36, 52.52, 46.97, 45.10, 31.37, 22.24, 20.51, 14.02. MS (m/z) [MH]+ calculated for C$_{19}$H$_{33}$N$_3$O 319.26; found 319.64.

2-(1H-imidazol-1-yl)-1-(4-isopropoxyphenyl)ethan-1-one (8i)

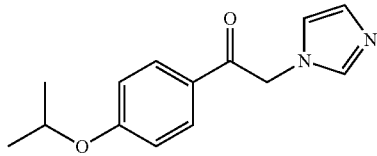 [SMILES: CC(C)Oc1ccc(C(=O)Cn2ccnc2)cc1]

C$_{14}$H$_{16}$N$_2$O$_2$ MW=244.29

Following general procedure 5 with 2-chloro-1-(4-isopropoxyphenyl)ethan-1-one (500 mg, 2.4 mmol) and imidazole (480 mg, 7.1 mmol), 2-(1H-imidazol-1-yl)-1-(4-isopropoxyphenyl)ethan-1-one 8i (160 mg, 27% yield) was obtained as a yellow oil.

$^1$H NMR (400 MHz, Chloroform-d) δ 8.07-7.74 (m, 2H), 7.54 (s, 1H), 7.16 (s, 1H), 7.04-6.73 (m, 3H), 4.70 (p, J=6.0 Hz, 1H), 1.41 (d, J=6.1 Hz, 6H). $^{13}$C NMR (101 MHz, CDCl$_3$) δ 190.00, 163.14, 130.51, 126.84, 120.44, 115.71, 70.56, 52.22, 21.99. MS (m/z) [MH]+ calculated for C$_{14}$H$_{16}$N$_2$O$_2$ 244.29; found: 244.60.

N-(2-(1H-imidazol-1-yl)-1-(4-isopropoxyphenyl)ethyl)butan-1-amine (9i)

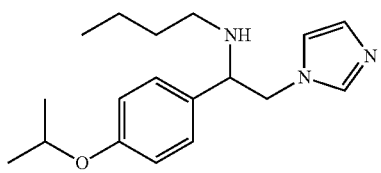 [SMILES: CCCCNC(Cn1ccnc1)c1ccc(OC(C)C)cc1]

C$_{18}$H$_{27}$N$_3$O MW=301.43

Following general procedure 6 with 2-(1H-imidazol-1-yl)-1-(4-isopropoxyphenyl)ethan-1-one (150 mg, 0.61 mmol) 8i, N-(2-(1H-imidazol-1-yl)-1-(4-isopropoxyphenyl)ethyl)butan-1-amine 9i (9 mg, 5% yield) was obtained as a yellow oil. Remaining starting material, 2-(1H-imidazol-1-yl)-1-(4-isopropoxyphenyl)ethan-1-one, was also obtained (11 mg, 7% yield), giving an amine/ketone ratio of 1:1.5.

$^1$H NMR (400 MHz, Chloroform-d) δ 7.32 (s, 2H), 7.14 (d, J=7.5 Hz, 2H), 6.98 (d, J=8.1 Hz, 2H), 6.93-6.70 (m, 2H), 4.68-4.43 (m, 1H), 4.14 (td, J=13.1, 6.5 Hz, 2H), 3.90 (s, 1H), 2.47 (ddt, J=18.6, 11.8, 5.3 Hz, 2H), 1.57-1.30 (m, 10H), 0.87 (t, J=7.1 Hz, 3H). $^{13}$C NMR (101 MHz, CDCl$_3$) δ 157.86, 152.78, 145.44, 138.51, 131.92, 128.28, 116.17, 70.06, 47.41, 32.20, 22.20, 20.45, 14.05. MS (m/z) [MH]+ calculated for C$_{18}$H$_{27}$N$_3$O 301.43; found: 301.62.

Metabolite Profiling 2 million HT-1080 cells were seeded in 10 cm culture dishes. The next day, cells were treated with 5 μg/mL erastin and incubated for 5 hours before metabolite extraction. 4 mL of cold 80% methanol was added to the cell monolayer to extract polar metabolites using a cell scraper. The cell lysate/methanol mixture was transferred to a 15 mL tube and centrifuged at 2,000×g at 4° C. for 10 minutes to pellet debris and proteins. The supernatant was transferred to a new tube and stored at −80° C. for liquid chromatography-mass spectrometry/mass spectrometry (LC-MS/MS) analysis. For lipid extract preparation, 3 mL of cold 100% isopropanol was added to the cell monolayer to scrape out cells. The resulting cell lysate/isopropanol mixture was transferred to a new 15 mL tube and centrifuged at 2,000×g at 4° C. for 10 minutes. The cleared supernatant was transferred to a new tube and stored at −20° C. for LC-MS/MS analysis.

RNAi Experiments

Small interfering RNA (siRNA) pools targeting ALOX15B and ALOXE3 were obtained from Dharmacon Technologies (Lafayette, Colo.). On the day of reverse-transfection, a cocktail of 1 mL of Opti-MEM (Invitrogen Corp., Carlsbad, Calif.), 6 μL of Lipofectamine RNAiMAX (Invitrogen), and 5 μL of 10 μM siRNA were prepared and transferred to each well of a 6-well plate. The 6-well plate was put in the tissue culture incubator for 20 minutes to allow the formation of transfection mixture. While the complex was forming, HT-1080 cells were trypsinized and the cell number was determined using ViCell (Trypan Blue). 200,000 cells were prepared in 1 mL of growth media with 2× serum, and then, the cell suspension was transferred to each well containing 1 mL of the transfection mix. The 6-well plate was returned to the incubator and the culture grown for 2 days. Then, cells were trypsinized and reverse-transfected again for two additional days to ensure knockdown. After a second round of reverse transfection, cells were trypsinized and treated with lethal compounds to examine the effect of the knockdown on drug sensitivity. RNA was harvested from a population of cells for RT-qPCR analysis.

GSH Depletion Assay 2 million cells were seeded on 10 cm dishes. The next day, cells were treated with compounds to induce GSH depletion followed by harvesting to determine cell number. Two million live cells from each sample were transferred to new tubes, and centrifuged at 1,000 rpm at 4° C. for 5 minutes. The cell pellet was resuspended in 1 mL of PB buffer (10 mM sodium phosphate buffer, 1 mM EDTA, pH 7) and sonicated using 60 Joule energy. The lysate was centrifuged at 13,200 rpm at 4° C. for 10 minutes, and then the cleared lysate was used to determine the amount of GSH in the sample. The QuantiChrome glutathione assay kit (BioAssay Systems, cat# DIGT-250) was used and the product instructions were followed to determine GSH level.

Cell Lines

The 4 BJ-derived cell lines, HT-1080 cells, and U-2-OS cells were maintained as described previously (Yang et al., 2008b).

RSL Testing

In order to test whether BSO and other antioxidant targeting agents exhibit the RSL phenotype, 4 BJ-derived cell lines, BJeH, BJeHLT, BJeLR, and DRD, were cultured and treated with compounds in a 2-fold dilution series as described previously (Yang et al., 2008a). Cell viability was determined using alamar blue and percent growth inhibition computed as described previously (Id.).

Cell Images

Bright field and fluorescence images were obtained using an EVOS$_{fl}$ fluorescence microscope.

Cellular ROS Assay Using Flow Cytometer 0.2 million cells were seeded in 6-well plates. The next day, culture media was replaced with 2 mL media containing 5 μM of CM-H$_2$DCF dye (Invitrogen, cat# C6827) and the culture was returned to the tissue culture incubator for 20 minutes. Cells were harvested in 15 mL tubes and washed twice with PBS followed by resuspending in 500 μL of PBS. The cell suspension was filtered through 0.4 μm nylon mesh and subjected to the flow cytometer analysis to examine the amount of ROS within cells. A C6 flow cytometry system (BD Accuri cytometers, BD Biosciences, San Jose, Calif.) was used for the flow cytometer analysis. When cells were prepared for flow cytometric analysis, different fluorescence intensities in the unstained samples were observed each time, indicating that cells had different autofluorescence upon passage. In order to compensate for changes in autofluorescence, the difference between the median fluorescence values of CM-H$_2$DCF stained samples and unstained samples were taken, and then the difference was divided by the median autofluorescence. The normalized ROS level was determined in this way for BJeH, BJeHLT, and BJeLR cells on the same day. The experiment was repeated 8 times on 8 different days.

Generating Stable Cell Lines Expressing GFP-ALOX5

A cDNA of ALOX5 (GeneBank ID: BC130332.1) was cloned into a pBabe-puro vector to express GFP fused ALOX5 (N-terminal GFP fusion) in cells. The plasmid was transfected into PLAT-GP cells (Cell Biolabs Inc., cat# RV-103, San Diego, Calif.) along with a pVSV-G helper plasmid to produce retrovirus harboring the expression plasmid. 0.2 million target cells (BJeH, BJeHLT, BJeLR or HT-1080 cells) were seeded in 10 cm tissue culture dishes and incubated in the tissue culture incubator for 1 day. A frozen stock of retrovirus solution was thawed at 37° C. for 2 minutes, and polybrene (Sigma, cat# H9268) was added at a final concentration of 8 μg/mL. Culture medium was replaced with virus/polybrene mix and the culture dish was incubated for two hours with rocking every 30 minutes. After 2 hours, 10 mL of growth media was added to culture dish, and the culture was incubated further for 2 days. Cell lines stably expressing GFP-ALOX5 protein were selected using 1.5 μg/mL puromycin and used for the GFP-ALOX5 translocation assay.

Lipid Peroxide Detection Using BODIPY-C11

Cells were treated with compounds, stained with 1 μM BODIPY-C11 (Invitrogen, cat# D3861), and subjected to flow cytometric analysis to determine the level of plasma membrane oxidation as described in the cellular ROS assay.

Cell Death Rescue by ALOX Inhibitors and COX Inhibitor

Lethal compounds were added to HT-1080 cells in the presence or absence of ALOX or COX inhibitors in a 2-fold dilution series. The concentrations of the inhibitors are listed along with vendor information in Table 2. Cell viability was determined using alamar blue and percent growth inhibition calculated as described above.

RT-qPCR

Total RNA from cells was prepared using an RNeasy kit (Qiagen, Germantown, Md.), and was reverse-transcribed using a High Capacity cDNA Reverse Transcription kit (Life Technologies, Inc., Grand Island, N.Y.). The resulting cDNA samples were mixed with TaqMan® probes for ALOX5, ALOX12, ALOX12B, ALOX15, ALOX15B and ALOXE3 and arrayed on a 96-well plate in triplicate. Each plate was loaded onto ViiA7 Real-Time PCR system (Life Technologies) for qPCR. Comparative analysis (delta delta Ct analysis) was performed using ACTB (human actin B) Ct value as a control.

Metabolic Stability Test

The mouse liver microsome assay on erastin and PE was performed at Shanghai Medicilon Inc. (Shanghai, China).

Mice Study

Athymic nude mice (8 weeks, Charles River) were injected with 4 million HT-1080 cells subcutaneously (SC). The next day, 400 μL of vehicle (0.625% DMSO/99.375% HBSS, pH 2) or 40 mg/kg PE were delivered to the SC site where HT-1080 cells were injected. Two days later, the SC injection was repeated. Three days later, 300$\mu$l of vehicle or 30 mg/kg PE were administered to the mice through a tail vein. The tail vein injection was repeated three times more, once every other day, before the final tumor size was measured in both groups.

Due to its poor solubility, erastin was prepared in 100% PEG-400 and delivered to nude mice with the same protocol as PE before the tail vein injection. 100% PEG-400 was toxic to nude mice, which prevented injection of erastin through the tail vein. Instead, erastin was injected through the SC route using the same schedule as PE until the tumor size was measured.

Statistics

To determine the significance between two groups, indicated in the figures by asterisks, comparisons were made using a Student's t-test, performed by Prism 5 software.

Example 2

Metabolite Profiling Reveals GSH Depletion as a Key Event Upon Erastin Treatment HT-1080 fibrosarcoma cells were treated with vehicle only or vehicle plus erastin, and polar metabolites and lipid samples extracted. The metabolite extract was subjected to LC-MS/MS analysis to determine the quantity of each metabolite in each sample. A total of 149 polar metabolites and 115 lipids were detected under these conditions (Table 5), and the fold change in each metabolite between vehicle-treated and erastin-treated sample was calculated (FIG. 1a).

TABLE 5

Changes in cellular metabolites upon erastin treatment.

| Metabolites | Erastin/DMSO | log2 (Erastin/DMSO) |
|---|---|---|
| glutathione reduced | 0.007019166 | −7.154484568 |
| alpha-glycerophosphocholine | 0.219393245 | −2.188408988 |
| glutathione oxidized | 0.323487361 | −1.628218751 |
| phosphocholine | 0.525200601 | −0.929059527 |
| isomer_of_erythrose-4-phosphate | 0.588678149 | −0.764449018 |
| glucuronate | 0.609972908 | −0.713182928 |
| C36:1 PC | 0.628637882 | −0.669698883 |
| C36:0 PC | 0.650147385 | −0.621161287 |
| phosphotyrosine | 0.65325359 | −0.614284946 |
| 2'-deoxyadenosine | 0.654860207 | −0.610741128 |
| C38:3 PC | 0.65972078 | −0.600072546 |
| 2-aminodipate | 0.664362669 | −0.589957085 |
| dUMP | 0.678665746 | −0.559226895 |
| C38:4 PC | 0.681438891 | −0.553343807 |
| dTMP | 0.698450125 | −0.517770996 |
| 5-HIAA | 0.728281128 | −0.457432634 |
| alpha-glycerophosphate | 0.755601314 | −0.404302884 |
| C22:6 CE | 0.784710293 | −0.349767971 |
| C20:3 CE | 0.786386118 | −0.346690241 |
| C14:0 CE | 0.78965845 | −0.340699315 |
| indoxylsulfate | 0.79128023 | −0.337739383 |
| serotonin | 0.792396909 | −0.335704842 |
| C32:0 PC | 0.794762338 | −0.331404587 |
| N-carbomoyl-beta-alanine | 0.795767915 | −0.329580363 |
| C34:0 PC | 0.797548892 | −0.326355132 |
| carnitine | 0.801997316 | −0.318330687 |
| NADH | 0.805068432 | −0.312816675 |
| triiodothyronine | 0.80664102 | −0.310001323 |
| C56:3 TAG | 0.810310731 | −0.303452849 |
| choline | 0.813880917 | −0.297110374 |
| taurine | 0.825870795 | −0.276012 |
| acetylcholine | 0.830711332 | −0.26758086 |
| kynurenic acid | 0.832177154 | −0.265037413 |
| C22:1 SM | 0.837383793 | −0.256039099 |
| C38:2 PC | 0.840512319 | −0.25065913 |
| C20:5 CE | 0.840682397 | −0.250367231 |
| OH-phenylpyruvate | 0.844239212 | −0.244276257 |
| GDP | 0.849679699 | −0.235008999 |
| ADMA | 0.858524915 | −0.220068092 |
| XMP | 0.859888851 | −0.217777906 |
| C54:1 TAG | 0.862815121 | −0.212876634 |
| creatine | 0.867524293 | −0.205023937 |
| C54:2 TAG | 0.869557029 | −0.201647447 |
| 5-hydroxytryptophan | 0.872515609 | −0.196747154 |
| C36:2 PC | 0.872862715 | −0.196173331 |
| C34:1 DAG | 0.882253588 | −0.180734703 |
| C38:5 PC | 0.883571889 | −0.178580575 |
| lactate | 0.883979768 | −0.177914745 |
| C54:10 TAG | 0.885067787 | −0.17614014 |
| thyroxine | 0.885869026 | −0.17483468 |
| cytosine | 0.886296508 | −0.174138665 |
| C24:1 SM | 0.893338826 | −0.16272063 |
| C30:0 PC | 0.895377526 | −0.159431988 |
| C52:1 TAG | 0.897011796 | −0.156801137 |
| ADMA/SDMA | 0.898537382 | −0.154349569 |
| C34:1 PC | 0.899331136 | −0.153075677 |
| UDP-galactose/UD-glucose | 0.900255041 | −0.151594322 |
| C36:4 PC | 0.902687749 | −0.147701067 |
| cotinine | 0.903721441 | −0.146049944 |
| C54:8 TAG | 0.906711066 | −0.141285202 |
| C56:10 TAG | 0.912891825 | −0.13148418 |
| C20:4 CE | 0.91405051 | −0.129654204 |
| NAD | 0.915714934 | −0.127029543 |
| C36:2 DAG | 0.916299532 | −0.126108813 |
| dCMP | 0.918389857 | −0.122821386 |
| C18:1 CE | 0.919786047 | −0.120629782 |
| C18:1 SM | 0.924983033 | −0.112501192 |
| C36:3 PC | 0.925067537 | −0.112369398 |
| C18:3 CE | 0.927653854 | −0.108341519 |
| niacinamide | 0.928866408 | −0.106456976 |
| C16:1 CE | 0.932056894 | −0.101510073 |
| C36:1 DAG | 0.933434013 | −0.099380057 |
| dimethylglycine | 0.933774768 | −0.09885349 |
| UDP-glucuronate | 0.933907721 | −0.09864809 |
| C36:2 PE | 0.93515925 | −0.09671603 |
| CMP | 0.937603038 | −0.092950851 |
| thiamine | 0.938498287 | −0.091573984 |
| sebacate | 0.941865852 | −0.086406501 |
| C46:0 TAG | 0.942410966 | −0.085571768 |
| C30:2 PC | 0.946705557 | −0.079012305 |
| ornithine | 0.948182209 | −0.076763771 |
| C18:2 CE | 0.948348099 | −0.076511386 |
| maleate/3-methyl-2-oxobutanoate | 0.94837736 | −0.076466872 |
| leucine | 0.949707988 | −0.074444106 |
| SDMA | 0.950466635 | −0.073292111 |
| C56:4 TAG | 0.950487716 | −0.073260113 |
| allantoin | 0.951233865 | −0.072128018 |
| histamine | 0.952625653 | −0.070018696 |
| isoleucine | 0.952635304 | −0.070004079 |
| betaine | 0.952796343 | −0.069760219 |
| C34:0 PE | 0.953254544 | −0.069066592 |
| C36:0 PE | 0.95381856 | −0.068213239 |
| C22:0 SM | 0.959998728 | −0.058895601 |
| ADP | 0.961640039 | −0.05643113 |
| C24:0 SM | 0.962145378 | −0.055673196 |
| C50:0 TAG | 0.962510978 | −0.0551251 |
| salicylurate | 0.963666252 | −0.053394512 |
| C16:0 CE | 0.964279781 | −0.052476297 |
| F1P | 0.96524394 | −0.051034503 |
| lysine | 0.9653934 | −0.050811131 |
| carnosine | 0.965734713 | −0.050301159 |
| C44:0 TAG | 0.968298141 | −0.04647677 |
| C54:3 TAG | 0.969176301 | −0.045168967 |
| methionine | 0.970222491 | −0.043612471 |
| C56:2 TAG | 0.970268868 | −0.043543512 |
| C38:6 PC | 0.970772017 | −0.042795573 |
| sorbitol | 0.970919029 | −0.042577109 |
| glucose | 0.971664149 | −0.041470356 |
| creatinine | 0.972042775 | −0.040908293 |
| glycine | 0.972285702 | −0.040547789 |
| citrate | 0.9739683 | −0.038053277 |
| histidine | 0.977875379 | −0.032277475 |
| xanthosine | 0.98003751 | −0.029091127 |
| C16:1 SM | 0.980789892 | −0.027983984 |
| 4-hydroxybenzoate | 0.981508946 | −0.026926678 |
| hypoxanthine | 0.981943367 | −0.026288275 |
| C34:2 PE | 0.982012323 | −0.026186967 |
| C32:0 PE | 0.982068705 | −0.026104136 |
| tyrosine | 0.982090761 | −0.026071736 |
| fumarate | 0.9821554 | −0.025976783 |
| valine | 0.982181785 | −0.025938027 |
| C38:4 PI | 0.982255832 | −0.025829266 |
| phosphoglycerate | 0.984827133 | −0.022057585 |
| C56:9 TAG | 0.986500661 | −0.019608077 |
| arginine | 0.98662075 | −0.019432465 |
| alpha-ketoglutarate | 0.98674206 | −0.019255089 |
| NMMA | 0.988556175 | −0.016605146 |
| tryptophan | 0.991129404 | −0.012854663 |
| threonine | 0.99243953 | −0.010948895 |
| C36:1 PE | 0.995288791 | −0.006812899 |
| C52:2 TAG | 0.996404827 | −0.005196084 |
| glycocholate | 0.997470442 | −0.003654004 |
| C32:1 PC | 0.999765803 | −0.000337915 |
| 4-pyridoxate | 1.000128453 | 0.000185307 |
| UDP | 1.002008092 | 0.00289416 |
| suberate | 1.003221833 | 0.004640651 |
| phenylalanine | 1.004872604 | 0.00701261 |
| hippurate | 1.005321858 | 0.007657461 |
| C36:0 PI | 1.006349047 | 0.009130783 |
| succinate/methylmalonate | 1.008198544 | 0.011779776 |
| C18:0 CE | 1.009518499 | 0.013667348 |
| glucose/fructose/galactose | 1.010633942 | 0.015260538 |
| C50:1 TAG | 1.011393801 | 0.016344841 |
| C30:1 PC | 1.013872124 | 0.019875703 |
| glutamine | 1.014636611 | 0.020963123 |
| quinolinate | 1.015210174 | 0.021778432 |
| aspartate | 1.017140543 | 0.024519037 |
| C32:2 PE | 1.017862786 | 0.025543091 |
| C18:0 SM | 1.017897199 | 0.025591866 |
| urate | 1.017972662 | 0.025698818 |

TABLE 5-continued

Changes in cellular metabolites upon erastin treatment.

| Metabolites | Erastin/DMSO | log2 (Erastin/DMSO) |
|---|---|---|
| oxalate | 1.018599015 | 0.026586227 |
| glutamate | 1.019332193 | 0.027624292 |
| C36:2 PI | 1.020645543 | 0.029481923 |
| pimelate/3-methyladipate | 1.021056242 | 0.030062336 |
| C32:1 PE | 1.023921785 | 0.034105516 |
| hydroxyphenylacetate | 1.024067694 | 0.034311085 |
| malonate | 1.025230038 | 0.035947654 |
| xanthine | 1.026812674 | 0.038173008 |
| C16:0 SM | 1.03011789 | 0.042809454 |
| folate | 1.032057885 | 0.045523889 |
| citrulline | 1.035673991 | 0.050569944 |
| aconitate | 1.036400242 | 0.051581258 |
| C34:1 PE | 1.040149897 | 0.056791452 |
| kynurenine | 1.040294446 | 0.056991928 |
| C52:0 TAG | 1.040694863 | 0.057547126 |
| C58:6 TAG | 1.047110675 | 0.066413937 |
| C56:6 TAG | 1.047483699 | 0.066927793 |
| C34:2 PC | 1.04850576 | 0.068334787 |
| UMP | 1.048921414 | 0.068906594 |
| ribulose-5-P | 1.050528526 | 0.071115337 |
| isocitrate | 1.051095653 | 0.071893965 |
| dGMP | 1.051722504 | 0.072754102 |
| serine | 1.053459932 | 0.075135443 |
| glycodeoxycholate | 1.053739818 | 0.075518692 |
| C32:1 DAG | 1.054515427 | 0.076580201 |
| glycerol | 1.058311744 | 0.081764661 |
| C48:1 TAG | 1.058553333 | 0.082093958 |
| alanine | 1.061199956 | 0.08569652 |
| C14:0 SM | 1.06154999 | 0.086172311 |
| C56:7 TAG | 1.061814078 | 0.086531175 |
| C54:7 TAG | 1.062074534 | 0.086885014 |
| IMP | 1.064629663 | 0.090351669 |
| GMP | 1.065877096 | 0.092041093 |
| glycochenodeoxycholate | 1.066841635 | 0.093346034 |
| asparagine | 1.069265793 | 0.096620515 |
| AMP | 1.071274609 | 0.099328346 |
| C58:7 TAG | 1.071364555 | 0.099449473 |
| C50:2 TAG | 1.073465707 | 0.102276104 |
| nicotinate | 1.085143298 | 0.11788557 |
| C34:4 PC | 1.085975817 | 0.118991978 |
| proline | 1.086372681 | 0.119519106 |
| C34:2 DAG | 1.088758408 | 0.122683861 |
| cystamine | 1.090375283 | 0.124824764 |
| adipate | 1.090949568 | 0.125584411 |
| C36:3 DAG | 1.091715359 | 0.126596754 |
| proprionate | 1.091955783 | 0.126914438 |
| taurolithocholate | 1.09332259 | 0.128719138 |
| C48:0 TAG | 1.098431827 | 0.135445333 |
| cis/trans hydroxyproline | 1.09933747 | 0.136634327 |
| taurocholate | 1.108372993 | 0.148443463 |
| ribos-5-P | 1.113413382 | 0.154989328 |
| C58:8 TAG | 1.117508568 | 0.160285893 |
| C48:2 TAG | 1.12096538 | 0.164741723 |
| C52:3 TAG | 1.123502729 | 0.168003629 |
| G6P | 1.133663732 | 0.180992771 |
| C56:5 TAG | 1.133971203 | 0.181384003 |
| C34:3 PC | 1.133988835 | 0.181406437 |
| phenylacetylglycine | 1.135117956 | 0.182842224 |
| orotate | 1.137904549 | 0.186379544 |
| malate | 1.143460137 | 0.193406072 |
| PEP | 1.146683618 | 0.197467392 |
| taurodeoxycholate | 1.167748017 | 0.223728996 |
| C46:1 TAG | 1.170876947 | 0.227589464 |
| GABA | 1.172608132 | 0.229720966 |
| phosphocreatine | 1.172975218 | 0.230172534 |
| C34:1 PI | 1.17332592 | 0.230603812 |
| C58:9 TAG | 1.175775533 | 0.233612662 |
| C54:4 TAG | 1.177998885 | 0.236338174 |
| C56:8 TAG | 1.178339088 | 0.23675476 |
| taurochenodeoxycholate | 1.180889408 | 0.23987386 |
| glyceraldehyde-3-phosphate | 1.191624534 | 0.252929733 |
| pantothenate | 1.19447216 | 0.256373229 |
| ascorbate | 1.196279953 | 0.258555047 |
| C32:2 PC | 1.218164138 | 0.284708538 |
| trimethylamine-N-oxide | 1.222211727 | 0.289494228 |
| DHAP | 1.227273271 | 0.295456523 |
| 5-HIAA | 1.230853823 | 0.299659437 |
| C50:3 TAG | 1.241015719 | 0.31152139 |
| Anthranilic acid | 1.242119129 | 0.312803546 |
| adenine | 1.25362125 | 0.326101541 |
| thymine | 1.257201762 | 0.330216199 |
| C32:1 PI | 1.261000876 | 0.334569278 |
| cystathionine | 1.262988673 | 0.336841701 |
| cAMP | 1.266090474 | 0.340380502 |
| C54:6 TAG | 1.266720903 | 0.341098691 |
| C50:5 TAG | 1.277049931 | 0.352814934 |
| C52:5 TAG | 1.27898172 | 0.354995644 |
| Pyruvate | 1.2826948 | 0.359177941 |
| C34:2 PI | 1.286345341 | 0.36327801 |
| F16DP/F26DP/G16DP | 1.302764118 | 0.38157589 |
| C52:4 TAG | 1.305344833 | 0.384430974 |
| C54:5 TAG | 1.315083914 | 0.395154859 |
| C54:9 TAG | 1.331382859 | 0.412925499 |
| Adenosine | 1.375972395 | 0.460451527 |
| C36:4 PI | 1.394818145 | 0.480077037 |
| Thymidine | 1.402373491 | 0.48787063 |
| Sucrose | 1.408292599 | 0.493947112 |
| C48:3 TAG | 1.520115971 | 0.604181392 |
| C46:2 TAG | 1.541893629 | 0.624703241 |
| C52:6 TAG | 1.601679465 | 0.679585459 |
| C44:1 TAG | 1.638829022 | 0.712665346 |
| C50:4 TAG | 1.681973845 | 0.750155272 |
| 2'-deoxycytidine | 1.737193761 | 0.796758677 |
| Inosine | 1.866736341 | 0.900518175 |
| C18:0 LPC | 3.335435273 | 1.737875045 |
| C14:0 LPC | 3.625332845 | 1.858113456 |
| C18:1 LPC | 3.743522467 | 1.904396413 |
| C16:0 LPC | 3.818006928 | 1.932819721 |
| Uridine | 4.368573078 | 2.127162124 |
| Guanosine | 4.509507284 | 2.172969811 |
| C16:1 LPC | 5.385771704 | 2.429153077 |
| Cytidine | 6.078961728 | 2.603824936 |
| C22:6 LPC | 8.455937356 | 3.079964689 |
| C20:4 LPC | 8.518404873 | 3.090583302 |

The name and fold change of the metabolites examined in FIG. 1a are listed here. The mean value of the abundance of each metabolite was calculated from four independent samples in each drug treatment condition and used to determine the fold change between erastin treatment and DMSO (the vehicle) treatment.

It was found that both reduced glutathione (GSH) and oxidized glutathione (GSSG) were depleted significantly upon erastin treatment, whereas the level of lysophosphatidyl choline (lyso-PC) was increased. This was intriguing, because lyso-PC has been reported to increase the permeability of cell membranes and to induce cell death involving oxidative species, which is rescued by antioxidants in fibroblasts (Colles et al., 2000). The effects of purified lyso-PC on erastin-induced cell death were tested in HT-1080 cells. The results show that lyso-PC modestly sensitized cells to erastin-induced cell death (FIGS. 5a and b), suggesting that lyso-PC contributes to erastin's lethality. However, lyso-PC did not show differential cytotoxicity between BJeH (BJ-TERT) and BJeLR (BJ-TERT/LT/ST/HRAS$^{V12}$) engineered cells (Yang et al., 2008a), suggesting that generation of lyso-PC is not sufficient to cause RAS synthetic lethality (FIG. 5c).

The significant depletion of GSH/GSSG, on the other hand, was intriguing, because erastin treatment induces the generation of reactive oxygen species (ROS), resulting in an oxidative form of cell death (Yagoda et al., 2007). GSH/GSSG constitutes a major cellular antioxidant system and provides reducing power to remove oxidative species. Three cell lines were treated with erastin, their GSH levels were determined using Ellman's reagent, and a dose-dependent, GSH-depleting effect of erastin was confirmed (FIG. 1b and FIG. 5d). Because GSH is a major antioxidant produced by cells, its depletion should make cells more sensitive to oxidative stress. Thus, U-2 OS cells were treated with tert-butylhydroperoxide (TBHP) in the presence of erastin, and observed that erastin made cells more sensitive to TBHP-induced cell death (FIG. 5e). Indeed, GSH depletion by erastin is necessary for erastin's lethality, because supplementing the culture medium with GSH itself or N-acetylcysteine (NAC), a precursor of GSH, rescued cells from erastin lethality (FIGS. 5f and 5g).

Whether the GSH-depleting activity of erastin was essential for its lethality was further tested. A synthetic route to access multiple erastin analogs was established, and these analogs were tested for potency and selectivity in BJ-derived tumorigenic cells (FIG. 1c). Three compounds (MEII, PE, AE) retained the RSL phenotype, whereas the other three (A8, PYR, dMK) did not display lethality (FIG. 1c). In addition, the following analogs were also made and tested for potency and selectivity.

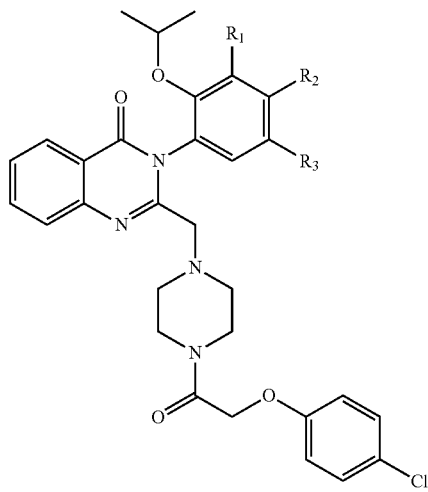

| Compound No. | $R_1 =$ | $R_2 =$ | $R_3 =$ | $EC_{50}$ | Selectivitey score |
|---|---|---|---|---|---|
| 51 | ⤳N(morpholine-CH2) | H | H | 1.17 μM | 4 |
| 52 | H | ⤳N(morpholine-CH2) | H | 4.7 μM | 3.3 |
| 40 | H | H | ⤳N(morpholine-CH2) | 0.13 μM | 9.2 |

* selectivity score = $EC_{50}$ (BJeH)/$EC_{50}$ (BJeLR)

Because changes at position $R_3$ of structure (100) above improved potency and selectivity, additional analogs were created and tested.
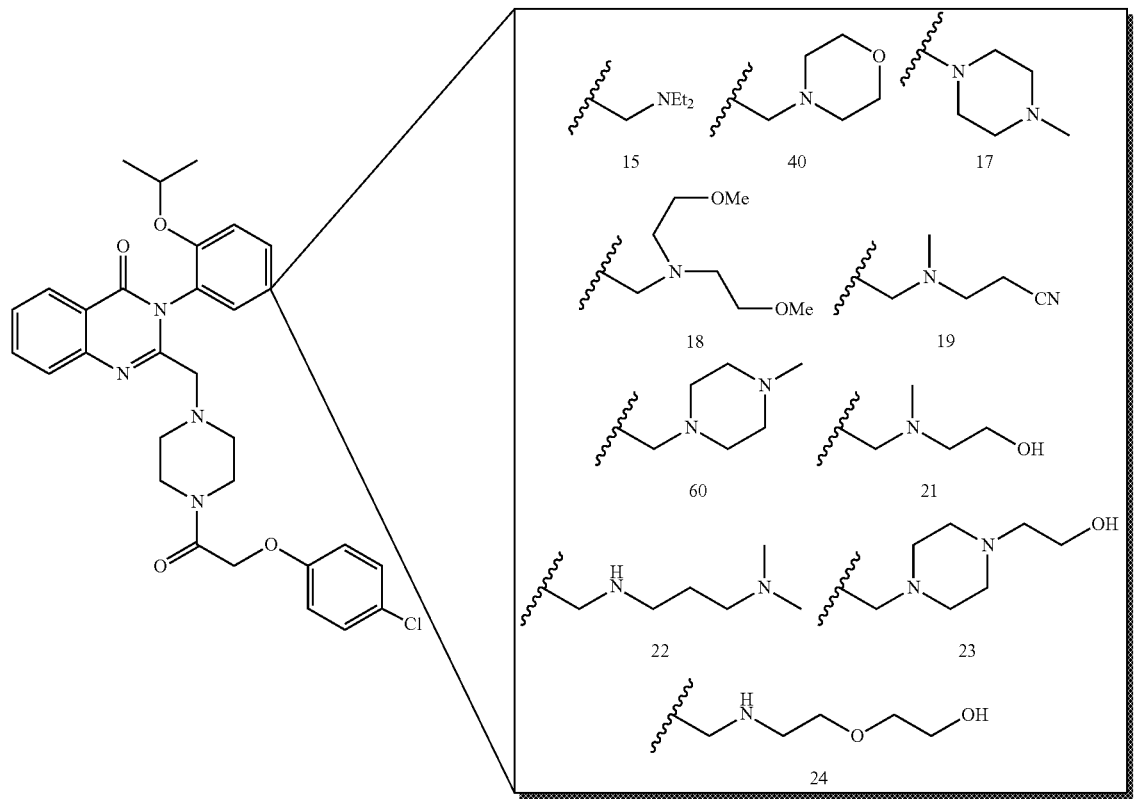
| Compound | EC$_{50}$ (BJeLR) | Selectivity score |
| --- | --- | --- |
| erastin | 1.78 μM | 4.7 |
| 15 | 1.68 μM | 4.1 |
| 40 | 0.13 μM | 9.2 |
| 17 | 0.90 μM | 7.3 |
| 18 | 0.14 μM | 5.9 |
| 19 | 0.26 μM | 5.1 |
| 60 | 0.60 μM | 3.8 |
| 21 | 0.36 μM | 3.7 |
| 22 | 2.30 μM | 3.3 |
| 23 | 1.20 μM | 2.8 |
| 24 | 2.10 μM | 2.5 |

Changes at other positions other than $R_3$ of structure (100) above generally lowered the selectivity and potency, as demonstrated by the testing of the following analogs.

(two with and two without oncogenic-HRAS), through which RSLs such as erastin were discovered (Dolma et al., 2003). When the four BJ-derived cells were treated with

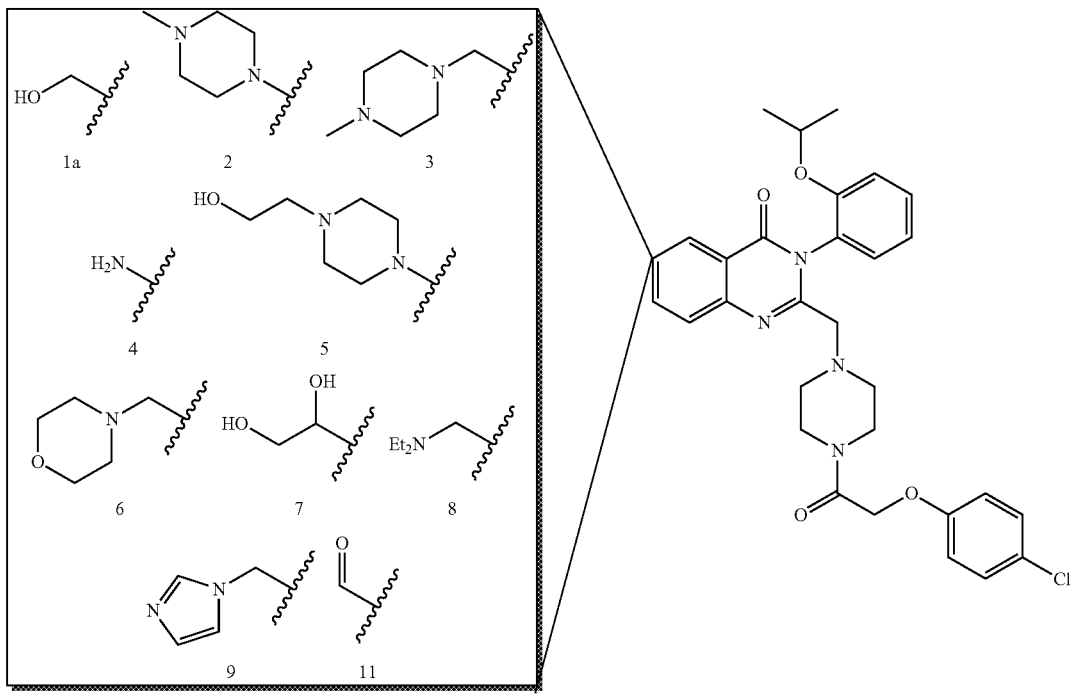

| Compound | $EC_{50}$ (BJELR) | Selectivity Score |
| --- | --- | --- |
| erastin | 1.8 µM | 4.7 |
| 1a | 4.8 µM | 3.5 |
| 2 | >10 µM | N/A |
| 3 | >10 µM | N/A |
| 4 | 0.9 µM | >25.0 |
| 5 | >10 µM | N/A |
| 6 | 2.7 µM | 3.8 |
| 7 | 3.7 µM | 4.5 |
| 8 | 4.4 µM | 2.4 |
| 9 | 0.47 µM | 6.3 |
| 11 | 2.0 µM | 6.8 |

Of these analogs, six analogs (MEII (Compound 40), PE (Compound 30), AE (Compound 50), A8, PYR, and dMK) were tested along with erastin in HT-1080 cells, and the relationship between the GSH-depleting activity and the lethality of each analog was examined (FIG. 1d). As set forth above, three compounds (MEII, PE, AE) retained the RSL phenotype, whereas the other three (A8, PYR, dMK) did not display lethality (FIG. 1c). Buthioninesulfoximine (BSO) was used as a positive control for GSH depletion. BSO is an irreversible inhibitor of γ-glutamyl cysteine synthetase, which catalyzes the first step in glutathione synthesis, and has been widely used for depleting GSH in a variety of experimental conditions. Active analogs of erastin depleted cellular GSH more effectively than inactive analogs of erastin (FIG. 1d), which further suggested that the GSH-depleting activity of erastin is necessary for erastin-induced cell death.

The inventors reasoned that if GSH depletion was sufficient for erastin lethality, then GSH depletion by other reagents should phenocopy erastin's selective lethality in the four BJ-cell line system, which consists of isogenic cell lines (two with and two without oncogenic-HRAS), through which RSLs such as erastin were discovered (Dolma et al., 2003). When the four BJ-derived cells were treated with BSO, an RSL phenotype was observed (FIG. 1e), suggesting that GSH depletion by erastin is sufficient for its oncogenic-RAS-selective lethality.

The cell death pathways activated by erastin and BSO appeared to be similar, as assessed by profiling a panel of cell death inhibitors against each compound in an adaptation of the recently reported modulatory profiling strategy (FIG. 1f) (Wolpaw et al., 2011). These results indicated that erastin likely acts through a dual targeting mechanism to induce synthetic lethality. First, it binds and perturbs mitochondrial VDACs as reported (Kumar et al., 2012), and second, it depletes GSH through preventing cystine uptake via inhibition of system $xc^-$ (Dixon et al., 2012). Both knockdown of VDAC2/3 (Kumar et al., 2012) and supplementation of GSH (FIG. 5g) were effective in rescuing cells from erastin's lethality.

Example 3

Targeting Antioxidants is not Sufficient to Induce Ferroptosis

Because GSH depletion appeared to be critical for erastin lethality, how GSH depletion by erastin induces synthetic lethality with RAS was investigated. It has been hypothesized that most cancer cells, including RAS-transformed cells (Irani et al., 1997), are under high levels of oxidative stress (Szatrowski et al., 1991), which needs to be balanced by increasing the ROS-scavenging capacity to prevent oxidative damage (Hussain et al., 2003). In this model, targeting ROS-scavenging systems, including GSH, could cause an imbalance in this equilibrium, leading to oxidative cell death (Chuang et al., 2003; Trachootham et al., 2006). In order to test whether this simple hypothesis could explain erastin's selective lethality, basal ROS levels in the four BJ-derived engineered cell lines was examined using $H_2DCF$, a ROS sensor. It was confirmed that BJeLR cells have elevated ROS compared to BJeH and BJeHLT (BJ-TERT/LT/ST) cells. However, the level of increase varied among passages (FIG. 2a). Initially, the inventors speculated that this finding could explain why GSH-depleting reagents such as erastin and BSO induce selective cell death in oncogenic-RAS expressing cells. If true, other anti-oxidant targeting reagents should also induce the RSL phenotype in these four BJ cell lines. To test this possibility, the four BJ cell lines were treated with a SOD inhibitor (DETC), a thiol-reactive reagent (DIA), a glutaredoxin inhibitor (IAA), a thiredoxinreductase inhibitor (DCNB), or a catalase inhibitor (ATZ) (FIG. 2b and FIG. 6). Erastin and BSO consistently showed an RSL phenotype in these four BJ cells; however, none of the other anti-oxidant targeting compounds displayed an RSL phenotype, which indicates that it is not possible to induce oncogenic-RAS-selective lethality by simply targeting the antioxidant system. Instead, these results suggested that unique biochemical changes downstream of GSH depletion were responsible for the synthetic lethality with oncogenic RAS.

One possibility for those results was that erastin selectively depletes GSH in tumor cells harboring oncogenic RAS. Thus, the degree of GSH depletion upon erastin treatment in the 4 BJ cell lines was examined (FIG. 2c). It was found that these four BJ-derived cell lines contained varying amounts of basal GSH in the absence of any treatment, as reported previously (Kang et al., 1992), but were depleted of GSH to a similar low level upon erastin treatment. The concentration of erastin used in this experiment was lethal to BJeLR and DRD cells (containing oncogenic HRAS), but was not lethal to BJeH and BJeHLT cells (with wild-type RAS proteins) even upon prolonged incubation (FIG. 2b). Therefore, the selective lethality among these cells was not caused by differential depletion of GSH or by differences in the basal level of GSH. Rather, downstream events occurring after GSH depletion were selectively activated in the sensitive cell lines.

Example 4

Selective Activation of ALOXs is Responsible for RSL Phenotype of Erastin

One consequence of GSH depletion could be activation of lipoxygenases (products of ALOX genes) (Li et al., 1997; Shornick et al., 1993). Lipoxygenases generate lipid peroxides from unsaturated lipids such as arachidonic acid, and use free iron as a cofactor. Oxidation of the catalytic iron is known to be an essential step in the enzyme reaction, making this a point of enzyme regulation. Depletion of GSH accelerates iron oxidation, leading to activation of lipoxygenases (Haeggstrom et al., 2011).

ALOX5 is one of the six human ALOX genes and plays a critical role in leukotriene synthesis. In the basal state, the ALOX5 protein remains in the nucleus; however, upon activation, it translocates to the nuclear membrane (Chen et al., 2001). In order to examine whether ALOX proteins are activated upon erastin treatment, GFP-tagged ALOX5 was expressed in the BJ-derived cell lines and whether erastin treatment had any effect on the location of GFP-ALOX5 was examined (FIG. 2d). A positive control for GFP-ALOX5 translocation, treatment with ionomycin, induced localization of GFP-ALOX5 to the nuclear membrane in all BJ-derived cell lines (FIG. 7). In contrast, only in BJeLR cells (harboring $HRAS^{G12V}$) was GFP-ALOX5 translocated to the nuclear membrane upon erastin treatment (FIG. 2d). These results suggested that activation of ALOX proteins after GSH depletion occurs selectively in oncogenic-RAS-expressing cells, leading to lipid peroxidation and oxidative cell death. GFP-ALOX5 was expressed in HT-1080 cells with oncogenic, mutant NRAS and the same translocation event upon erastin treatment was observed (FIG. 2e). It is unlikely that erastin activates lipoxygenases through calcium upregulation, as ionomycin does, for multiple reasons. First, the kinetics of GFP-ALOX5 translocation in response to erastin differed from that seen upon ionomycin treatment (FIG. 2e). Second, calcium chelators were not effective in suppressing erastin-induced cell death (Wolpaw et al., 2011). Third, flow cytometer analysis with Fluo-4, an intracellular calcium reporter, did not show any increase in calcium after erastin treatment (data not shown).

The three BJ-derived cell lines were stained with BODIPY-C11, a membrane targeted lipid ROS sensor, and fluorescence was monitored using flow cytometry to detect lipid peroxidation caused by the activation of ALOX proteins (FIG. 2f). BJeLR cells (with oncogenic $HRAS^{V12}$) exhibited a stronger BODIPY-C11 fluorescence than BJeH and BJeHLT cells (with wild-type RAS proteins), which further supported the hypothesis that activation of ALOXs occurs selectively in cells expressing oncogenic RAS (FIG. 2f). The activation of ALOX proteins was required for lethality, as five different ALOX inhibitors were able to prevent erastin-induced cell death (FIG. 2g). Indomethacin, a cyclooxygenase inhibitor, was only minimally effective in suppressing erastin lethality, highlighting the importance of lipoxygenases, but not cyclooxygenases, in erastin-mediated cell death.

Example 5

RSL3 Also Activates ALOX-Dependent Ferroptosis

The inventors examined whether GSH depletion and activation of lipoxygenases was applicable to RSL3, another oncogenic-RAS-selective lethal compound (Yang et al., 2008a), or whether this mechanism was unique to erastin. The cell death induced by erastin and RSL3 share common features, such as iron-, MEK-, and ROS-dependence; however, tumor cells had different responses to erastin and RSL3 in the presence of cobalt, TLCK, cycloheximide, and, N-acetyl-cysteine (FIG. 8). Importantly, RSL3 is not dependent on VDAC2/3 (Yang et al., 2008) or system xc− (Dixon et al., 2012), implying that a different initiating mechanism can converge on a similar form of ferroptotic cell death.

When cellular GSH levels during RSL3-induced cell death were examined, it was found that GSH remained unaffected by a lethal RSL3 dose in BJeLR cells, which was in sharp contrast to erastin's effect (FIG. 3a). However, RSL3 caused GFP-ALOX5 translocation to the nuclear membrane in BJeLR cells, suggesting that activation of ALOX proteins could be a common lethal event between erastin and RSL3 (FIG. 3b). As with erastin, five different ALOX inhibitors, but not a COX inhibitor, suppressed cell death induced by RSL3, reinforcing the importance of ALOX proteins in the lethal mechanism of both of these two compounds (FIG. 3c). Furthermore, BODIPY-C11 staining demonstrated the generation of lipid peroxides in RSL3-treated cells (FIG. 3d).

Example 6

Synthetic Lethality with RAS Occurs Through an ALOX-Dependent Pathway

In order to validate the critical role of ALOX proteins in inducing selective lethality, cellular lipoxygenase was activated by knocking down GPX4, which is a phospholipid hydroperoxidase (Imai et al., 2003) and known to counter the effects of lipoxygenases by reducing lipid hydroperoxides, but also to negatively regulate lipoxygenases through a feedback mechanism; i.e. lipid peroxides cause further activation of ALOXs (Imai et al., 2003). Deletion of Gpx4 in mice is embryonic lethal. However, mouse embryo fibroblasts (MEFs) from Gpx4$^{+/-}$ mice have increased lipid peroxide levels compared to wild-type MEFs (Ran et al., 2003).

Knockdown of GPX4 caused an increase in the level of lipid peroxides, and induced cell death in HT-1080 cells (FIG. 3e and FIG. 9a). Cell death induced by siGPX4 accompanied translocation of GFP-ALOX5 to the nuclear membrane, as was seen with erastin and RSL3 (FIG. 3f). This translocation was specific to siGPX4, because cell death induced by a pool of siRNAs targeting multiple essential genes (siDeath) did not translocate GFP-ALOX5. Moreover, the cell death induced by siGPX4 was rescued by an iron chelator (DFOM), a MEK inhibitor (U0126), an antioxidant (Vit. E), and an ALOX inhibitor (ZIL), which suggested that GPX4 knockdown induced ferroptotic cell death (FIG. 3g). Finally, siGPX4 induced selective cell death in BJeLR and DRD cells (with oncogenic HRAS), but not BJeH and BJeHLT cells (lacking oncogenic HRAS) (FIG. 3h and FIG. 9b). In a separate study, cellular binding proteins for RSL3 were characterized using chemoproteomic approaches (data not shown). The unbiased search for RSL3-binding proteins identified GPX4 as the highest priority target. Taken together, these results indicate that GSH-depletion by erastin and GPX4 inhibition by RSL3 or siGPX4 are two mechanisms for activating lipoxygenases, leading to cell death involving oxidative lipid damage.

To determine the generality of these findings, lipid peroxidation levels and the degree of cell death suppression by ALOX inhibitors upon treatment of BJeLR cells or HT-1080 cells with other RSL compounds were examined. In a larger screening campaign to find additional RSL compounds, 14 RSLs were identified out of more than a million compounds tested (FIG. 10a) (Weiwer et al., 2012; Yang et al., 2012). The RSL activity of these 14 compounds was confirmed in the four BJ-derived cell lines (FIG. 10b). This four-BJ-cell-line testing has been productive in discovering genuine RSL compounds. For example, natural cancer cell lines with NRAS or KRAS mutations were sensitive to the RSL compounds, and knockdown of mutant RAS genes rescued cells from RSL-induced cell death (Yang et al., 2008a; Yagoda et al., 2007). Furthermore, there was a correlation between the sensitivity of erastin and phospho-ERK levels, a surrogate marker for RAS activation, in 12 natural cancer cell lines (Yagoda et al., 2007), highlighting the oncogenic RAS selectivity of RSL compounds in genuine tumor cell lines, despite the fact that they were identified from the four engineered BJ-derived cell lines.

The degree of structural similarity among these 14 RSL compounds, erastin and RSL3 was determined using the Tanimoto coefficient, in order to quantitatively define which of these 14 RSL compounds are simple analogs of each other. Most were structurally diverse, which led to the definition of 12 independent RSL groups, including erastin and RSL3 (FIG. 10c). Ten structurally diverse and representative RSLs were chosen to use in subsequent experiments.

BJeLR cells treated with the 10 additional RSL compounds exhibited an increase in BODIPY-C11 fluorescence, indicating that lipid peroxides were generated (FIG. 11). 11 non-RSL lethal compounds with diverse lethal mechanisms were tested to see whether they induced lipid peroxide generation. These 11 lethal compounds were confirmed to be non-RSL compounds previously (Root et al., 2003). It was found that 10/11 of the non-RSL compounds did not generate lipid peroxides, implying a specificity of lipid peroxidation to RSL compound treatment (FIG. 11). Of note, phenylarsine oxide (PAO) increased the BODIPY-stained cell population, albeit significantly less than the RSL compounds. It is likely that the known ROS-generating activity of PAO oxidized the BODIPY-C11 dye (Fanelus, 2008).

In order to examine the requirement of ALOX proteins for the lethality of each compound, HT-1080 cells were treated with each lethal compound (RSLs and non-RSLs) in the presence or absence of baicalein (BAI) or zileuton (ZIL), the two ALOX inhibitors. Both ALOX inhibitors strongly suppressed cell death induced by all RSL compounds (FIG. 12). The rescuing effect of these ALOX inhibitors was specific to RSL compounds, because the ALOX inhibitors were not able to suppress cell death induced by eleven non-RSL compounds (FIG. 8). The degree of cell death suppression was quantified by calculating the normalized differences in the AUC (Area Under the Curve) of the compound alone curve and compound with zileuton curve. Combined with the BODIPY-C11 staining data, these results revealed that all RSL compounds are mechanistically distinct from the 11 non-RSL compounds (FIG. 4a).

Figure 13:
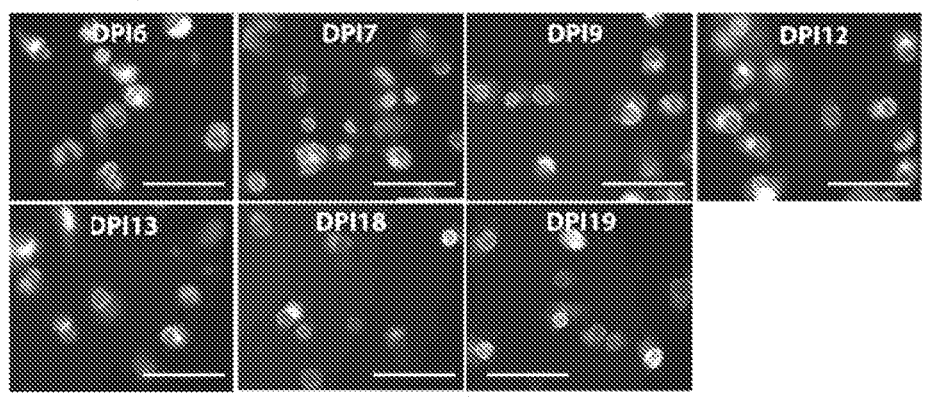
Figure 13:
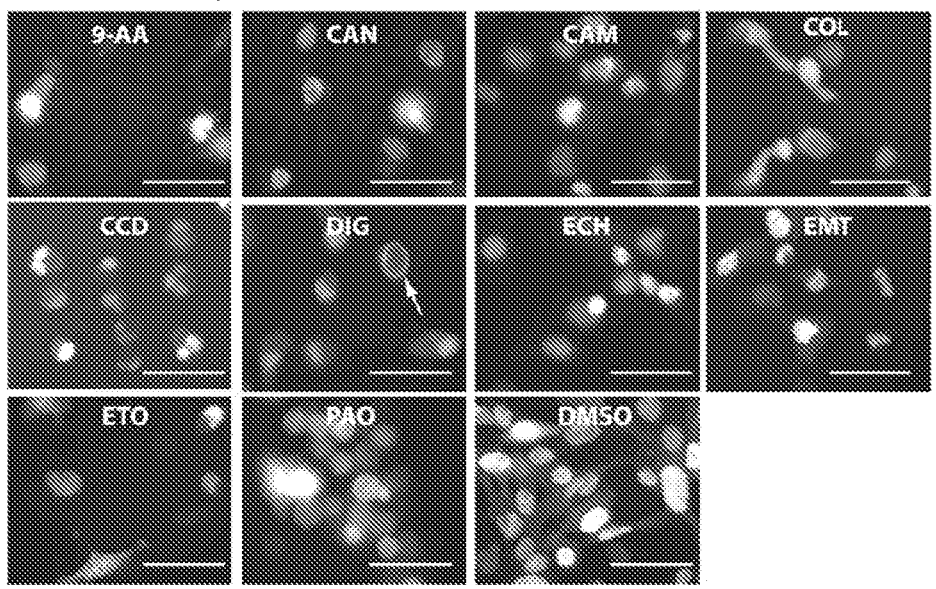
Figure 13:
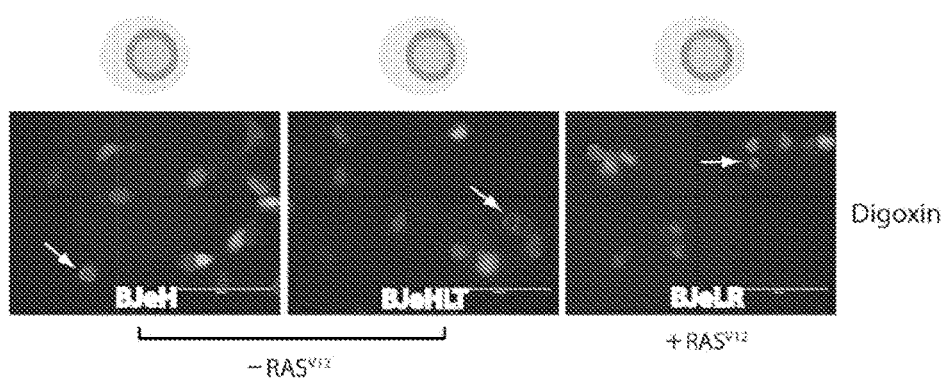

Next, GFP-ALOX5-expressing HT-1080 cells were treated with these non-RSL and RSL compounds and changes in the location of GFP-ALOX5 were monitored as a measure of ALOX protein activation. All RSL compounds induced translocation of GFP-ALOX5 to the nuclear membrane, whereas of the eleven different non-RSL compounds, only digoxin induced GFP-ALOX5 translocation (FIG. 4b and FIG. 13). Digoxin is known to elevate intracellular calcium (McGarry et al., 1993), which is likely to cause the translocation of GFP-ALOX5, similar to ionomycin. Note that ionomycin and digoxin are not RSL compounds and induce translocation of GFP-ALOX5 non-specifically in the BJ-derived cell lines (FIGS. 7 and 13). The results highlight the importance of selective ALOX activation for the induction of the RSL phenotype.

The suppression of RSL-induced cell death by lipoxygenase inhibitors implied that knocking down ALOX expression using RNA interference (RNAi) might rescue cells from RSL-induced cell death, if there is a lack of functional redundancy among ALOX genes. There are six ALOX genes in humans—ALOX5, ALOX12, ALOX12B, ALOX15, ALOX15B, and ALOXE3. These genes have different expression patterns among different tissues; therefore, which ALOX genes were expressed in the BJ cell lines and in HT-1080 cells were examined using qPCR. Of the six isoforms, ALOX15B and ALOXE3 were consistently expressed in these cell lines, whereas ALOX5, ALOX12, ALOX12B, and ALOX15 did not show consistent expression in the qPCR analysis (FIG. 14a). Accordingly, pools of small interfering RNAs (siRNAs) targeting ALOX15B and ALOXE3 were prepared, and the effect of each siRNA pool on the lethality of the RSL compounds was tested. The siRNA pools targeting ALOX15B and ALOXE3 were able to decrease their target mRNA levels by greater than 6-fold and 20-fold, respectively (FIG. 14b). Knocking down ALOX15B prevented erastin-induced cell death, but sensitized cells to RSL3-induced cell death (FIG. 4c). On the other hand, knockdown of ALOXE3 suppressed both erastin and RSL3-induced cell death (FIG. 4c). When the experiment was expanded to 10 additional RSL compounds, siRNAs targeting ALOXE3 consistently suppressed cell death induced by all RSLs, demonstrating a critical role for ALOXE3 in inducing the RSL phenotype (FIG. 4c and FIG. 15). Moreover, ALOXE3 knockdown exerted minimal effect on cell death induced by 10 non-RSL compounds (FIG. 4c and FIG. 15). The effect of ALOXE3 knockdown was not as specific to RSL compounds as small molecule ALOX inhibitors. The differences in isoform specificity, and the different mechanisms of RNAi and small molecules, may explain these differences (Luo et al., 2012; Weiss et al., 2007; Yang et al., 2012).

Example 7

Erastin Analogs are Selective Against Cells Expressing HRAS, as Shown in Isogenic BJ Cell Lines and the HT-1080 Cell Line The carbonyl erastin analogs were tested in 4 isogenic cell lines: HRAS$^{G12V}$ overexpressing artificially transformed fibroblasts (BJeLR, BJeDRD) and non-transformed isogenic cells without mutant HRAS expression (BJeHLT, BJeH).
General Procedure: Generation of Concentration-Dependent Curve of Carbonyl Erastin Analogs Empty 384-well plates were filled with 30 µL growth media, except for column 5, where 60 µL of compound solution (erastin analogs) was transferred. After transferring a solution containing carbonyl erastin analog compounds, 2-fold dilution series across columns 5 through 20 was made by transferring 30 µL of compound solution to the next column successively (16-point dilution series), with extensive mixing. Assay plates were prepared by seeding either BJ-derived cell lines or HT-1080 cells at 1,500 cells per well concentration in 36 µL growth medium. Cells in the assay plates were treated with compounds by transferring 4 µL volume from the compound plate. The final concentration of compound was typically 30 µM to 0.9 nM in this 16-point, 2-fold dilution series. Assay plates were returned to the culture incubator and maintained for 2 days before adding alamar blue. 10 µL of 50% alamar blue solution in cell growth media was transferred to the assay plates, which resulted in 10% final concentration alamar blue. Plates were incubated further for 16 hours to allow reduction of alamar blue, which results in the generation of red fluorescence. The fluorescence intensity was determined using a Victor 3 plate reader (Perkin Elmer) with a 535 nm excitation filter and a 590 nm emission filter.

Percent growth inhibition (% GI) was calculated from the following formula using the alamar blue fluorescence intensity values.

% GI=100*(1−(X−N)/(P−N))

X, cells treated with lethal compound; N, no cells—growth media only; P, no lethal compound—cells only.

The concentration-dependent curves were generated using Prism software. Percent growth inhibition, measured using alamar blue is shown. Error bars indicate one standard deviation of triplicate data.

Figure 16:
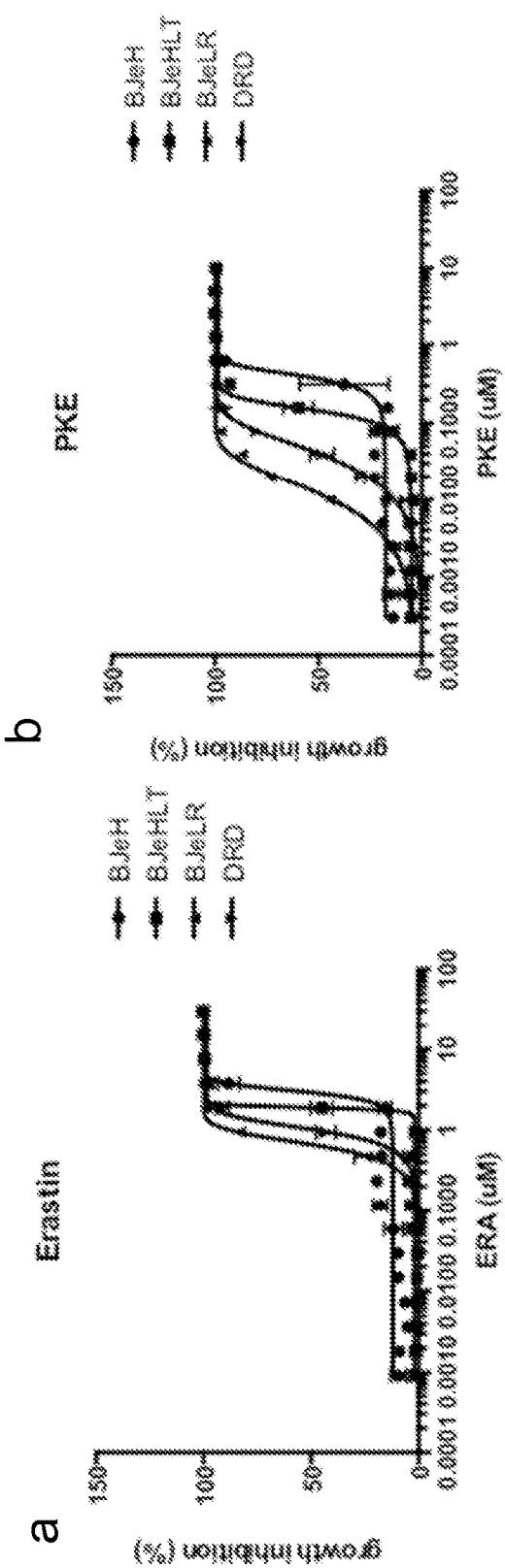
Figure 16:
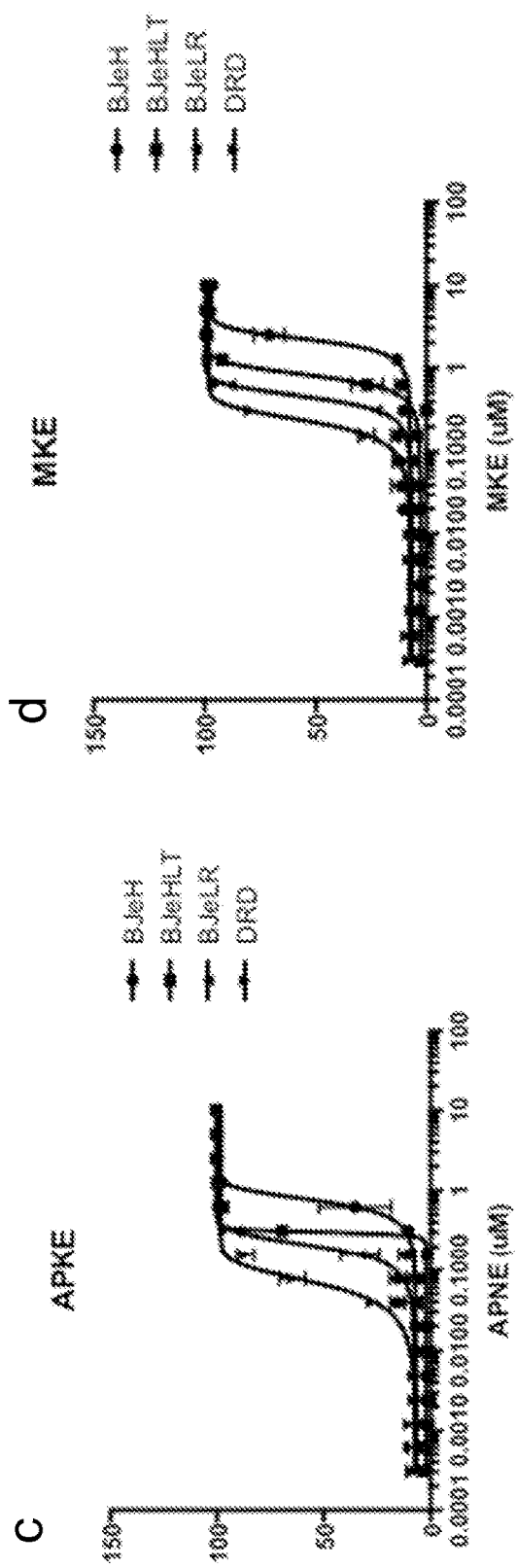
Figure 16:
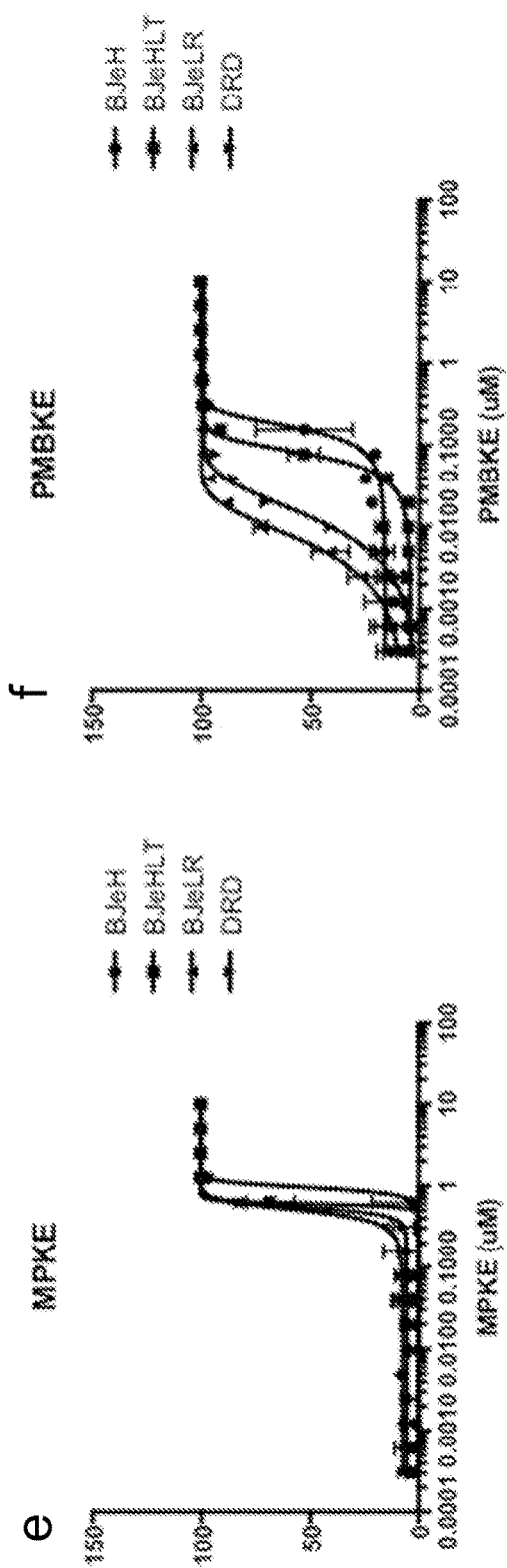
Figure 16:
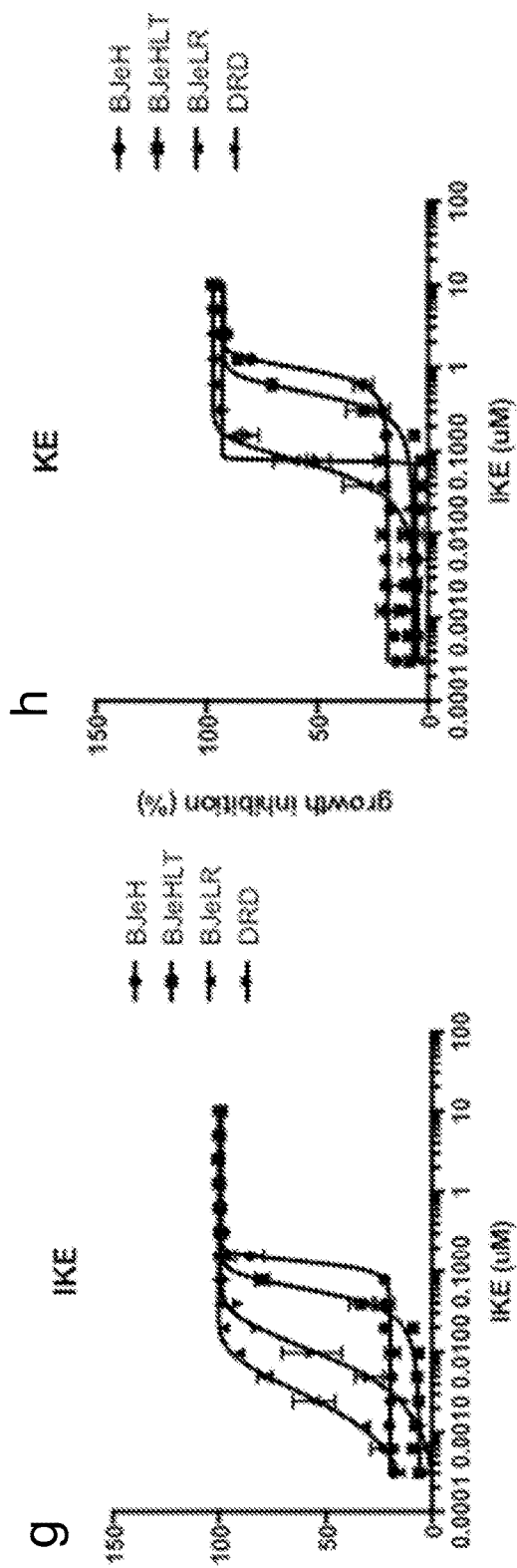
Figure 16:
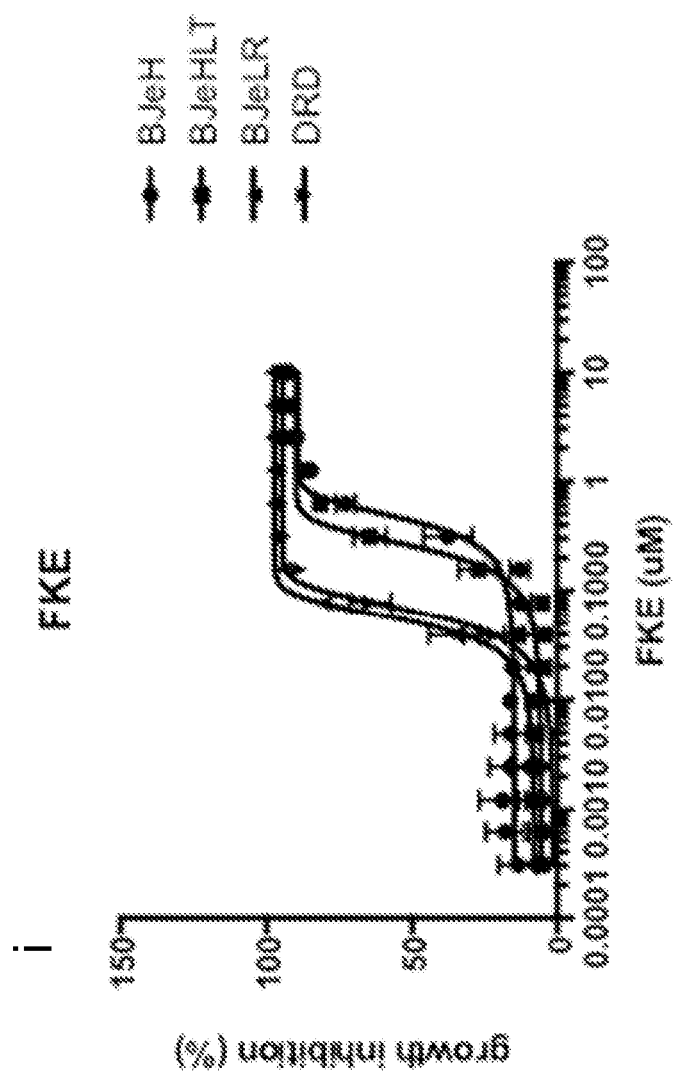

The results are shown in FIG. 16 and in Table 6 below.

TABLE 6

| Analog | IC$_{50}$ BJeLR (nM) | Selectivity (IC$_{50}$BJeH/IC$_{50}$BJeLR) |
|---|---|---|
| Erastin | 625 | 4.6 |
| PE | 300 | 3 |
| AE | 8 | 15 |
| KE | 65 | 15 |
| FKE | 51 | 8.3 |
| MKE | 427 | 5 |
| MPKE | 474 | 1.9 |
| APKE | 195 | 1.5 |
| PMB-PKE | 13 | 13 |
| PKE | 12 | 32 |
| IKE | 3 | 42 |

Figure 17:
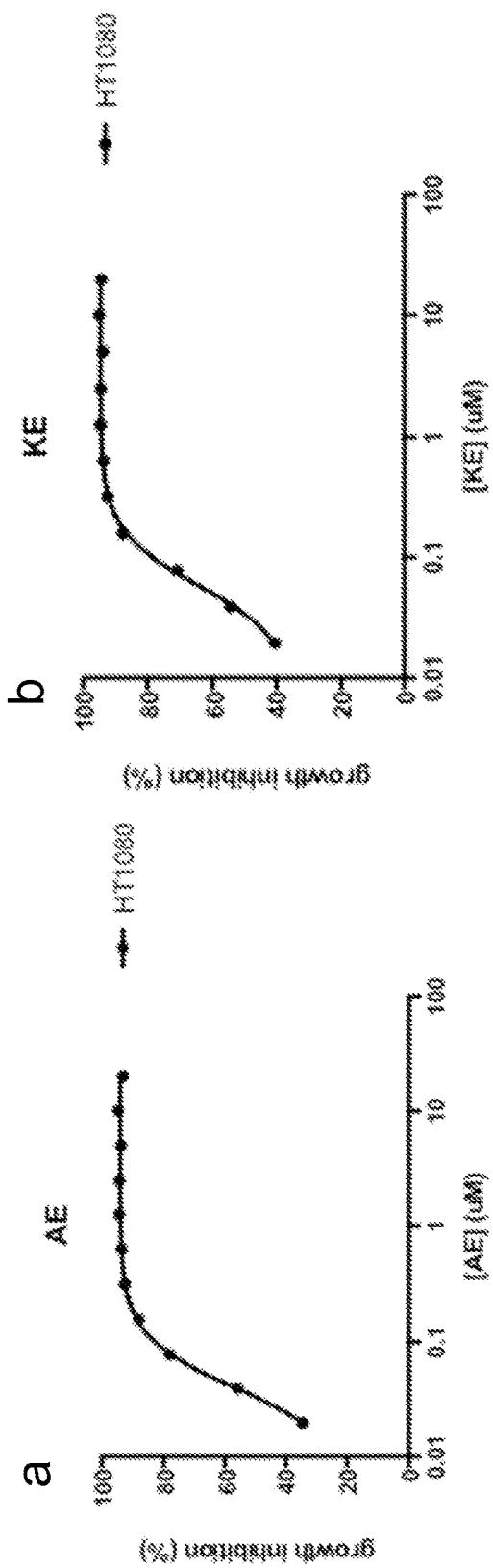
Figure 17:
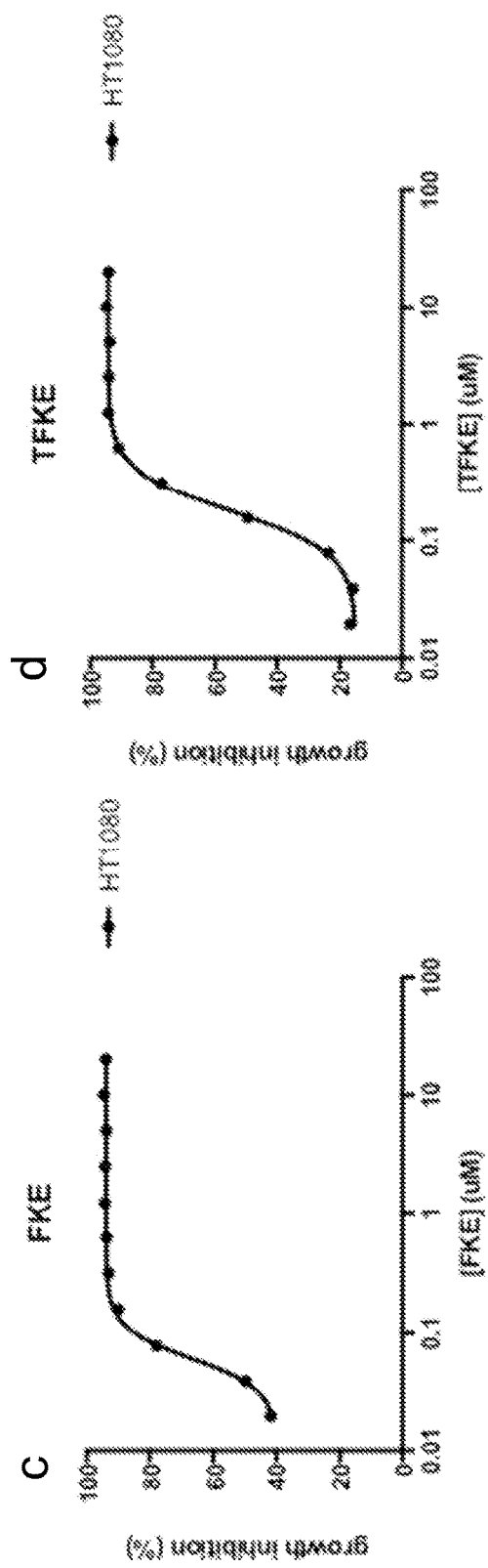
Figure 17:
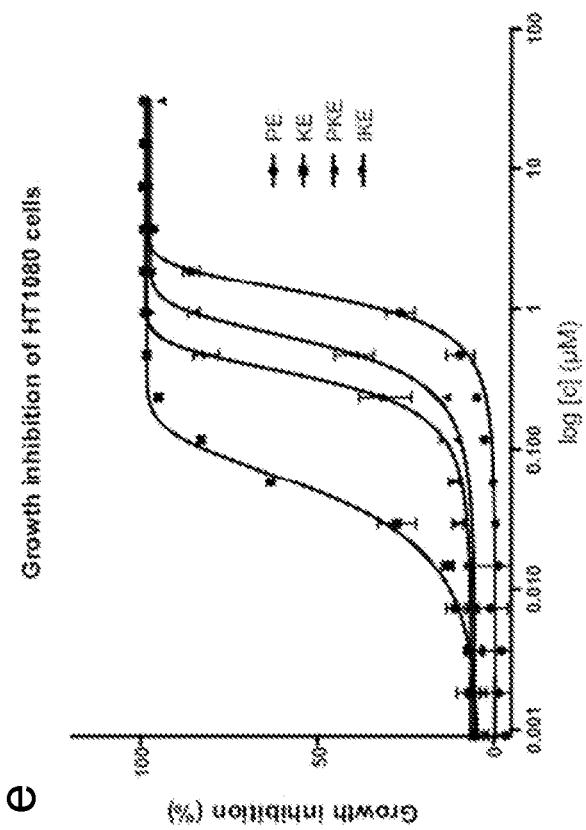

Using the same general procedure described for BJ cells, the human fibrosarcoma cell line, HT1080, was treated with AE, KE, FKE, TFKE, PE, IKE, PKE. The results are shown in FIG. 17 and in Table 7 below.

TABLE 7

| Analog | IC$_{50}$ HT1080 (nM) |
|---|---|
| PE | 1196 |
| AE | 39 |
| KE | 59 |
| FKE | 61 |
| TFKE | 178 |
| PKE | 550 |
| IKE | 314 |

Example 8

Metabolic Stability of Carbonyl Erastin Analogues in Mice Liver Microsomes

General Procedure:—Assessment of Compound Half-Life in Liver Microsomes

Test compound (0.5 µM) was incubated at 37° C. for up to 45 minutes in 50 mM of potassium phosphate buffer (pH 7.4) containing mouse liver microsomal proteins (0.5 mg/mL) and an NADPH generating system (0.34 mg/mL β-nicotinamide adenine dinucleotide phosphate (NADP), 1.56 mg/mL glucose-6-phosphate, 1.2 units/mL glucose-6-phosphate dehydrogenase). At 0, 5, 15, 30 and 45 minute intervals an aliquot was taken and quenched with acetonitrile (ACN) containing internal standard. No-cofactor controls at 45 minutes were prepared. Following completion of the experimentation, the samples were analyzed by LC-MS/MS. The LC-MS/MS method was developed for each compound individually. The instruments used include Shimadzu HPLC, Applied Biosystem API4000 QTrap.

The half-life ($t_{1/2}$) is calculated using the following equation:

$t_{1/2}=0.693/k$ where, k is the elimination rate constant of test compounds obtained by fitting the data to the equation:

$C=\text{initial}\times\exp(-k\times t)$

Intrinsic clearance (Clint) is calculated as liver clearance from the half-life using the following equation:
where:
rate=k/min
0.5 mg protein/mL incubation
52.5 mg protein/g liver Results were reported as peak area ratios of analyte to internal standard. The intrinsic clearance (CLint) was determined from the first order elimination constant by non-linear regression. The results are shown in FIG. 18 and in Table 8 below.

TABLE 8

| Analog | Half-life in liver microsomes (min) |
|---|---|
| PE | 55 |
| KE | 3.8 |
| FKE | 4.7 |
| MKE | 23.4 |
| APKE | 4.2 |
| PMB-PKE | 3.4 |
| PKE | >90 |
| IKE | 79 |

As predicted, both the aldehyde analog (FIG. 18, AE) and the methyl ketone analog (FIG. 18, KE) were rapidly metabolized and had half-lives <5 minutes. Several other carbonyl erastin analogs (FIG. 18: FKE, MKE, APKE, PMB-PKE) displayed medium to poor metabolic stability. On the other hand, two carbonyl erastin analogues, piperazine ketone erastin (FIG. 18, PKE, T½>90 min) and imidazole ketone erastin (FIG. 18, IKE, T½=79 min) demonstrated exceptionally high metabolic stability that even surpassed that of piperazine erastin, which does not possess a carbonyl functionality (FIG. 18, PKE, T½=55 min).

In addition, we assessed the plasma stability and PK profile of IKE and PKE in mice. Stability of PKE and IKE in mouse plasma was determined by dissolving each compound in the mouse plasma at 500 ng/mL concentration followed by incubation at 37° C. Both PKE and IKE remained stable up until 120 minutes under this condition (Table 9, below). The pharmacokinetic profiles of PKE and IKE in vivo were determined by administering to adult mice (C57BL/6) 20 mg/kg PKE or 5 mg/kg IKE via a single IV bolus injection or a single oral gavage. Both PKE and IKE exhibited poor oral bioavailability (0.75% and 2.49% each), which suggested IP delivery of the compound should be used for drug efficacy studies.

Example 9

Carbonyl Erastin Analogues are Potent System xc– Inhibitors

Ten ketone erastin analogs were evaluated in a glutamate release assay, which reports on system xc– activity. Human astrocytoma cells (CCF-STTG1) were used, which contain the system xc–. Following a 2 hour incubation period, glutamate released into the medium was detected fluorometrically using glutamate oxidase, horseradish peroxidase and Amplex UltraRed. Dramatic improvement of the half-maximal inhibitory constants ($IC_{50}$) for system xc– inhibition was observed for all ketone analogs, compared to erastin and PE (Table 9). Several analogs, such as MKE (Table 9, entry 7, $IC_{50}$=10 nM) and IKE (Table 9, entry 12, $IC_{50}$=30 nM) even had improved potency over aldehyde erastin (Table 9, entry 3, $IC_{50}$=60 nM).

TABLE 9

| Entry | Compound | R | $IC_{50}$ glutamate release (nM) |
|---|---|---|---|
| 1 | Erastin | — | 200 |
| 2 | PE | — | 800 |
| 3 | AE | H | 60 |
| 4 | KE | Me | 30 |
| 5 | FKE | $CH_2F$ | 40 |
| 6 | TFKE | $CF_3$ | 20 |
| 7 | MKE | morpholinomethyl | 10 |
| 8 | MPKE | 4-methylpiperazinylmethyl | 300 |
| 9 | APKE | 4-allylpiperazinylmethyl | 10 |
| 10 | PMB—PKE | 4-(4-methoxybenzyl)piperazinylmethyl | 4 |
| 11 | PKE | piperazinylmethyl | 100 |
| 12 | IKE | imidazolylmethyl | 30 |

Example 10

IKE Inhibits Tumor Growth in a Mouse Xenograft Tumor Model

To test our hypothesis that IKE represented a candidate of choice for in vivo studies, we treated xenograft tumors generated from BJeLR cells in nude mice and with IKE compared to vehicle or doxorubicin treatments (as a positive growth suppression control). After an 8 day study, consisting of seven once-daily doses of IKE, we observed tumors that were on average about one third of the size of vehicle-treated tumors (P=0.035), (FIG. 19a). Comparing IKE to doxorubicin treatment, there was no significant difference (P=0.73). No overt toxicity was observed in either IKE or doxorubicin-treated mice throughout the study (as gauged by monitoring body weight, FIG. 20). To confirm that growth suppression caused by IKE was due to ferroptotic cell death, we looked at levels of expression of PTGS2, a gene expression marker of ferroptosis. We observed a three-fold average increase in expression of PTGS2 in IKE-treated mice relative to doxorubicin or vehicle-treated mice (FIG. 19b). As a control, we also analyzed expression of CDKN1A, a marker of doxorubicin exposure, and found a 5-fold increase in expression relative to IKE-treated or vehicle-treated mice.

Example 11

Comparative Reactivities of Carbonyl Moities with n-butylamine

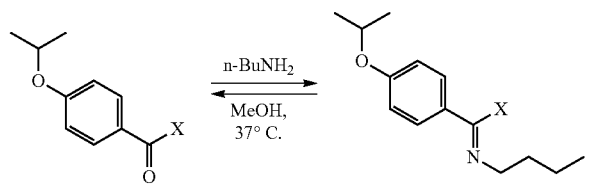

α-substituted ketones can form imines with lysine side chains. In order to define the structural requirements for facile imine formation, we compared the reactivity of aryl aldehydes and α-substituted aryl ketones towards a simple model of lysine side chain. Our idea was to use n-butyl amine to mimic the reactive side chain of lysine and determine whether this moiety could react with α-substituted ketones at 37° C. Reaction of aryl aldehyde 8a with n-butylamine in MeOH produced imine 9a with >90% conversion after 24 hours at 37° C. High conversion to the imine adduct were also obtained with methyl ketone 8b and α-fluoromethyl ketone 8c. We observed that when the methyl ketone was α-substituted with heterocycles, the formation of the imine adduct could still be observed, although the conversion was lower under these conditions.

We tested in total a set of 9 carbonyl-containing moieties after 24 hours at 37° C. Carbonyl derivatives 8a-i were reacted with n-butylamine in MeOH, and the imine adduct to starting material ratio (imine/SM) was measured after 24 hours by treating the mixture with NaBH3CN, and isolating the corresponding amine and SM. (Table 10). We found that α-substituted ketones could be used as an electrophile for imine formation, and the relative reactivity of each carbonyl moiety was determined.

TABLE 10

| Probe, X | Imine/SM ratio |
|---|---|
| 8a, X = H | 10/1 |
| 8b, X = Me | 3/1 |
| 8c, X = CH$_2$F | 1/1 |
| 8d, X = (morpholinomethyl) | 1/1.2 |
| 8e, X = (4-methylpiperazinylmethyl) | 1/2.5 |
| 8f, X = (4-allylpiperazinylmethyl) | 1/1.2 |
| 8g, X = (4-(4-methoxybenzyl)piperazinylmethyl) | 1/4 |
| 8h, X = (piperazinylmethyl) | 1/7 |
| 8i, X = (imidazolylmethyl) | 1/1.5 |

DOCUMENTS

BABIJ, C. et al. STK33 kinase activity is nonessential in KRAS-dependent cancer cells. *Cancer Res* 71, 5818-5826 (2011).

BARBIE, D. A. et al. Systematic RNA interference reveals that oncogenic KRAS-driven cancers require TBK1. *Nature* 462, 108-112(2009).

BODEN, S. E., Bertsche, T., Ammon, H. P. & Safayhi, H. MEK-1/2 inhibition prevents 5-lipoxygenase translocation in N-formylpeptide-challenged human neutrophils. *Int J Biochem Cell Biol* 32, 1069-1074 (2000).

CHEN, B. K., Liu, Y. W., Yamamoto, S. & Chang, W. C. Overexpression of Ha-ras enhances the transcription of human arachidonate 12-lipoxygenase promoter in A431 cells. *Biochim Biophys Acta* 1344, 270-277 (1997).

CHEN, X. S. & Funk, C. D. The N-terminal "beta-barrel" domain of 5-lipoxygenase is essential for nuclear membrane translocation. *J Biol Chem* 276, 811-818(2001).

CHUANG, J. I., Chang, T. Y. & Liu, H. S. Glutathione depletion-induced apoptosis of Ha-ras-transformed NIH3T3 cells can be prevented by melatonin. *Oncogene* 22, 1349-1357(2003).

COLLES, S. M. & Chisolm, G. M. Lysophosphatidylcholine-induced cellular injury in cultured fibroblasts involves oxidative events. *J Lipid Res* 41, 1188-1198 (2000).

DIXON, S. J., Costanzo, M., Baryshnikova, A., Andrews, B. & Boone, C. Systematic mapping of genetic interaction networks. *Annu Rev Genet* 43, 601-625 (2009).

DIXON, Scott J. et al. Ferroptosis: An Iron-Dependent Form of Nonapoptotic Cell Death. *Cell* 149, 1060-1072 (2012).

DOLMA, S., Lessnick, S. L., Hahn, W. C. & Stockwell, B. R. Identification of genotype-selective antitumor agents using synthetic lethal chemical screening in engineered human tumor cells. *Cancer Cell* 3, 285-296 (2003).

DOWNWARD, J. Targeting RAS signalling pathways in cancer therapy. *Nat Rev Cancer* 3, 11-22 (2003).

FANELUS, I. & Desrosiers, R. R. Reactive oxygen species generated by thiol-modifying phenylarsine oxide stimulate the expression of protein L-isoaspartyl methyltransferase. *Biochem Biophys Res Commun* 371, 203-208 (2008).

HAEGGSTROM, J. Z. & Funk, C. D. Lipoxygenase and leukotriene pathways: biochemistry, biology, and roles in disease. *Chemical reviews* 111, 5866-5898(2011).

HAHN, W. C. et al., "Creation of human tumour cells with defined genetic elements," Nature 400 (1999): 464-468

HARTWELL, L. H., Szankasi, P., Roberts, C. J., Murray, A. W. & Friend, S. H. Integrating genetic approaches into the discovery of anticancer drugs. *Science* 278, 1064-1068 (1997).

HUSSAIN, S. P., Hofseth, L. J. & Harris, C. C. Radical causes of cancer. *Nat Rev Cancer* 3, 276-285(2003).

IMAI, H. & Nakagawa, Y. Biological significance of phospholipid hydroperoxide glutathione peroxidase (PHGPx, GPx4) in mammalian cells. *Free Radic Biol Med* 34, 145-169 (2003).

IRANI, K. et al. Mitogenic signaling mediated by oxidants in Ras-transformed fibroblasts. *Science* 275, 1649-1652 (1997).

JI, Z. et al. Chemical genetic screening of KRAS-based synthetic lethal inhibitors for pancreatic cancer. *Frontiers in bioscience: a journal and virtual library* 14, 2904-2910 (2009).

KAELIN, W. G., Jr. The concept of synthetic lethality in the context of anticancer therapy. *Nat Rev Cancer* 5, 689-698 (2005).

KAMPHORST, J. J., Fan, J., Lu, W., White, E. & Rabinowitz, J. D. Liquid chromatography-high resolution mass spectrometry analysis of fatty acid metabolism. *Analytical chemistry* 83, 9114-9122 (2011).

KANG, Y. J. & Enger, M. D. Buthionine sulfoximine-induced cytostasis does not correlate with glutathione depletion. *Am J Physiol* 262, C122-127 (1992).

KUMAR, M. S. et al. The GATA2 Transcriptional Network Is Requisite for RAS Oncogene-Driven Non-Small Cell Lung Cancer. *Cell* 149, 642-655 (2012).

LEBEAU, A., Terro, F., Rostene, W. & Pelaprat, D. Blockade of 12-lipoxygenase expression protects cortical neurons from apoptosis induced by beta-amyloid peptide. *Cell Death Differ* 11, 875-884(2004).

LI, Y., Maher, P. & Schubert, D. A role for 12-lipoxygenase in nerve cell death caused by glutathione depletion. *Neuron* 19, 453-463 (1997).

LUO, J. et al. A genome-wide RNAi screen identifies multiple synthetic lethal interactions with the Ras oncogene. *Cell* 137, 835-848(2009).

LUO, T. et al. STK33 kinase inhibitor BRD-8899 has no effect on KRAS-dependent cancer cell viability. *Proc Natl Acad Sci USA* 109, 2860-2865, (2012).

MALUMBRES, M. & Barbacid, M. RAS oncogenes: the first 30 years. *Nat Rev Cancer* 3, 459-465 (2003).

MCGARRY, S. J. & Williams, A. J. Digoxin activates sarcoplasmic reticulum Ca(2+)-release channels: a possible role in cardiac inotropy. *Br J Pharmacol* 108, 1043-1050 (1993).

PATEL, N. S. et al. Reduction of renal ischemia-reperfusion injury in 5-lipoxygenase knockout mice and by the 5-lipoxygenase inhibitor zileuton. *Mol Pharmacol* 66, 220-227(2004).

PRICE, B. D., Morris, J. D., Marshall, C. J. & Hall, A. Stimulation of phosphatidylcholine hydrolysis, diacylglycerol release, and arachidonic acid production by oncogenic ras is a consequence of protein kinase C activation. *J Biol Chem* 264, 16638-16643 (1989).

RAN, Q. et al. Embryonic fibroblasts from Gpx4+/− mice: a novel model for studying the role of membrane peroxidation in biological processes. *Free Radic Biol Med* 35, 1101-1109 (2003).

ROOT, D. E., Flaherty, S. P., Kelley, B. P. & Stockwell, B. R. Biological mechanism profiling using an annotated compound library. *Chemistry & biology* 10, 881-892 (2003).

SCHOLL, C. et al. Synthetic lethal interaction between oncogenic KRAS dependency and STK33 suppression in human cancer cells. *Cell* 137, 821-834(2009).

SEILER, A. et al. Glutathione peroxidase 4 senses and translates oxidative stress into 12/15-lipoxygenase dependent- and AIF-mediated cell death. *Cell Metab* 8, 237-248(2008).

SHAW, A. T. et al. Selective killing of K-ras mutant cancer cells by small molecule inducers of oxidative stress. *Proc Natl Acad Sci USA* 108, 8773-8778 (2011).

SHORNICK, L. P. & Holtzman, M. J. A cryptic, microsomal-type arachidonate 12-lipoxygenase is tonically inactivated by oxidation-reduction conditions in cultured epithelial cells. *J Biol Chem* 268, 371-376 (1993).

SZATROWSKI, T. P. & Nathan, C. F. Production of large amounts of hydrogen peroxide by human tumor cells. *Cancer Res* 51, 794-798 (1991).

TRACHOOTHAM, D. et al. Selective killing of oncogenically transformed cells through a ROS-mediated mechanism by beta-phenylethyl isothiocyanate. *Cancer Cell* 10, 241-252(2006).

WEISS, W. A., Taylor, S. S. & Shokat, K. M. Recognizing and exploiting differences between RNAi and small-molecule inhibitors. *Nat Chem Biol* 3, 739-744(2007).

WEIWER, M. et al. Development of small-molecule probes that selectively kill cells induced to express mutant RAS. *Bioorg Med Chem Lett* 22, 1822-1826 (2012).

WOLPAW, A. J. et al. Modulatory profiling identifies mechanisms of small molecule-induced cell death. *Proc Natl Acad Sci USA* 108, E771-780(2011).

YAGODA, N. et al. RAS-RAF-MEK-dependent oxidative cell death involving voltage-dependent anion channels. *Nature* 447, 864-868 (2007).

YANG, W. S. & Stockwell, B. R. Synthetic Lethal Screening Identifies Compounds Activating Iron-Dependent, Non-apoptotic Cell Death in Oncogenic-RAS-Harboring Cancer Cells. *Chemistry & biology* 15, 234-245 (2008a).

YANG, W. S. & Stockwell, B. R. Inhibition of casein kinase 1-epsilon induces cancer-cell-selective, PERIOD2-dependent growth arrest. *Genome biology* 9, R92 (2008b).

YANG, W. S. et al. Identification of Simple Compounds with Microtubule-Binding Activity That Inhibit Cancer Cell Growth with High Potency. *ACS Med Chem Lett* 3, 35-38 (2012).

YU, Z., Schneider, C., Boeglin, W. E., Marnett, L. J. & Brash, A. R. The lipoxygenase gene ALOXE3 implicated in skin differentiation encodes a hydroperoxide isomerase. *Proc Natl Acad Sci USA* 100, 9162-9167 (2003).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound according to formula (I):

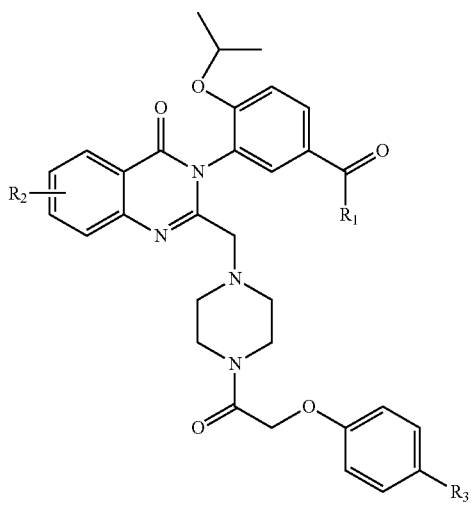

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$alkyl-aryl-O—C$_{1-4}$alkyl;

R$_2$ is selected from the group consisting of H, halo, and C$_{1-6}$aliphatic; and R$_3$ is a halo atom;

or an N-oxide, crystalline form, hydrate, or pharmaceutically acceptable salt thereof.

2. A compound according to claim 1 having the structure of formula (II):

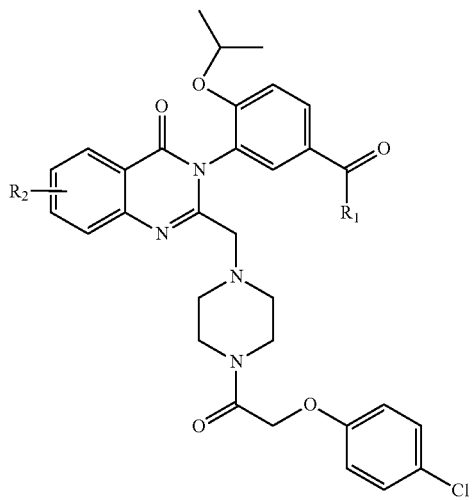

(II)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$ alkyl-aryl-O—C$_{1-4}$ alkyl; and R$_2$ is selected from the group consisting of H, halo, and C$_{1-6}$aliphatic;

or an N-oxide, crystalline form, hydrate, or pharmaceutically acceptable salt thereof.

3. A compound according to claim 1 having the structure of formula (III):

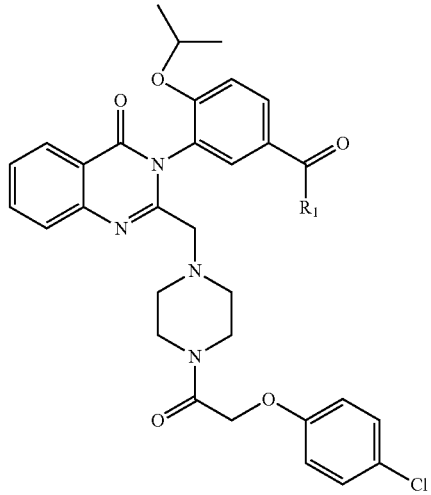

(III)

wherein R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$ aliphatic may be optionally substituted with an C$_{1-4}$ alkyl-aryl-O—C$_{1-4}$ alkyl or an N-oxide, crystalline form, hydrate, or pharmaceutically acceptable salt thereof.
4. A compound according to claim 1, which is selected from the group consisting of:
KE
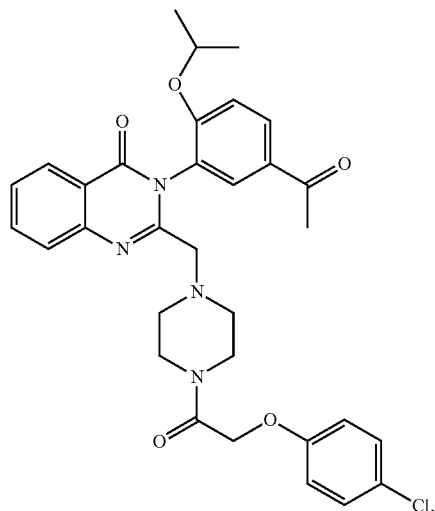
FKE
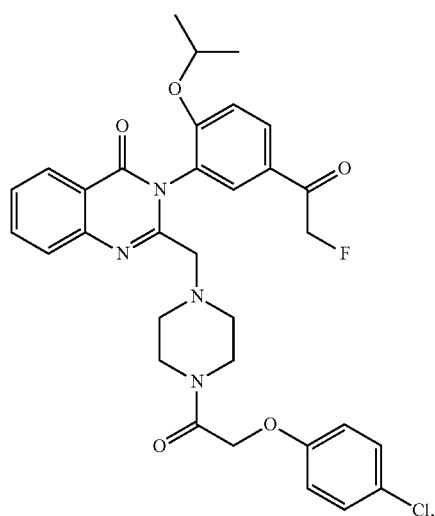
TFKE
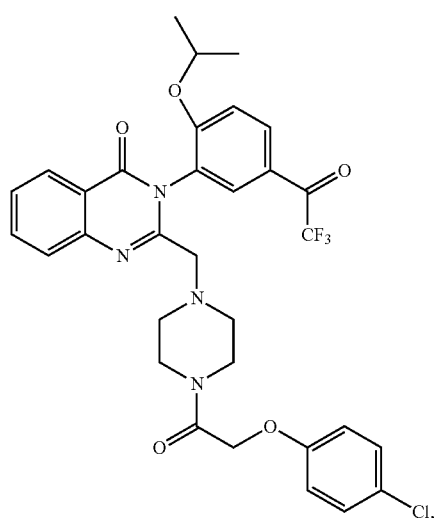
MKE
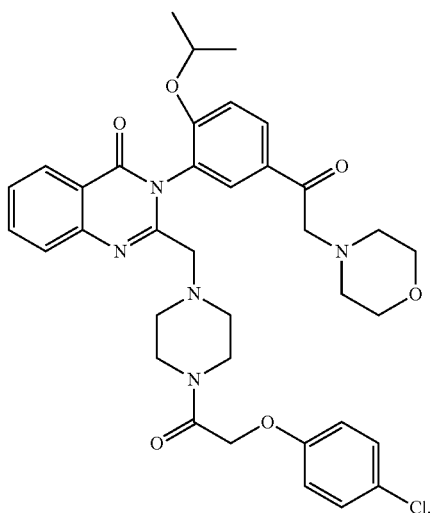
MPKE
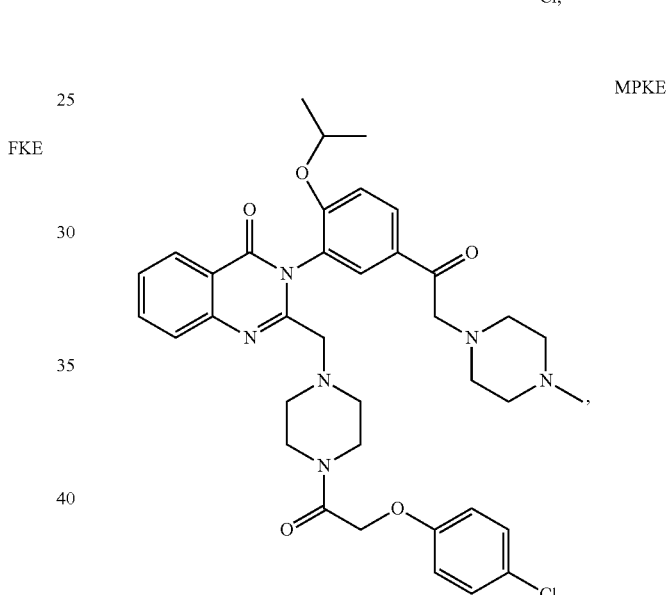
APKE
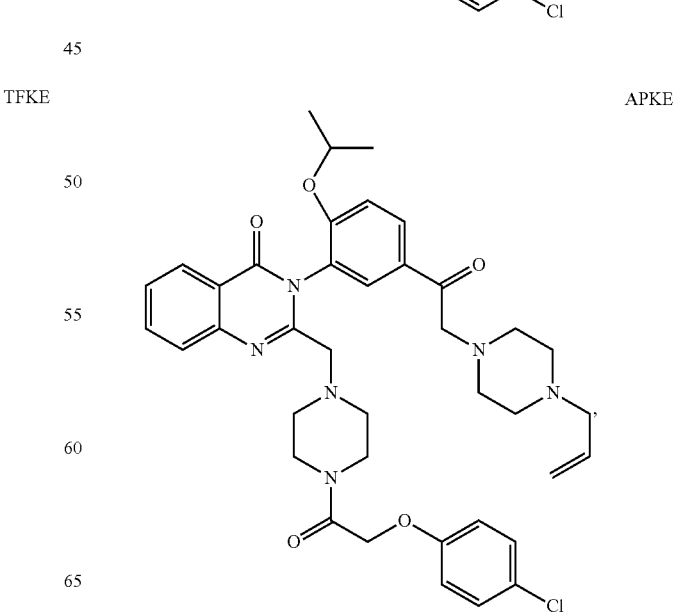

-continued
PMB-PKE
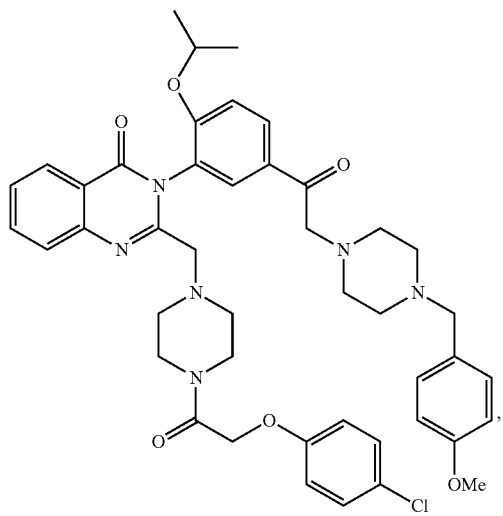
PKE
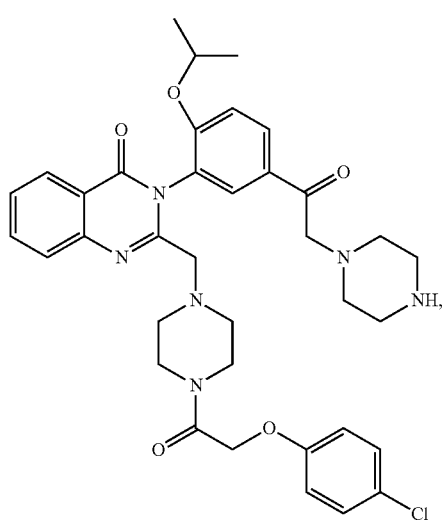
IKE
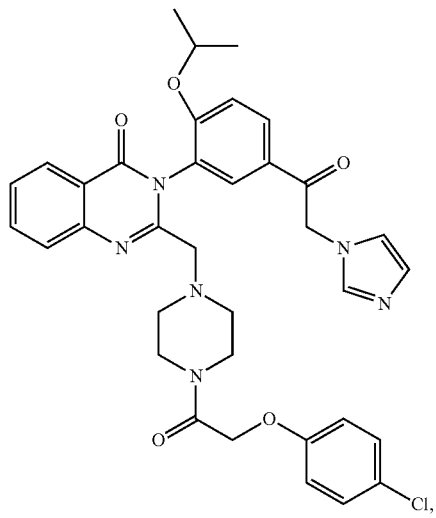
and combinations thereof or an N-oxide, crystalline form, hydrate, or pharmaceutically acceptable salt thereof.
5. A compound according to claim 1, which is selected from the group consisting of:
KE
PKE
IKE
and combinations thereof, or an N-oxide, crystalline form, hydrate, or pharmaceutically acceptable salt thereof.

6. A pharmaceutical composition comprising a pharmaceutically acceptable carrier or diluent and a compound according to formula (I):

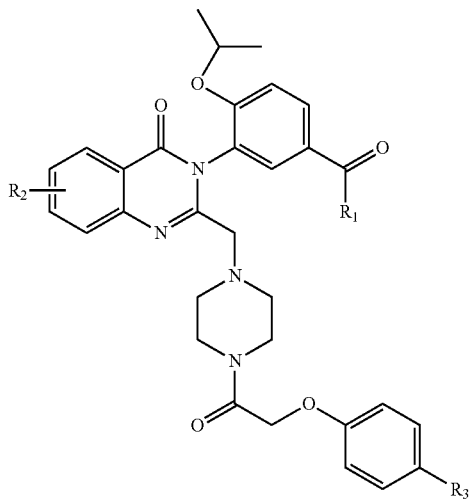

(I)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$ alkyl-aryl-O—C$_{1-4}$ alkyl;
R$_2$ is selected from the group consisting of H, halo, and C$_{1-6}$aliphatic; and
R$_3$ is a halo atom;
or an N-oxide, crystalline form, hydrate, or pharmaceutically acceptable salt thereof.

7. A pharmaceutical composition according to claim 6, wherein the compound has the structure of formula (II):

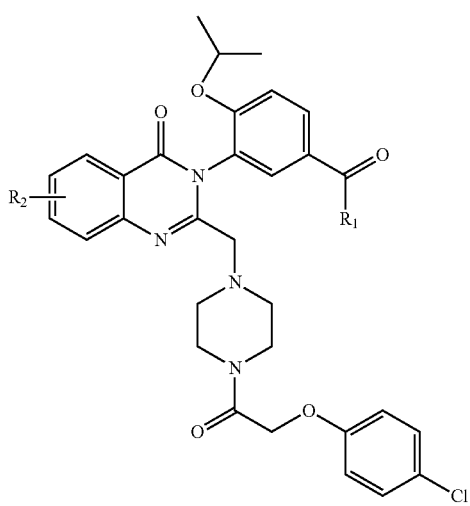

(II)

wherein:
R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$aliphatic may be optionally substituted with an C$_{1-4}$ alkyl-aryl-O—C$_{1-4}$ alkyl; and
R$_2$ is selected from the group consisting of H, halo, and C$_{1-6}$aliphatic;
or an N-oxide, crystalline form, hydrate, or pharmaceutically acceptable salt thereof.

8. A pharmaceutical composition according to claim 6, wherein the compound has the structure of formula (III):

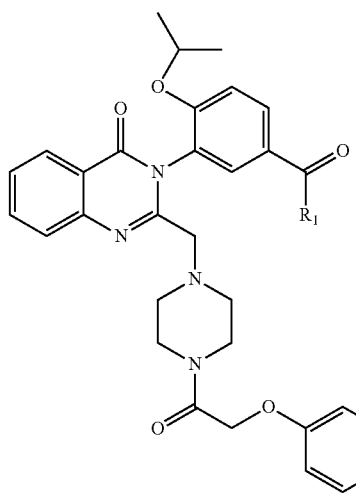

(III)

wherein R$_1$ is selected from the group consisting of H, C$_{1-6}$alkyl, and CF$_3$, wherein each C$_{1-6}$alkyl may be optionally substituted with an atom or a group selected from the group consisting of a halogen atom, a saturated or unsaturated C$_{3-6}$-heterocycle and an amine, each heterocycle optionally substituted with an atom or group selected from the group consisting of C$_{1-4}$aliphatic, which C$_{1-4}$ aliphatic may be optionally substituted with an C$_{1-4}$ alkyl-aryl-O—C$_{1-4}$ alkyl or an N-oxide, crystalline form, hydrate, or pharmaceutically acceptable salt thereof.

9. A pharmaceutical composition according to claim 6, wherein the compound has a structure that is selected from the group consisting of:

101
KE
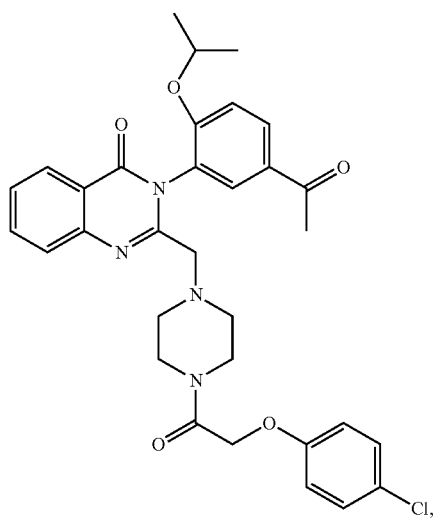
FKE
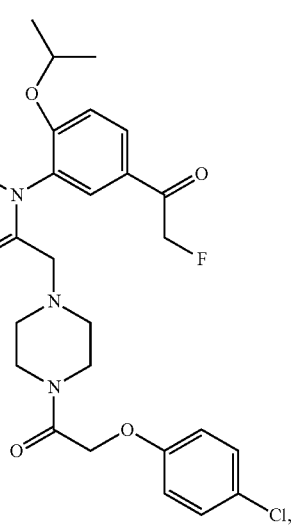
TFKE
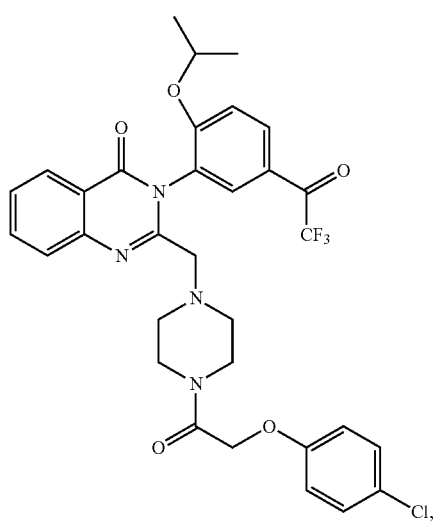
102
-continued
MKE
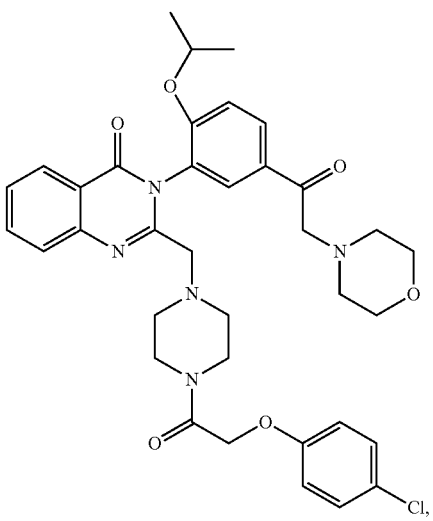
MPKE
APKE -continued
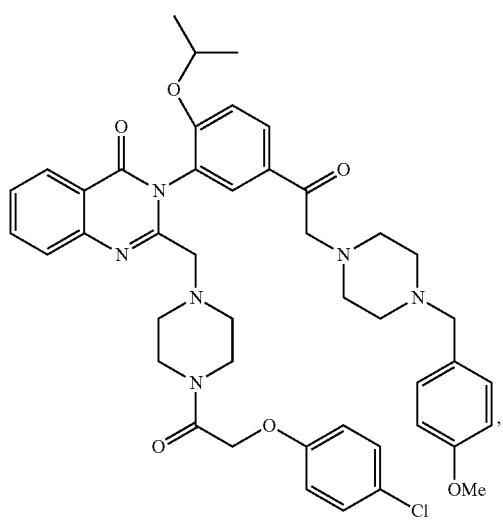
PMB-PKE
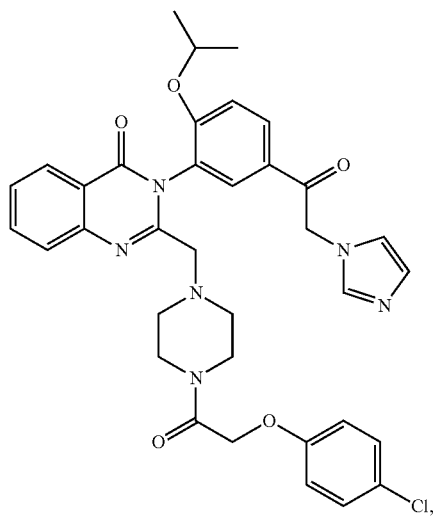
PKE
IKE
and combinations thereof, or an N-oxide, crystalline form, hydrate, or pharmaceutically acceptable salt thereof.
10. A pharmaceutical composition according to claim 6, wherein the compound has a structure that is selected from the group consisting of:
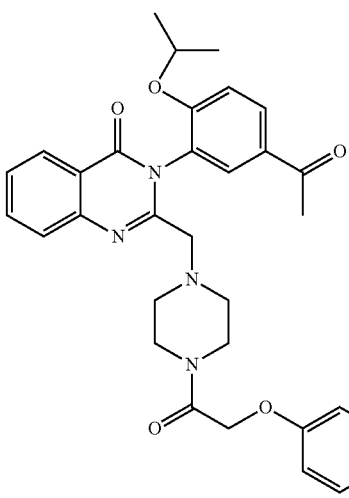
KE
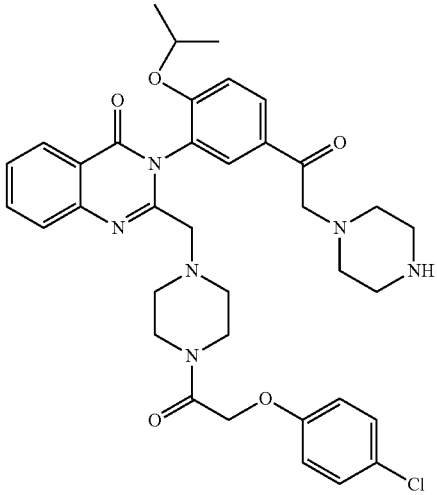
PKE
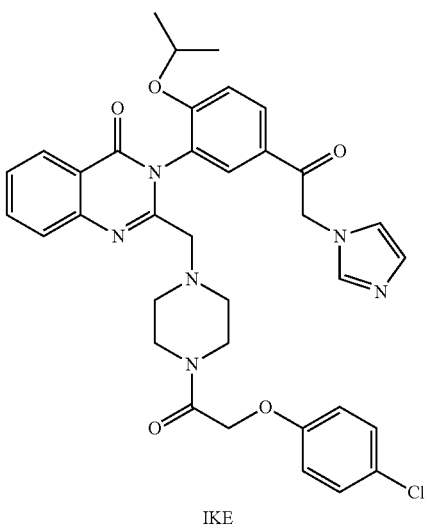 [SMILES: CC(C)Oc1ccc(C(=O)Cn2ccnc2)cc1-n1c(CN2CCN(C(=O)COc3ccc(Cl)cc3)CC2)nc2ccccc2c1=O]
IKE and combinations thereof or an N-oxide, crystalline form, hydrate, or pharmaceutically acceptable salt thereof.

11. A method for treating or ameliorating the effects of a cancer comprising a cell that harbors an oncogenic RAS mutation, the method comprising administering to a subject in need thereof a therapeutically effective amount of a compound according to claim 1.

12. A method for treating or ameliorating the effects of a cancer comprising a cell that harbors an oncogenic RAS mutation, the method comprising administering to a subject in need thereof a therapeutically effective amount of a pharmaceutical composition according to claim 6.

13. A method for treating or ameliorating the effects of a cancer comprising a cell that harbors an oncogenic RAS mutation, the method comprising administering to a subject in need thereof a therapeutically effective amount of a pharmaceutical composition comprising a compound having a structure that is selected from the group consisting of:

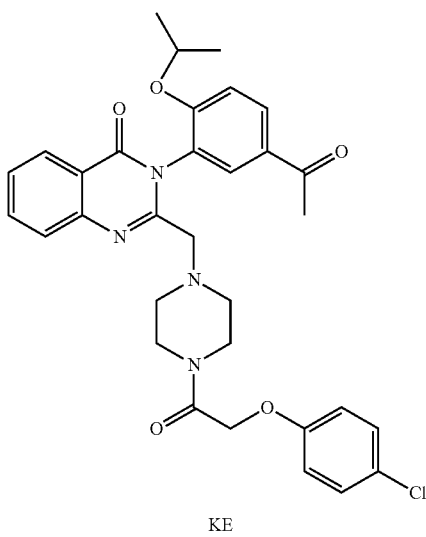

KE

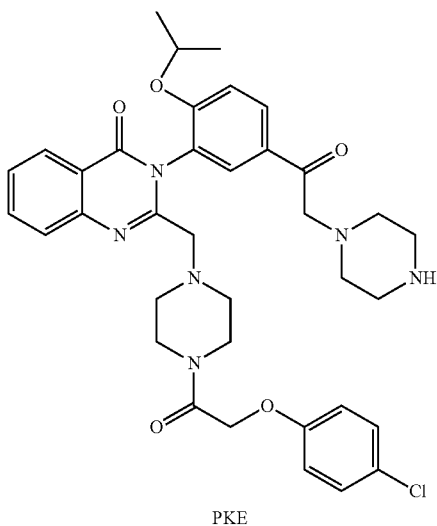

PKE

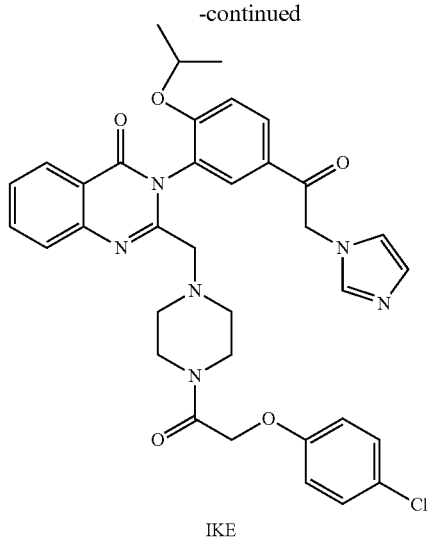

IKE and combinations thereof or an N-oxide, crystalline form, hydrate, or pharmaceutically acceptable salt thereof.

14. A method for modulating a lipoxygenase in a ferroptosis cell death pathway comprising contacting a cell with an effective amount of a compound having the structure of formula (I):

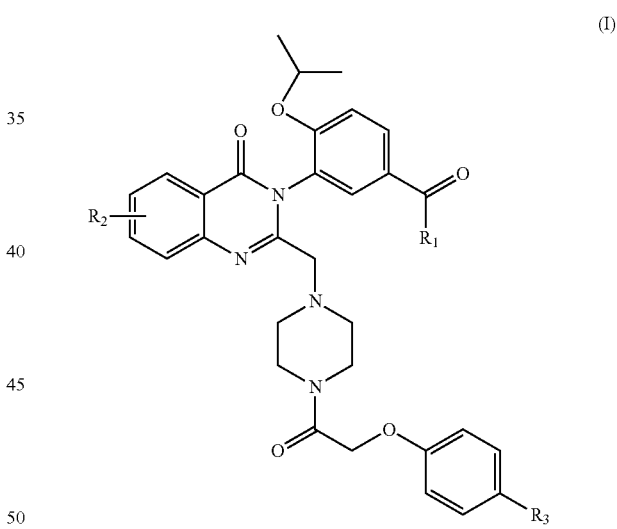

(I)

wherein:
$R_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl;
$R_2$ is selected from the group consisting of H, halo, and $C_{1-6}$aliphatic; and
$R_3$ is a halo atom;
or an N-oxide, crystalline form, hydrate, or pharmaceutically acceptable salt thereof.

15. The method according to claim 14, wherein the compound has the structure of formula (II):

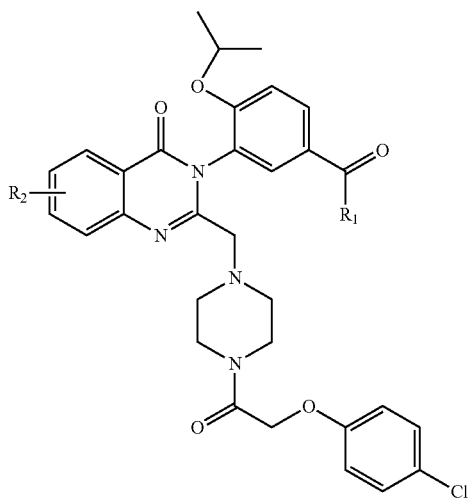

(II)

wherein:
R₁ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$ alkyl-aryl-O—$C_{1-4}$ alkyl; and R₂ is selected from the group consisting of H, halo, and $C_{1-6}$aliphatic;

or an N-oxide, crystalline form, hydrate, or pharmaceutically acceptable salt thereof.

16. The method according to claim 14, wherein the compound has the structure of formula (III):

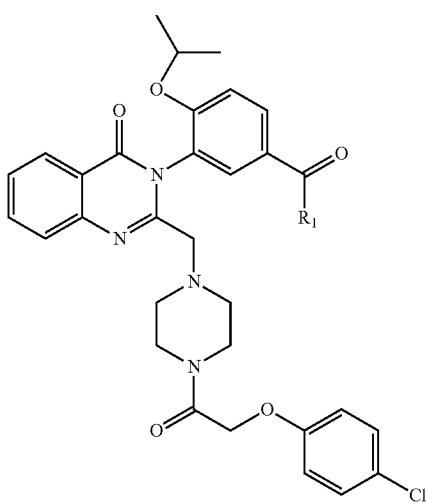

(III)

wherein R₁ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$alkyl-aryl-O—$C_{1-4}$alkyl or an N-oxide, crystalline form, hydrate, or pharmaceutically acceptable salt thereof.

17. The method according to claim 14, wherein the compound has a structure that is selected from the group consisting of:

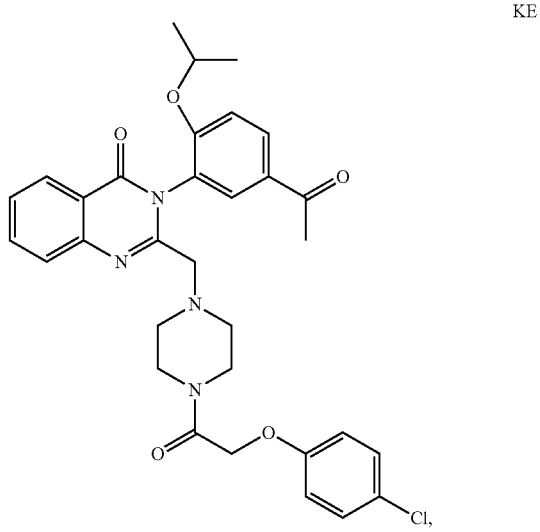

KE

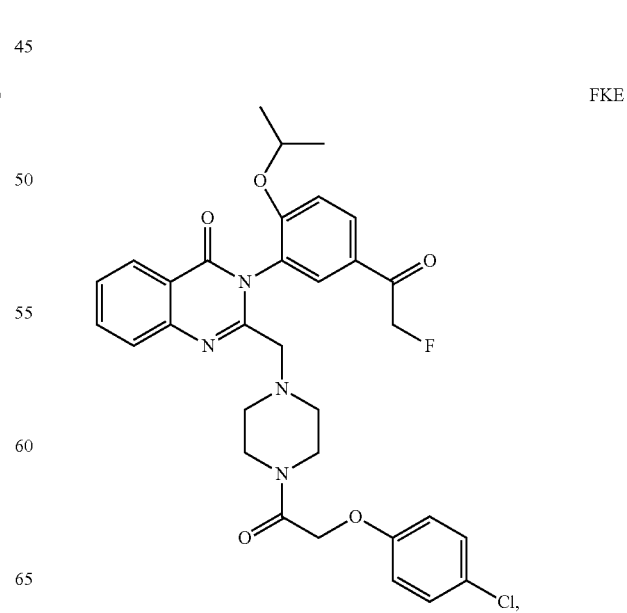

FKE

109
-continued
TFKE
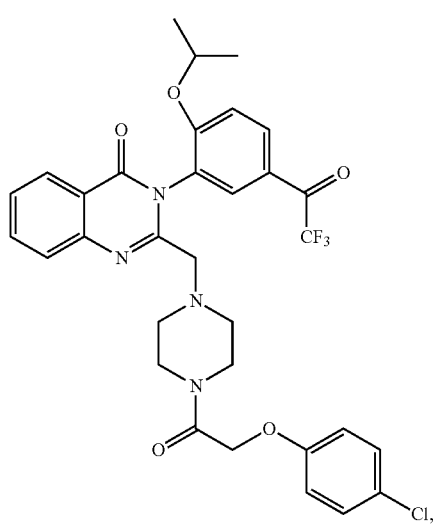
MKE
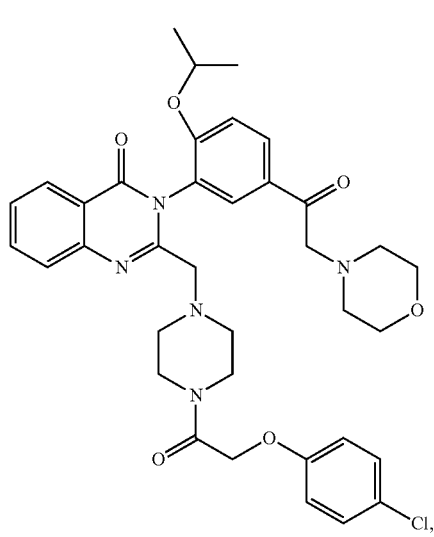
MPKE
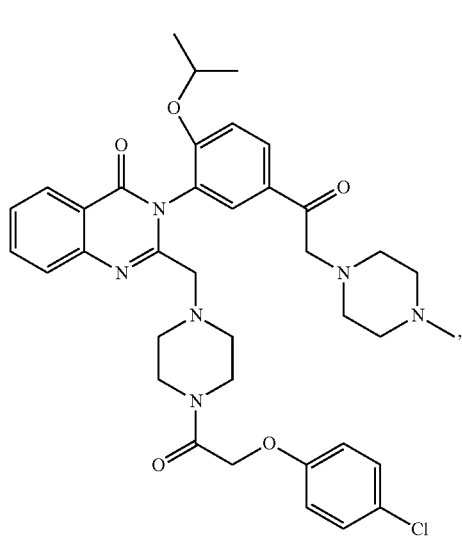
110
-continued
APKE
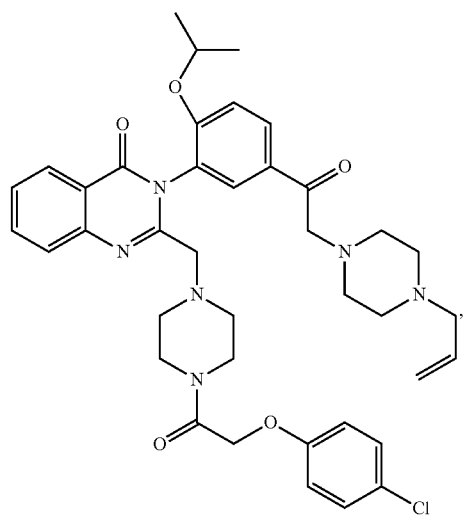
PMB-PKE
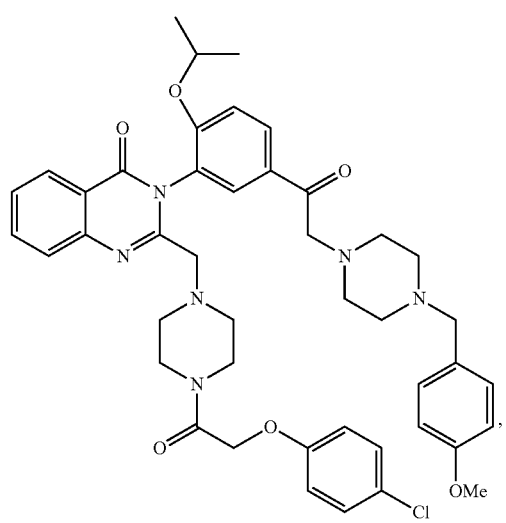
PKE
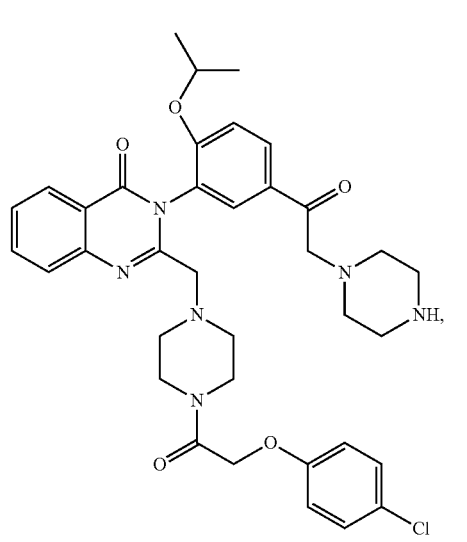

111
-continued

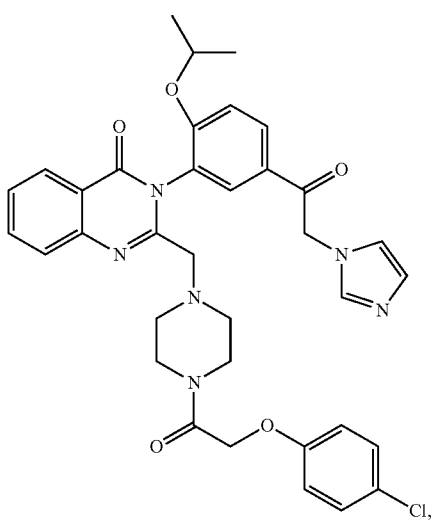
IKE and combinations thereof, or an N-oxide, crystalline form, hydrate, or pharmaceutically acceptable salt thereof.

18. The method according to claim 14, wherein the compound has a structure that is selected from the group consisting of:

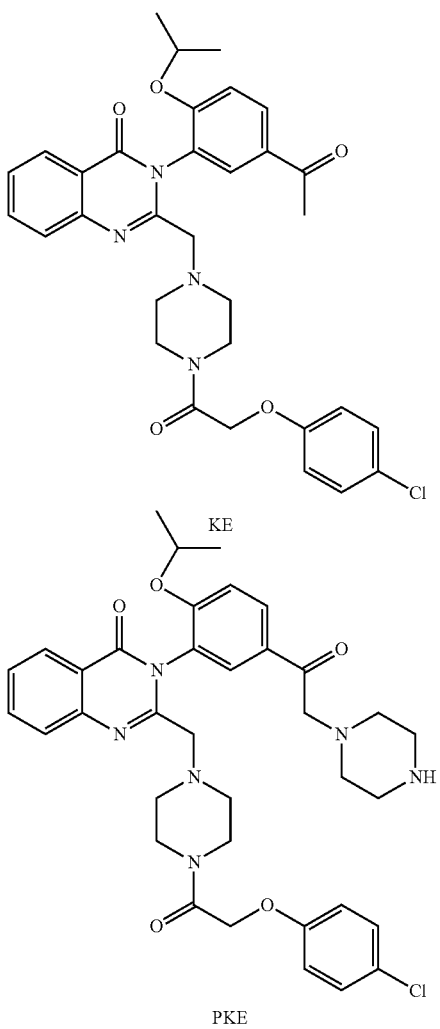
KE

PKE

112
-continued

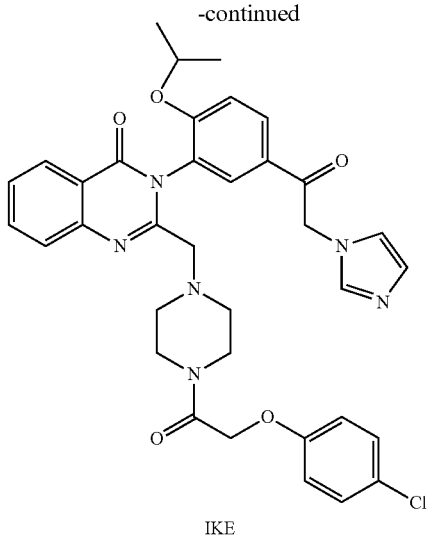
IKE and combinations thereof or an N-oxide, crystalline form, hydrate, or pharmaceutically acceptable salt thereof.

19. The method according to claim 14, wherein the modulation comprises activation of one or more polypeptides encoded by ALOX genes.

20. A method for depleting reduced glutathione (GSH) in a cell harboring an oncogenic RAS mutation comprising administering to the cell an effective amount of a compound having the structure of formula (I):

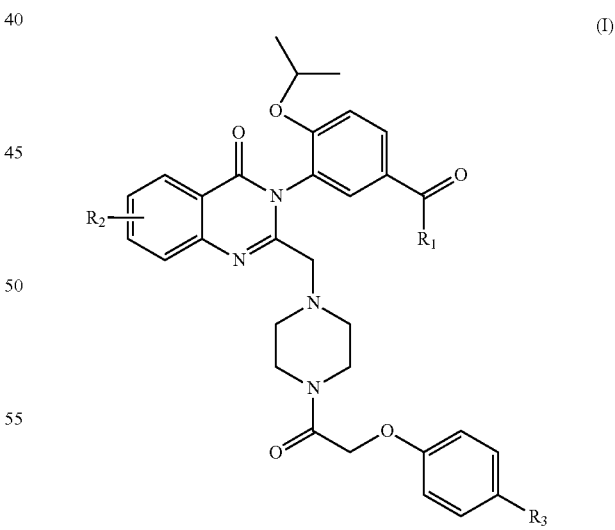
(I)

wherein:

$R_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each het erocycle optionally substituted with an atom or group selected from the group consisting of $C_{1-4}$aliphatic, which $C_{1-4}$aliphatic may be optionally substituted with an $C_{1-4}$ alkyl-aryl-O—$C_{1-4}$ alkyl;

$R_2$ is selected from the group consisting of H, halo, and $C_{1-6}$aliphatic; and $R_3$ is a halo atom;

or an N-oxide, crystalline form, hydrate, or pharmaceutically acceptable salt thereof.

21. A method of inhibiting system xc⁻ in a subject in need thereof comprising administering to the subject an effective amount of a compound having the structure of formula (I):

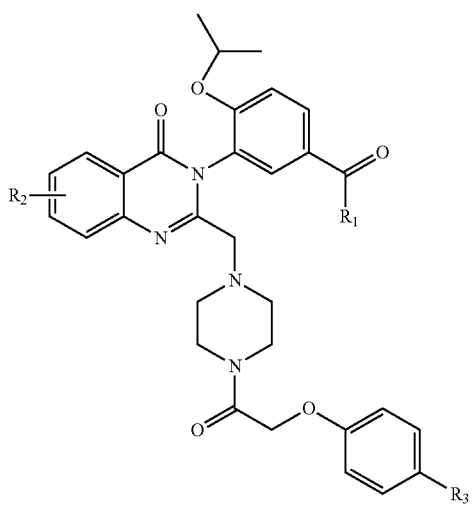

(I)

wherein:

$R_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$ alkyl-aryl-O—$C_{1-4}$ alkyl;

$R_2$ is selected from the group consisting of H, halo, and $C_{1-6}$aliphatic; and $R_3$ is a halo atom;

or an N-oxide, crystalline form, hydrate, or pharmaceutically acceptable salt thereof.

22. A method of selectively killing a cell having a Ras$^{v12}$ mutation comprising contacting the cell with an effective amount of a compound having the structure of formula (I):

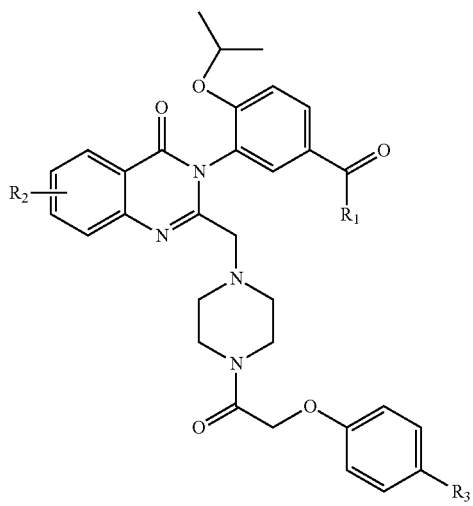

(I)

wherein:

$R_1$ is selected from the group consisting of H, $C_{1-6}$alkyl, and $CF_3$, wherein each $C_{1-6}$alkyl may be optionally substituted with an atom or a group selected from the group consisting of a halogen atom, a saturated or unsaturated $C_{3-6}$-heterocycle and an amine, each heterocycle optionally substituted with an atom or group selected from the group consisting of $C_{1-4}$aliphatic, which $C_{1-4}$aliphatic may be optionally substituted with an $C_{1-4}$ alkyl-aryl-O—$C_{1-4}$ alkyl;

$R_2$ is selected from the group consisting of H, halo, and $C_{1-6}$aliphatic; and $R_3$ is a halo atom;

or an N-oxide, crystalline form, hydrate, or pharmaceutically acceptable salt thereof.

23. A kit comprising a compound according to claim 1 together with instructions for the use of the compound.

24. A kit comprising a pharmaceutical composition according to claim 6 together with instructions for the use of the pharmaceutical composition.

25. A compound having the structure:

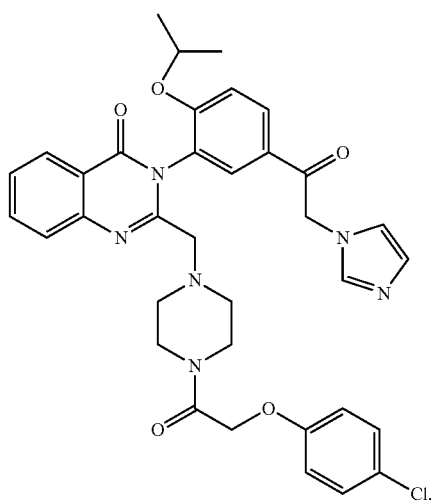

IKE

* * * * *